US012618067B2

(12) United States Patent
Engelhardt et al.

(10) Patent No.: US 12,618,067 B2
(45) Date of Patent: May 5, 2026

(54) TARGETED DELIVERY OF AN INHIBITOR OF miR-21 TO MACROPHAGES FOR THE TREATMENT OF PULMONARY FIBROSIS

(71) Applicant: Technische Universität München, Munich (DE)

(72) Inventors: Stefan Engelhardt, Munich (DE); Deepak Prabhu Ramanujam, Munich (DE)

(73) Assignee: Technische Universität München, Munich (DE)

( * ) Notice: Subject to any disclaimer, the term of this patent is extended or adjusted under 35 U.S.C. 154(b) by 808 days.

(21) Appl. No.: 17/995,722

(22) PCT Filed: Apr. 9, 2021

(86) PCT No.: PCT/EP2021/059360
§ 371 (c)(1),
(2) Date: Oct. 7, 2022

(87) PCT Pub. No.: WO2021/205032
PCT Pub. Date: Oct. 14, 2021

(65) Prior Publication Data

US 2023/0287413 A1 Sep. 14, 2023

(30) Foreign Application Priority Data

Apr. 9, 2020 (EP) .................................... 20169160

(51) Int. Cl.
*A61K 47/60* (2017.01)
*A61K 47/54* (2017.01)
*A61P 11/00* (2006.01)
*C12N 15/113* (2010.01)

(52) U.S. Cl.
CPC .......... *C12N 15/113* (2013.01); *A61K 47/549* (2017.08); *A61P 11/00* (2018.01); *C12N 2310/141* (2013.01)

(58) Field of Classification Search
None
See application file for complete search history.

(56) References Cited

U.S. PATENT DOCUMENTS

2013/0289093 A1 10/2013 Bhat et al.
2016/0333341 A1* 11/2016 Bhat .................... C12N 15/113
2018/0216170 A1 8/2018 Lee et al.

FOREIGN PATENT DOCUMENTS

AU 2014256406 11/2014
WO WO2015/061536 4/2015
WO WO2015/154002 10/2015

OTHER PUBLICATIONS

Molyneaux et al. The role of infection in the pathogenesis of idiopathic pulmonary fibrosis. Eur Respir Rev 2013; 22: 376-381.*
Zhu et al. Preparation and evaluation of mannose receptor mediated macrophage targeting delivery system. Journal of Controlled Release 152 (2011) e133-e191.*
Adam et al., "Role of miR-21 in pathogenesis of atrial fibrosis", *Basic Res Cardio*, 107:278, 2012.
Altshuler et al., "Generation of Recombinant Antibodies and Means for Increasing Their Affinity", *Biochemistry*, 75:13, 1584-1605, 2010.
Anonymous: "MRC1 mannose receptor C-type 1 [*Homo sapiens* (human)]—Gene—NCBI", XP055817974, retrieved from the internet: url:https://www.ncbi.nlm.nih.gov/gene/4360.
Bahit et al., "Post-Myocardial Infarction Heart Failure", *JACC: Heart Failure*, 6:3, 2018.
Bartel, "Metazoan MicroRNAs", *Cell*, 173, Mar. 22, 2018.
Bashore, et al., "2012 American College of Cardiology Foundation/ Society for Cardiovascular Angiography and Interventions Expert Consensus Document on Cardiac Catheterization Laboratory Standards Update", *Journal of the American College of Cardiology*, 59:24, 2012.
Basson et al., "Endogenous miRNA and Target Concentrations Determine Susceptibility to Potential ceRNA Competition", *Mol Cell*, 56(3):347-359, Nov. 6, 2014.
Brennan et al., "Preparation of Bispecific Antibodies by Chemical Recombination of Monoclonal Immunoglobulin $G_1$ Fragments", *Science*, 229, 81-83, 1985.
Brown et al., "Endogenous microRNA can be broadly exploited to regulate transgene expression according to tissue, lineage and differentiation state", *nature biotechnology*, 25(123)1457-1467, 2007.
Cardin et al., "Role for MicroRNA-21 in Atrial Profibrillatory Fibrotic Remodeling Associated with Experimental Postinfarction Heart Failure", *Dirc. Arrhythm Electrophysiol*, 6:1027-1035, 2012.
Carter et al., "High Level *Escherichia coli* Expression and Production of a Bivalent Humanized Antibody Fragment", *Bio/Technology*, 10, 163-167, 1992.
Cole, et al., "Antibody Production by Human x Human Hybridomas in Serum-Free Medium", *Journal of Immunological Methods*, 78, 271-278, 1985.
Harlow et al., "Antibodies a Laboratory Manual", 88-13983, 1988.
Harlow et al., "Using Antibodies a Laboratory Manual", 98-42802, 1998.
Hinkel et al., "Inhibition of MicroRNA-92a Protects Against Ischemia/ Reperfusion Injury in a Large-Animal Model", *Circulation*, 128-1066-1075, 2013.
Holliger et al., "Engineered antibody fragments and the rise of single domains", *nature biotechnology*, 23(9), 1126-1136, 2005.
International Search Report and Written Opinion for PCT/EP2021/ 059360 dated Jul. 7, 2021, 13 pages.

(Continued)

*Primary Examiner* — Nianxiang Zou
(74) *Attorney, Agent, or Firm* — pH IP Law

(57) ABSTRACT

The present invention relates to a composition for use in the treatment of pulmonary fibrosis of a subject, wherein the composition comprises an inhibitor of miR-21 and a moiety that delivers said inhibitor of miR-21 to a macrophage. Further, the composition may be administered by a pulmonary administration. In particular aspects, said subject to be treated suffers from pulmonary fibrosis and further has a lung disease or disorder, wherein the lung disease or disorder may be a corona virus disease. Furthermore, the invention relates to a composition, wherein the composition comprises an inhibitor of miR-21 and a moiety that delivers said inhibitor of miR-21 to a lung macrophage.

17 Claims, 71 Drawing Sheets

Figure 1:
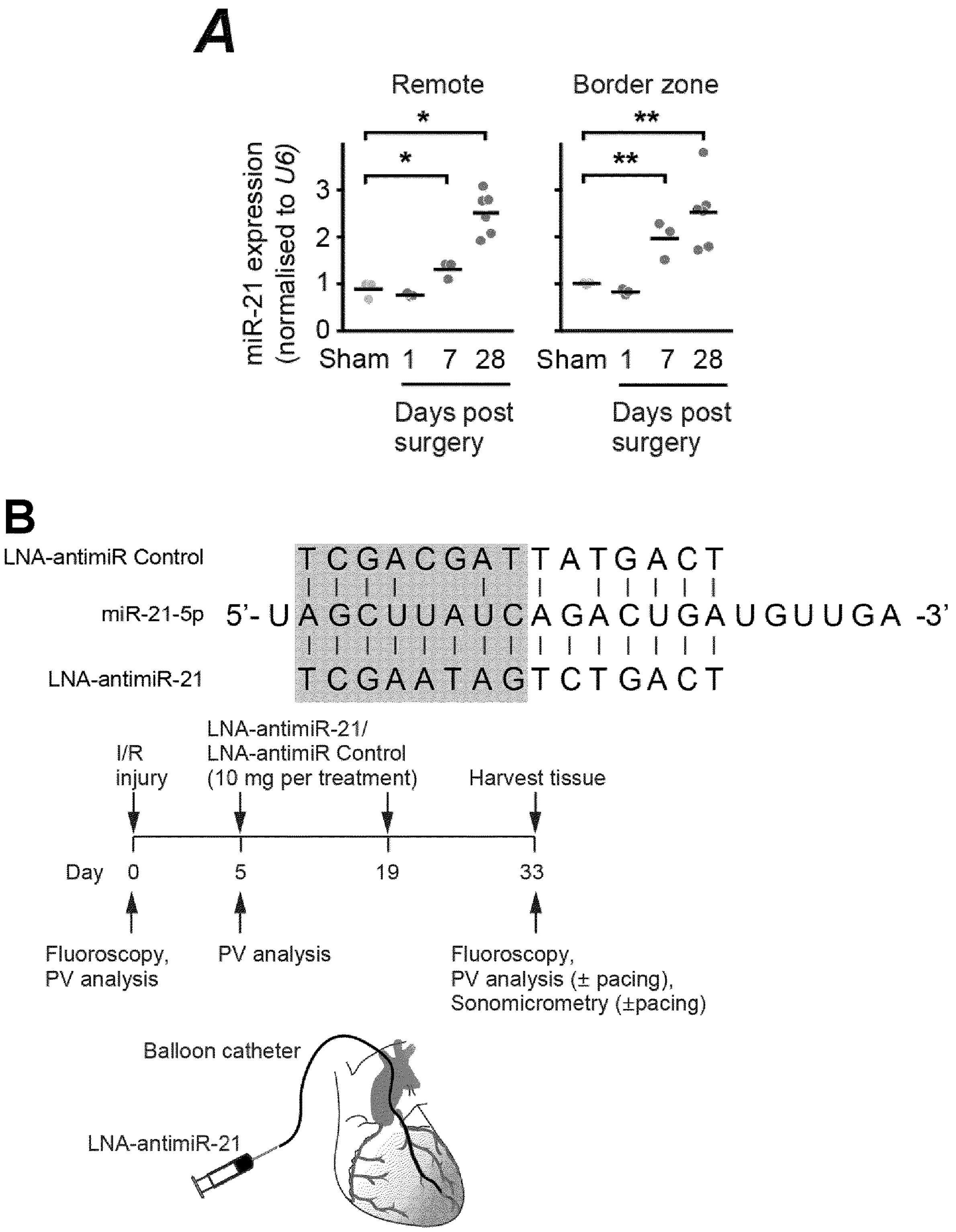
Figure 1:
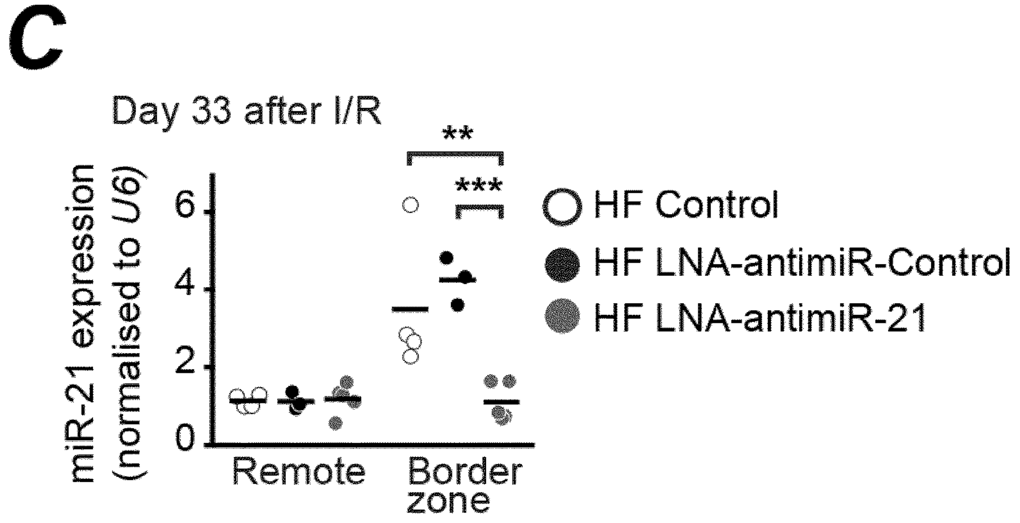

Specification includes a Sequence Listing.

(56) References Cited

OTHER PUBLICATIONS

International Preliminary Report on Patentability for PCT/EP2021/059360 dated Oct. 6, 2022, 10 pages.
Jones et al., "Replacing the complementarity-determining regions in a human antibody with those from a mouse", *Nature*, 321, 822-826, 1986.
Juliano, "Survey and Summary, The delivery of therapeutic oligonucleotides", *Nucleic Acids Research*, 44(14), 6518-6548, 2016.
Khvorova et al., "The chemical evolution of oligonucleotide therapies of clinical utility", *nature biotechnology*, 35(3), 238-248, 2017.
Koehler et al., "Continuous cultures of fused cells secreting antibody of predefined specificity", *Nature*, 256, 495-497, 1975.
Kozbor et al., "The production of monoclonal antibodies from human lymphocytes", *Immunology Today*, 4(3), 72-79, 1983.
Li et al., "Therapeutic targeting of microRNAs: current status and future challenges", *Nature Reviews*, 13, 622-638, 2014.
Lu et al., "RNA-based diagnostic and therapeutic strategies for cardiovascular disease", *Nature Reviews Cardiology* 16: 661-674, 2019.
Martinez-Pomares, "The mannose receptor", *Journal of Leukocyte Biology*, 92, 1176-1186, 2012.
Mendell et al., "MicroRNAs in Stress Signaling and Human Disease", *Cell*, 148, 1172-186, 2012.
Milstein et al., "Hybrid hybridomas and their use in immunohistochemistry", *Nature*, 305, 537-540, 1983.
Morimoto et al., "Transcriptional Regulation of Heat Shock Genes", *The Journal of Biological Chemistry*, 267(31), 21987-21990, 1992.
Patrick et al., "Stress-dependent cardiac remodeling occurs in the absence of micrRNA-21 in mice", J. Clin Invest, 120(11), 3912-3916, 2010.
Pellicori et al., "New perspectives and future directions in the treatment of heart failure", *Heart Failure Reviews*, 25, 147-159, 2020.
Potere et al., "Low Density Lipoprotein Receptor-Related Protein-1 in Cardiac Inflammation and Infarct Healing", *frontiers in Cardiovascular Medicine*, 6(51), 1-18, 2019.
Presta, "Antibody engineering", *Current Opinion in Biotechnology*, 3:394-398, 1992.
Ramanujam et al., "Viral Vector-Based Targeting of miR-21 in cardiac Nonmyocyte Cells Reduces Pathologic Remodeling of the Heart", *Molecular Therapy*, 24(11): 1939-1948, 2016.
Ramilowski et al., "A draft network of ligand-receptor-mediated multicellular signaling in human", *nature communications*, 6:7866, 1-11, 2015.
Riechmann et al., "Reshaping human antibodies for therapy", *Nature*, 332, 232-327, 1988.
Rupaimoole et al., "MicroRNA therapeutics: towards a new era for the management of cancer and other diseases", *Nature Reviews Drug Discovery*, 19, 203-221, 2017.
Sambrook et al., "Molecular Cloning, a Laboratory Manual", 00-064380, 2001.
Sayed et al., "MicroRNA-21 is a Downstream Effector of AKT That Mediates Its Antiapoptotic Effects via Suppression of Fas Ligand", *The Journal of Biological Chemistry*, 285(26), 20281-20290, 2010.
Sgalla et al., "Idiopathic pulmonary fibrosis: pathogenesis and management", *Respiratory Research*, 19:32, 2018.
Shalaby et al., "Development of Humanized Bispecific Antibodies Reactive with Cytotoxic Lymphocytes and Tumor Cells Overexpressing the HER2 Protooncogene", *J. Exp. Med.*, 175, 217-225, 1992.
Skelly et al., "Single-Cell Transcriptional Profiling Reveals Cellular Diversity and Intercommunication in the Mouse Heart", *Cell Reports*, 22, 600-610, 2018.
Sood et al., "Cell-type-specific signatures of microRNAs on target mRNA expression", *PNAS*, 103(8), 2746-2751, 2006.
Stenvang et al., "Inhibition of microRNA function by antimir oligonucleotides", *Science*, 3:1, 2012.
Stephens, "False discovery rates: a new deal", *Biostatistics*, 18(2), 275-294, 2017.
Thum et al., "MicroRNA-21 contributes to myocardial disease by stimulating MAP kinase signaling in fibroblasts", *Nature*, 456(18), 2008.
Tutt et al., "Bispecific F(ab'$\gamma$)$_3$ antibody derivatives for redirecting unprimed cytotoxic T cells*", Eur. J. Immunol., 21: 1351-1358, 1991.
Wessels et al., "Global identification of functional microRNA-mRNA interactions in *Drosophila", nature communications*, 10(1): 1626, 2019.
Xu et al., "Clinical and computed tomographic imaging features of novel coronavirus pneumonia caused by SARS-CoV2", *Journal of Infection*, 80, 394-400, 2020.
Yang et al., "Three-Dimensional Quantitative Co-Mapping of Pulmonary Morphology and Nanoparticle Distribution with Cellular Resolution in Nondissected Murine Lungs", *ACS Nano*, 13, 1029-1041, 2019.
Yona et al., "Fate Mapping Reveals Origins and Dynamics of Monocytes and Tissue Macrophages under Homeostasis", *Immunity*, 38, 79-91, 2013.
Byrne et al., "Pulmonary Macrophages: A New Therapeutic Pathway in Fibrosing Lung Disease?", *Trends in Molecular Medicine*, 22(4):303-316, 2016.
Sheng et al., "Viral Infection Increases the Risk of Idiopathic Pulmonary Fibrosis A Meta-Analysis", Chest, 157(5):1175-1187, 2019.

* cited by examiner

A

Figure 3:
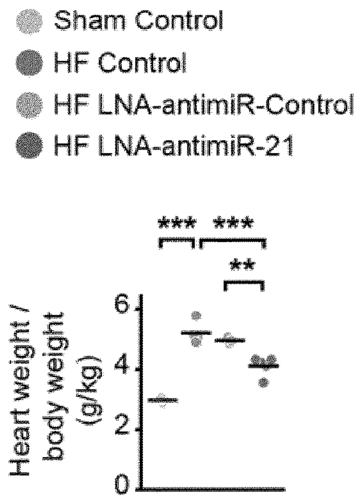
Figure 3:
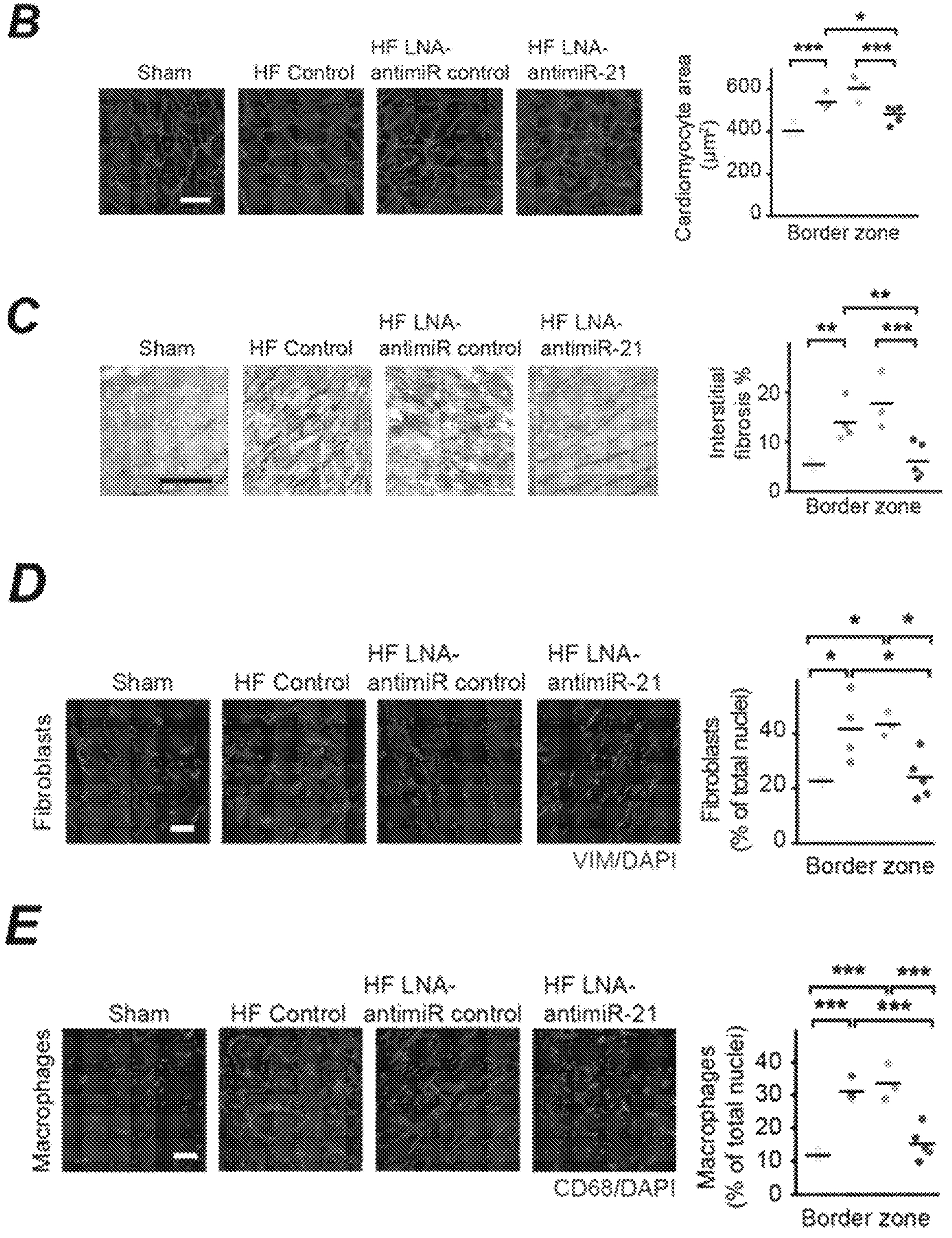

Figure 3 cont.
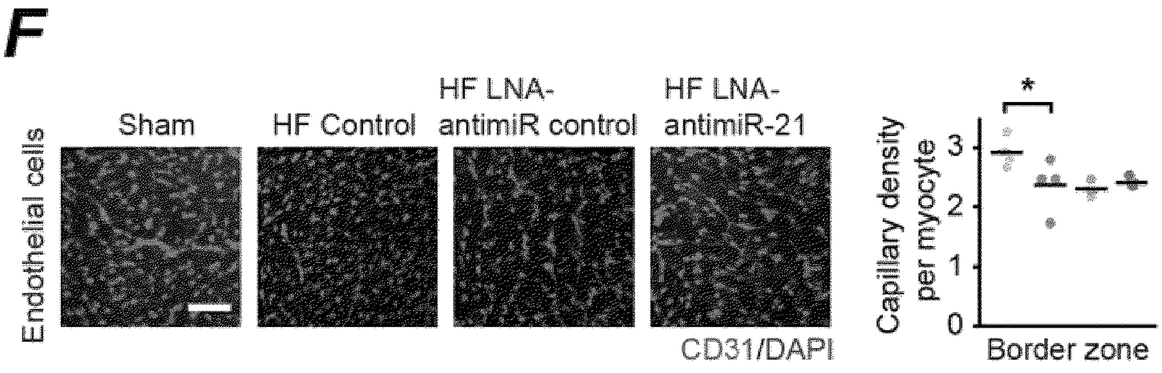
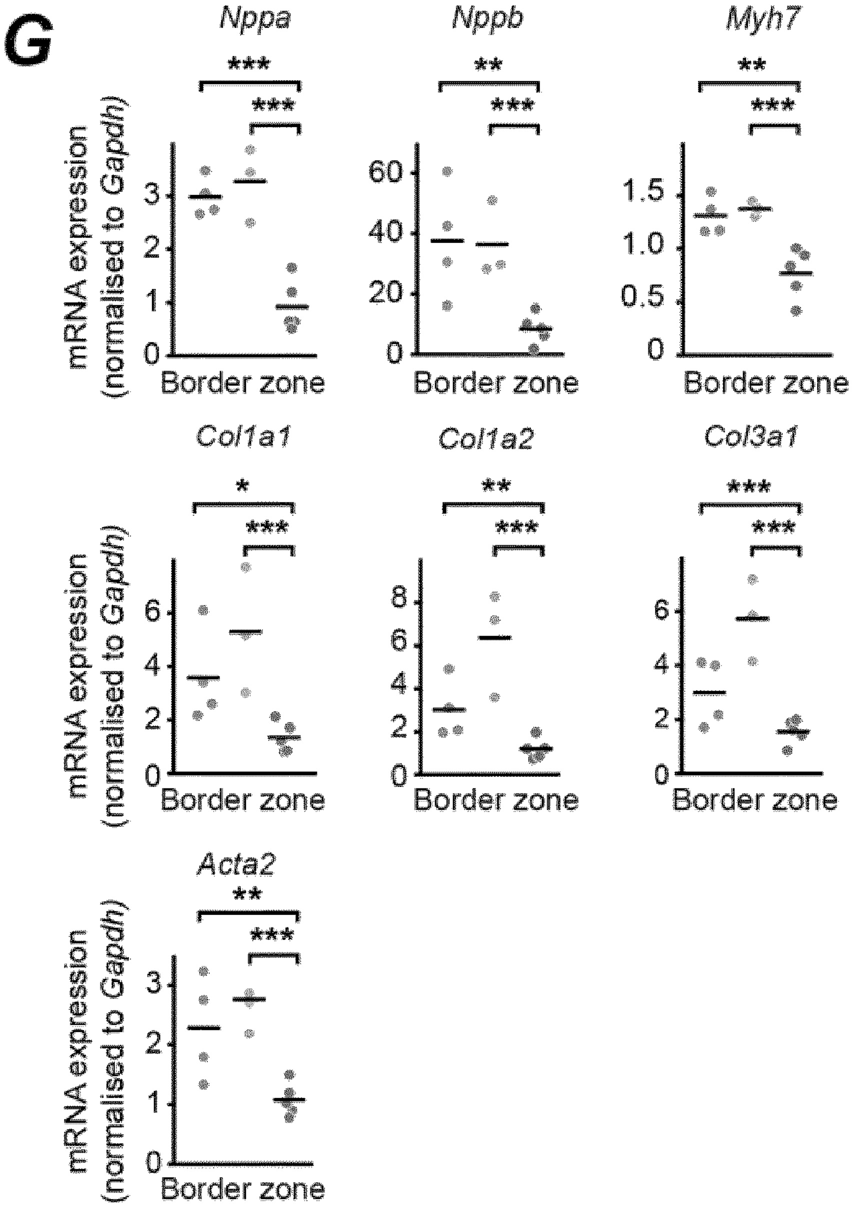

Figure 4:
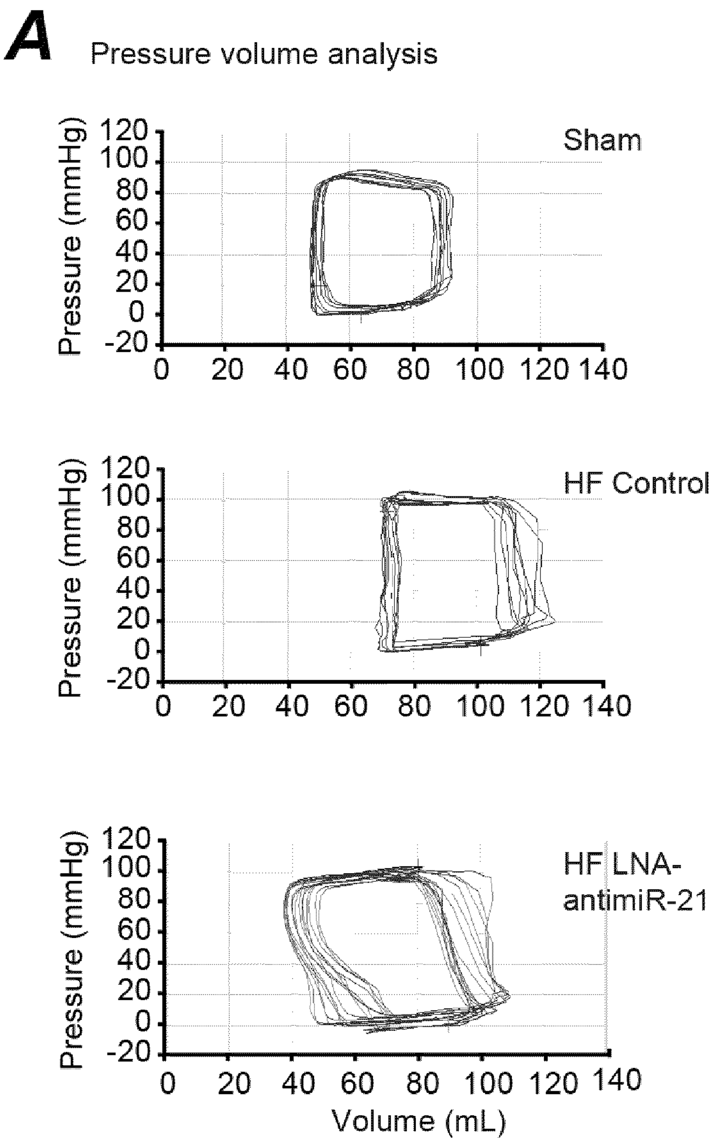
Figure 4:
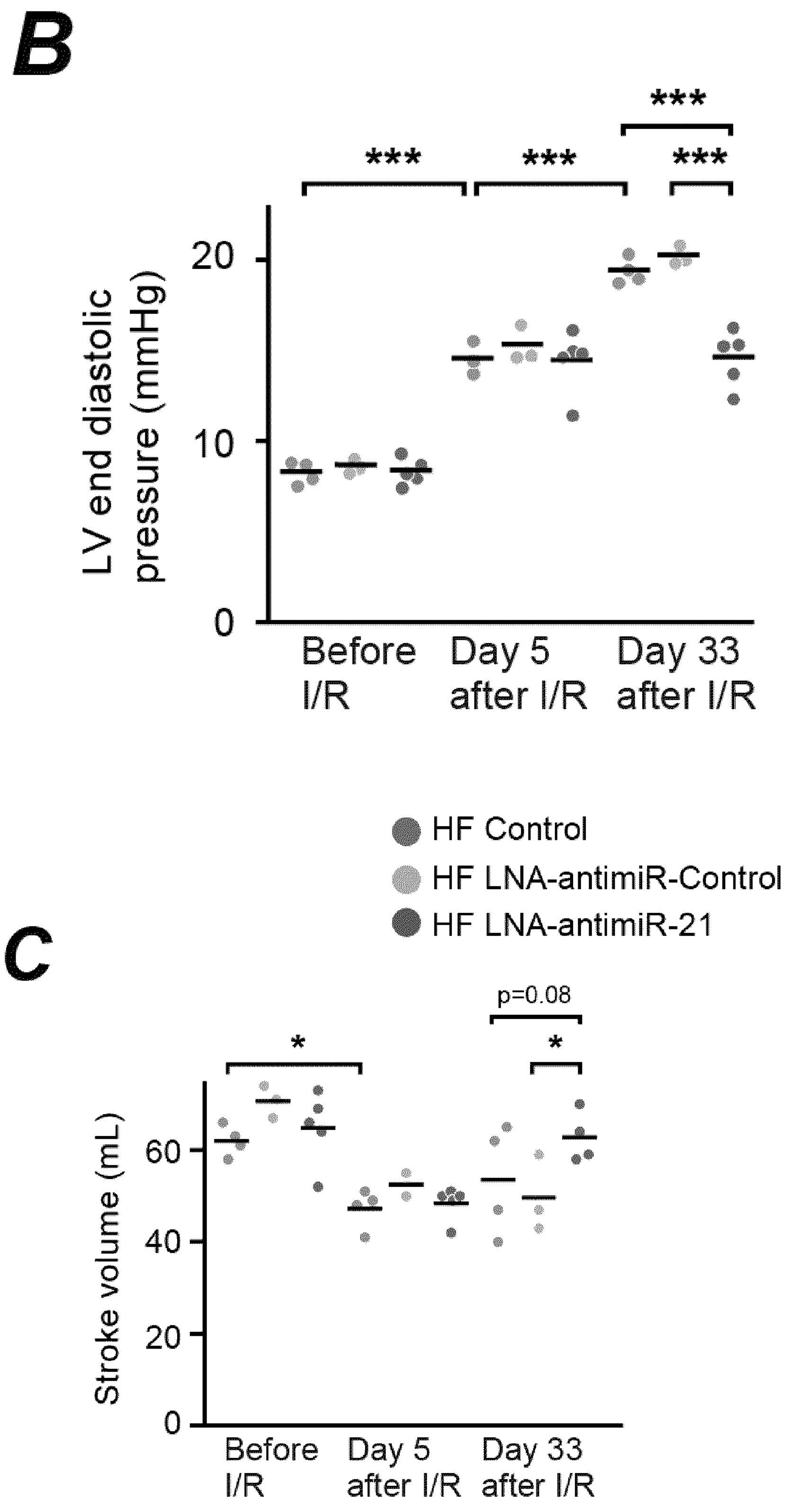

Figure 4 cont.
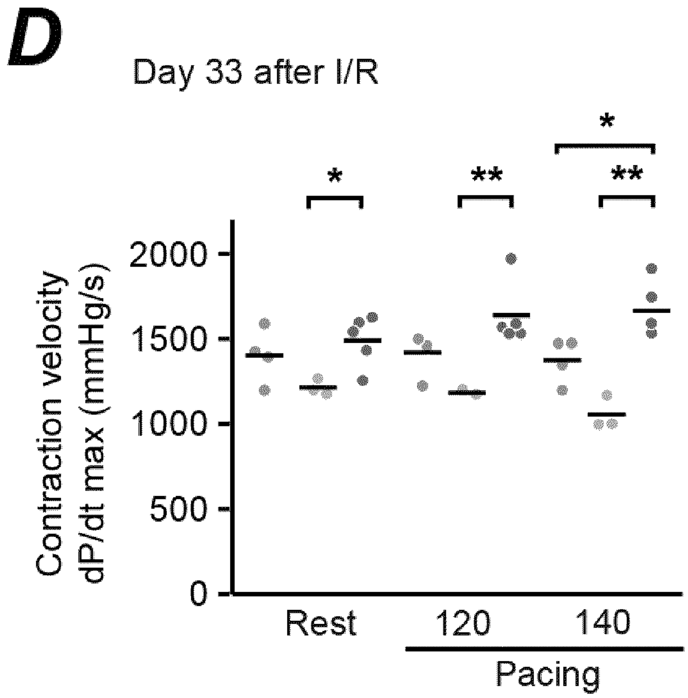
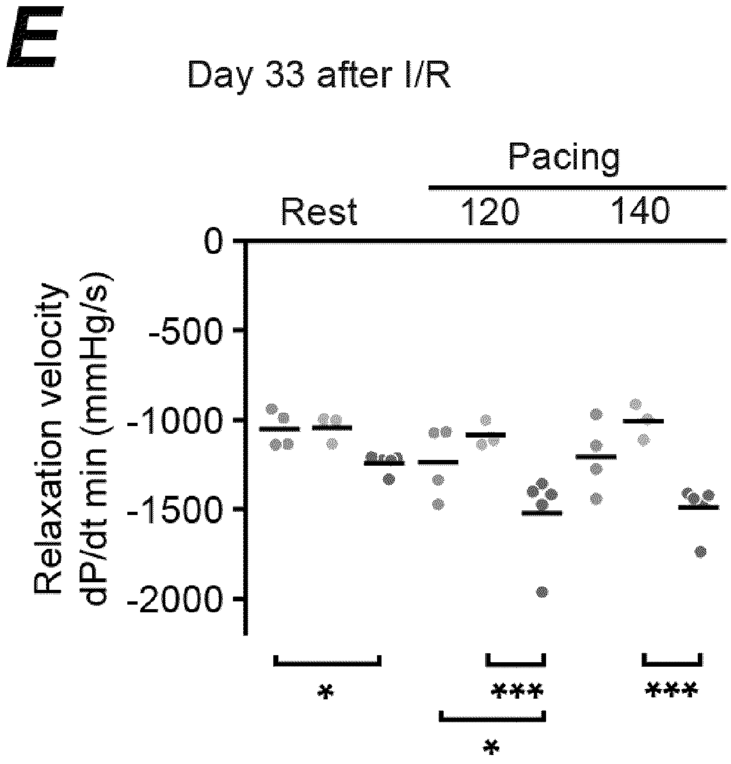

Figure 4 cont.
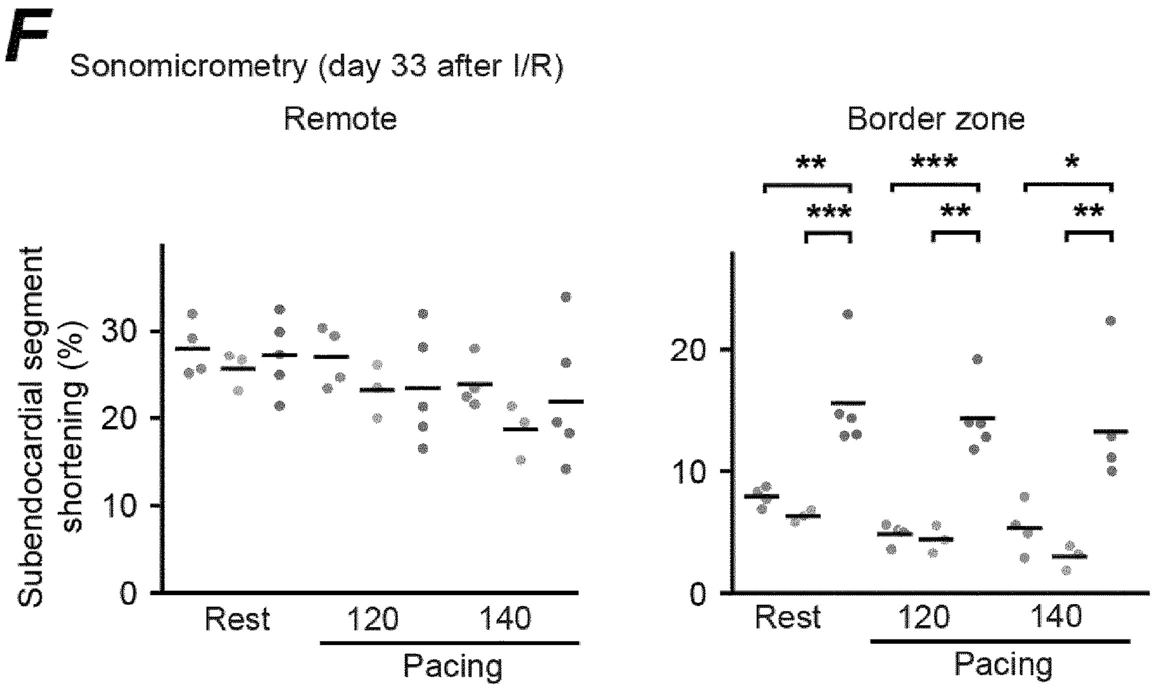
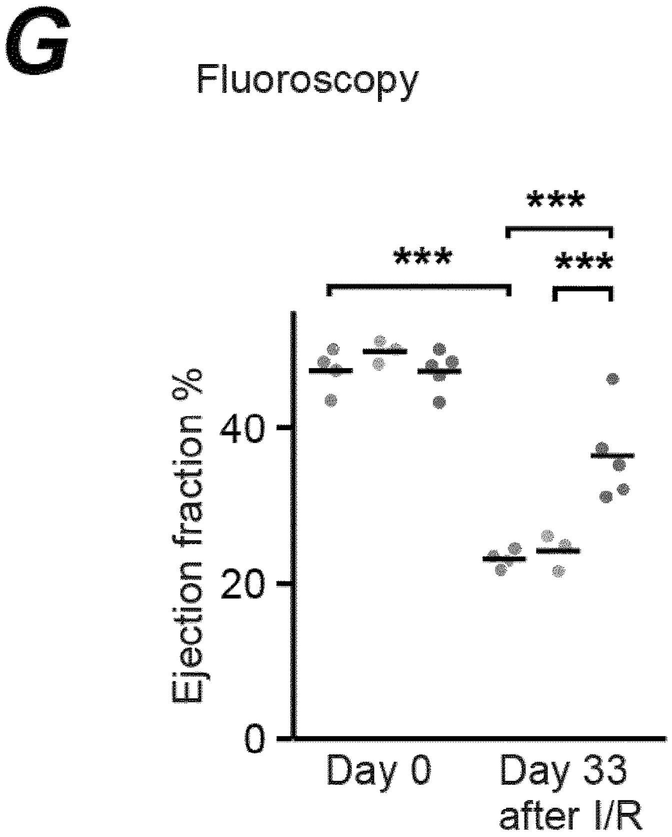

E

Figure 6:
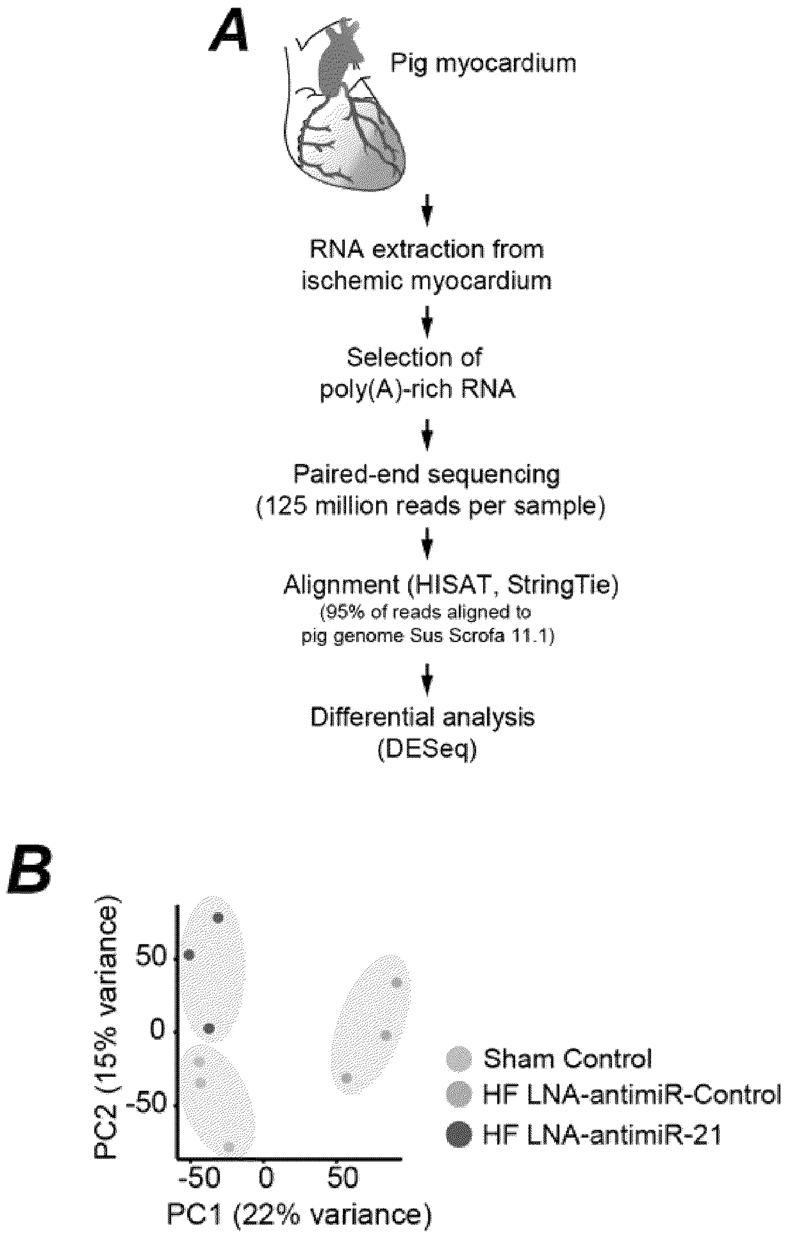
Figure 6:
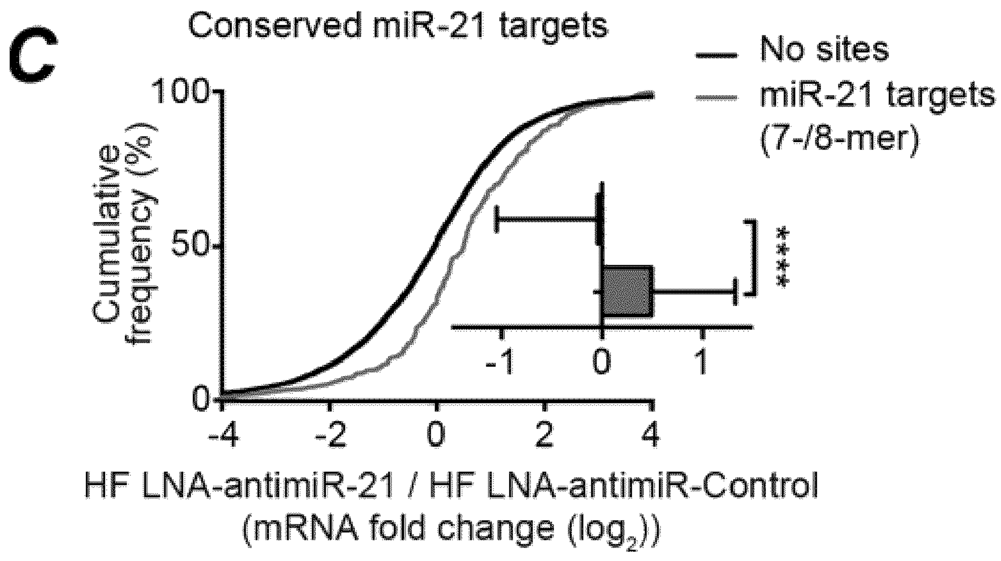
Figure 6:
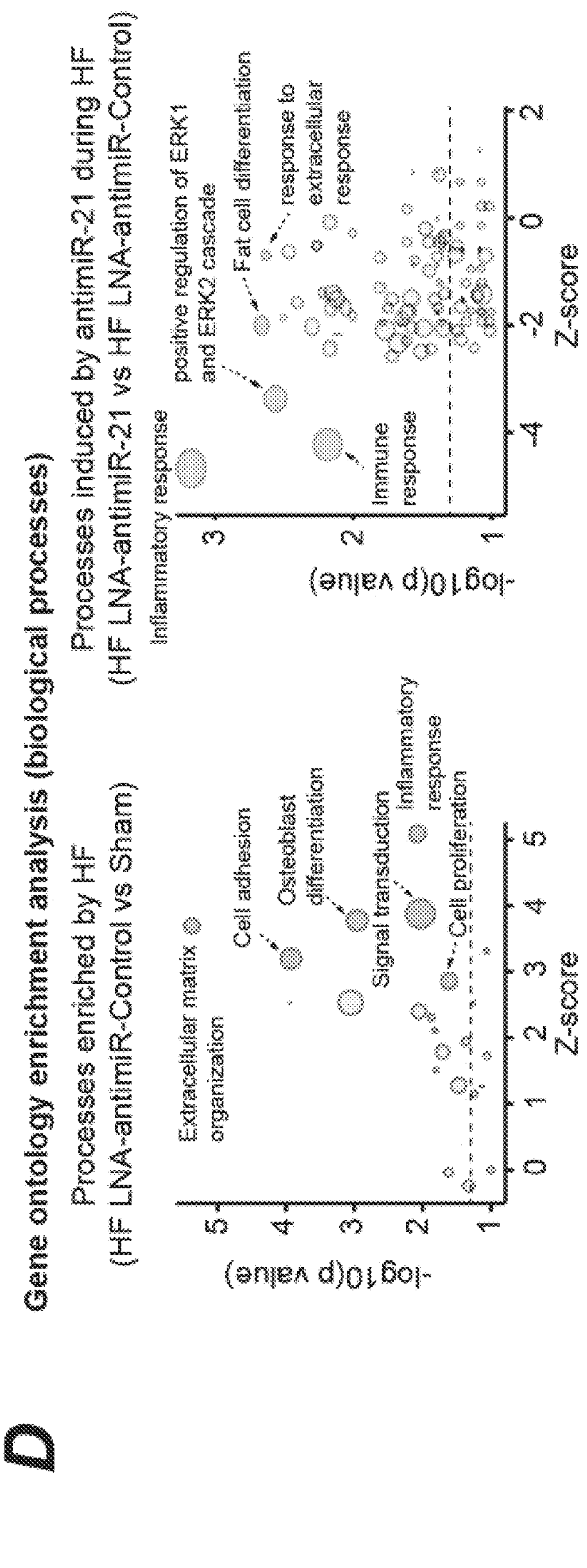
Figure 6:
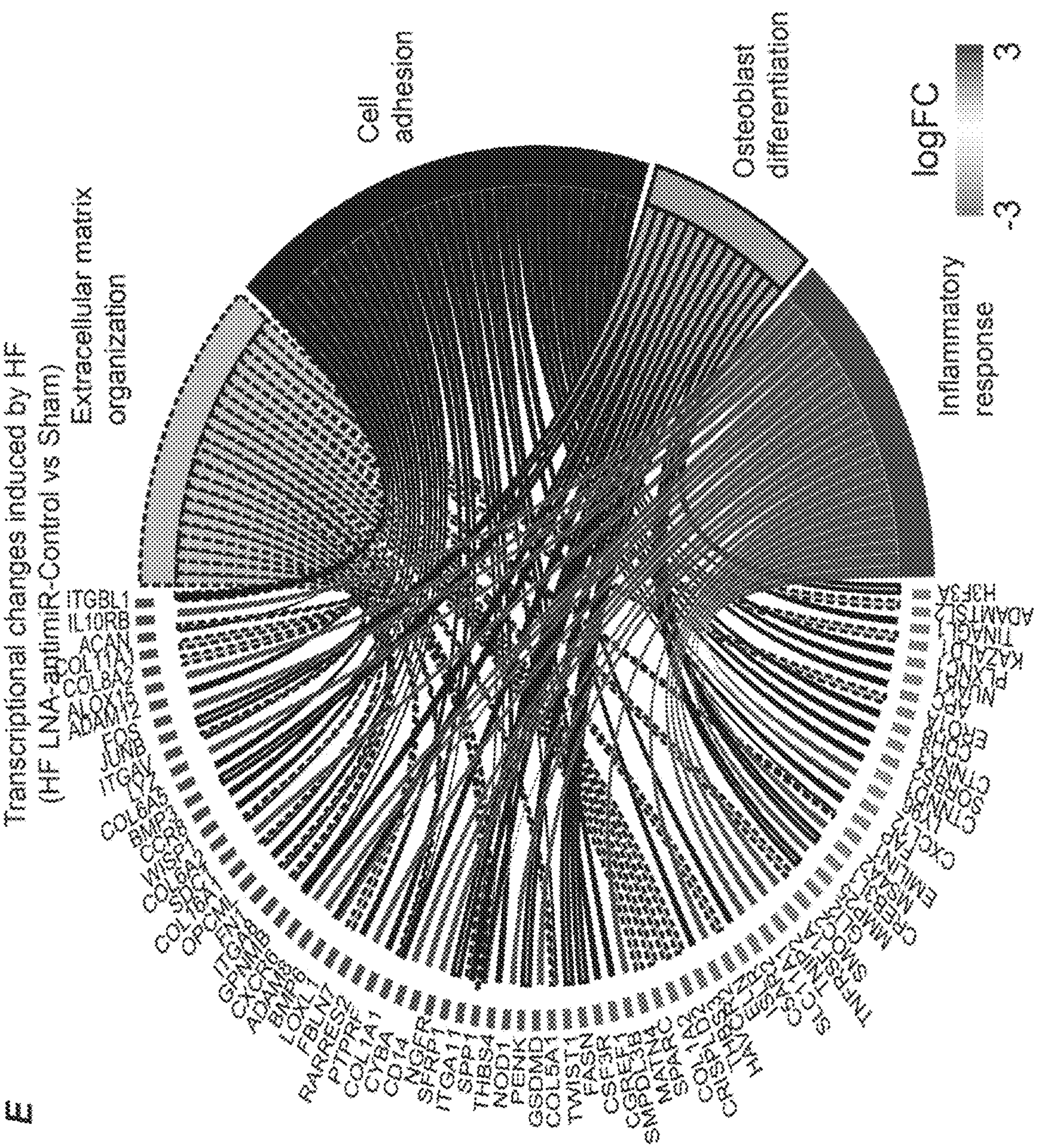
Figure 6E:
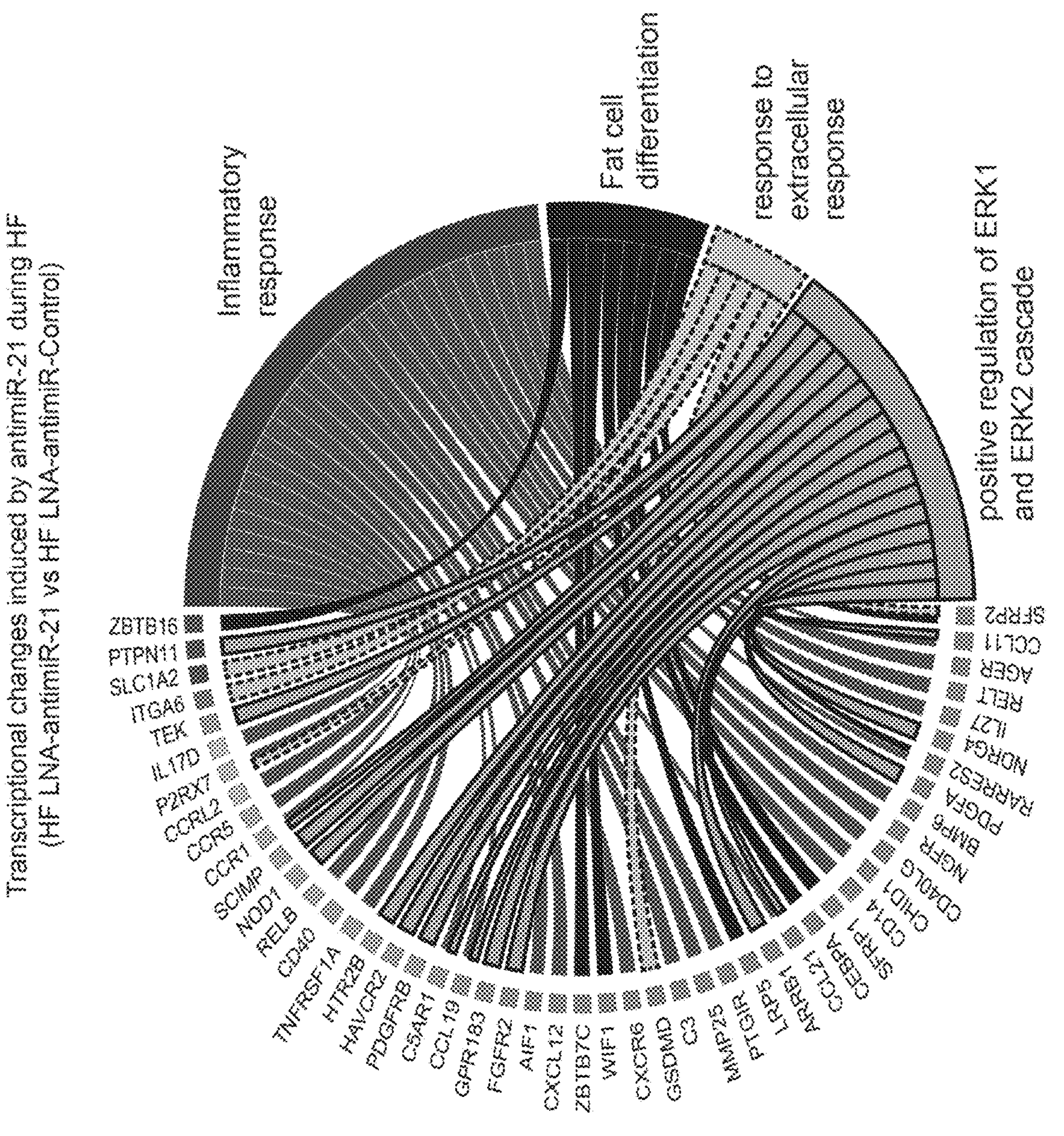

Figure 6 cont.
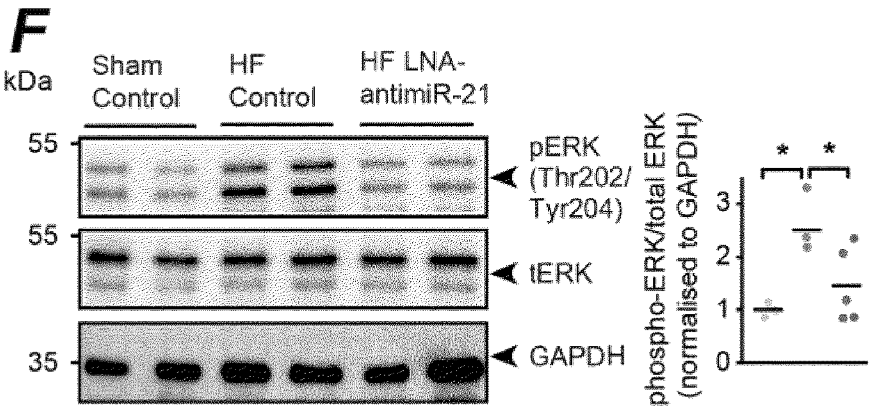
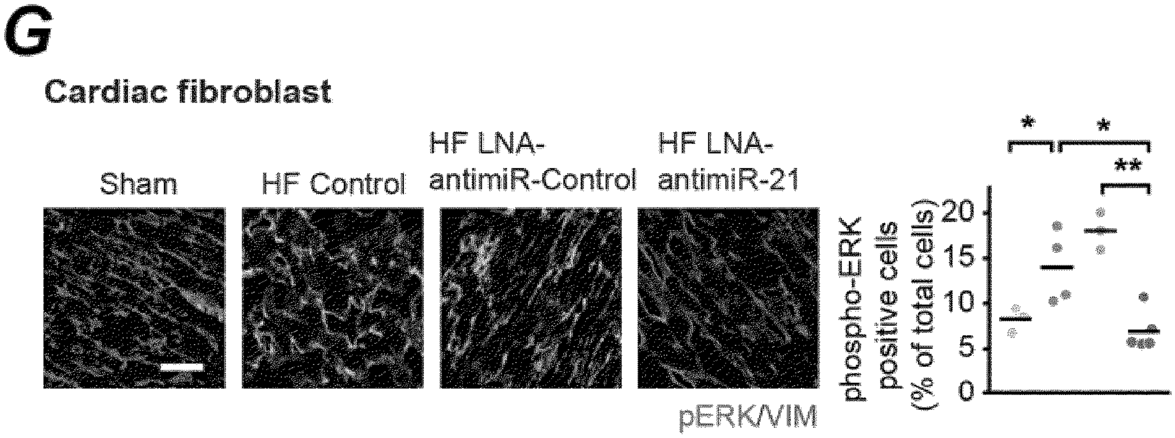

A

Figure 8:
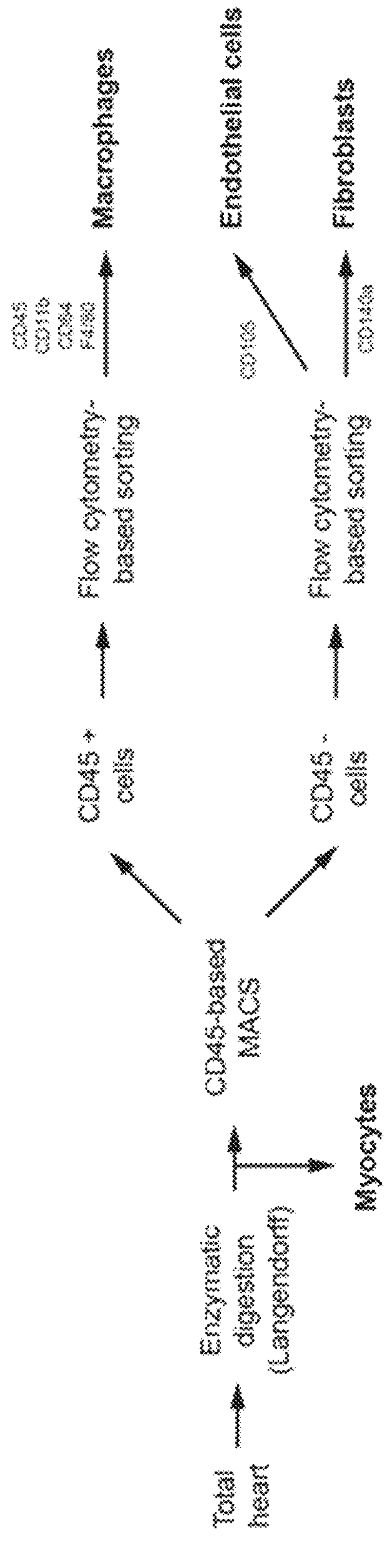
Figure 8:
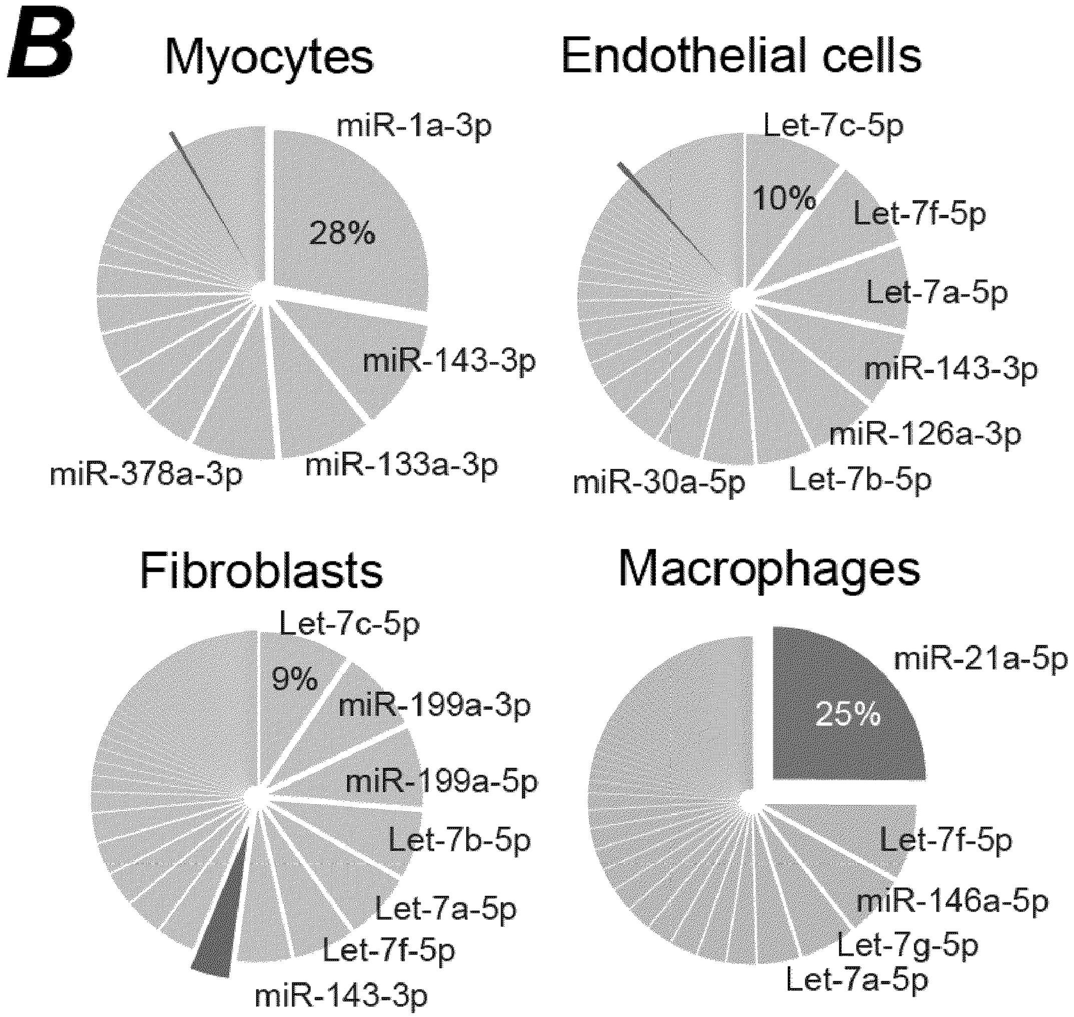
Figure 8:
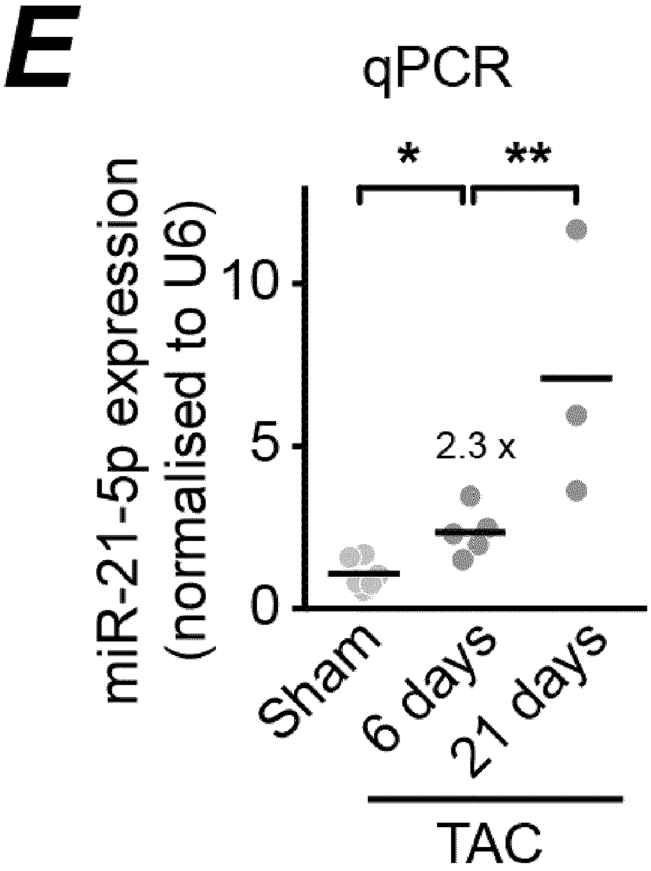

Figure 8 cont.
C
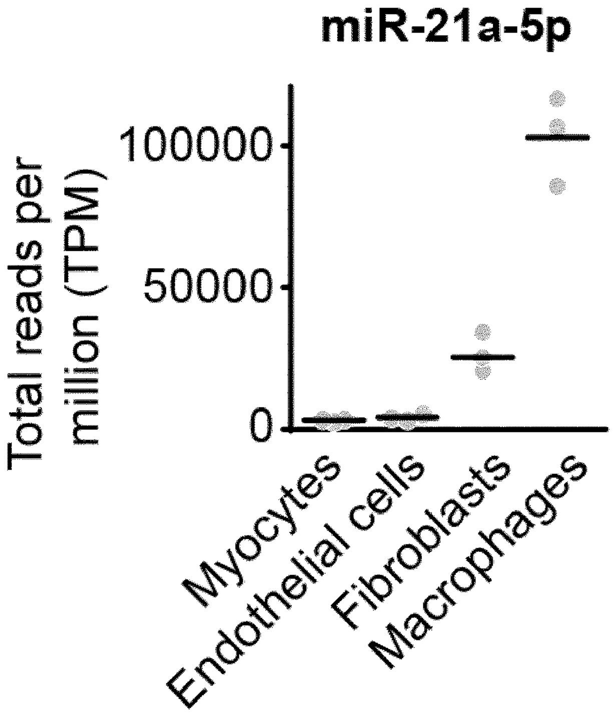
D
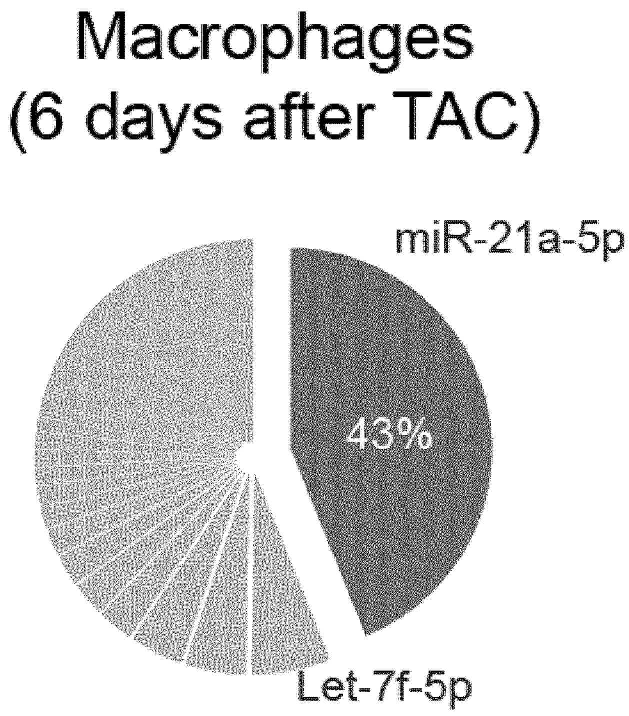

Figure 8 cont.
F
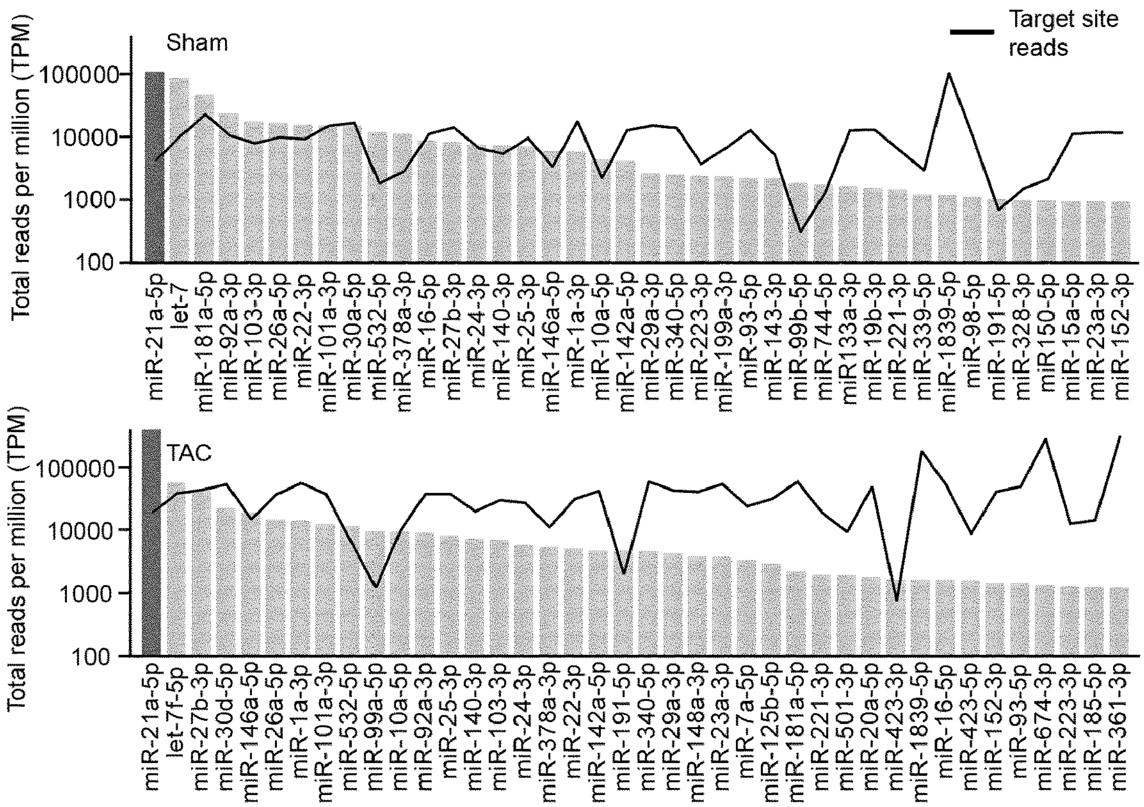
G
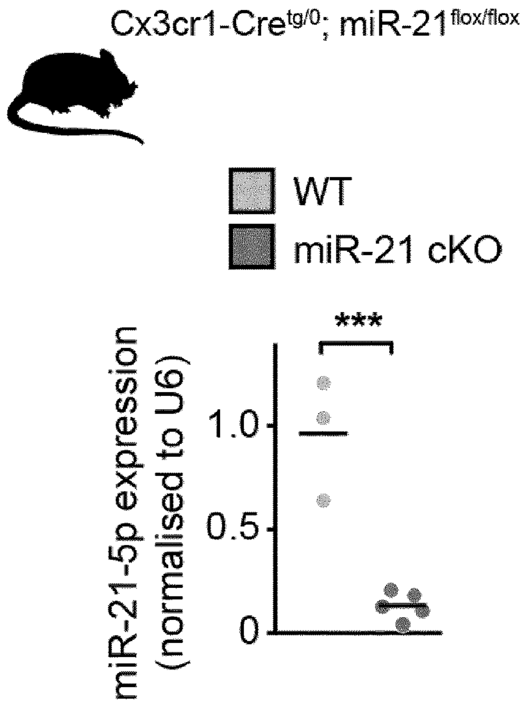

Figure 9:
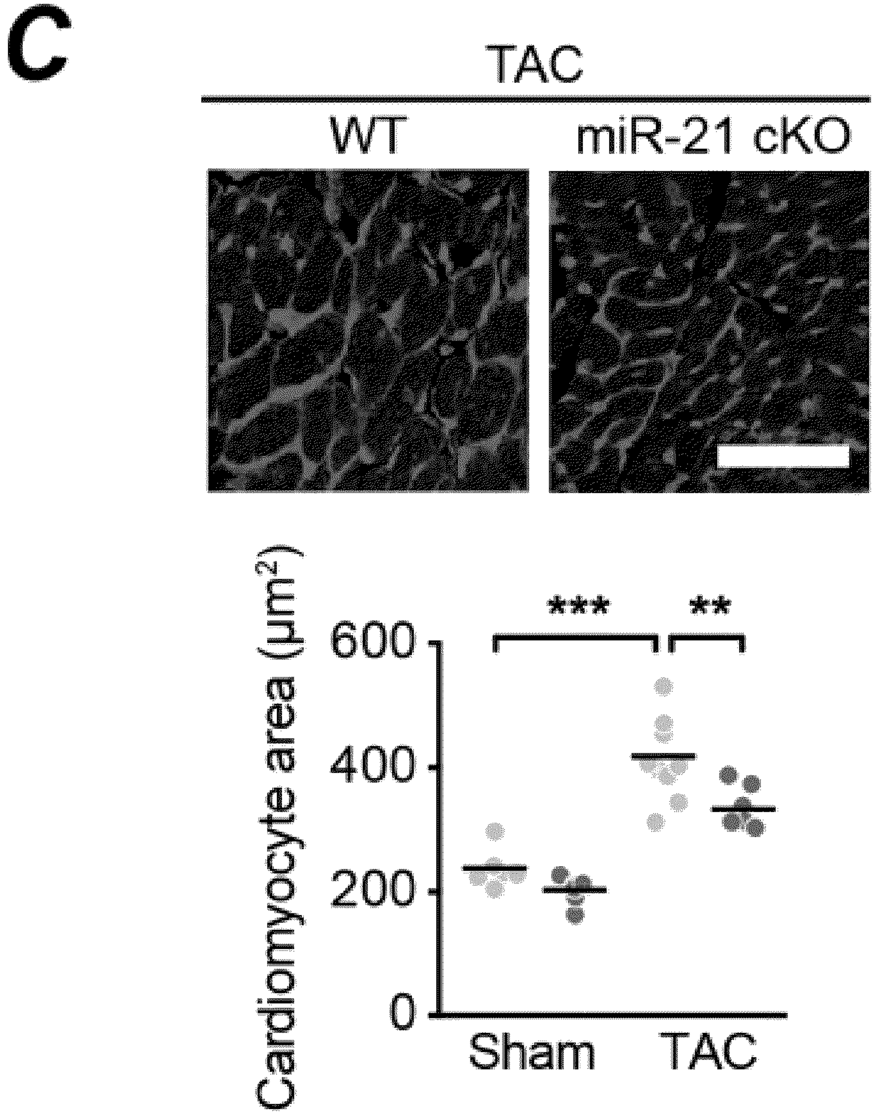

Figure 9
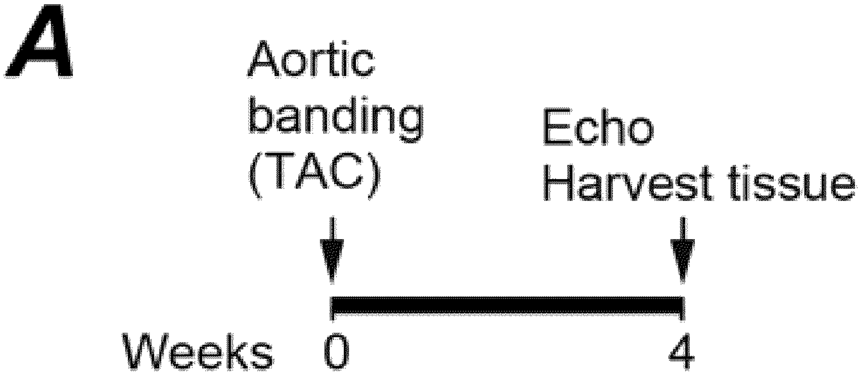
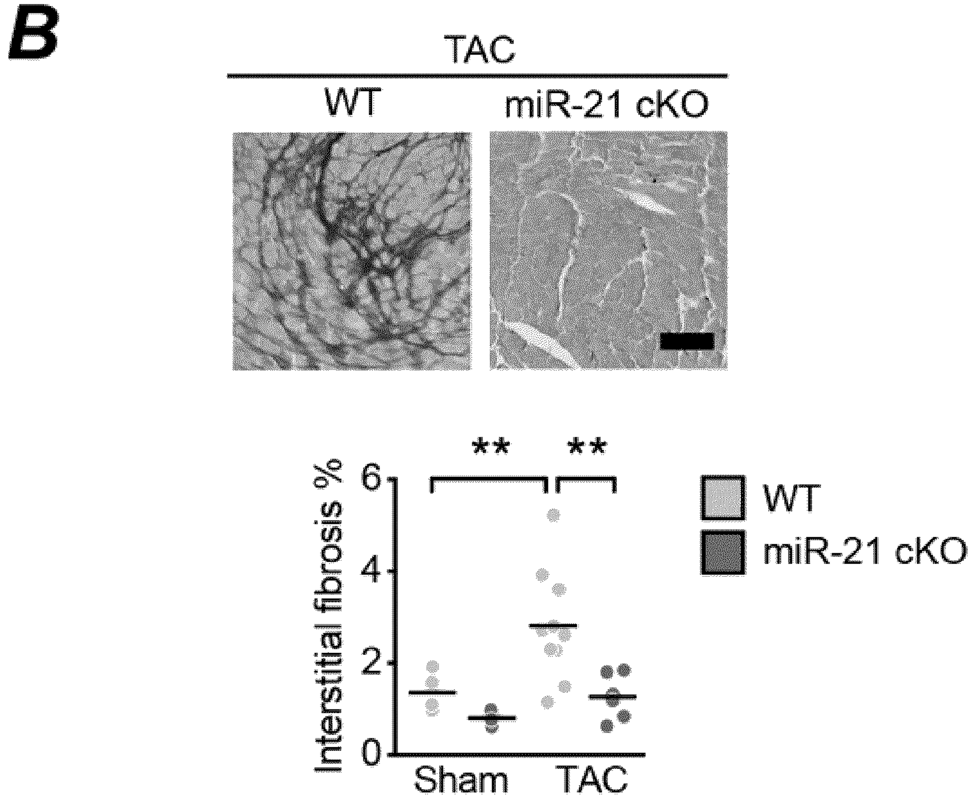

Figure 9 cont.
D
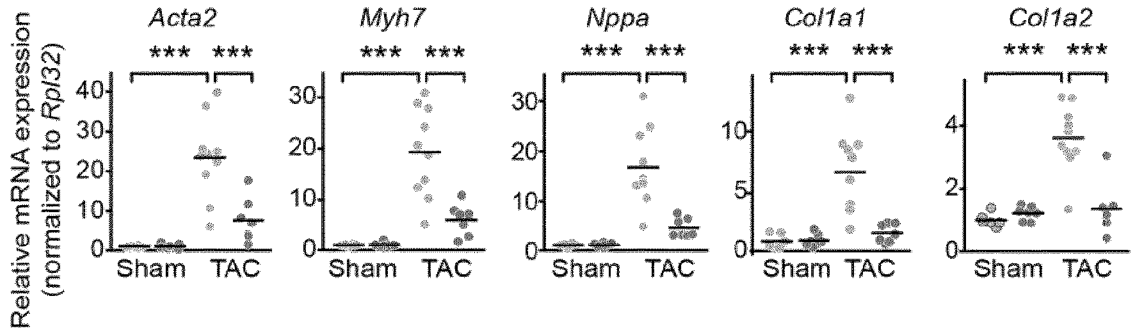
E
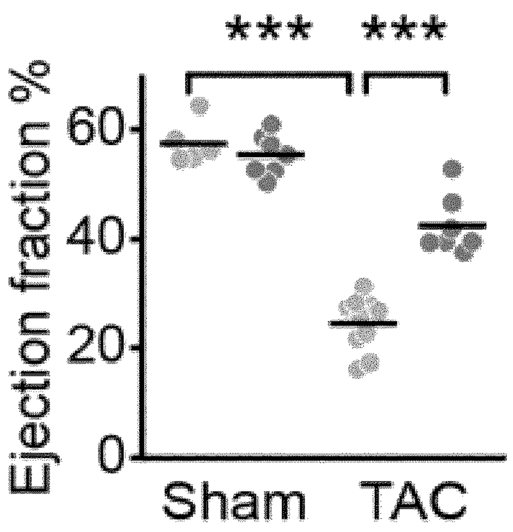

Figure 10:
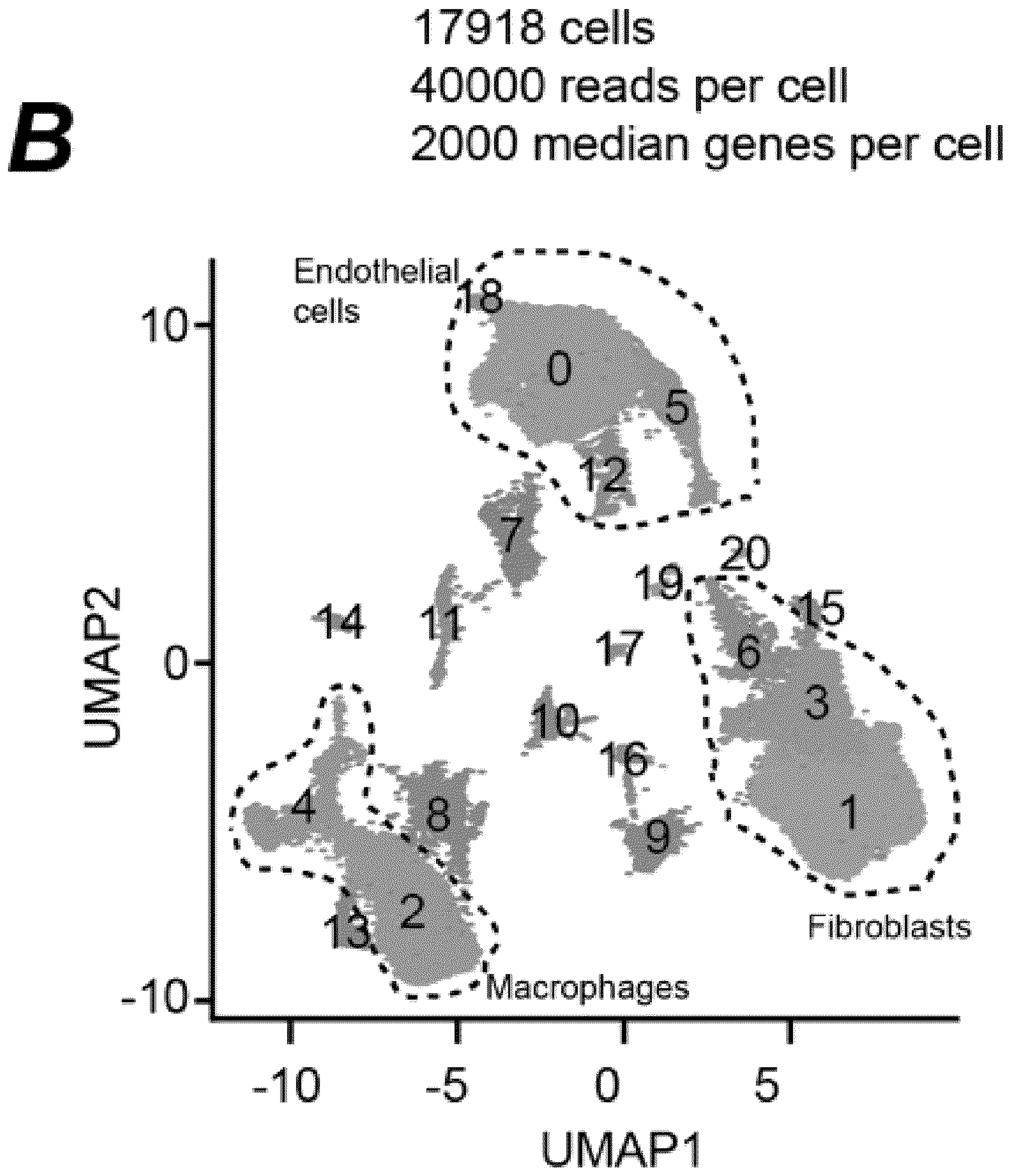
Figure 10:
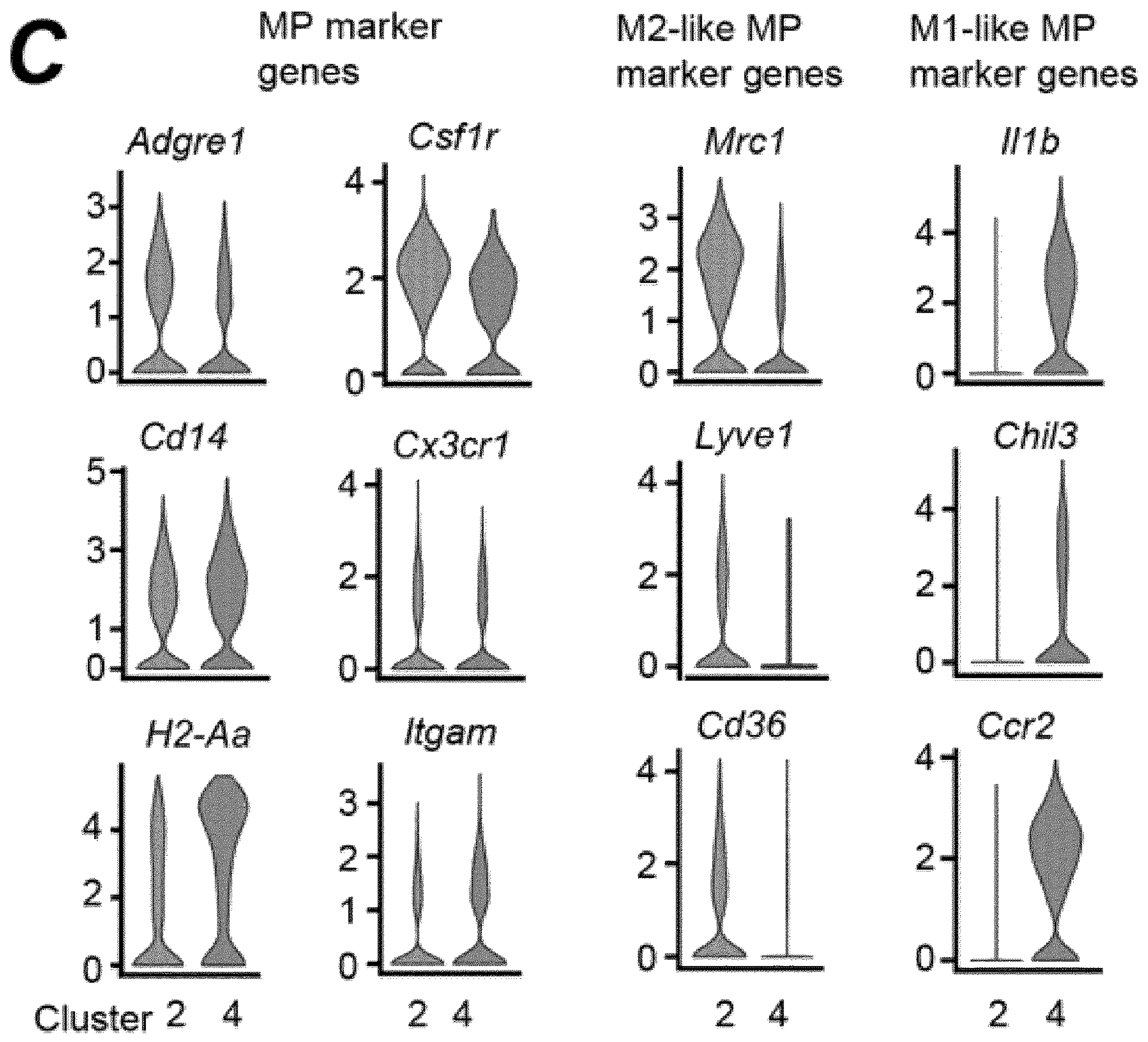
Figure 10:
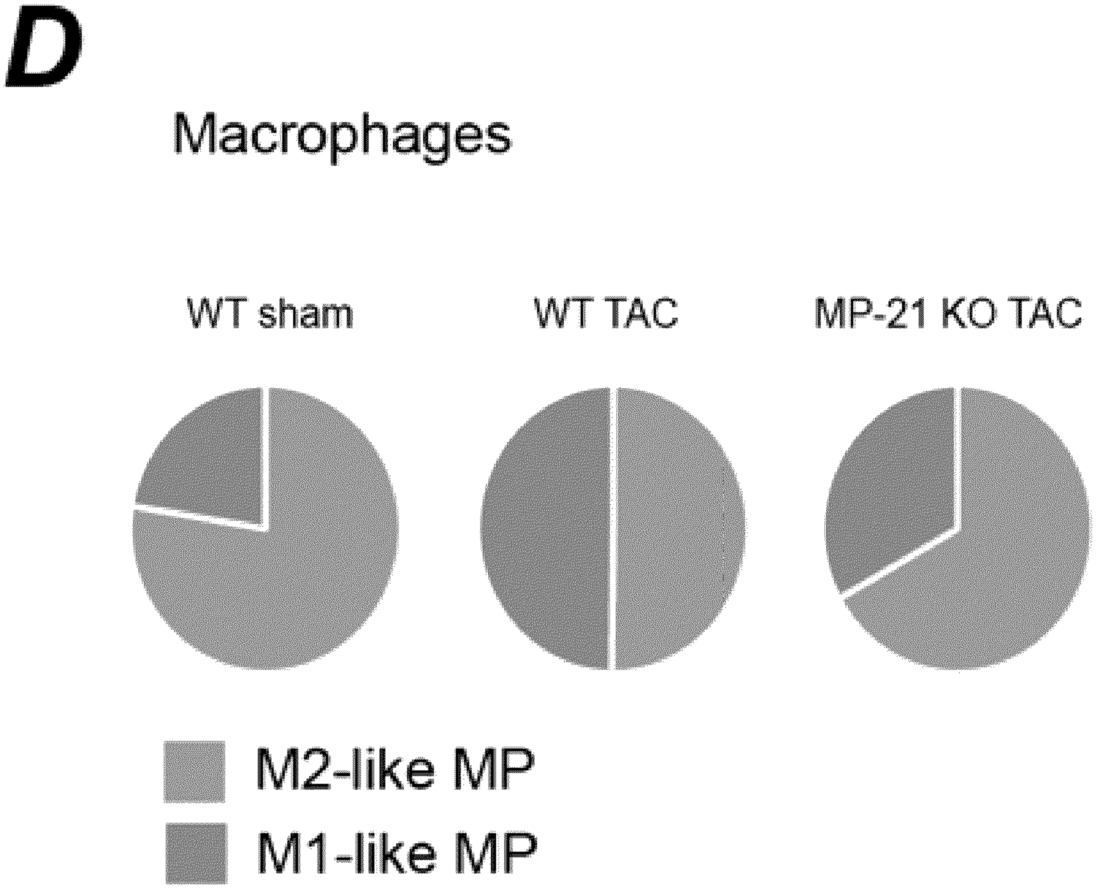
Figure 10:
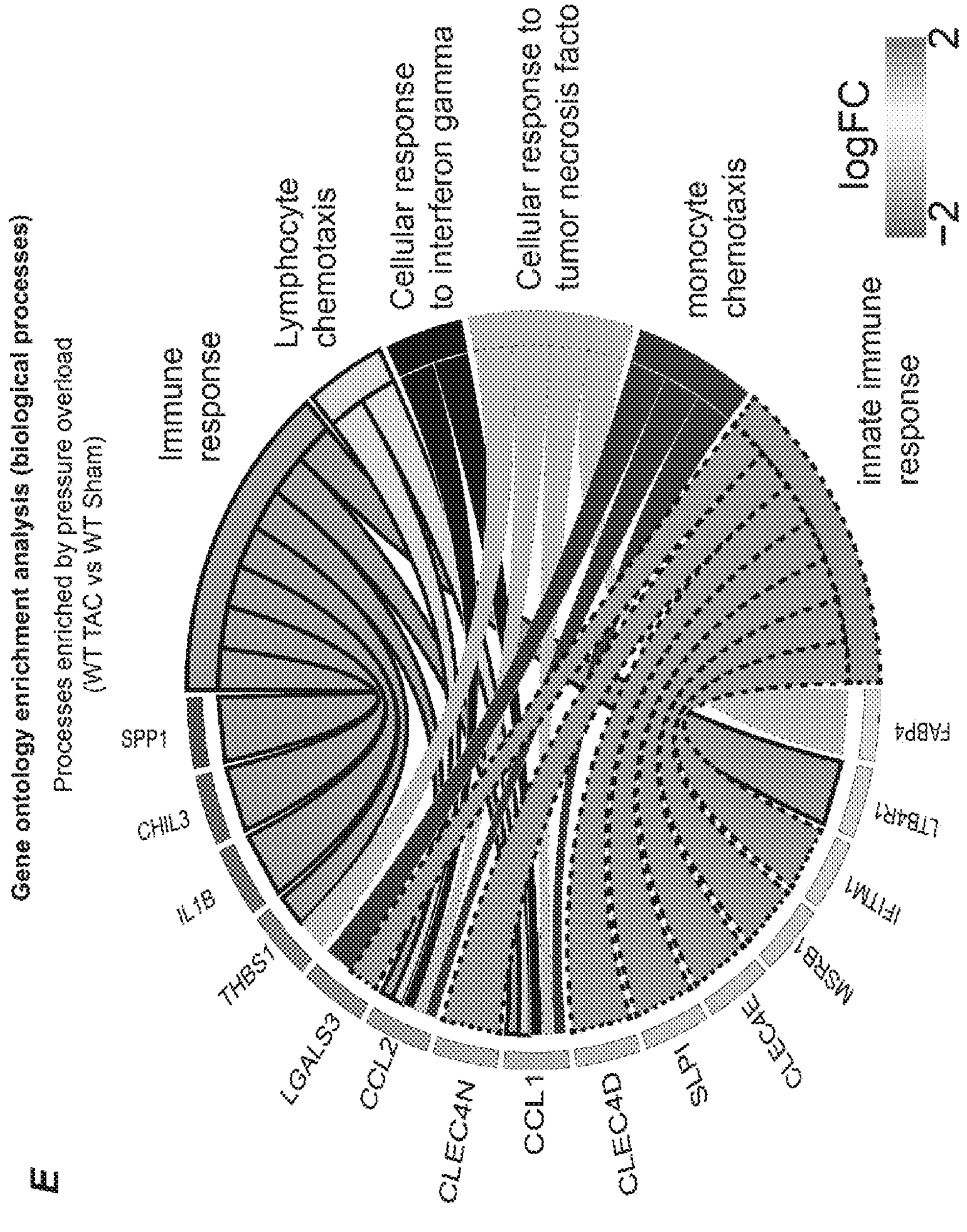

Figure 9 cont.
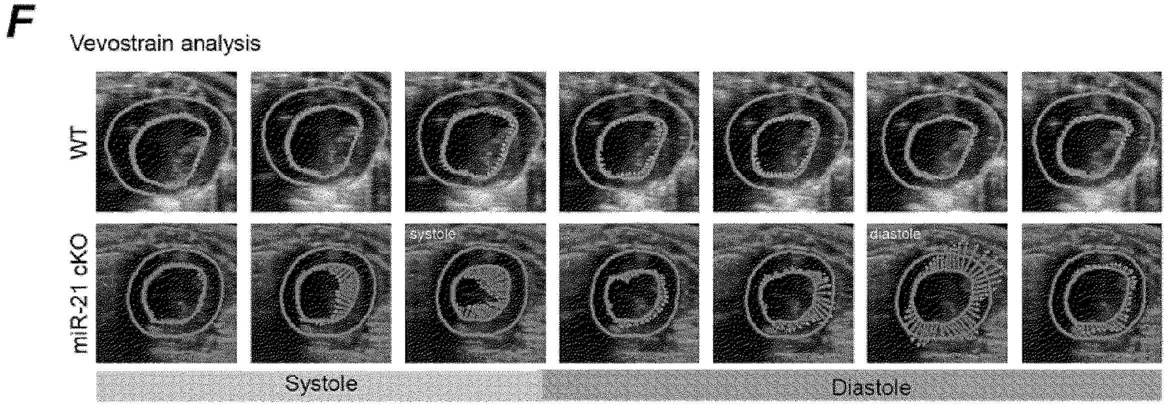
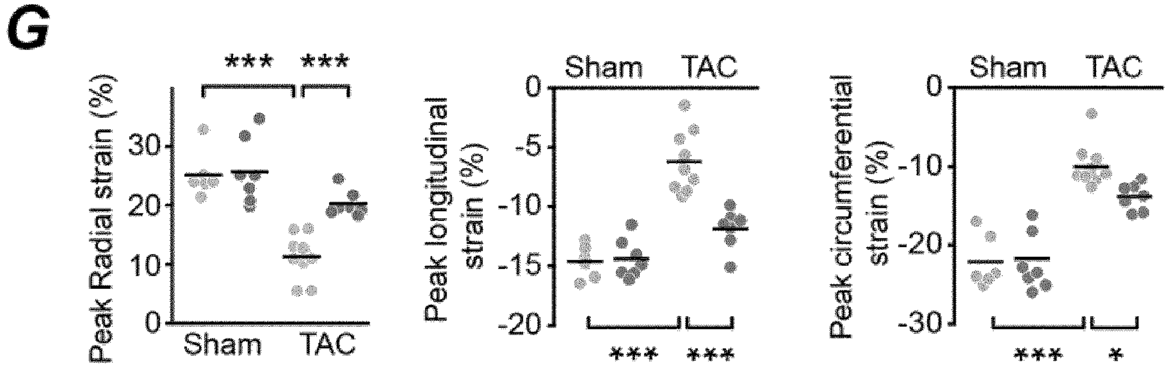
Figure 10
*A*
Isolation of cardiac non-myocytes by Langendorff perfusion (6 days after TAC)
↓
Single cell sequencing library preparation using 10X genomics
↓
Sequencing analysis (Seurat, RNA velocity, Monocle)

E

A

LR pairs upregulated by
pressure overload
(WT TAC vs WT Sham)

LR pairs upregulated by miR-21
deletion during pressure overload
(miR-21 cKO TAC vs WT TAC)

Quiescent
fibroblasts
(Tcf21+)

Activated
fibroblasts
(Postn+)

Myofibroblasts
(Postn+ Acta2+)

Non
macrophages

Myocytes

Endothelial
cells

Lymphatic
endothelial
cells

M1-like
macrophages

M2-like
macrophages

Figure 11:
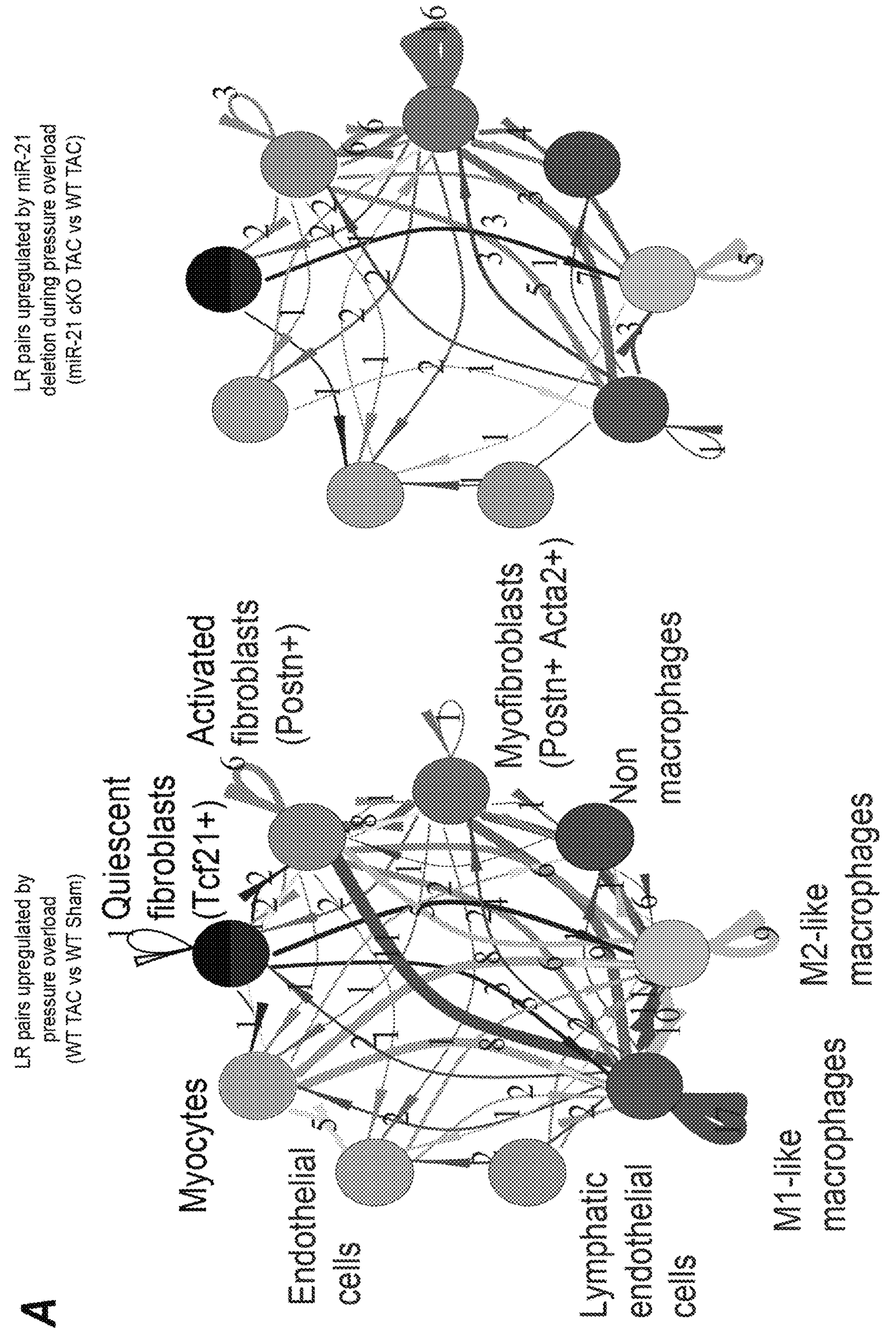
Figure 11:
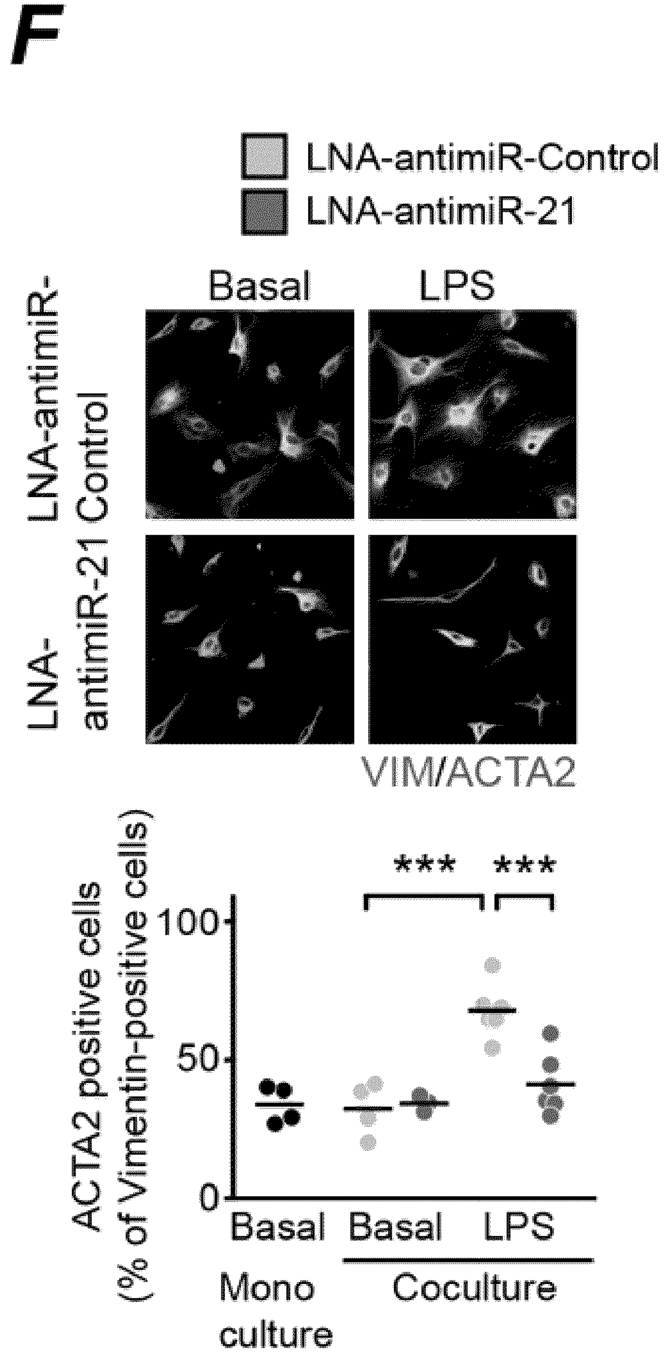

Figure 11 cont.
B
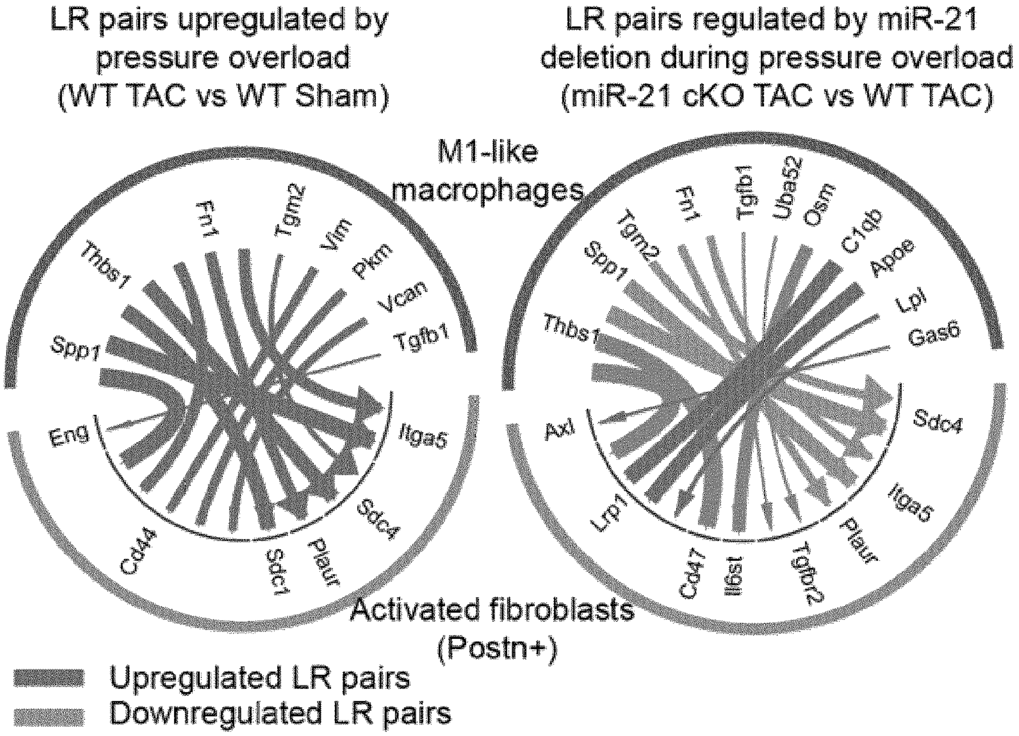
C
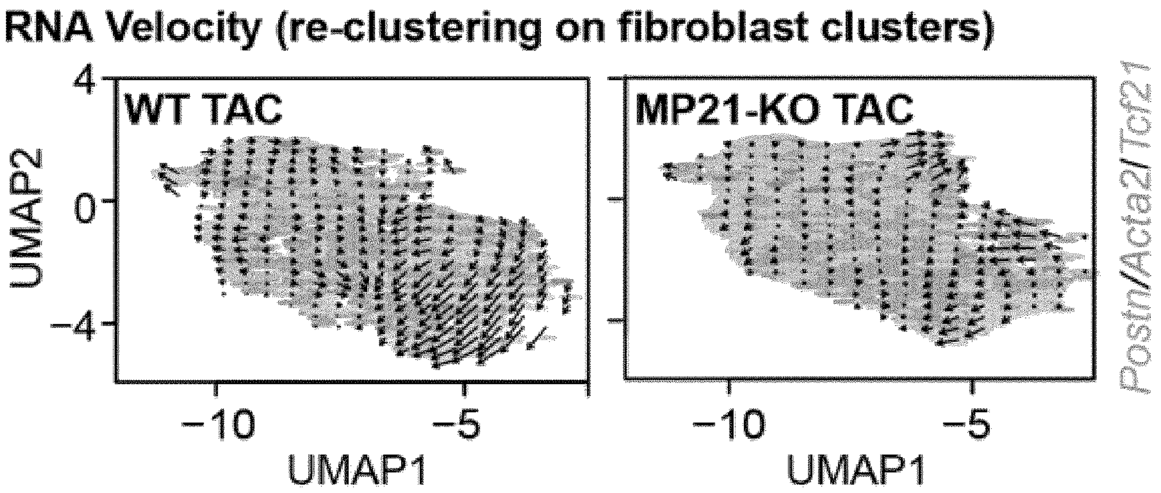
*B*
LR pairs upregulated by
pressure overload
(WT TAC vs WT Sham)
LR pairs regulated by miR-21
deletion during pressure overload
(miR-21 cKO TAC vs WT TAC)
Upregulated LR pairs
Downregulated LR pairs
*C*
RNA Velocity (re-clustering on fibroblast clusters)

Figure 11 cont.
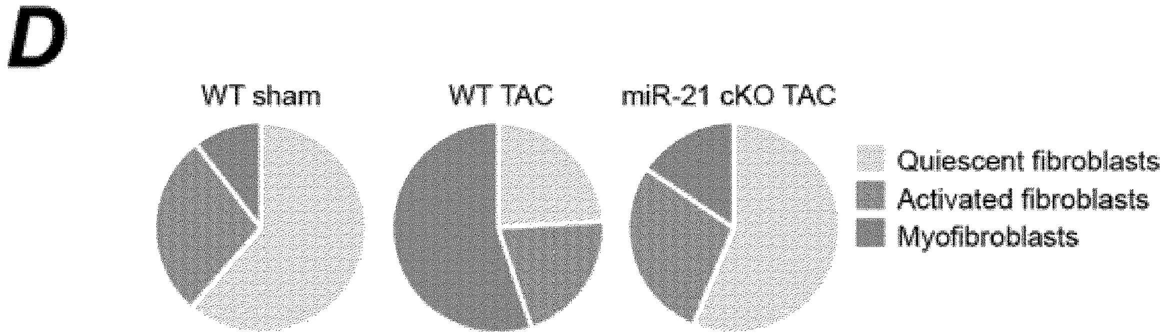
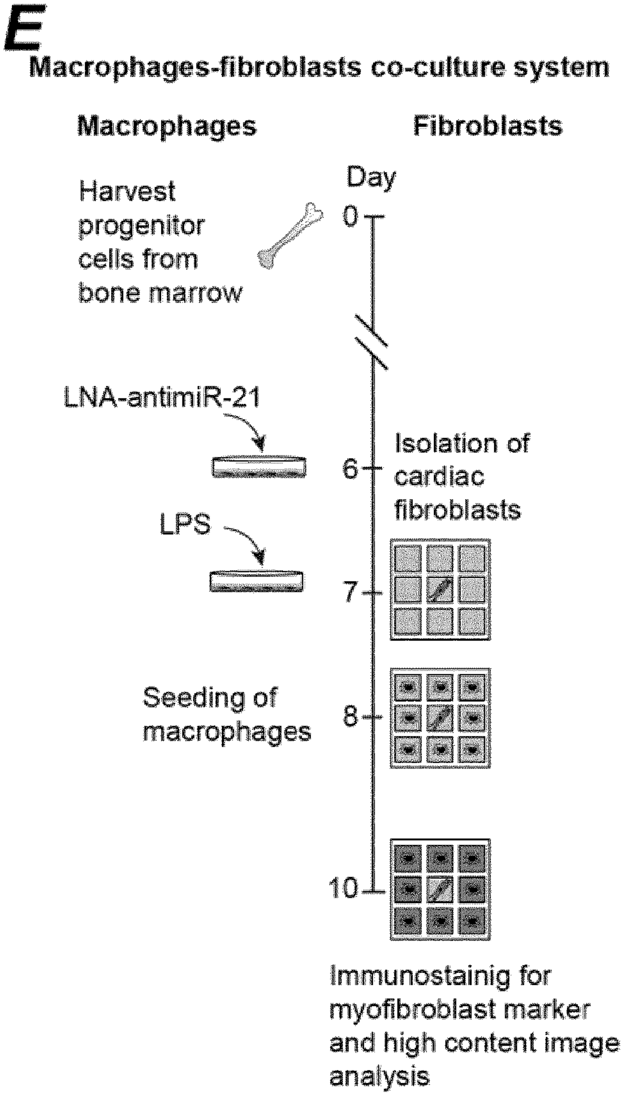
D
WT sham          WT TAC          miR-21 cKO TAC
Quiescent fibroblasts
Activated fibroblasts
Myofibroblasts
E
Macrophages-fibroblasts co-culture system
Macrophages          Fibroblasts
Harvest progenitor cells from bone marrow
Day 0
LNA-antimiR-21
6    Isolation of cardiac fibroblasts
LPS
7
Seeding of macrophages
8
10
Immunostainig for myofibroblast marker and high content image analysis

A

Figure 12:
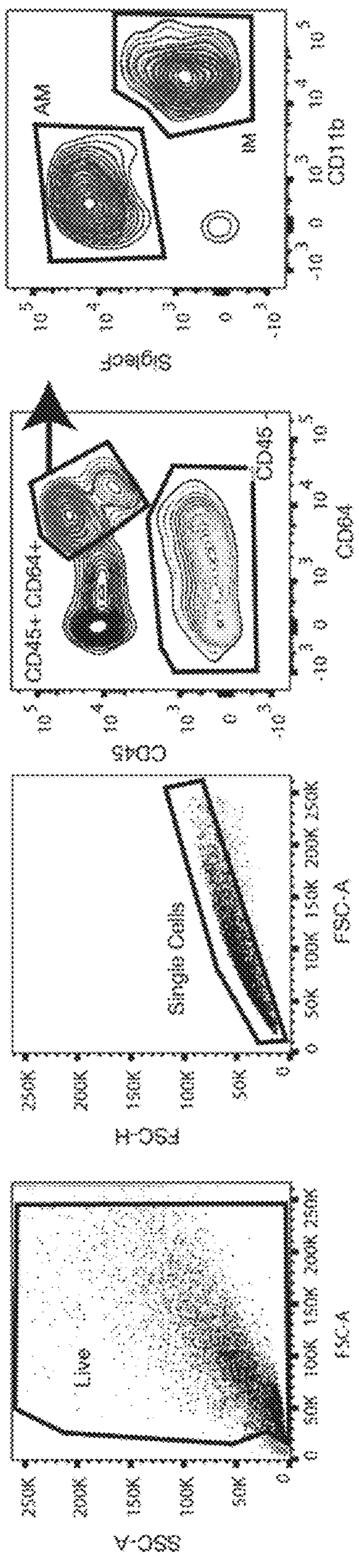

Figure 12 cont.
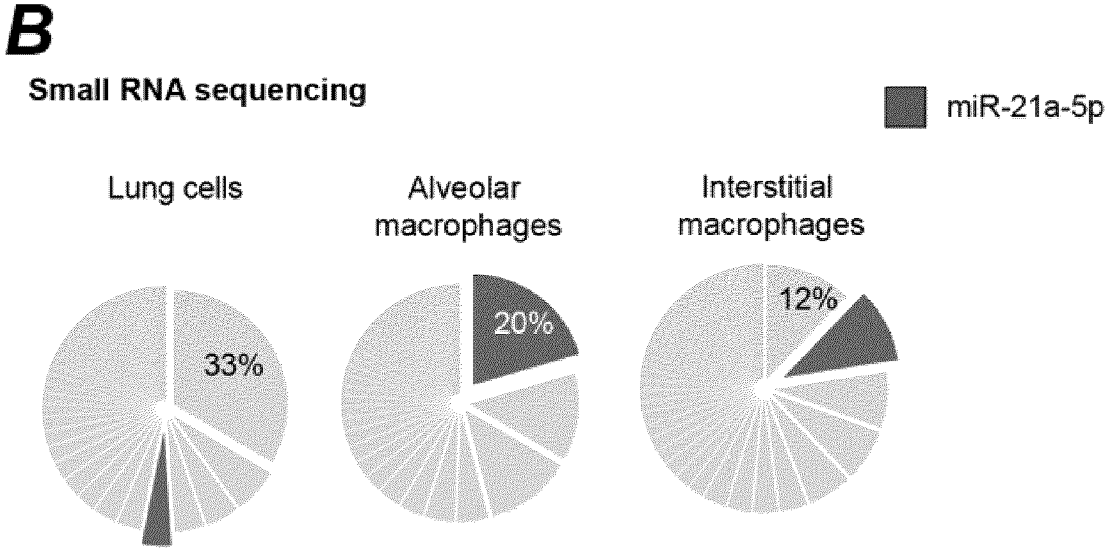
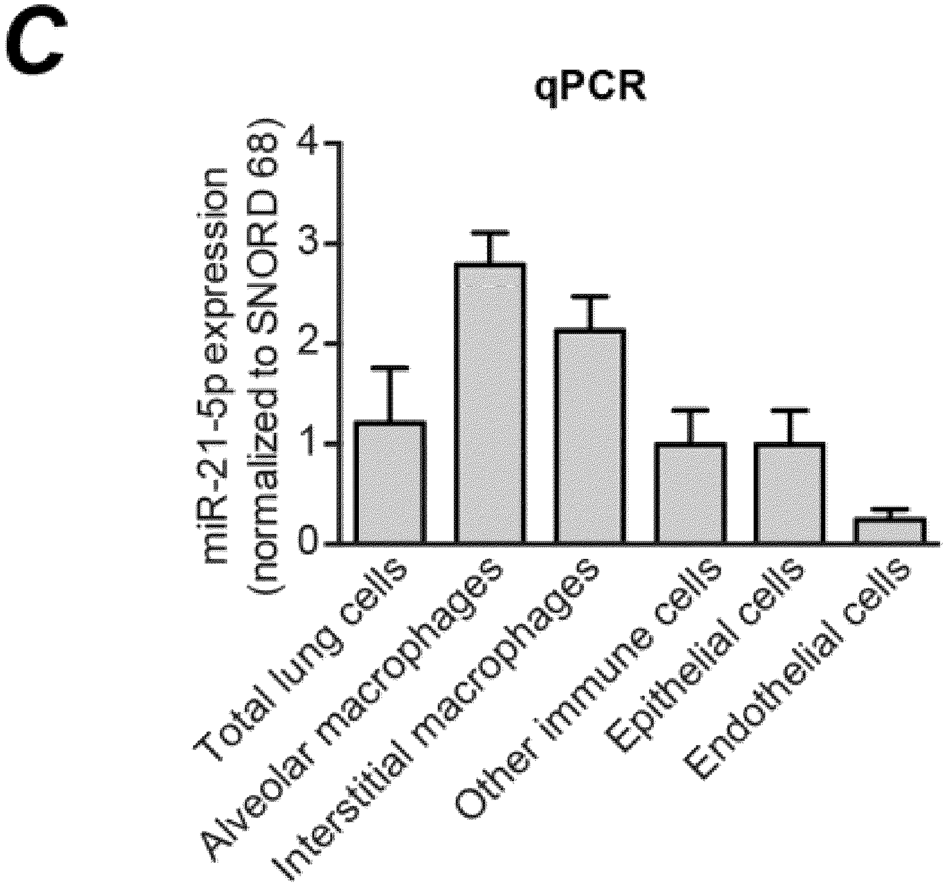

Figure 13:
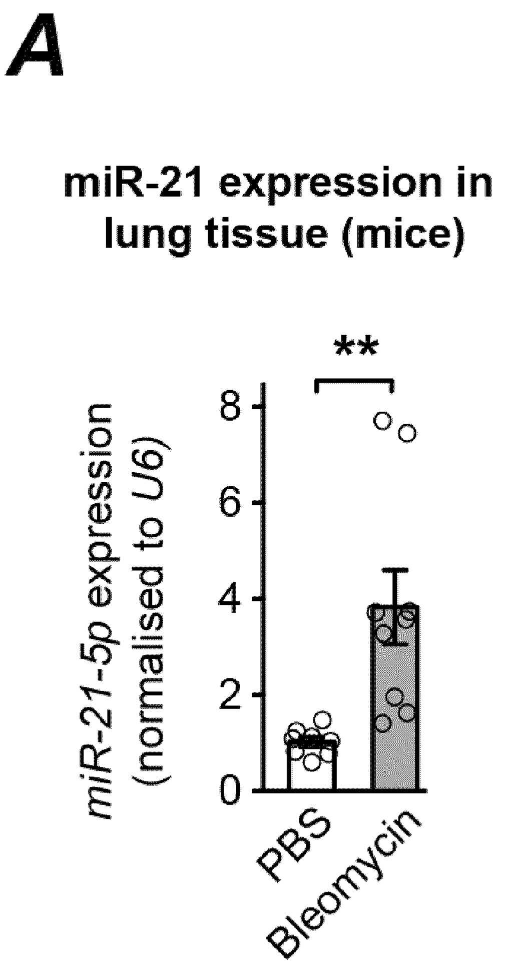
Figure 13:
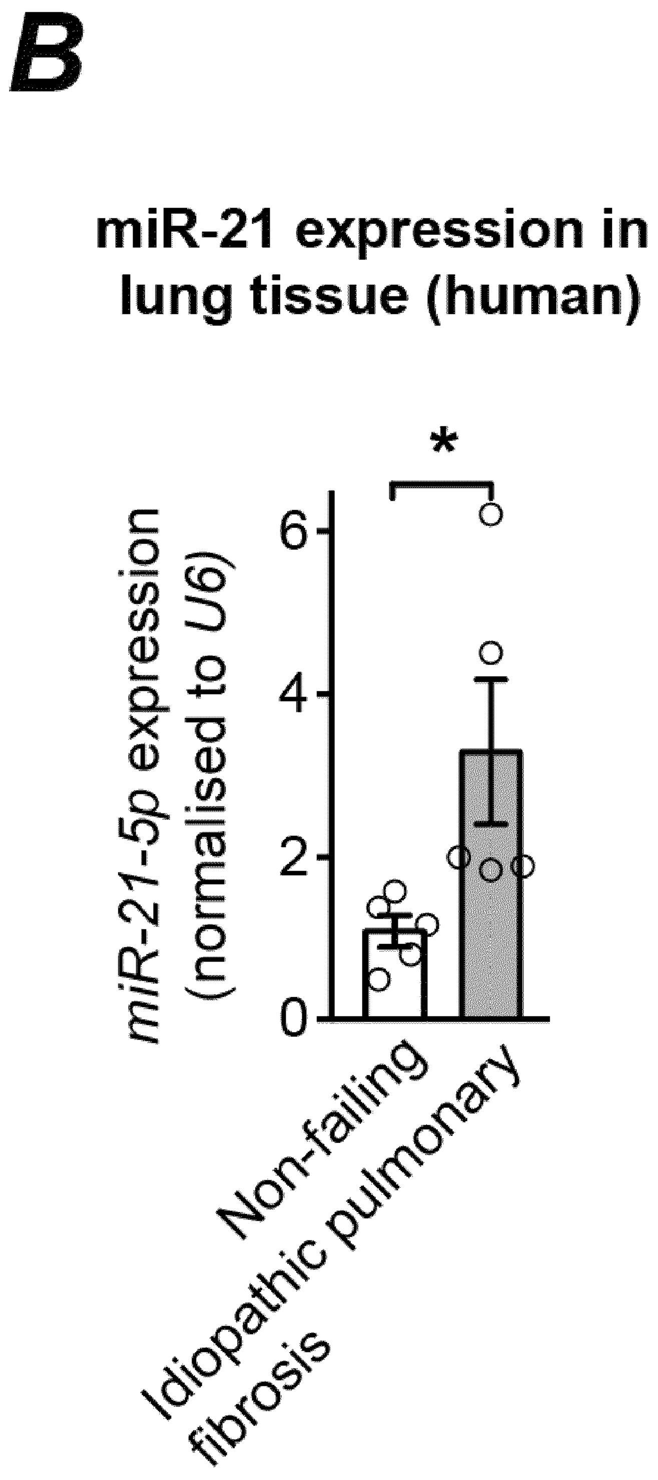

Figure 13 cont.
C
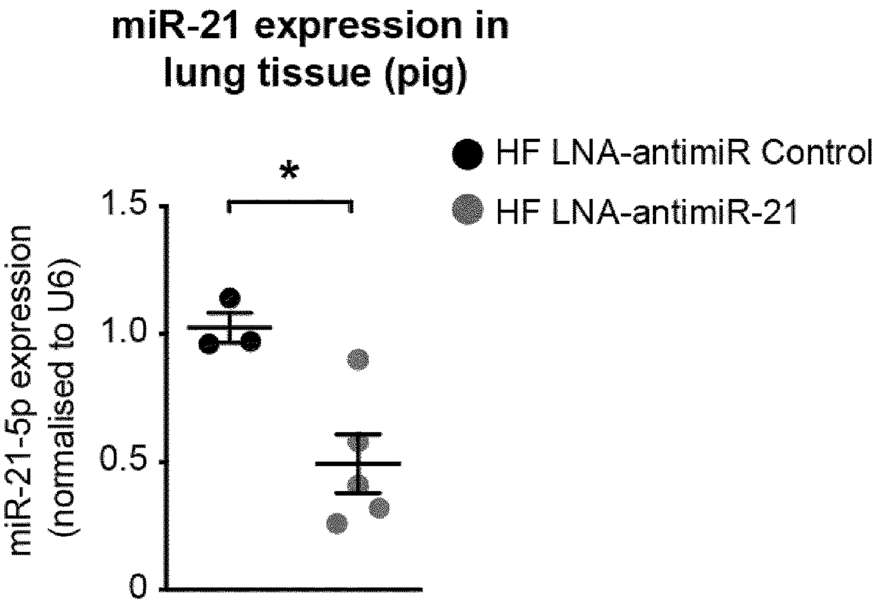
D
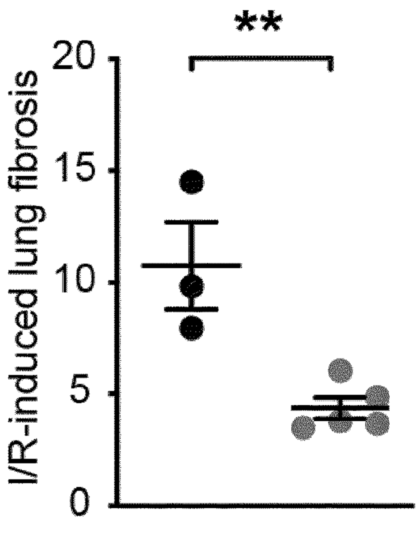

Figure 14:
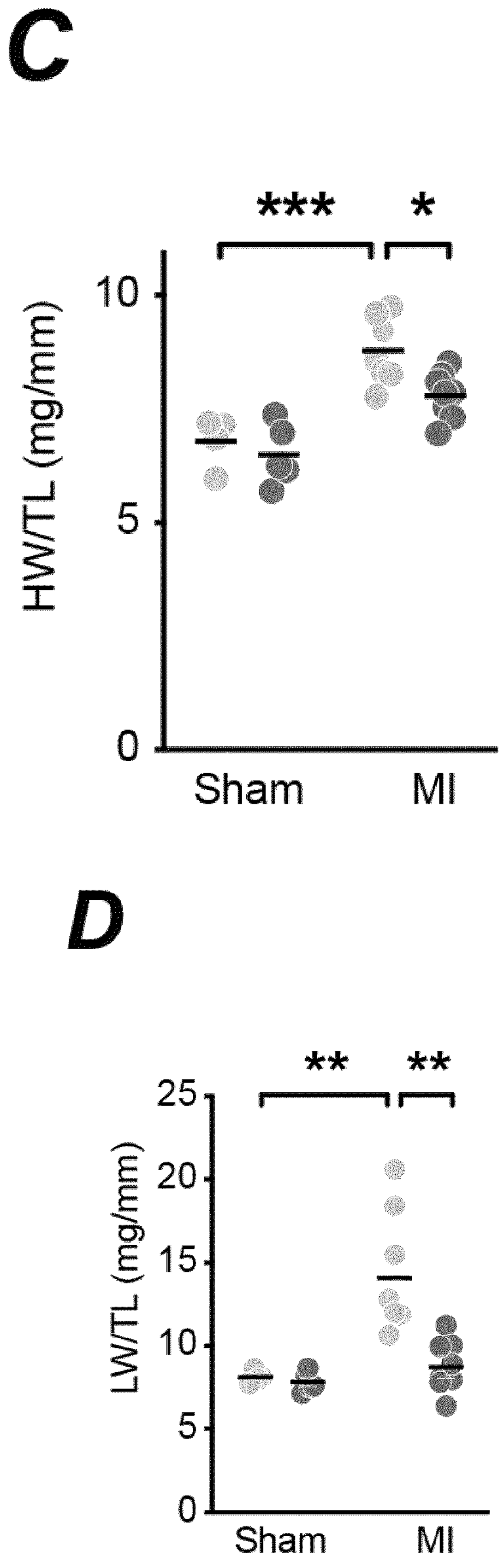
Figure 14:
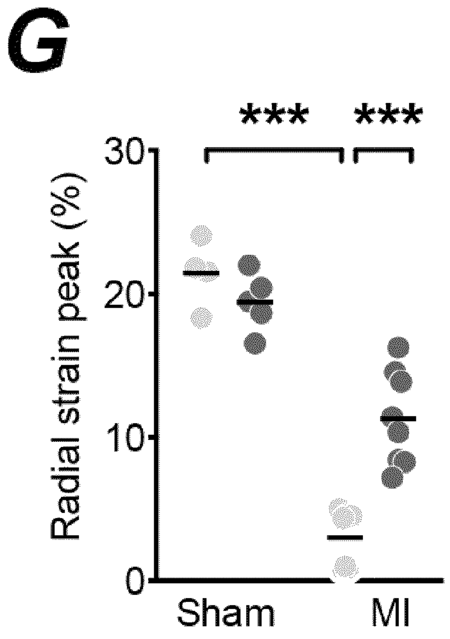

Figure 14
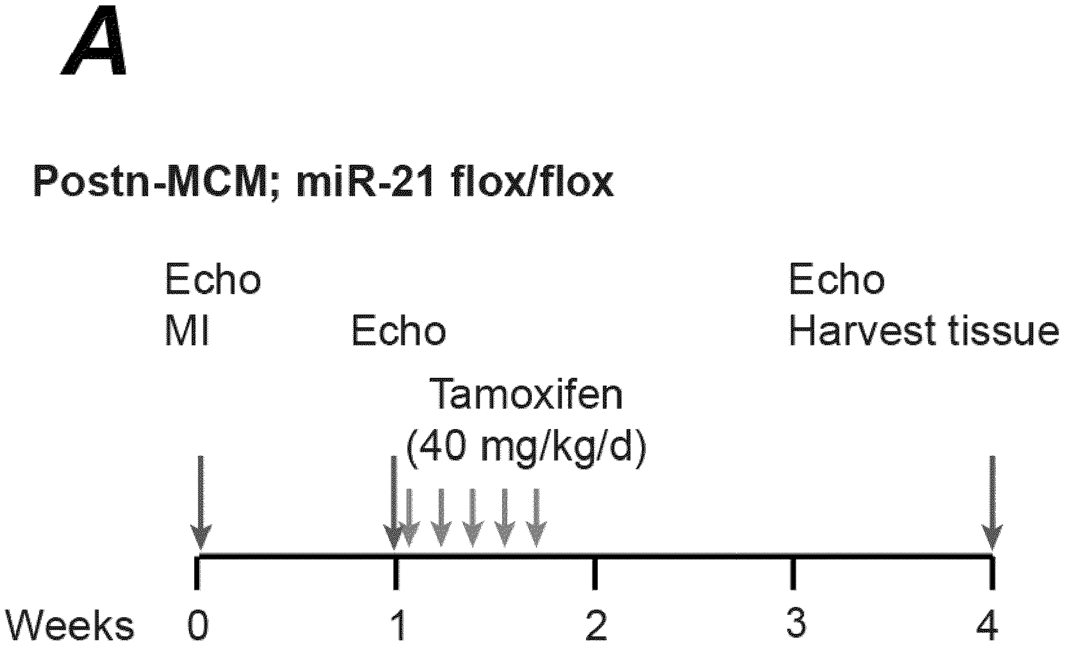
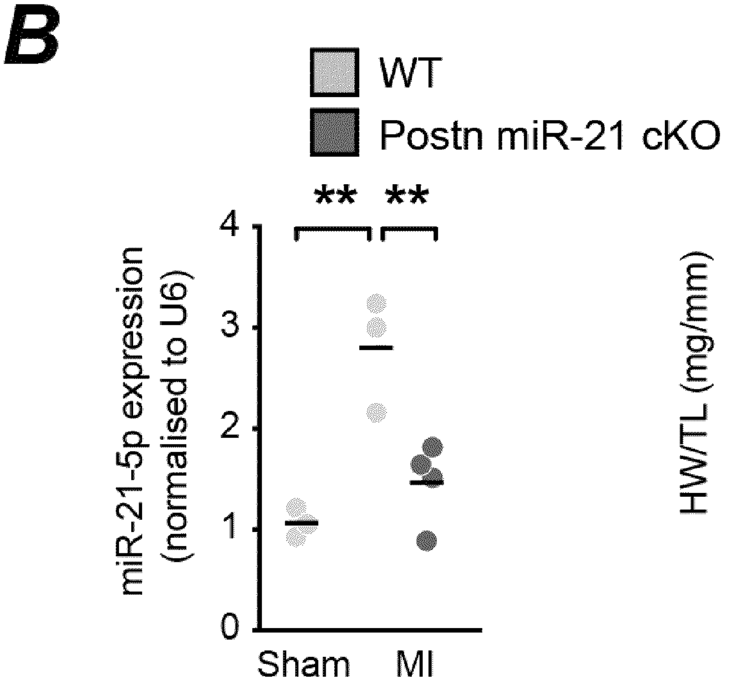

Figure 14 cont.
E
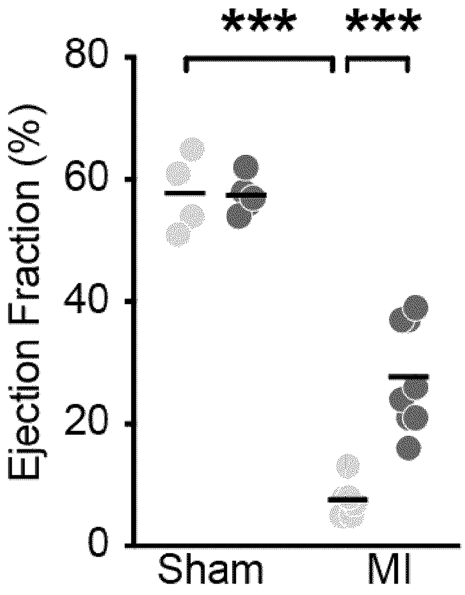
F
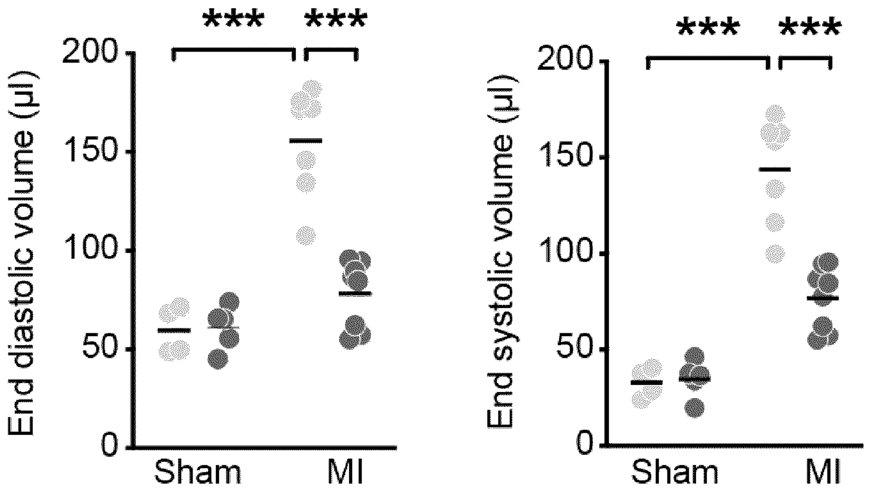

Figure 16
Table 1
Serological analysis of selected biochemical parameters of liver and kidney function

| | HF Control | HF LNA-antimiR-Control | HF LNA-antimiR-21 | p-value |
|---|---|---|---|---|
| n | 3 | 3 | 5 | |
| **Day 0** | | | | |
| AST (GOT) (U/l) | 32 ± 3.8 | 23 ± 3.1 | 29 ± 3.8 | n.s. |
| ALT (GPT) (U/l) | 42 ± 5.0 | 36 ± 3.7 | 46 ± 8.8 | n.s. |
| γ-GT (U/l) | 33 ± 10.7 | 28 ± 8.4 | 30 ± 7.5 | n.s. |
| Creatinine (µmol/l) | 87 ± 5.9 | 72 ± 5.4 | 88 ± 2.4 | n.s. |
| Urea (mmol/µl) | 2.5 ± 0.6 | 3.6 ± 0.7 | 3.1 ± 0.9 | n.s. |
| **Day 5** | | | | |
| AST (GOT) (U/l) | 33 ± 7.1 | 32 ± 7.3 | 30 ± 1.3 | n.s. |
| ALT (GPT) (U/l) | 47 ± 7.4 | 55 ± 1.2 | 63 ± 10.6 | n.s. |
| γ-GT (U/l) | 48 ± 22.8 | 23 ± 3.5 | 32 ± 7 | n.s. |
| Creatinine (µmol/l) | 93 ± 10.5 | 58 ± 5.2 | 99 ± 5.4 | n.s. |
| Urea (mmol/µl) | 2.7 ± 0.6 | 3.9 ± 0.3 | 3.2 ± 0.6 | n.s. |
| **Day 33** | | | | |
| AST (GOT) (U/l) | 31 ± 3.3 | 22 ± 7.3 | 27 ± 4.9 | n.s. |
| ALT (GPT) (U/l) | 44 ± 12.6 | 22 ± 3.7 | 53 ± 9.5 | n.s. |
| γ-GT (U/l) | 49 ± 11.7 | 25 ± 4.7 | 33 ± 4.8 | n.s. |
| Creatinine (µmol/l) | 120 ± 20.7 | 97 ± 0.8 | 111 ± 2.3 | n.s. |
| Urea (mmol/µl) | 3.3 ± 0.8 | 3.4 ± 0.2 | 4.3 ± 0.7 | n.s. |

(MEAN±SEM, p-value HF Control vs. HF LNA-antimiR-21)

Reference values: AST (GOT) (<59 U/l); ALT (GPT) (<68 U/l); γ-GT (<54 U/l); Creatinine (<160 µmol/l); Urea (2.5-6.7 mmol/µl).

Figure 17
Table 2
Cardiovascular events

| | Sham | HF Control | HF LNA-antimiR-21 |
|---|---|---|---|
| | **Day0** | | |
| Ventricular extrasystoly | 0% | 67% | 85% |
| Reanimation (Defibrillation) | 0% | 33% | 14% |
| Cardiac death | 0% | 16% | 14% |
| | **Day 5** | | |
| Ventricular extrasystoly | | 20% | 16% |
| Reanimation (Defibrillation) | | 20% | 16% |
| Cardiac death | | 20% | 16% |
| | **Day 19** | | |
| Ventricular extrasystoly | | 0% | 0% |
| Reanimation (Defibrillation)n | | 0% | 0% |
| Cardiac death | | 0% | 0% |
| | **Day 33** | | |
| Ventricular extrasystoly | 0% | 0% | 0% |
| Reanimation (Defibrillation) | 0% | 0% | 0% |
| Cardiac death | 0% | 0% | 0% |

(MEAN±SEM, p-value HF Control vs. HF LNA-antimiR-21)

Figure 22:
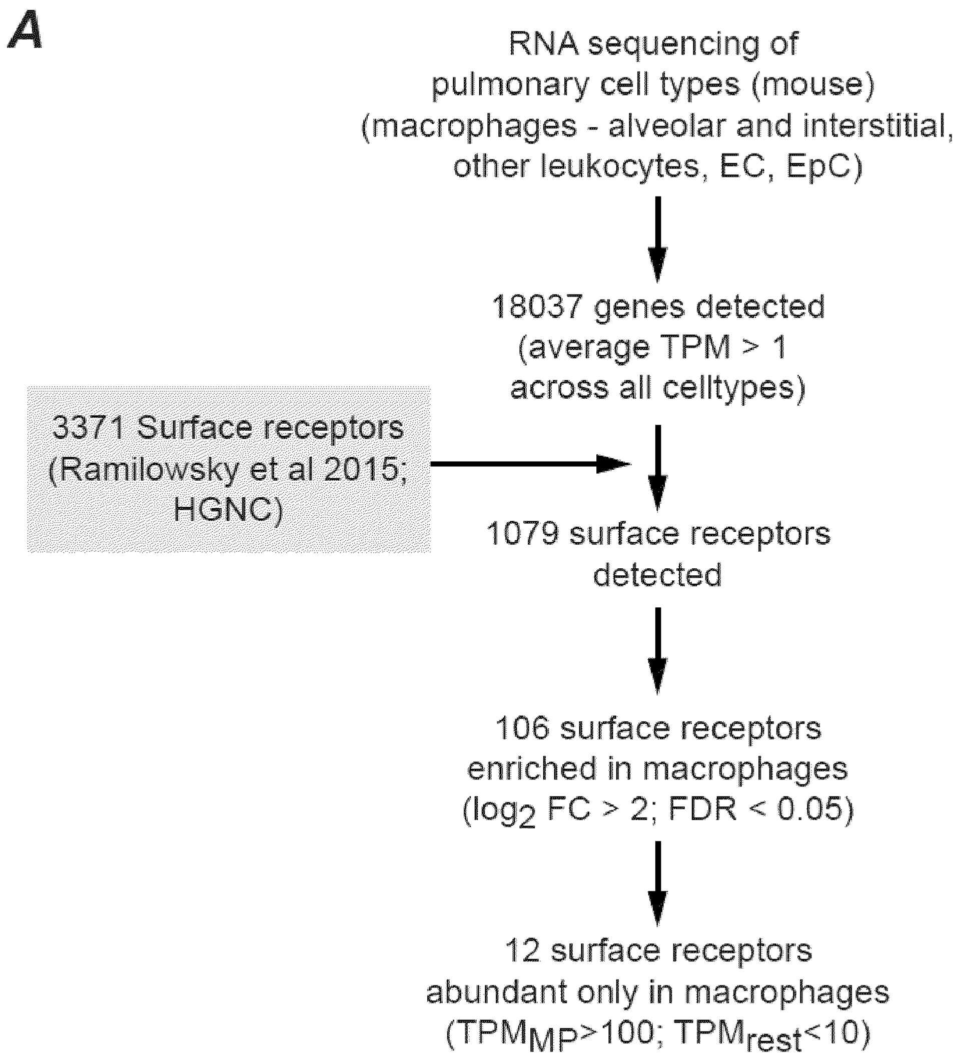
Figure 22:
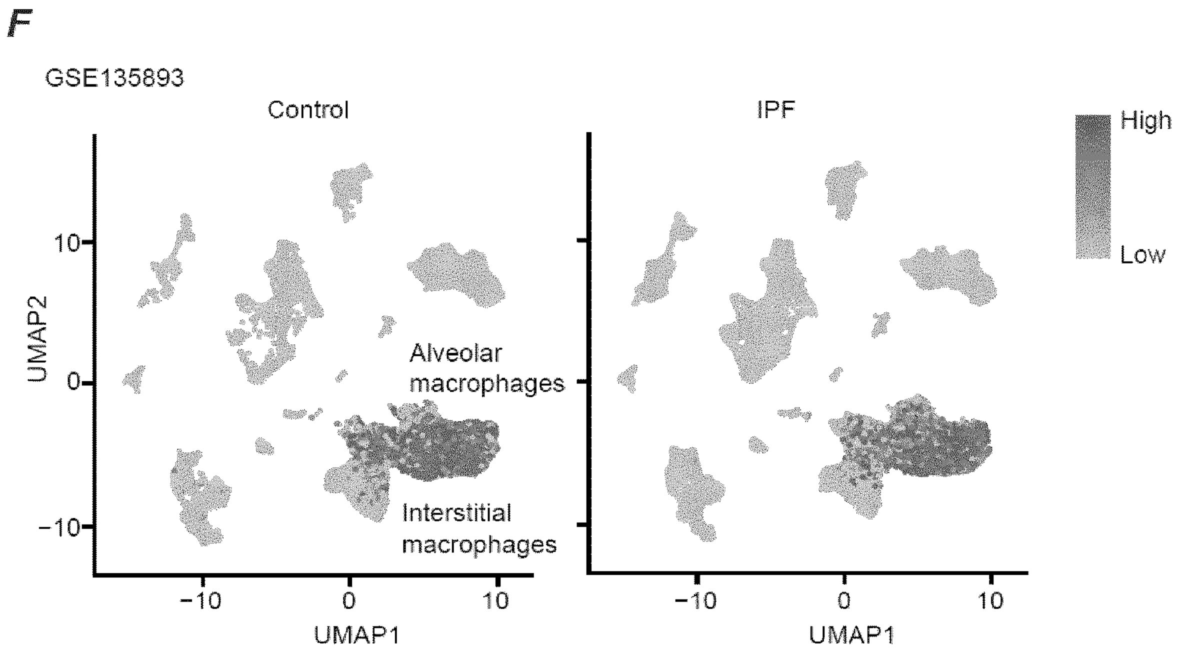

Figure 22 cont.
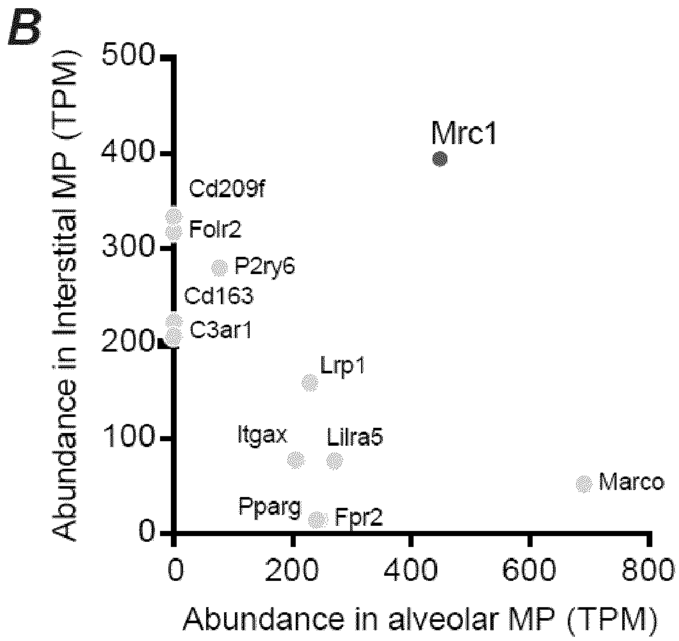
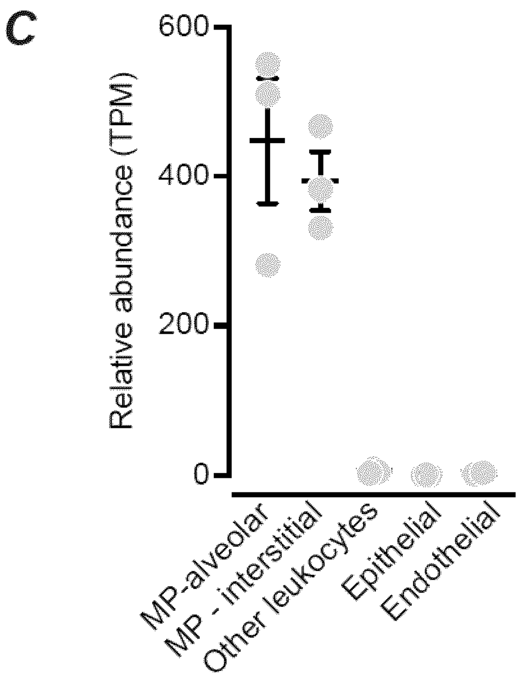

Figure 22 cont.
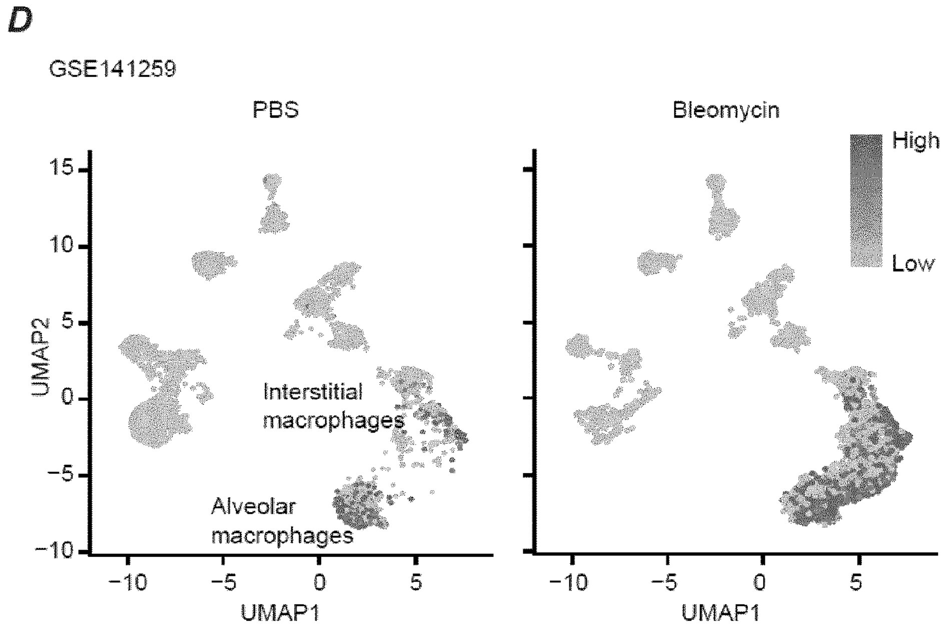
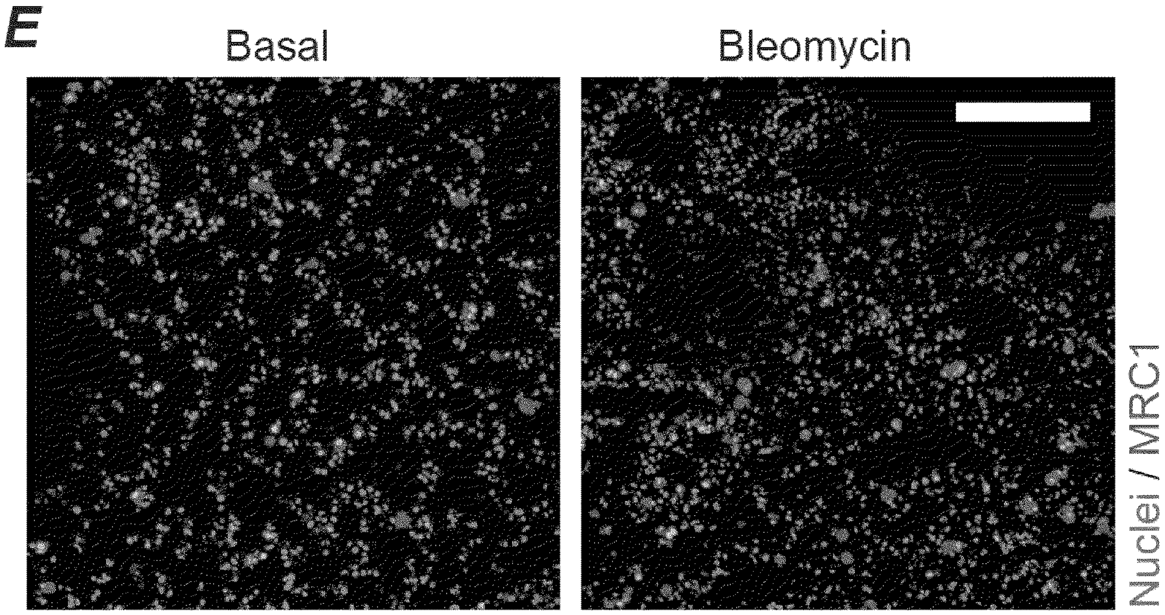

Mannose-conjugated LNA-antimiR-21

Tri-mannose

LNA-antimiR-21

TCAGTCTGATAAGCT

N-acetylglactosamine-conjugated LNA-antimiR-21-FAM

A

Figure 24:
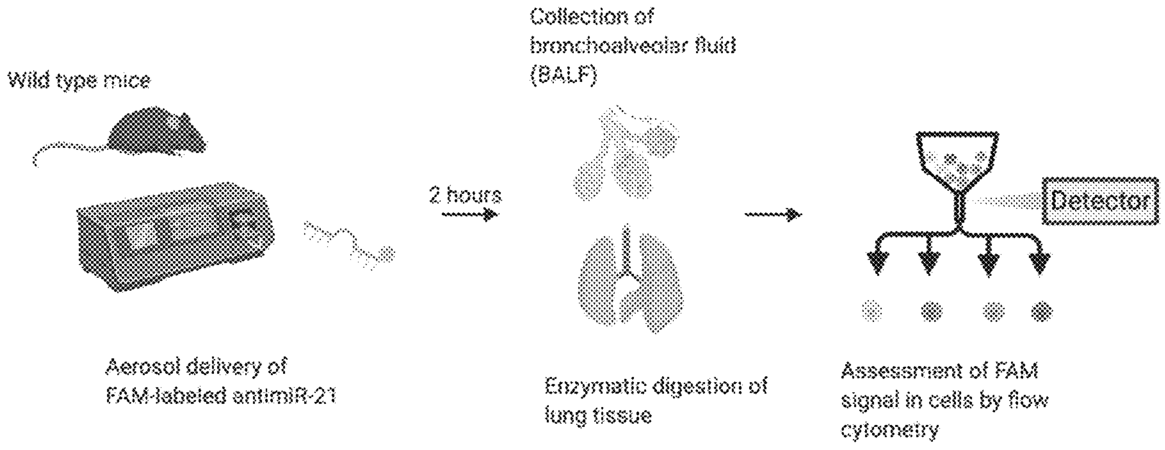

Figure 24 cont.
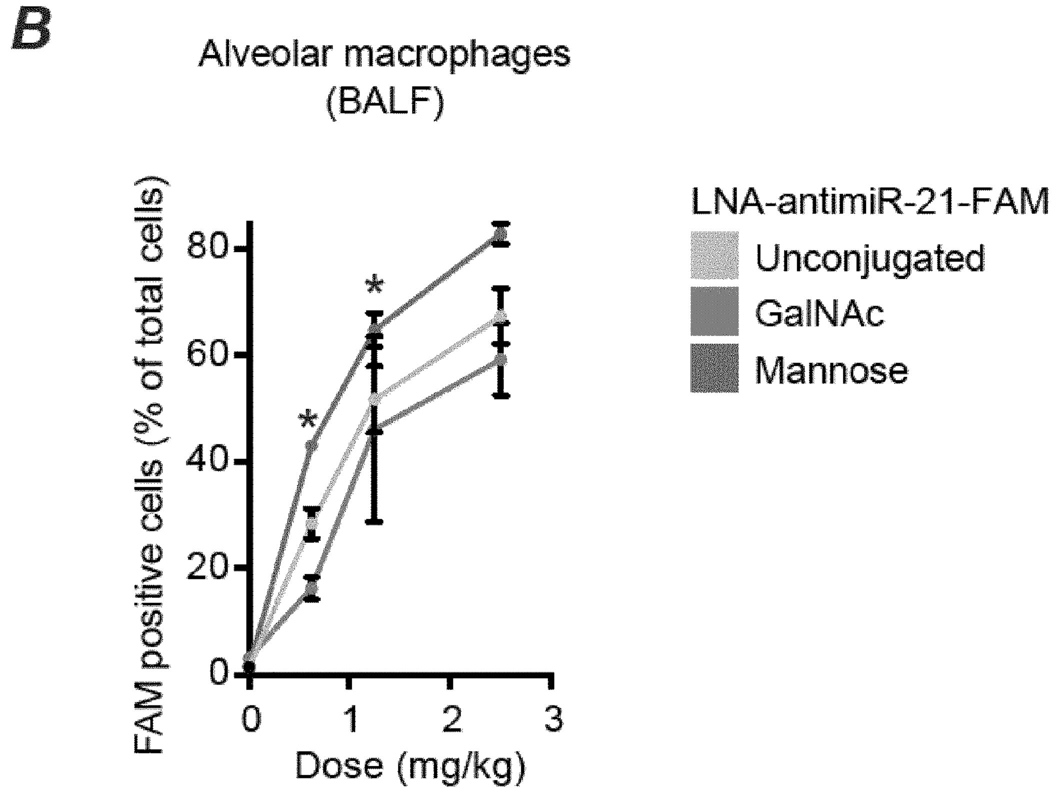
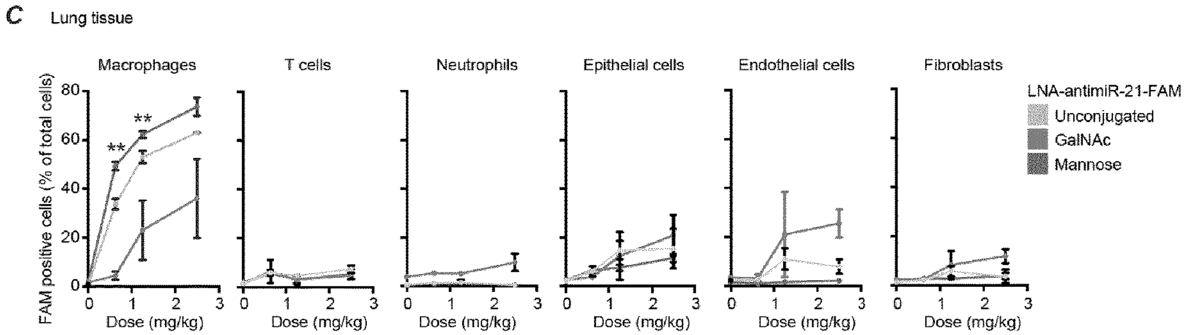

Figure 25
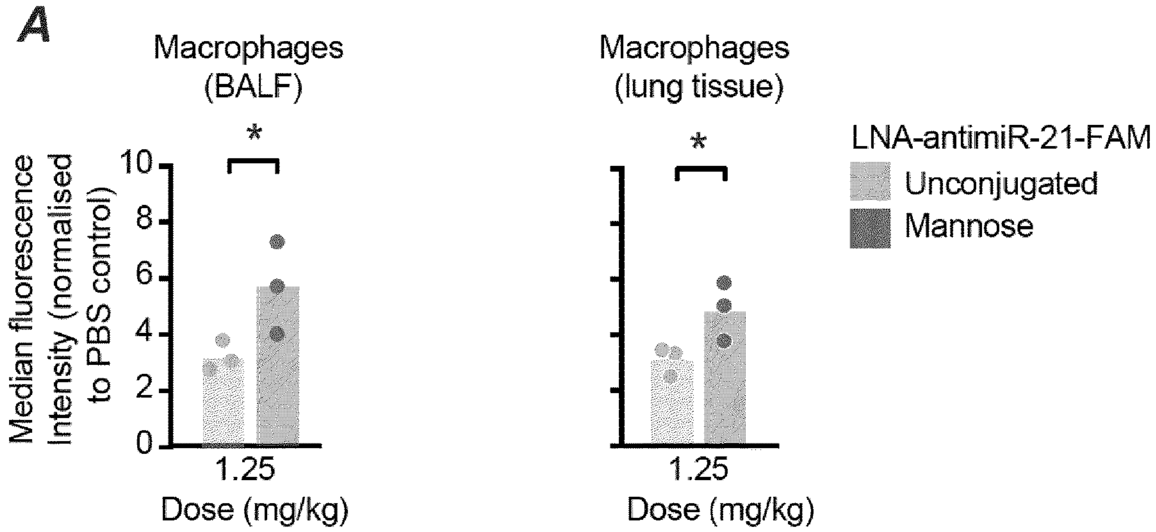
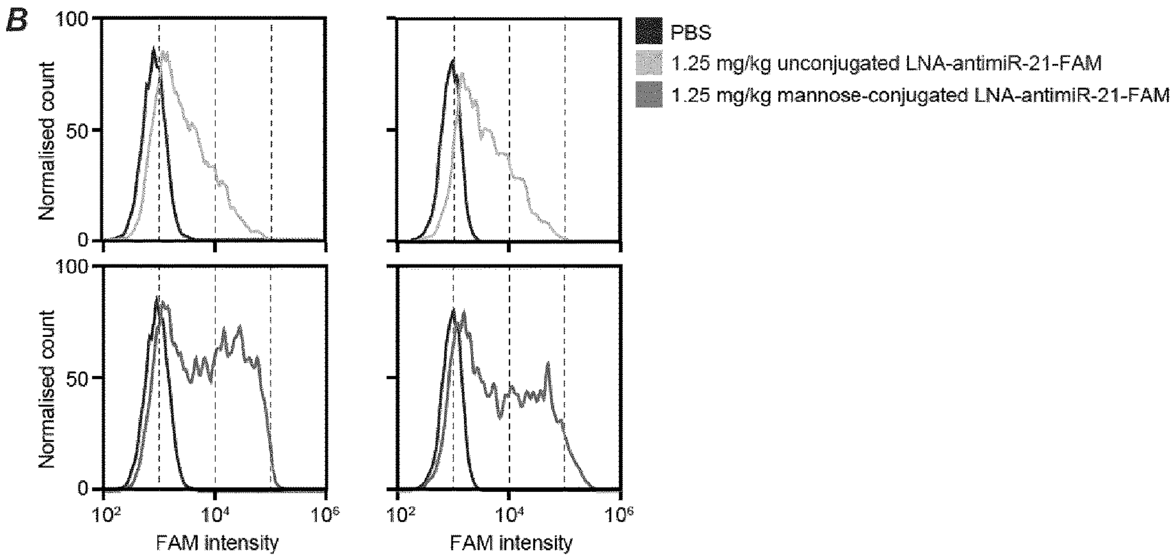

Figure 26
A
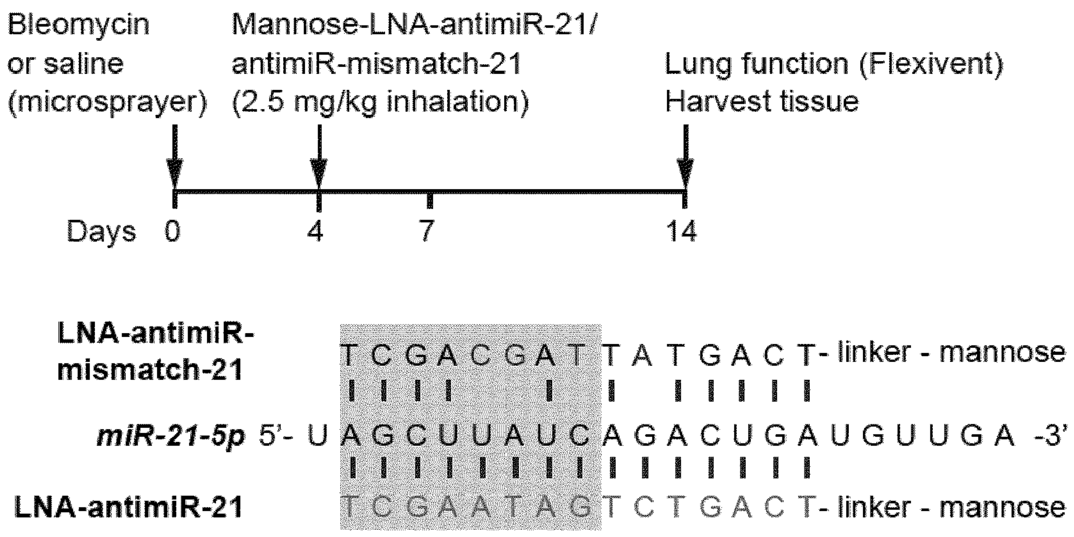
B
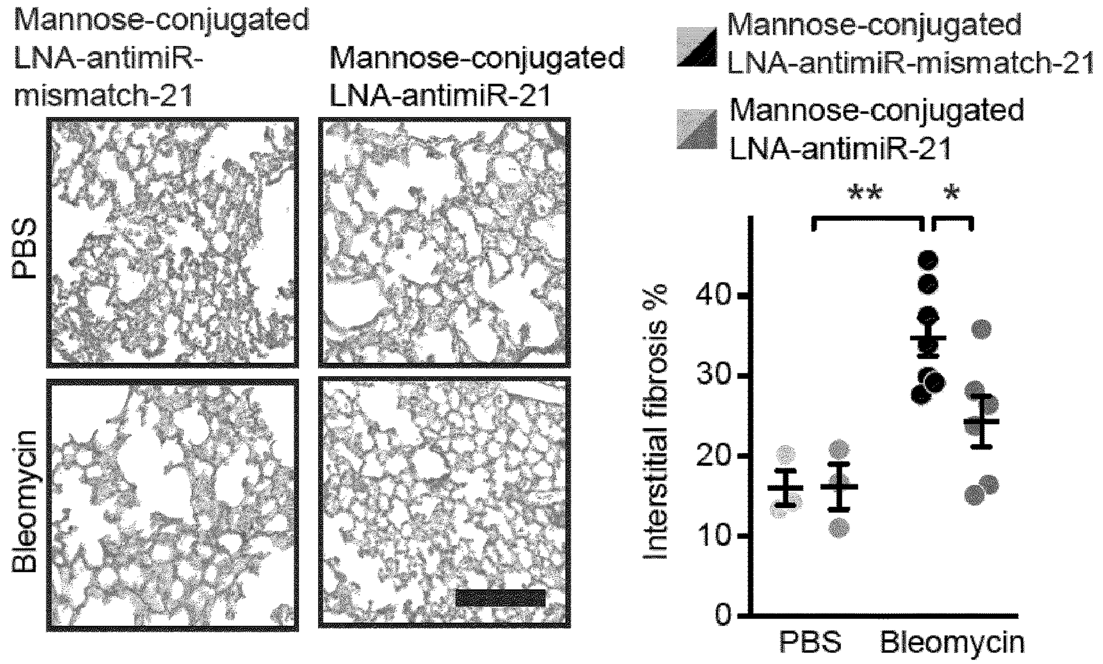

Figure 26 cont.
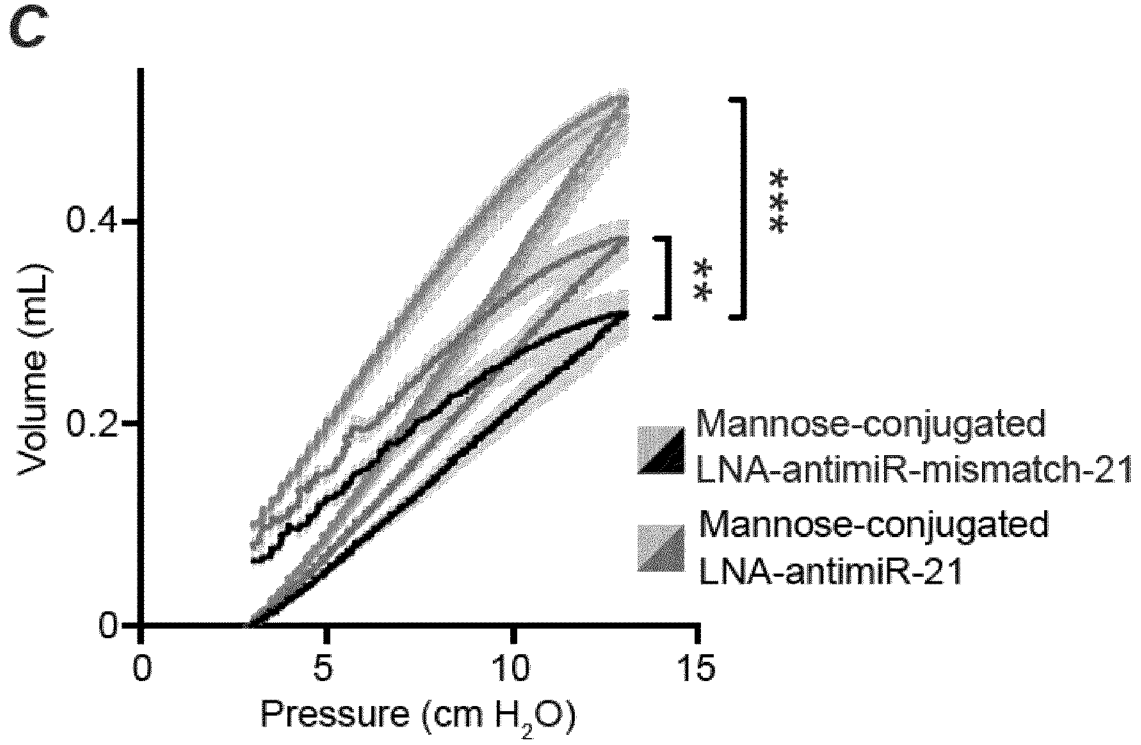
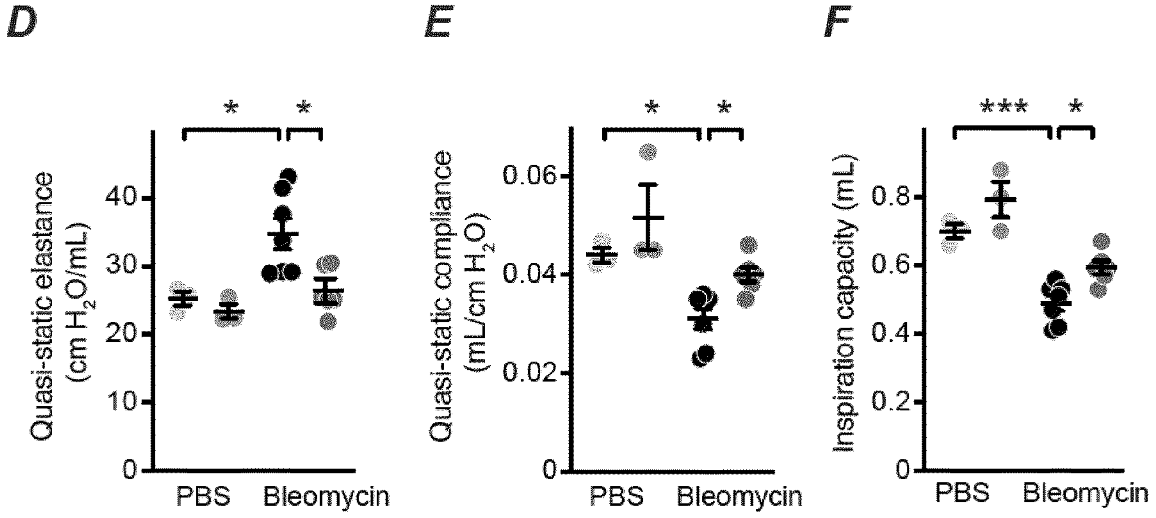

Figure 27:
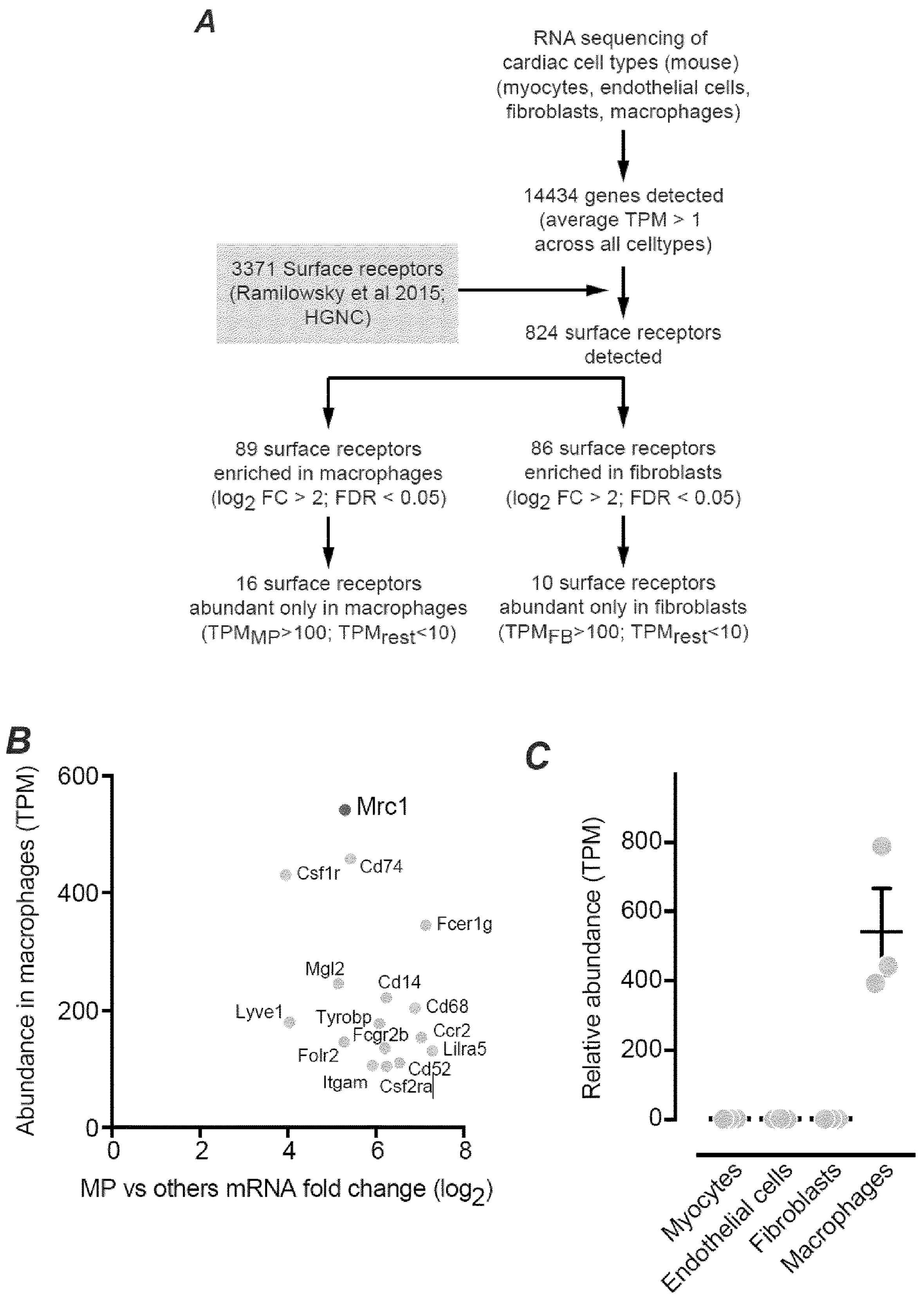

Figure 27 cont.
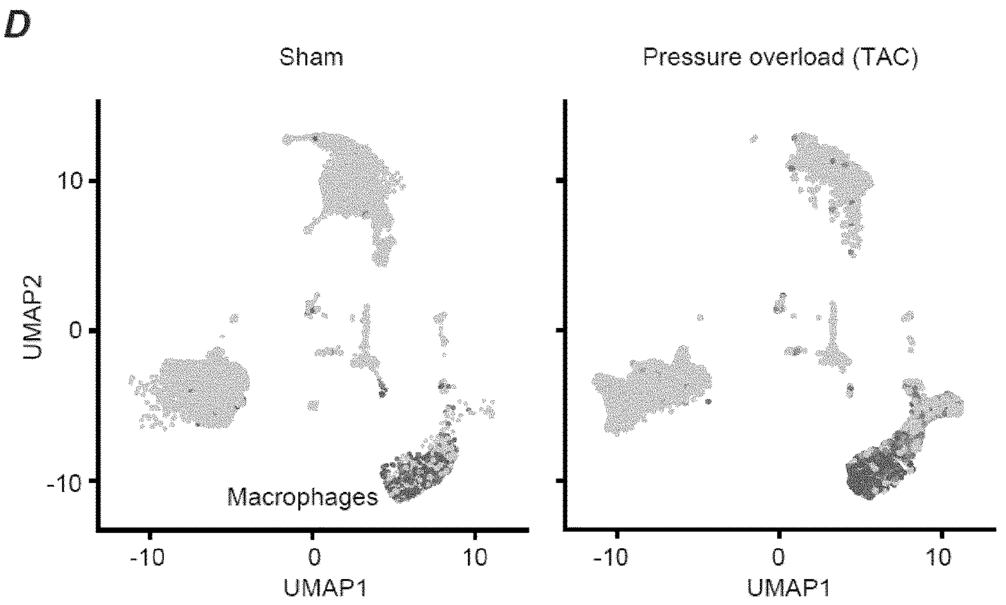
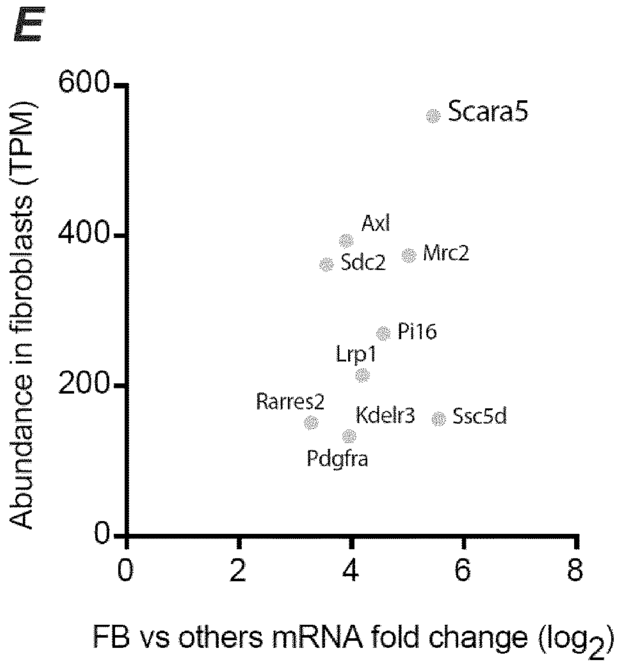

TARGETED DELIVERY OF AN INHIBITOR OF miR-21 TO MACROPHAGES FOR THE TREATMENT OF PULMONARY FIBROSIS

This application is a national phase application under 35 U.S.C. § 371 of International Application No. PCT/EP2021/059360, filed Apr. 9, 2021, the entire contents of which are hereby incorporated by reference. International Application No. PCT/EP2021/059360 claims benefit of European Application No. 20169160.7, filed Apr. 9, 2020.

The present invention relates to a composition for use in the treatment of pulmonary fibrosis of a subject, wherein the composition comprises an inhibitor of miR-21 and a moiety that delivers said inhibitor of miR-21 to a macrophage. Further, the composition may be administered by a pulmonary administration. In particular aspects, said subject to be treated suffers from pulmonary fibrosis and further has a lung disease or disorder, wherein the lung disease or disorder may be a corona virus disease. Furthermore, the invention relates to a composition, wherein the composition comprises an inhibitor of miR-21 and a moiety that delivers said inhibitor of miR-21 to a lung macrophage.

There is a high need of the treatment of organ fibrosis, for example pulmonary fibrosis. With regard to pulmonary fibrosis, viral infections, such as the corona virus infections, like COVID-19, are often followed by consolidation of the lung and fibrosis (Xu et al., 2020). Pulmonary fibrosis severely compromises pulmonary function and is largely untreatable with the current treatment and treatment regimens (Sgalla et al., 2018). Therefore, there is also an urgent need for new therapeutic strategies targeting alternative mechanisms and molecules involved in pulmonary fibrosis.

Furthermore, fibrosis plays further key roles in the pathologies of further diseases, such as cardiac diseases or disorders. Although acute survival after myocardial infarction has considerably improved within the last decades (Bahit et al., 2018), post-ischemic heart failure (HF) remains a very frequent (approx. 50%) consequence and constitutes one of the most common causes for hospitalization and death (Bahit et al., 2018). While current medical management of HF largely relies on vasodilating agents and inhibitors of neurohumoral activation, the clinical efficacy of these therapeutic principles has been suggested of having reached a level, where further increases in clinical benefit are increasingly difficult to achieve (Pellicori et al., 2019). Still, there is an urgent need for new therapeutic strategies targeting alternative mechanisms and molecules involved in HF pathology.

Microribonucleic acids (MiRNAs or miRs) are approximately 20-22 nucleotides long RNA molecules that bind to antisense complementary regions in the 3'-untranslated regions of the majority of protein-encoding mRNAs (Bartel, 2018). Next to their pivotal role in almost any cellular process investigated to date, they are important regulators in a large and growing list of disease entities, including cancer, immunological and cardiovascular disease (Mendell & Olson, 2012).

A major obstacle, which till date prevented the clinical development of inhibitors of miR-21, in particular oligonucleotide-based therapies, is the relatively low extent to which these molecules enter cells upon systemic delivery. Consistently, the prior art suggests to use comparably high doses of oligonucleotides, ranging from 2-80 mg/kg body weight. Such doses cannot be scaled to humans, both for economic reasons and for side effects that can be expected with such high substance loads (Li & Rana, 2014; Lu & Thum, 2019).

Accordingly, the underlying technical problem is the provision of an improved therapy of pulmonary fibrosis.

The technical problem is solved by provision of the embodiments provided herein below and as characterized in the appended claims.

In particular, and as documented in the appended examples, it was surprisingly found that inhibition of miR-21 reduces pulmonary remodeling and/or dysfunction in diseased and/or damaged lungs. Accordingly, the present invention relates to the medical and/or pharmaceutical use of an inhibitor of miR-21 in the treatment and/or amelioration of a lung disease, a lung damage and/or of a lung disorder. Said lung disease, said lung damage and/or said lung disorder may be, may be the cause of and/or may be accompanied by pulmonary fibrosis. In a particular embodiment, the present invention relates to a composition for use in the treatment of pulmonary fibrosis, wherein said composition comprises an inhibitor of miR-21 and a moiety that delivers said inhibitor of miR-21 to a macrophage. In context of this invention the term "composition" also comprises compounds, wherein said "compound" may be a single molecule that has at least two functional moieties/parts, i.e., (a) a functional moiety/part that is an inhibitor of miR-21 and (b) a functional moiety/part that delivers said inhibitor of miR-21 to said macrophage. In context of this invention, the term composition and compound may be used interchangeably. Accordingly, and in one embodiment, said composition comprising said inhibitor of miR-21 and comprising said moiety that delivers said inhibitor of miR-21 to a macrophage may be a single molecule, i.e. said "inhibitor" and said "targeting moiety to (a) macrophage(s) may be physically linked, for example by covalent binding, conjugation and the like. Such a compound/molecule may also comprise a "linker" structures that links the "inhibitor of miR21" and the moiety that delivers said inhibitor of miR-21 to a macrophage. Corresponding exemplified and non-limiting linkers are provided herein. It is also envisaged that the inventive composition/compound also comprises, further moieties/parts, like, e.g. a moiety/a part as defined herein below and capable of targeting the inhibitor of miR-21 to other target cells like, in particular (and in one embodiment) to fibroblasts.

Accordingly, in a particular embodiment, the present invention also relates to a composition/compound, wherein said composition/compound comprises an inhibitor of miR-21 and a moiety that delivers said inhibitor of miR-21 to a, preferably to a lung macrophage. A further embodiment of this invention is a composition/compound, wherein said composition/compound comprises an inhibitor of miR-21, a moiety that delivers said inhibitor of miR-21 to a (lung) macrophage and a further moiety that delivers said inhibitor of miR-21 to a fibroblast, preferably to a lung fibroblast. In context of this invention the term "delivers said inhibitor of miR-21 to . . . " also means "targets said inhibitor of miR-21 to . . . ". Corresponding, non-limiting examples of such "moieties" are provided herein below and are also illustrated in the appended non-limiting examples. Accordingly, it is understood in context of this invention that the composition/compound to be used in the inventive medical means and methods is a composition/compound wherein said inhibitor of miR-21 is conjugated to said moiety/moieties that deliver(s) said inhibitor of miR-21 to macrophage(s) and/or fibroblast(s). Accordingly, the terms "compound" and "composition" may be employed interchangeably and relate to the fact that in a preferred embodiment of this invention said compound/composition comprises said inhibitor of miR-21 and said moiety that delivers said inhibitor of miR-21 to a macrophage and/or a fibroblast. In a preferred embodiment, said inhibitor of miR-21 and said moiety that delivers the inhibitor to macrophages and/or fibroblasts are conjugated/covalently bound.

As detailed herein, the inhibitor of miR-21 may be conjugated to moiety that delivers said inhibitor of miR-21 to a macrophage. For example, but with being limiting, said inhibitor of miR-21 may be conjugated to an antibody or to a functional fragment thereof that binds to/interacts with preferably with a (specific) cell surface receptor(s) on macrophages. The inhibitor of miR-21 may also be conjugated to cell type-specific targeting moieties in context of this invention. As also envisaged and shown herein in the appended examples, the inhibitor of miR-21 may be conjugated to a "ligand" of said cell surface markers/receptors. Non-limiting examples of such cell markers/receptors are provided in Table 3 herein. Such "ligands" may comprise small molecule ligands and/or (proteinaceous) ligands or to functional fragments thereof which are capable of interacting with their corresponding "receptors" on the corresponding desired target cell. An example of such an "ligand-receptor" interaction may be the herein employed and exemplified interaction of "mannose" (an example of a "small molecule ligand" with MRCI1 on the target macrophages. An example of a proteinaceous ligand may the peptide CSPGAKVRC (SEQ ID No. 6) as described also below that is an interacting peptide for MRC1, i.e. a cell surface receptor on macrophages.

The inventors surprisingly found in context of this invention that miR-21 is a strongly expressed miRNA in specific cell types of lung and heart tissue, and in particular so under pathologic conditions, such as cardiac diseases or disorders, or pulmonary diseases or disorders.

In particular and based on the prior art, the inventors considered that the delivery to the myocardium or the lung is difficult and thus hampered the use of miRNA-based therapies. Accordingly, the inventors elucidated in this uncertain scientific and medical field the applicability and therapeutic efficacy of (anti-) miRNA-based medical interventions to macrophages and/or fibroblasts, in particular to macrophages and/or fibroblasts residing in the heart and/or in the lung, like alveolar macrophage(s) and/or interstitial macrophage(s). Accordingly, such macrophages residing and/or found in lung tissue, like alveolar macrophage(s) and/or interstitial macrophage(s) are "lung macrophage(s)" in context of this invention. The term "lung macrophage(s) also comprises the term "pulmonary macrophages". As illustrated in the experimental part, the inventors also elucidated surface receptors/surface markers of pulmonary macrophages. These receptors/markers, which are specific for "lung macrophages" comprise, but are not limited to, e.g., mannose receptor C type 1 (MRC1; ENSG00000260314), macrophage receptor with collagenous structure (MARCO; ENSG00000019169), CD68 antigen (CD68; ENSG00000129226), adhesion G protein-coupled receptor E1 (ADGRE1; ENSG00000174837), C—C motif chemokine receptor 2 (transient) (CCR2; ENSG00000121807), integrin subunit alpha M (ITGAM; ENSG00000169896) and Fc receptor, IgG, high affinity (FCGR1A; ENSG00000150337).

A marker specific for alveolar macrophages may be sialic acid binding Ig like lectin 1 (SIGLEC1; ENSG00000088827) and macrophage receptor with collagenous structure (MARCO; ENSG00000019169). A marker specific for interstitial macrophages may be CD163 molecule (CD163; ENSG00000177575). Receptors/markers, which are specific for fibroblasts comprise, but are not limited to, e.g., platelet derived growth factor receptor (PDGFRA; ENSG00000134853), transcription factor 21 (TCF21; ENSG00000118526), periostin (POSTN; ENSG00000133110) and actin alpha 2 (ACTA2; ENSG00000107796). Receptor/markers on the surface of macrophages that are particularly useful in the context of this invention are also provided and identified herein below by their stable identifiers in the ENS format (Ensembl Gene ID); see also table 3. Table 3 also comprises further receptors/markers on macrophages and/or fibroblasts, which are particularly useful in the context of this invention as interaction partner for the herein defined "moiety that delivers the inhibitor of miR-21 to (a) macrophage(s) (and, optionally also to fibroblast(s))". Whereas the above recited "markers" relate to markers that are predominantly expressed in macrophages and/or fibroblasts, respectively, most preferred "targets" for the herein defined "moiety that delivers an inhibitor of miR-21 to a macrophage (and/or to a fibroblast)" are surface markers/receptors on these cells. In a preferred embodiment, these surface markers/receptors mediate endocytosis upon interaction with said "moiety that delivers said inhibitor of miR-21"). Accordingly, said moiety/part delivering the inhibitor of miR-21 to macrophages (and, optionally to fibroblasts) may, inter alia, comprise ligands (e.g. small molecule ligands or proteinaceous ligands) that are capable of specifically interacting with said receptors/markers. Yet, it is also envisage, in context of this invention that the "inhibitor of miR-21" is delivered to said macrophages, preferably lung macrophages, via (specific) binding molecules that are capable of (specifically) interacting with said receptors/markers. Such binding molecules may comprise, but are not limited to, e.g., specific antibodies (binding to antigens comprised on said receptors/markers) and functional fragments thereof. Most preferably, said receptors/markers are cell-surface receptors on said macrophages (and/or fibroblast). As illustrated herein below and in the appended examples, a useful "receptor/marker" in context of this invention may be Mannose receptor C type 1 that is encoded by the MRC 1 gene and that is a membrane receptor mainly expressed on the surface of macrophages and that mediates the endocytosis of glycoproteins by macrophages. Mannose receptor C type 1, is known to preferably bind to sugars structures, in particular (high-)mannose structures. Accordingly, and in context of this invention, "a moiety that delivers an inhibitor of miR-21 to a macrophage" may be a ligand that interacts with mannose receptor C type 1. Such a ligand may be a small molecule, like a sugar molecule or a derivative thereof, for example mannose (herein below also branched tri-mannose structures), dimannosylmannose or the amino sugar derivative of galactose (GalNAc; N-acetylgalactosamine). As documented in the appended examples, the inventors could successfully deliver (in particular via inhalation) inhibitors of miR-21 "anti-miR-21") to (lung-) macrophages via mannose structures (here, e.g. tri-mannose) as well as via GalNAc as "moiety delivering an inhibitor of miR-21 to a macrophage".

The inventors surprisingly found that miR-21 is the most abundant and enriched microRNA in lung macrophages; as illustrated and, e.g., in particular in Examples 3 and 5. In particular, it is documented herein below that miR-21 represents most abundant fraction of miRs comprising approx. 20% of all miR expressed in lung alveolar macrophages; see, e.g. appended FIG. 12 B. Thus, miR-21 is the most abundant miR in the lung macrophages. Such high levels were also found in the lung interstitial macrophage, where more than 10% of all miRNA reads could be attributed to miR-21. Accordingly, the macrophages, in particular lung macrophages, are used as a target cell in the means and methods of medical intervention/treatment provided herein. As is also illustrated herein below, it was also surprisingly found in context of this invention that miR-21 is dramatically increased in human lung tissues that show pulmonary fibrosis-like structural damage. In this context, it was for example found that miR-21 is among the top upregulated miRNAs in the lungs from COVID-19 victims. Without being bound by theory, in context of this invention and based on the scientific evidence provided herein, it is that miR-21 in pulmonary macrophages plays a critical role in the pathophysiology of e.g. and in particular lung damage seen in infections, like the pulmonary damage induced by infection with SARS-CoV-2/COVID-19-induced lung damage. Based on this scientific evidence, the present invention relates to the composition comprising an inhibitor of miR-21 and a moiety that delivers said inhibitor of miR-21 to a macrophage, preferably to a (lung) macrophage. In a preferred, yet not limiting embodiment of the present invention, the compounds as provided herein, i.e. the composition/compound that comprises an inhibitor of miR-21 and a moiety that delivers said inhibitor of miR-21 to a macrophage, is delivered to the diseased lung tissue via inhalation. Accordingly, said compound/composition may be comprised in an inhalable composition, like a pharmaceutical composition. Accordingly, the composition (for medical use) that comprises an inhibitor of miR-21 and a moiety that delivers said inhibitor of miR-21 to a macrophage may be in, e.g. aerosol form. The appended examples also comprise an in vivo study wherein in a model of pulmonary fibrosis, the targeted delivery of an inhibitor of miR-21 to macrophages in the lung (via inhalation) was significantly effective against pulmonary dysfunction and also pulmonary fibrosis (also compared to targeted control and inactive (mismatch) anti-miR-21).

Therefore, in particular aspects of this invention, the inhibitor of miR-21 is to be delivered to (a) lung macrophage(s). In other words, the “moiety” comprised in the compositions/compounds described herein (and also comprising the inhibitor of miR-21) delivers/targets the inhibitor of miR-21 to (a) macrophage(s), in particular to (a) lung macrophage(s). In very particular aspects, the moiety comprised in the composition delivers/targets the inhibitor of miR-21 to (a) alveolar macrophage(s) and/or interstitial macrophage(s). As provided herein below, the moiety comprised in the composition may deliver the inhibitor of miR-21 exclusively, or predominantly to the target cell type, e.g. exclusively or predominantly to (a) macrophage(s), preferably exclusively or predominately to (a) lung macrophage(s), or in particular aspects exclusively or predominately to (a) alveolar macrophage(s) and/or interstitial macrophage(s). As is known in the art, “exclusively” as used herein in the context of the binding of biomolecules does not indicate that the moiety only detectably binds a target molecule/cell. Rather, it is well known that dependent on the assay system the moiety may exhibit some (weak) binding to an irrelevant molecule. Thus, “exclusively”, indicates that the moiety binds predominantly to the target cell type, i.e. that the binding is selective (selective binding). That is, the moiety selectively and preferentially binds target cells, i.e. macrophages and, optionally, fibroblasts, over non-target cells, e.g., T-cells or neutrophils, epithelial cells, etc.; see also illustrative, appended FIG. 24 (C) wherein it is documented that an exemplified compound of the present invention targets selectively macrophages (and not e.g. T-cells, epithelial cell, neutrophils, etc.) As also discussed herein below, such a selective and preferential binding may be achieved with moieties that specifically interact with and/or specifically bind to the herein defined (a) cell surface receptor(s) on said target cells.

The delivery of the inhibitor of miR-21 to macrophages is most preferred herein. The herein provided composition/compound can be thus used in the treatment of pulmonary fibrosis. The herein provided composition/compound can also be used in the treatment of macrophage-associated fibrosis in the lung but also in the treatment of cardiac disease, wherein the present invention documents that miR-21 has its highest expression in cardiac tissue macrophages (compared to all other cell types of the heart) in mice that had been subjected to pressure overload-induced cardiac dysfunction (TAC model, a relevant animal model for human cardiac diseases/disorders). As is documented in the appended examples, the mice with macrophage-specific deletion of miR-21 were found to be protected from cardiac hypertrophy and dysfunction. Unexpectedly, the transgenic animals also showed much less fibrosis of the myocardium in response to pressure overload as compared to their control littermates. Based on these data, the inventors speculated that antimir-21-based therapies (therapies with an inhibitor of miR-21) may exert relevant and important therapeutic efficacy primarily through the inhibition of miR-21 in macrophages. The examples also provide for the novel and inventive finding that miR-21 in macrophages also determines fibrotic events in other organs besides the heart, namely the lung and that in particular in the lungs from COVID-19 victims, miR-21 is one of the top upregulated miRNAs (also and in particular in lung macrophages). Based on these surprising findings, the inventors provide herewith the contribution to the art that specific delivery of an anti-miR-21 (inhibitor to miR-21) to macrophages provides for superior anti-fibrotic therapies and it is speculated that such a specific delivery has advantages for the patients to be treated, e.g. treatment with fewer non-desired side-effects is feasible and a preferred treatment of the lung can be obtained via inhalation administration of the compositions/compounds of the invention which target the inhibitor of miR-21 to macrophages.

In preferred aspects of this invention, the composition/the compound of this invention is used in the treatment of pulmonary fibrosis, wherein the composition/compound comprises both the inhibitor of miR-21 and the moiety that delivers the inhibitor of miR-21 to lung macrophage(s) and/or lung fibroblast(s). In most preferred aspects, the composition is used in the treatment of pulmonary fibrosis, wherein the composition comprises the inhibitor of miR-21 and the moiety that delivers the inhibitor of miR-21 to lung macrophage(s). In further preferred aspects, the inhibitor of miR-21 is delivered to lung macrophage(s) and/or lung fibroblast(s), more preferably wherein the inhibitor of miR-21 is delivered to lung macrophage(s).

The macrophage-targeted inhibitor of miR 21 as provided herein may be used to prevent or treat various kinds of pulmonary disease, where macrophages and/or fibroblasts contribute to the diseased status. Such pulmonary disease includes, but is not limited to (fibrotic) lung disease caused by toxic substances (including SMOG, cigarette smoke, etc.), medications (such as bleomycin, busulfan, amiodaron, etc.), connective tissue diseases, interstitial lung diseases and, in particular infections (including SARS infections, like COVID-19). In this context, present invention documents for the first time that in lungs of COVID-19 victims (harvested post-mortem) miR-21 is among the top upregulated miRNAs. Accordingly, the present invention also relates to the medical/pharmaceutical use of the compositions/compounds described herein and comprising an inhibitor of miR-21 and comprising a moiety that delivers said inhibitor of miR-21 to a macrophage in the treatment of lung disease or disorder caused by a corona virus, in particular by SARS-CoV-2. Therefore, and also based on herein provided technical information and based on the appended scientific evidence/experimental data, the inventors envisage that pulmonary fibrosis, in particular when associated with or caused by a viral infection and/or a bacterial infection (for example caused or induced by SARS-CoV-2 or another coronavirus), can be treated with the herein provided means and methods since such diseased subjects have increased levels of miR-21 in their lungs. As discussed above and concerning one embodiment of the present invention, the inventors surprisingly found that miR-21 is among the top upregulated miRNAs in the lungs from human COVID-19 victims. This is herein, inter alia, demonstrated by analysing the small RNAomes of human lungs harvested post mortem from patients that had died of and/or with a COVID-19 infection, see, e.g. Example 5 and FIG. 19.

These surprising results document that miR-21 expression in lungs, and in particular in pulmonary macrophages plays a critical role in the pathophysiology of pulmonary fibrosis. In particular and based on the surprising findings of the present invention, it is documented herein that miR-21 (and/or its expression in macrophages, i.e. macrophages of the lung) plays a substantial role in the pathophysiology pulmonary fibrosis in patients, particularly in humans, that suffer further from a lung disease, lung damage or lung disorder and wherein said fibrosis is a consequence of said lung disease, lung damage or lung disorder. As also discussed herein below, the present medical invention relating to the medical and/or pharmaceutical use of an inhibitor of miR-21 in the treatment of pulmonary fibrosis is based in part on the surprising finding that the expression of miR-21 is particularly high in the macrophages in or of diseased and/or damaged tissue. Accordingly, the present invention relates in a particular embodiment to the provision of means and methods for the treatment of pulmonary fibrosis, wherein said treatment comprises the administration of a composition that inhibits miR-21 in macrophages, in particular and in context of this invention of macrophages in or of the lung. Yet, as also illustrated herein, the it is also beneficial if miR-21 is inhibited in fibroblasts in the diseased or damaged tissue, like in diseased or damaged lung(s). Accordingly, the present invention relates, in one aspect to the medical and/or pharmaceutical use of a compound and/or composition that comprises an inhibitor of miR-21 and a moiety that delivers said inhibitor of miR-21 to a macrophage. In one aspect, said compound and/or composition for medical and/or pharmaceutical use may further comprise a moiety that is able to deliver/that delivers said inhibitor of miR-21 to a fibroblast. The moiety that delivers the said inhibitor of miR-21 to macrophages and the moiety that delivers the said inhibitor of miR-21 to fibroblasts may be the same moiety or may be a different one. Accordingly, and in a further aspect of the herein provided means and methods for the treatment of pulmonary fibrosis said moiety delivers said inhibitor of miR-21 selectively to macrophages, or wherein the moiety delivers said inhibitor of miR-21 selectively to macrophages and to fibroblasts. As already discussed herein above, said "selective delivery"/ "selective targeting" means that the moiety selectively and preferentially binds to target cells, i.e. macrophages and, optionally, fibroblasts, over non-target cells, e.g., T-cells or neutrophils, epithelial cells, etc.

As illustrated herein below and as evidenced in the appended examples, the means and methods of the present invention, i.e. the medical and/or pharmaceutical use of a compound and/or composition that comprises an inhibitor of miR-21 and a moiety that delivers said inhibitor of miR-21 to a macrophage is particularly envisaged in the treatment of subject that suffers from pulmonary fibrosis further has a lung disease or disorder. In a preferred embodiment of the invention, said the lung disease or disorder may cause or may be associated with fibrosis, preferably said lung disease or disorder may be caused by a virus and/or a bacterium. As illustrated herein, the means and methods of the present invention are also and surprisingly useful in the medical intervention of a lung disease, lung damage and/or lung disorder wherein said lung disease, lung damage and/or lung disorder to be treated is caused by a viral infection, like by a corona virus disease. In a preferred embodiment of the present invention said miR-21 inhibitor is to be used in the treatment of pulmonary fibrosis and/or in the treatment of pulmonary fibrosis that is associated and/or that is caused by a lung disease, a lung damage or lung disorder wherein the basis of the diseases or damaged status is an infection with a virus or a bacterium. In a preferred embodiment of the present invention, a pulmonary fibrosis in a (human) patient and/or a pulmonary fibrosis in a (human) patient who suffers from a pulmonary fibrosis and also from a further lung disease, a lung damage or lung disorder is to be treated by the means and methods provided herein. Said pulmonary fibrosis in said (human) patient may also be caused by said (further) lung disease, a lung damage or lung disorder. The means and methods provided as herein relate in particular to the medical and/or pharmaceutical use(s) of an inhibitor of miR-21. In preferred embodiment said medical and/or pharmaceutical use(s) comprise(s) the administration of an inhibitor of miR-21 to a (human patient) in need of such medical intervention, i.e. a (human) patient who suffers from or who is prone to suffer from a pulmonary fibrosis as herein defined. In further embodiment, the present invention relates to said medical and/or pharmaceutical use(s) wherein a compound and/or a composition is to be administered to said patient wherein said compound and/or said composition comprises an inhibitor of miR-21 and a moiety that delivers said inhibitor of miR-21 to a macrophage. It is also envisaged in context of this invention, that said inhibitor of miR-21 also comprises a further moiety that delivers said inhibitor of miR-21 to a fibroblast. Accordingly, the invention also relates to the herein defined medical and/or pharmaceutical uses of an inhibitor of miR-21 (and/or a compound/composition comprising the same) that also comprises a moiety that delivers said inhibitor of miR-21 exclusively to macrophages. As detailed herein below, it is also envisaged, that said compound/composition to be employed in context of the present invention comprises the mir-21 inhibitor and a moiety delivers said inhibitor of miR-21 selectively to macrophages and to fibroblasts.

In context in particular the appended examples, it is envisaged that the inhibitor of miR-21 is employed in the medical intervention of pulmonary fibrosis, in particular in the medical intervention of a pulmonary fibrosis caused by or relating to a lung disease, a lung damage or lung disorder. Said lung disease, a lung damage or lung disorder may be the infection of the lung, in particular an infection caused by a bacterium and/or a virus. As documented herein, said virus may be a coronavirus, like, MERS or SARS, e.g. SARS-CoV-2 or SARS-CoV-1. Other lung diseases, lung damages or lung disorders to be treated with the means and methods of the present invention may be, without being limiting, an infection with influenza A virus, influenza B virus, other coronaviruses (e.g., CoV-229, CoV-NL63, CoV-OC43 or CoV-HKU1), rhinoviruses, parainfluenza viruses, adenoviruses, respiratory syncytial virus, human metapneumovirus or human bocavirus. In further context of the invention and in light of the appended examples, the lung disease/damage/disorder to be treated, i.e. the pulmonary fibrosis, may be a SARS-CoV-2/COVID-19-induced lung damage. Further, as documented herein, the anti-miR-21 (i.e. the inhibitor of miR-21) that is to be targeted to macrophages may further constitute a superior therapeutic principle to prevent or cure pulmonary damage induced by infection with an infective agent that causes such pulmonary damage. The example provided herein relates in particular to a SARS-CoV-2 infection. Yet, said lung disease/damage/disorder to be treated with the means and methods of the present invention may also be another lung condition, like, e.g., chronic obstructive lung disease or idiopathic pulmonary fibrosis, etc.

As documented herein, the inventors also surprisingly found that miR-21 is increased in the lung of subjects suffering from a lung disease or disorder; see FIGS. 13 A and B, below. The treatment with the inhibitor of miR-21 reduced the pulmonary fibrosis. As demonstrated herein below, the inhibition of miR-21 in macrophages or fibroblasts reduces and/or prevents fibrosis. Thus, the delivery of the inhibitor of miR-21 to macrophages and/or fibroblasts is rendered plausible. Accordingly, the composition and the use thereof provided herein can be used in the treatment of pulmonary fibrosis caused by and/or associated with a lung disease or disorder, e.g. a viral and/or bacterial lung infection. The pulmonary fibrosis treated in the present invention may be caused by or associated with pulmonary support or mechanical ventilation. Infections (bacterial and/or viral), pressure and/or (artificial) ventilation may lead to ARDS (Acute Respiratory Distress Syndrome) that is followed by pulmonary fibrosis. Thus, the composition and the use of the composition provided herein may be suitable in the prevention or treatment of pulmonary fibrosis. Thus, the composition provided herein may also be suitable in prevention or treatment of pulmonary fibrosis. Thus, the composition may be used in the treatment of a subject that has not manifested a pulmonary fibrosis. For example, the miR-21 inhibitor as defined herein, the composition/compounds provided herein may also be used in the treatment of lung diseases, lung disorder, lung damage and/or ARDS. It is also envisaged that the means and methods provided herein are used in the prevention of lung disease, lung damage and/or ARDS before their manifestation. For example, "Coronavirus viral infections", like SARS-CoV-2 infections, are also associated with pulmonary fibrosis. This is indeed documented in the appended examples wherein it was also surprisingly found that miR-21 is not only enriched in (alveolar/lung) macrophages from diseased/damaged lungs but also, and even more surprisingly, that miR-21 is upregulated in lung tissue obtained from individuals infected with SARS-CoV-2, i.e. human Covid-19 patients Accordingly, the miR-21 inhibitor as defined herein and in particular the herein defined compounds/composition comprising an inhibitor of miR-21 and a moiety that delivers said inhibitor of miR-21 to a (lung) macrophage may be used in the treatment of infection caused or induced by, inter alia, influenza A virus, influenza B virus, rhinoviruses, parainfluenza viruses, adenoviruses, respiratory syncytial virus, human metapneumovirus or human bocavirus, MERS or SARS, e.g. SARS-CoV-2 or SARS-CoV-1, other coronaviruses (e.g., CoV-229, CoV-NL63, CoV-OC43 or CoV-HKU1). The composition/compound provided herein may also be used in the treatment and/or prevention of pulmonary fibrotic diseases associated with such (viral) infections. Yet, it is of note the present invention is not limited to the treatment of pulmonary fibrotic diseases associated with viral infections. As discussed herein, based on the surprising findings of the present invention, it is also plausibly documented that inhibitor(s) of miR-21, in particular when linked to a moiety that delivers said inhibitor of miR-21 to macrophage, and, in one embodiment, also to fibroblasts, of the diseased/damaged/infected tissue (i.e. the diseased/damaged/infected lung) are medically/pharmaceutically useful in the treatment of other pulmonary fibrotic disorders, like pulmonary fibrosis associated with bacterial infections, or chronic obstructive lung disease, idiopathic pulmonary fibrosis, etc. It is also evident form this invention that the compounds and compositions provided herein and comprising the inhibitor of miR-21 are particular useful in the medical/pharmaceutical intervention of fibrotic events that are related to, caused by or associated to pulmonary support or mechanical ventilation, for example and in particular pulmonary support/mechanical ventilation following Adult Respiratory Distress Syndrome (ARDS). Accordingly, the present invention also relates to the medical/pharmaceutical use of the compounds/compositions as described herein and comprising said inhibitor of miR-21 in the treatment of Adult Respiratory Distress Syndrome (ARDS).

As used herein, the term "pulmonary fibrosis" or "lung fibrosis" can be used interchangeably.

As surprisingly demonstrated herein in the appended examples and scientific data, also the intravascular (intracoronary) application of an inhibitor of miR-21 in a large animal model of cardiac disease reduced the pulmonary fibrosis; see, e.g. FIG. 13 D, below. Accordingly, in particular aspects, the inventive compound/composition comprising the inhibitor of miR-21 is for the use in the treatment of pulmonary fibrosis/lung fibrosis of a subject suffering from a heart condition. Accordingly, the present invention also relates to the medical/pharmaceutical use of the herein provided compositions/compounds in the treatment of lung fibrosis in a subject the subject suffering from a cardiac disease or disorder. In one embodiment, the cardiac disease or disorder causes or is associated with fibrosis. Such a cardiac disease or disorder may be selected from, but is not limited to, the group consisting of heart failure, ischemia, postischemic heart failure, cardiac hypertrophy, hypertensive heart failure, diastolic heart failure, systolic heart failure, heart related storage disease, cardiomyopathy, constrictive pericarditis, coronary artery disease, acute myocardial infarction, chronic myocardial infarction, right heart failure, cardiac arrhythmias, myocarditis-related fibrosis, and heart valve disease.

As discussed above and plausibly documented by means of the appended examples, the pulmonary fibrosis may also be a mechanical ventilation-associated lung fibrosis. In even more preferred aspects, the pulmonary fibrosis to be treated may be a mechanical ventilation-associated lung fibrosis and/or a pulmonary support-associated lung fibrosis in Acute Respiratory Distress Syndrome (ARDS). This is also of particular relevance in subjects suffering from viral infections and in need of mechanical ventilation, like COVID-19 patients.

In a further in vivo experiment, the inventors also analyzed the specific inhibition of miR-21 in fibroblasts; see, e.g. appended and non-limiting Example 4; FIG. 14. The inventors demonstrated that the inhibition of miR-21 in fibroblasts prevents cardiac remodeling and dysfunction; see FIG. 14. As is also illustrated in the appended examples, specific inhibition of miR-21 in a lung injury model reduced undesired pulmonary remodeling and dysfunction; see, e.g. appended and non-limiting Example 6 and FIG. 26. Thus, the composition/compound of the present invention and comprising the inhibitor of miR-21 and the moiety that delivers the inhibitor to (a) macrophage(s) and/or to (a) fibroblast(s) provides the beneficial therapeutic use(s) as described and documented herein. As indicated above, the moiety comprised in the composition may deliver the inhibitor of miR-21 exclusively to the target cell type, e.g. exclusively to (a) macrophage(s) and/or (a) fibroblast(s), preferably exclusively to (a) lung macrophage(s) and/or (a) fibroblast(s), or in particular aspects exclusively to (a) alveolar macrophage(s) and/or fibroblasts and/or interstitial macrophage(s) and/or (a) fibroblast(s). Furthermore, the inventors found that miR-21 is increased in subjects suffering from pulmonary fibrosis compared to subjects that do not suffer from pulmonary fibrosis; see FIGS. 13 A and B. It is documented herein below that miR-21 is increased in human subjects (FIG. 13B) and also in an animal model suffering from pulmonary fibrosis.

The inventors also administered an inhibitor of miR-21, in particular an antisense-miR-21 (for example LNA-anti-miR-21, as also used and employed in the appended examples), to animal models suffering from pulmonary fibrosis. The inventors surprisingly found that the inhibitor of miR-21 reduces, prevents, and/or ameliorates pulmonary fibrosis (or the fibrosis of the lung). This beneficial therapeutic effect was very strong. Accordingly, the herein provided composition and the therapeutic use/method provides an advantageous, safe and effective treatment, as demonstrated further herein below.

As further documented herein below, administration of an inhibitor of miR-21 in a large-animal model led to a reduction in macrophage infiltration as well as fibroblast proliferation. Therefore, the herein provided in vivo data show that the inhibitor of miR-21 reduces fibrosis through its activity in fibroblasts and macrophages; see Example 1. A further in vivo study is herein below described. It was unexpectedly shown that miR-21 has its strongest expression in cardiac macrophages among all miRNAs; FIG. 8B, below.

In view of these experimental results, the inventors further analyzed whether specifically inhibiting of miR-21 in macrophages is a beneficial treatment in fibrosis; see Example 2. As a representative for an inhibitor of miR-21 delivered to macrophages and/or fibroblasts, miR-21 was deleted in macrophages or fibroblasts of an animal disease model; see herein above and below. The inhibition of miR-21 in macrophages prevents pro-inflammatory polarization in macrophages and prevents inflammation. Moreover, the inhibition of miR-21 in macrophages reduces fibrosis, in particular cardiac fibrosis, e.g. pressure overload-induced fibrosis. Further, it is herein below shown that the inhibition of miR-21 in macrophages improves dysfunction of the organ, e.g. heart dysfunction. It is also demonstrated that the inhibition of miR-21 in macrophages improves heart function in a cardiac disease or disorder. Moreover, it is herein below shown that in the in vivo animal model, the inhibition of miR-21 in macrophages reduces hypertrophy-related genes and fibrosis-related genes. In addition, it is shown herein that macrophage-dependent myofibroblast transformation is reduced by the inhibition of miR-21 in macrophages. As shown in the appended examples, the fibroblasts are the primary recipient for intercellular signaling from macrophages. Therefore, fibroblasts are controlled by miR-21 comprised in/expressed in macrophages. Thus, the inhibitor of miR-21 in macrophages controls paracrine and pro-fibrotic signaling towards fibroblasts. As documented in the appended examples, the macrophage-derived, pro-fibrotic secretory signal is strong enough to control pathological fibrosis.

As set out above and as shown herein below, the inhibition of miR-21 in fibroblasts prevents cardiac remodeling and dysfunction; see appended FIG. 14.

Accordingly, the exclusive inhibition of miR-21 in macrophages or fibroblasts provides a strong medical potential in the therapy of fibrosis, in particular pulmonary fibrosis.

A specific targeting/inhibition of miR-21 comprised in macrophages and/or fibroblasts is considered advantageous compared to a systemic inhibition of miR-21. For example, a specific delivery of the inhibitor of miR-21 and thus a specific inhibition of miR-21 in macrophages and/or fibroblasts reduces the risk of an overall inhibition in all cell types, e.g. myocytes or non-myocytes. For example, an inhibition in myocytes is detrimental, in particular in an acute disease state. Accordingly, as documented in the appended examples and as explained herein, prevention and reduction of fibrosis by a specific inhibition of miR-21 in macrophages and/or fibroblasts renders the advantageous therapy of fibrosis by the inventive composition/compound comprising an inhibitor of miR-21 and a moiety that delivers said inhibitor of miR-21 to (a) macrophage and, optionally, in addition, to (a) fibroblast(s) plausible. As documented in the appended examples, the targeted delivery of the inhibitor of miR-21 to macrophages leads to a surprisingly high anti-fibrotic effect (higher than the previously described effect with non-targeted anti-miR-21/non-targeted inhibitor of miR-21). This is a non-expected finding of the present invention. That the preferential delivery/preferential targeting of the inhibitor of miR-21 (anti-miR-21) to macrophages and its relative exclusion from fibroblasts as documented in the experimental part was expected to result in a less pronounced anti-fibrotic effect, based on the fibroblast hypothesis of the site of action of miR-21 as provided in the prior art. This "fibroblast hypothesis" was proposed by Liu (2010); J Exp Med. 207:1589-97) who thought that miR-21 expression was increased in pulmonary myofibroblasts in bleomycin-treated lungs as well as in fibroblastic foci of patients suffering from idiopathic pulmonary fibrosis. The authors of Liu (2010), loc cit., administered an miR-21 antisense probe intraperitoneally after a bleomycin administration and an attenuated collagen deposition in the lungs was observed. Yet, a direct effect on fibrosis was not documented and the authors saw an increased miR-21 expression in pulmonary (myo-)fibroblasts in bleomycin-treated lungs as well as in fibroblastic foci of patients suffering from idiopathic pulmonary fibrosis. In contrast to these findings by Liu (2010), loc cit, the present inventors could, inter alia, document an even more relevant expression of miR-21 in macrophages of diseased tissues (not only in the lung, but also in the heart). In particular, the present inventors surprisingly found that miR-21 is among the top upregulated miRNAs in the lungs from COVID-19 victims, see, e.g. appended FIG. 19, as well as in the lungs after bleomycin administration, see, e.g. appended FIG. 21. Said miR-21 is unexpectedly also the most abundant and enriched microRNA in lung macrophages, see, e.g. appended FIGS. 12 and 20. Due to the very high abundance of macrophages in the mammalian lung, the inventors concluded that the vast majority of miR-21 of the lung derives from lung macrophages. It is, therefore, one of the surprising findings of the present invention that targeting miR-21 specifically in macrophages (via an inhibitor of miR-21 that is specifically delivered to said macrophages) constitutes a superior therapeutic principle to prevent or cure pulmonary damage, for example also pulmonary damage, induced by infections, like infections by viruses, e.g. infections with SARS-CoV-2. As also documented in the appended examples, it was also surprisingly found that the delivery of an inhibitor of miR-21 specifically to macrophages via (aerosolized) inhalation efficiently attenuates pulmonary fibrosis, the decline of pulmonary functions was prevented by the macrophage-specific inhibition of miR-21, see, e.g. FIG. 26. This high efficiency of the compositions/compounds of the present invention was neither foreshadowed nor expected form the prior art. As provided in the appended examples and as discussed herein, the inventors identified surface receptors of pulmonary macrophages that are highly expressed, relatively selective for this cell type and suitable for the uptake of (specific) ligands to that specific receptor. Such a ligand may be a small molecule ligand and may also comprise a proteinaceous ligand (or a functional, fragment thereof). Said small molecule ligand, said proteinaceous ligand (or said functional, fragment thereof) is preferably capable of specifically interacting with a (surface) molecule on the cell surface of macrophages (and, optionally also on fibroblasts). In one embodiment such an interaction may also lead to internalization of the composition/compounds of the present invention, for example, via endocytosis. Also envisaged herein is the use of antibodies (or functional fragments thereof, like scFvs. etc) as moiety that delivers said inhibitor of miR-21 to a macrophage. Such an antibody (or functional fragment thereof) may specifically bind to a (surface) marker/receptor on macrophages (and, optionally, but also on fibroblasts). In the appended examples, single cell sequencing of pulmonary and cardiac primary cells and deep RNA sequencing of sorted, purified cell fractions was performed. Bioinformatics analysis of these data yielded a few surface molecules that fulfilled the above criteria (see appended table 3). Among them, MRC1 (Macrophage receptor C type 1) proved as highly specific and highly expressed on pulmonary macrophages. The expression of mannose receptor C type 1 on lung macrophages was further verified by immunofluorescence staining of lung tissue, see, appended and non-limiting Example 5 and Figure. 22. Appended FIG. 27 also confirms the high expression of mannose receptor C type 1 on heart macrophages.

The inventors used MRC1 to specifically deliver an miR-21 inhibitor to (human) macrophages. In addition, the inventors realized that a macrophage-specific targeting of the miR-21 inhibitor combined with a local delivery via inhalation constitutes a superior therapeutic principle to prevent or treat pulmonary fibrosis. As shown below, the inventors conjugated ligands for MRC1 (here Tri-Mannose, GalNAc) with a chemical linker to the inhibitor of miR-21, see, appended but non-limiting Example 5 and FIG. 23.

In an in vivo experiment, the inventors confirmed the delivery of these compounds to the lung and their fate was traced through fluorescent labelling followed by the detection via fluorescent cell cytometry. Compared to the composition comprising an unlabelled inhibitor of miR-21, the composition comprising the mannose-coupled inhibitor of miR-21 was delivered to a higher fraction of alveolar macrophages, reached higher levels in macrophages and reached lower levels in non-macrophage cell types such as endothelial cells see Example 5 and FIGS. 24 and 25.

In a further in vivo experiment, the inventors tested the efficiency of the composition comprising the macrophage-targeting, mannose-coupled inhibitor of miR-21. For this purpose, a mouse model of pulmonary fibrosis was employed, wherein the mice received the aerosolized composition via inhalation 4 days after lung injury induction. As shown below in Example 5 and FIG. 26, the mice that received said composition attenuated pulmonary fibrosis. Accordingly, this therapeutic principle was significantly effective against pulmonary dysfunction and also pulmonary fibrosis as determined by the most relevant functional and structural parameters.

In accordance with the scientific evidence provided herein and in particular aspects, the invention relates to a composition/a compound as defined herein, i.e. comprising an inhibitor of miR-21 and comprising a moiety that delivers an inhibitor of miR-21 to a macrophage. These inventive compositions/compounds are to be used in particular in the medical intervention of pulmonary fibrosis. The composition/compound comprising an inhibitor of miR-21 and a moiety that delivers said inhibitor of miR-21 to a macrophage may be also used in the prevention of pulmonary fibrosis. It is, for example, envisaged that the compounds/compositions of the invention are used in early stages of disorders/diseases which may lead to a damage of the lung, for example in early stages of an infection and/or at stages of a disease wherein pulmonary support or mechanical ventilation is warranted. Accordingly, the present invention is also useful in the medical intervention as well as in prevention of, e.g., pulmonary fibrosis following Adult Respiratory Distress Syndrome (ARDS).

In certain aspects, the invention relates to a composition and the use thereof in the treatment of pulmonary fibrosis, wherein the composition comprises an inhibitor of miR-21 and a moiety that delivers said inhibitor of miR-21 to a macrophage and/or a fibroblast.

The definitions and explanations provided herein below and above apply to the composition/compound for use in the treatment of fibrosis, in particular pulmonary fibrosis, the composition/compound provided herein, the method of producing the composition/compound, the use of the composition/compound in the treatment of pulmonary fibroses, and the method of treatment provided herein.

As used herein, the term "miR" can be used interchangeably with the term "a micro-ribonucleic acid" or "miRNA".

As used herein, miR-21 refers to the miRNA-21, in particular miR-21a-5p or miR-21-5p as illustrated in appended FIG. 1 B), below.

As used herein, the "inhibitor of miR-21" refers to a molecule that specifically binds to and inhibits endogenous miR-21. Thus, the target of the inhibitor of miR-21 may be miR-21. A target of miR-21 may also be understood to encompass a downstream target of miR-21. The inhibitor of miR-21 increases the level of target mRNAs and/or of at least one target mRNA of miR-21. The inhibition of miR-21, e.g. via an oligonucleotide with a sequence at least complementary to miR-21 will lead to a derepression or even an overexpression of targets of miR-21, like Sprouty (a developmental protein involved in cell signaling) and the like. The effect of inhibition of miR-21 following the administration of the inhibitor of miR-21 can be assessed by a variety of methods known in the art. For example, the miRNA level can be quantitated/determined in cells or tissues in vitro or in vivo. Changes in miRNA levels can be measured by microarray analysis. Changes in miRNA levels can be measured by one of several commercially available PCR assays, such as the TaqMan® MicroRNA Assay (Applied Biosystems). For example, inhibition of miR-21 upon administration of the inhibitor of miR-21 is assessed by measuring the mRNA and/or protein level of a target of the miRNA. As demonstrated in the appended examples, the inhibition of miR-21 induced by deletion of miR-21 provided a drastic decrease of about >90% in the levels of miR-21. Moreover, inhibitors of miR-21 are known in the prior art; see, e.g., Thum (2008); Nature 456: 980-984, Zhang (2015); Cancer Res 75(9): 1-9 or Ardite (2012); J Cell Biol 196(1): 163-175. Further inhibitors of miR-21 can be identified without further ado. Examples of miR-21inhibitors that are composed of an oligonucleotide with a sequence at least partially complementary to miR-21 are proved here, see. e.g. appended FIG. 1B (showing a LNA-anti-miR-21 oligonucleotide), appended FIG. 23B (showing two exemplified compounds/constructs of the present invention which do comprise the "anti-miR-21 part" (inhibitor of miR-21) as well as the moiety that delivers said inhibitor of miR-21 to a macrophage, namely here tri-mannose or N-acetylgalactosamine) or appended FIG. 26 A (showing, inter alia, an exemplified construct of the invention in the format "LNA-antimiR-21 linker-mannose" and comprising the oligonucleotide as also shown in appended SEQ ID NO: 3. Accordingly, exemplified "anti-miR-21" oligonucleotides comprise, but are not limited to an antisense-miR-21 3'-tCgAaTaGtCtGaCT-5' (SEQ ID NO:1), and/or an antisense-miR-21 3'-TCgAaTagTCtgAcT-5' (SEQ ID NO: 2), whereby here an LNA-DNA construct is shown (called herein "mixmer"). Capital letters represent locked-nucleic acid nucleotides (LNA), lower case letters refer to DNA bases and every capital "C" denotes here 5-Methyl-Cytosine. Accordingly, these two sequences 3'-tCgAaTaGtCtGaCT-5' and 3'-TCgAaTagTCtgAcT-5' constitute "mixmers". i.e. constructs that comprise LNA and DNA nucleotides-SEQ ID NO: 3 also represents a useful "anti-MIR-21" which represents a LNA oligonucleotide (accordingly, exemplified SEQ ID NO:3 represents a LNA construct comprising the same nucleotide sequence as SEQ ID Nos: 1 and 2, but with all nucleotides locked, 5'-Methyl-Cytosine modifications and a phosphorothioate backbone). Further useful, yet non limiting "anti-miR-21" oligonucleotides comprise SEQ ID Nos. 7 to 9. SEQ ID NO: 7 is a LNA construct comprising the same nucleotide sequence as SEQ ID Nos: 1 and 2, but with all nucleotides locked, with 5'-Methyl-Cytosine modifications, but without a phosphorothioate backbone. SEQ ID NO:8 is a LNA construct comprising the same nucleotide sequence as SEQ ID Nos: 1 and 2, but with all nucleotides locked, with a phosphorothioate backbone, but without 5'-Methyl-Cytosine modifications. SEQ ID NO: 9 is a LNA construct comprising the same nucleotide sequence as SEQ ID Nos: 1 and 2, but with all nucleotides locked and without any 5'-Methyl-Cytosine modifications and without a phosphorothioate backbone. Again, in the sequences provided herein, capital letters refer to LNA, lower case letters refer to DNA bases. Every capital C denotes 5-Methyl-Cytosine. The antisense miRs against miR-21 may have a fully PS (Phosphorothioate) backbone; see also, e.g. SEQ ID NO. 1. As also discussed herein below, particularly useful antisense-miR-21 molecules are provided in SEQ ID NO: 1 and 2, most preferred and as illustrated in the appended examples is the "anti-miR-21" as follows: 3'-tCgAaTaGtCtGaCT-5' (SEQ ID NO:1). Ye, the present invention is by no means limited to these specific oligonucleotides. The person skilled in the art is aware that also further "anti-miR-21" constructs/oligonucleotides may be employed in context of this invention. Such "anti-miR-21" constructs/oligonucleotides may comprise, for example RNA constructs, PNAs (peptide nucleic acids) and the like. Also further modifications on said anti-miR-21 oligonucleotides are envisaged, like morpholino-oligomers (phosphorodiamidate morpholino oligomers), antagomirs/blockmirs, ZEN (N,N-diethyl-4-(4-nitronaphthalen-1-ylazo)-phenylamine)-modifications of the anti-micro RNA oligonucleotides. Further useful modifications are also described, inter alia, in the review of Khvorova (2017) Nature Biotech 35, 238-248.

As discussed in Sun (2019), https://doi.org/10.1155/2019/6782653, inhibition of miR-21 can be also be achieved by means like miRNA sponges, miRNA masks, and, as also detailed herein by anti-miRNA oligonucleotides (anti-miRs). Anti-miRs are single-stranded synthetic oligonucleotides designed to bind directly to the endogenous miRNAs of interest and block the miRNA-induced repression of mRNA translation through disruption of the miRISC complex. miRNA sponges are transcripts with multiple binding sites which function as a decoy to sequester miRNAs from their endogenous targets. They can be designed to target a single specific miRNA or a whole family of related miRNAs sharing a common seed region.

miRNA masks are single-stranded modified oligonucleotides which are completely base-pairing with the proleptic miRNA-binding site in the 3UTR of the target mRNA. Whereas it is envisaged in context of this invention that "miRNA sponges" or "miRNA masks" are employed to inhibit miR-21, it is preferred to use anti-miRNA oligonucleotides (anti-miRs) that specifically target miR-21 in context of this invention.

As used herein, the "moiety that delivers the inhibitor of miR-21 to a macrophage" or grammatical variants thereof refer to a carrier, and/or a moiety that delivers the inhibitor of miR-21 to a macrophage. The carrier and/or moiety enrich(es) the inhibitor of miR-21 at the macrophage or the target cell. As used herein, the target cell(s) is/are (a) macrophage(s) and/or (a) fibroblast(s), preferably the target cell(s) is/are (a) macrophage(s). In preferred aspects, the macrophage(s) and/or fibroblast(s) is/are lung macrophages(s) and/or lung fibroblast(s). In more preferred aspects, the macrophage(s) and/or fibroblast(s) is/are alveolar macrophage(s) and/or alveolar fibroblast(s); and/or interstitial macrophage(s) and/or interstitial fibroblast(s). In certain aspects, the carrier and/or moiety leads to an endocytosis of the inhibitor of miR-21. The endocytosis can increase the uptake of the inhibitor of miR-21. In particular aspects, the moiety and/or carrier comprised in the composition deliver(s) said inhibitor of miR-21 to a macrophage or macrophages. The moiety and/or carrier comprised in the composition may further deliver said inhibitor of miR-21 to a fibroblast or fibroblasts. As demonstrated herein below, the deletion of miR-21 in fibroblasts provides a beneficial effect. Thus, the moiety and/or carrier comprised in the composition may deliver said inhibitor of miR-21 to a macrophage or macrophages and/or to a fibroblast or fibroblasts. In particular aspects, the moiety and/or carrier comprised in the composition deliver(s) said inhibitor of miR-21 to a macrophage or macrophages and to a fibroblast or fibroblasts. In preferred aspects, the carrier and/or a moiety that delivers the inhibitor of miR-21 to a macrophage is linked to the inhibitor of miR-21, i.e. both parts of the compounds of the invention, i.e. the "inhibitor of miR-21" and the "moiety that delivers the inhibitor of miR-21 to a macrophage" are comprised in one molecule. Said molecule may also comprise additional "moieties" and/or parts, like "linkers" and/or "markers" (like fluorescence markers). Such markers may also be part of the "linker" structure(s). Corresponding examples are provided herein below, and one example is shown in the upper part of appended FIG. 23B (a GalNAcconjugated-LNA-antimiR-21-FAM, whereby the "linker" comprises a "fluorescein amidite derivative"/FAM)

In particular preferred aspects, the carrier and/or moiety comprised in the composition deliver(s) said inhibitor of miR-21 exclusively to the relevant target cell, here in particular macrophages. Thus, in particular aspects, the carrier and/or moiety comprised in the composition deliver(s) said inhibitor of miR-21 exclusively to the macrophages and/or fibroblasts. In the appended examples, miR-21 was deleted in macrophages or fibroblasts. Accordingly, the appended examples show a specific deletion/inhibition of miR-21 in macrophages. Thus, and as used herein, the term "delivers said inhibitor of miR-21 exclusively to macrophages" means that the inhibitor is only delivered to macrophages. Thus and as used herein, the term "delivers said inhibitor of miR-21 exclusively to fibroblasts" means that the inhibitor is only delivered to fibroblasts. Therefore, the moiety and/or carries does not deliver said inhibitor of miR-21 to other cell types that are not macrophages and/or fibroblasts. In particular, the moiety and/or carrier comprised in the inventive composition does not deliver said inhibitor of miR-21 to myocytes. Thus, in particular aspects, the carrier and/or moiety comprised in the composition deliver(s) said inhibitor of miR-21 exclusively to macrophages, wherein the moiety and/or carrier do(es) not deliver said inhibitor of miR-21 to myocytes. The appended examples and as explained herein below document that the inhibitor of miR-21 in macrophages controls paracrine and pro-fibrotic signaling towards fibroblasts. Thus, in particular aspects, the moiety and/or carrier deliver(s) said inhibitor of miR-21 exclusively to macrophages and to fibroblasts. In certain aspects, the moiety and/or carrier deliver(s) said inhibitor of miR-21 to macrophages and to fibroblasts, wherein the moiety and/or carrier do(es) not deliver said inhibitor of miR-21 to myocytes.

In particular aspects, the inhibitor of miR-21 is delivered to a lung macrophage and/or lung fibroblast. In particular aspects, the inhibitor of miR-2.1 is delivered to lung cells. In most preferred aspects, the inhibitor of miR-21 is delivered to a lung macrophage. The administration of the composition provided herein provides a delivery to the lung or the lung target cells. In particular aspects, the inhibitor of miR-21 is delivered to a lung macrophage and to a lung fibroblast. In preferred aspects, the delivery to lung cells is provided by administration of the composition to the lung. Thus, the composition is to be administered by a pulmonary administration. For example, the composition is to be administered by an aerosolized composition to the lung of the subject. In particular, the composition may be administered by an aerosolized composition to the lung of the subject by inhalation or by other means of local administration to the lung, bronchi and/or airways. In certain embodiments, a composition is prepared for administration by inhalation. Certain of such compositions for inhalation are prepared in the form of an aerosol spray in a pressurized pack or a nebulizer. Certain of such compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of the composition and a suitable powder base such as lactose or starch. Formulations and methods for modulating the size of droplets using nebulizer devices to target specific portions of the respiratory tract and lungs are well known to those skilled in the art. Additional suitable devices include dry powder inhalers or metered dose inhalers.

The herein provided composition can also be administered by intraarterial administration, preferably by intracardial administration, and more preferably by intracoronary administration. As demonstrated herein below, the intracoronary administration of the inhibitor of miR-21 reduces the pulmonary fibrosis. Thus, in certain embodiments, administering to a subject comprises intraarterial administration. In certain embodiments, administering to a subject comprises intracardial administration. Suitable means for intracardial administration include the use of a catheter, or administration during open heart surgery.

Furthermore, the inhibitor of miR-21 may also be delivered to (a) cardiac macrophage(s). As shown in the appended examples, a delivery of the inhibitor of miR-21 to cardiac macrophages reduced the pulmonary fibrosis; see FIG. 13 D. therefore, the inhibitor of miR-21 is delivered to (a) cardiac macrophage(s) in a particular aspect. In a further particular aspect, the inhibitor of miR-21 is delivered to (a) lung macrophage(s) and/or to (a) cardiac macrophage(s). In further certain aspects, the inhibitor of miR-21 is delivered to (a) lung macrophage(s) and/or lung fibroblast(s) and/or to (a) cardiac macrophage(s) and/or (a) cardiac fibroblast(s). Yet, in context of this invention, it is also envisaged that such compounds/compositions of the invention that comprises an inhibitor of miR-21 and a moiety that delivers said inhibitor of miR-21 to a cardiac macrophage are not only used in the medical intervention of pulmonary fibrosis but also in other fibrotic events, for examples fibrosis of the heart.

As demonstrated herein below, the cardiac administration of an inhibitor of miR-21 reduced the pulmonary fibrosis; see, e.g. appended FIG. 13 D, below. As used herein, the term "pulmonary fibrosis" or "lung fibrosis" can be used interchangeable. Accordingly, in particular aspects, the composition is for the use in the treatment of pulmonary fibrosis/lung fibrosis of a subject. In more particular aspects, the pulmonary fibrosis may be a mechanical ventilation-associated lung fibrosis. In even more preferred aspects, the pulmonary fibrosis may be a mechanical ventilation-associated lung fibrosis in Acute Respiratory Distress Syndrome (ARDS). The composition provided herein may particularly be suitable in the use of the treatment of lung damage (e.g. induced by infection, pressure and/or ventilation) that is followed by ARDS (Acute Respiratory Distress Syndrome), and that is then followed by fibrosis. The composition provided herein may also suitable in the prevention or treatment of fibrosis. Thus, the composition provided herein may also suitable in the treatment or prevention of treatment of lung damage and/or ARDS preceding the outbreak of the pulmonary fibrosis.

The subject that suffers from pulmonary fibrosis may further have/suffer/be diagnosed from a lung disease or disorder. The lung disease or disorder may cause or may be associated with fibrosis, preferably pulmonary fibrosis. In preferred aspects, the lung disease or disorder is caused by a virus and/or a bacterium, is related to inflammation, is chronic obstructive lung disease, or is idiopathic pulmonary fibrosis. Fibrosis may also lead to inflammation and the composition provided herein may be used for the treatment of such inflammation. In more preferred aspects, the lung disease or disorder is viral infection and/or the lung disease or disorder is based or linked to a viral infection. In a further aspect, the lung disease or disorder is a viral infection and/or bacterial infection. Accordingly said subject to be treated in accordance with the invention may suffer from a lung disease/disorder related to viral infection and/or bacterial infection, i.e. the subject may also suffer from both kind of infections. In more preferred aspects, the lung disease or disorder is viral pneumonia infection. In more preferred aspects, the lung disease or disorder is a corona virus disease. In more preferred aspects, the lung disease or disorder is a COVID, and/or caused or associated with SARS, or MERS. In more preferred aspects, the lung disease or disorder is caused or induced by SARS-CoV-2 or SARS-CoV-1. In particularly preferred aspects, the lung disease or disorder is COVID-19. The inventors envisaged that pulmonary fibrosis associated with or caused by viral infection and/or bacterial infection, for example caused or induced by SARS-CoV-2 or SARS-CoV-1, can be treated since such subjects have increased levels of miR-21. The inventors surprisingly found that miR-21 is increased in the lung of subjects suffering from a lung disease or disorder; see FIGS. 13 A and B, below. The treatment with the inhibitor of miR-21 reduced the pulmonary fibrosis. As demonstrated herein below, the inhibition of miR-21 in macrophages or fibroblasts reduces and/or prevents fibrosis. Thus, the delivery of the inhibitor of miR-21 to macrophages and/or fibroblasts is rendered plausible. Accordingly, the composition and the use thereof provided herein can be used in the treatment of pulmonary fibrosis caused by and/or associated with a lung disease or disorder. In particular aspects, the invention relates to the use of the composition in the treatment of pulmonary fibrosis of a subject, wherein the subject suffers from a lung disease or disorder, and wherein the composition comprises an inhibitor of miR-21 and a moiety that delivers said inhibitor of miR-21 to a macrophage. In further particular aspects, the invention relates to the use of the composition in the treatment of pulmonary fibrosis of a subject, wherein the subject suffers from a lung disease or disorder, and wherein the composition comprises an inhibitor of miR-21 and a moiety that delivers said inhibitor of miR-21 to a macrophage and/or fibroblast.

In even more preferred aspects, the lung disease or disorder is caused by or is associated with SARS-CoV-2 or SARS-CoV-1.

In particular aspects, the pulmonary fibrosis treated in the present invention is caused or associated by pulmonary support or mechanical ventilation. In further aspects, the pulmonary fibrosis treated in the present invention follows or is associated with Adult Respiratory Distress Syndrome (ARDS).

In further aspects, the herein provided composition can be used in the treatment of fibrosis that is selected from the group consisting of cardiac fibrosis, pulmonary fibrosis, liver fibrosis, kidney fibrosis, skin fibrosis, age-related fibrosis, and/or spleen fibrosis. For example, the composition provided herein may be used in the treatment of a pulmonary fibrosis and/or cardiac fibrosis. As demonstrated herein below, the treatment of cardiac fibrosis by an inhibitor of miR-21 further reduced/alleviated the pulmonary fibrosis. In certain aspects, the herein provided composition can be used in the treatment of macrophage associated fibrosis–

The herein provided treatment may also be administered to a subject that suffers from fibrosis, preferably pulmonary fibrosis, and further has at least one disease or disorder selected from a lung disease or disorder, a cardiac disease or disorder, and a liver disease or disorder, in particular wherein the fibrosis, preferably the pulmonary fibrosis, is associated to a lung disease or disorder and/or cardiac disease or disorder. In particular aspects, the subject has a lung disease or disorder and further has a cardiac disease or disorder, and/or a liver disease or disorder.

As used herein, the subject to be treated is preferably a human, i.e. a human patient.

In certain aspects, the cardiac disease or disorder causes or is associated with fibrosis, e.g. pulmonary fibrosis. In further aspects, the cardiac disease or disorder is selected from the group consisting of heart failure, ischemia, postischemic heart failure, cardiac hypertrophy, hypertensive heart failure, diastolic heart failure, systolic heart failure, heart related storage disease, cardiomyopathy, constrictive pericarditis, coronary artery disease, acute myocardial infarction, chronic myocardial infarction, right heart failure, cardiac arrhythmias, myocarditis-related fibrosis, and heart valve disease. Accordingly, the subject that is administered the herein provided treatment of pulmonary fibrosis may suffer from any further disease or disorder/condition that causes or is associated with pulmonary fibrosis.

In particular aspects, the herein provided composition/compound described herein in context of the invention prevents and/or reduces fibrosis, in particular pulmonary fibrosis. In more particular aspects, the herein provided composition/compound prevents or reduces macrophage pro-inflammatory polarization, prevents inflammation, myofibroblast transformation, and/or fibrosis in the lung (i.e. pulmonary fibrosis). The pulmonary fibrosis to be treated may, accordingly also be stimulated by regulation of fibroblast-activating and/or fibroblast-inhibiting factors secreted from macrophages.

In it certain aspects, the composition/compound described herein in context of the invention is to be administered to the subject/patient at least about 5 days after the acute injury/disease/disorder. In particular aspects, the composition is to be administered to the subject at least about 5 days after Adult Respiratory Distress Syndrome (ARDS). However, it is envisaged that the patient in need of medical intervention receives the compounds/compositions of the present invention at the earliest feasible time point. In further particular aspects, the composition is to be administered to the subject at least about 5 days after ischemia. As demonstrated herein below, the administration of the inhibitor of miR-21 at least 5 days after ischemia (heart) unexpectedly provided an increased uptake and therapeutic efficacy in postischemic myocardium. The finding of the increased uptake of the inhibitor of miR-21 was unexpected at 5 days after ischemia since an increased uptake of the inhibitor of miR-21 was only expected directly after ischemia. In an acute injury/disease/disorder situation uptake of the inhibitor of miR-21, in particular antisense miR-21, is increased, potentially due to leakiness of endothelia and dissolution of the extracellular matrix (without being bound by theory). Thus, it is surprisingly documented herein that the administration of the inhibitor of miR-21 results in an increased uptake of the inhibitor of miR-21 even about 5 days after the acute injury/disease/disorder (e.g. ischemia or ARDS). Therefore, the administration of the inhibitor of miR-21 at least about 5 days after the acute injury/disease/disorder (e.g. ischemia or ARDS) may be safer compared to an administration at the acute injury/disease/disorder (e.g. ischemia or ARDS) since such a delayed administration avoids the detrimental effects in the acute setting. As used herein, the acute injury/disease/disorder refers to a situation where the uptake of the inhibitor of miR-21 is increased in the subject due to injury/disease/disorder. Thus, in an acute situation the uptake of the inhibitor of miR-21 is increased compared to the state where the subject does not suffer from the injury/disease/disorder.

In certain aspects, the composition/compound of the invention is to be administered to the subject/patient at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, or at least about 19 days after the acute injury/disease/disorder, in particular after Adult Respiratory Distress Syndrome (ARDS) or ischemia. In particular, the composition is further to be administered to the subject at least about 19 days after Adult Respiratory Distress Syndrome (ARDS). In certain aspects, the composition is to be administered to the subject at least about 19, 20, 30, or 40 days after acute injury/disease/disorder, in particular after Adult Respiratory Distress Syndrome (ARDS) or ischemia. In general, it was herein surprisingly demonstrated that a belated administration, i.e. after the acute event, e.g. ischemia or ARDS, provides the beneficial therapeutic effects. Accordingly, such an administration after the acute event is advantageous compared to the administration in the acute disease or disorder. Thus, in particular aspects, the composition/compound provided herein is not administered in the acute disease or disorder, e.g. the acute cardiac disease or disorder, and/or the acute lung disease or disorder. Accordingly, it is preferred that the composition/compound comprising said inhibitor of miR-21 and the moiety that delivers said inhibitor of miR-21 to a macrophage and/or fibroblast is to be administered in the chronic phase of said lung disease or disorder, and/or said cardiac disease or disorder. It is, accordingly and as an example envisaged to provide a patient in need of the compounds/compositions of the present invention with the composition/compound comprising said inhibitor of miR-21 and comprising said moiety that delivers said inhibitor of miR-21 to a macrophage during the chronic phase of, e.g. a pulmonary fibrosis. A corresponding scenario is for example the medical/pharmaceutical use of the compounds/compositions of the present invention in pulmonary fibrosis caused by an infection (like, e.g. SARS-CoV-2) when the infective agent is not detectable in the patient anymore but the (lung) damages persist or even worsen. This may be the case, for example, with so called “Long-COVID” patients. Yet, it of note that it is envisaged that the patients in need of medication is provided the same at the earliest possible time point, even for example in prevention of a lung damage, like a pulmonary fibrosis caused by an infection.

It is also surprisingly demonstrated herein below that the administration of the composition in a single dose comprising about 10 mg of the inhibitor of miR-21 provides the therapeutic effect and reduced fibrosis, e.g. a single dose of the inhibitor of miR-21 reduced miR-21 and burden caused by miR-21. Thus, in particular aspects, the composition is to be administered in a single dose comprising about 10 mg of the inhibitor of miR-21. In further particular aspects, the composition is to be administered in a single dose comprising about 10 mg of the inhibitor of miR-21 or less. For example, composition is to be administered in a single dose comprising about 1 mg, about 2 mg, about 3 mg, about 4 mg, about 5 mg, about 6 mg, about 7 mg, about 8 mg, or about 9 mg of the inhibitor of the miR-21. The inventor envisages that the pulmonary administration of the composition requires less than 10 mg of the inhibitor of miR-21. In further aspects, the composition/compound of the invention is to be administered to a patient in need of medical intervention in a dose comprising about 1 mg to about 1 g of the composition/compound of the invention. Said dose to be administered, may be a single dose. The administration may be, for example, via inhalation/as an aerosol. In further particular aspects, the composition/compound is to be administered in a single dose comprising about 10 mg to about 900 mg of said composition/compound of the invention. For example, composition/compound may be administered in a single dose comprising about 100 mg to about 800 mg of the composition. The inventors, accordingly envisage that the pulmonary administration of the composition/compound requires about 1 mg to about 1 g of the composition/compound of the invention per individual dose. Said pulmonary administration may be achieved via inhalation, for example in form of an aerosol.

As provided herein above and below the composition comprises the inhibitor of miR-21 and the moiety that delivers the inhibitor of miR-21 to a macrophage. As described above, the carrier and/or moiety enrich(es) the inhibitor of miR-21 at the macrophage or the target cell. Thus, the carrier and/or moiety enrich(es) the composition at the macrophage or the target cell, e.g. the carrier and/or moiety enrich(es) the composition at the macrophage(s) and the fibroblast(s). In certain aspects, the moiety and/or carrier comprised in the composition may deliver the composition to a fibroblast or fibroblasts. In certain further aspects, the moiety and/or carrier comprised in the composition may deliver the composition to a macrophage or macrophages and/or to a fibroblast or fibroblasts. In certain further aspects, the moiety and/or carrier comprised in the composition deliver(s) the composition to a macrophage or macrophages and to a fibroblast or fibroblasts. Accordingly, the particular aspect is that the inhibitor of miR-21 is delivered to the target cell. For example, the carrier and/or moiety that delivers the inhibitor of miR-21 to the target does not necessarily enter the target cell, preferably wherein the target cell is the macrophage and/or fibroblast, or more preferably wherein the target cell is the macrophage.

As used herein, the “carrier”, “moiety” or “part” that delivers the inhibitor of miR-21 to the macrophage is not necessarily limited as long as the “carrier”, “moiety” or “part” provides an enrichment of the inhibitor of miR-21 at the cell surface of the target cell, preferably wherein the target cell is the macrophage and/or fibroblast, or more preferably wherein the target cell is the macrophage. The targeting of macrophages and/or fibroblasts is known in the art. More preferably, the “carrier” or “moiety” provides an enrichment of the inhibitor of miR-21 at the cell surface of the target cell and the inhibitor of miR-21 enters the target cell, preferably wherein the target cell is the macrophage and/or fibroblast, or more preferably wherein the target cell is the macrophage. Even more preferably, the “carrier”, “moiety” or “part” provides an enrichment of the inhibitor of miR-21 at the cell surface of the target cell, the inhibitor of miR-21 enters the target cell and the inhibitor of miR-21 derepresses or overexpresses the targets of miR-21, preferably wherein the target cell is the macrophage and/or fibroblast, or more preferably wherein the target cell is the macrophage.

In particular aspects, the moiety or carrier is selected from the group consisting of a nanoparticle, a liposome, a lipid nanoparticle (LNP), a mesoporous silica nanoparticles (MSN), an antibody or a functional fragment thereof, and a small molecule ligand (like in the appended examples, wherein sugar or modified sugar moieties are employed as ligands) and a (proteinaceous) ligand or a functional fragment thereof. (Small molecule) ligands may also comprise chemicals and/or pharmaceuticals that are able to interact with markers/receptors on the surface of macrophages (and, optionally, also the surface of fibroblasts).

The same applies, *mutatis mutantis*, for (proteinaceous) ligands or (a) functional fragment(s) thereof that are able to interact with their corresponding (surface) markers/receptors on the surface of macrophages (and, optionally, also the surface of fibroblasts). For example, such "proteinaceous ligands" may comprise also antibodies (or functional fragments thereof) that specifically interact with and/or specifically bind to the herein defined (a) cell surface receptor(s). Yet, the term "ligands" also comprise smaller peptides or peptide structures. An example of such a "peptide ligands may be the peptide "C-S-P-G-A-K-V-R-C" (SEQ ID NO: 6; CSPGAKVRC) as disclosed in Scodeller (2017); Sci Rep 7: 14655. Said peptide is an interacting peptide for MRC1, i.e. a cell surface receptor on macrophages. The "moiety" that delivers said inhibitor of miR-21 to a macrophage may also comprise nanobodies and the like as well as lipid structures that are able to interact with/bind to relevant cell surface receptor on macrophages (and/or, optionally to fibroblasts).

The delivery of an inhibitor to macrophages is known to the skilled person; e.g. (Juliano, 2016) Juliano R L; The delivery of therapeutic oligonucleotides. Nucleic Acids Res. 2016 Aug. 19; 44(14):6518-48. doi: 10.1093/nar/gkw236. Epub 2016 Apr. 15). In the following non-limiting examples are provide for the delivery of the inhibitor of miR-21 to the target cell. In further aspects, the moiety binds to at least one antigen that is found on: a macrophage; a fibroblast and a macrophage; a lung macrophage; or a lung fibroblast and a lung macrophage. In further particular aspects, the moiety binds to at least one antigen that is exclusively found on: a macrophage; a fibroblast and a macrophage; a lung macrophage; or a lung fibroblast and a lung macrophage. In further particular aspects, the moiety specifically binds to at least one antigen that is exclusively found on: a macrophage; a fibroblast and a macrophage; a lung macrophage; or a lung fibroblast and a lung macrophage. The terms "specifically binds" and/or "specifically and/or predominantly binds to or interacts with" as used herein means that the moiety has a stronger binding affinity to the least one antigen and/or receptor/marker on the surface of the target cell (i.e. here in particular on macrophages) than to any other or other peptide or polypeptide.

For example, a moiety may be a small molecule ligand or a proteinaceous ligand or a functional fragment thereof (specifically and/or predominantly) binding to (a) cell surface receptor(s) that are selected from the group consisting of antagonist(s), agonist(s), beta adrenergic receptor(s), G-protein-coupled receptor(s), and cytokine(s) binding to (a) receptor(s). As discussed herein, a "small molecule ligand" may also comprise a chemical or pharmaceutical that (specifically or predominantly) binds to or (specifically or predominantly) interacts with such (a) cell surface receptor(s) of the macrophage (and/or to fibroblasts, and macrophages and fibroblasts). Said "small molecule ligand" or said "proteinaceous ligand or a functional fragment thereof" may be the natural ligand of the corresponding (cell surface) receptor. An example is provided herein: here one or more sugar or modified sugar moieties are employed as "delivery moiety" (in the present exemplified case e.g. tri-mannose or N-acetylgalactosamine (GalNAc) and the "targeting structure is the Mannose receptor C type 1, a surface receptor for such sugars/modified sugar moieties on macrophages.

In table 3, exemplary surface receptor/markers are provided that can provide a delivery to the indicated target cell, e.g. macrophages, fibroblasts, and macrophages and fibroblasts. These a surface receptor/markers may also be the target of antibodies (or functional fragments thereof) which may be employed in context of this invention as a "moiety that delivers said inhibitor of miR-21 to a macrophage; to a fibroblast and to a macrophage; to a lung macrophage; and/or a to lung fibroblast and a to lung macrophage".

TABLE 3

Exemplified receptors/markers for the targeting/delivery of the inhibitor of miR-21 to macrophages and/or fibroblasts in human lung and heart tissue as identified by RNA sequencing of purified primary cell fractions. Selection is based on abundance, cell type-specificity and receptor characteristics.

| Ensembl Gene ID | Ensembl Gene ID version | Gene name | Gene description | Cell type | Tissue |
|---|---|---|---|---|---|
| ENSG00000260314 | ENSG00000260314.3 | MRC1 | Mannose receptor C type 1 | Heart and Lung | macrophages |
| ENSG00000165457 | ENSG00000165457.14 | FOLR2 | Folate receptor beta | Heart and Lung | Macrophages |
| ENSG00000278355 | ENSG00000278355.4 | LILRA5 | Leukocyte immunoglobulin like receptor A5 | Heart and Lung | Macrophages |
| ENSG00000132514 | ENSG00000132514.14 | CLEC10A | C-Type lectin domain containing 10A | Heart and Lung | Macrophages |
| ENSG00000019169 | ENSG00000019169.11 | MARCO | Macrophage receptor with collagenous structure | Lung | Macrophages |
| ENSG00000171049 | ENSG00000171049.9 | FPR2 | Formyl peptide receptor 2 | Lung | Macrophages |
| ENSG00000140678 | ENSG00000140678.17 | ITGAX | Integrin subunit alpha X | Lung | Macrophages |
| ENSG00000132170 | ENSG00000132170.23 | PPARG | Peroxisome proliferator activated receptor gamma | Lung | Macrophages |
| ENSG00000019582 | ENSG00000019582.16 | CD74 | CD74 antigen | Heart | Macrophages |
| ENSG00000182578 | ENSG00000182578.13 | CSF1R | Colony stimulating factor 1 receptor | Heart | Macrophages |
| ENSG00000158869 | ENSG00000158869.11 | FCER1G | Fc receptor | Heart | Macrophages |
| ENSG00000170458 | ENSG00000170458.14 | CD14 | CD14 antigen | Heart | Macrophages |
| ENSG00000129226 | ENSG00000129226.14 | CD68 | CD68 antigen | Heart | Macrophages |
| ENSG00000134853 | ENSG00000134853.12 | PDGFRA | Platelet derived growth factor receptor | Heart and Lung | Fibroblasts |

TABLE 3-continued

Exemplified receptors/markers for the targeting/delivery of the inhibitor of miR-21 to macrophages and/or fibroblasts in human lung and heart tissue as identified by RNA sequencing of purified primary cell fractions. Selection is based on abundance, cell type-specificity and receptor characteristics.

| Ensembl Gene ID | Ensembl Gene ID version | Gene name | Gene description | Cell type | Tissue |
|---|---|---|---|---|---|
| ENSG00000168079 | ENSG00000168079.17 | SCARA5 | Scavenger receptor class A member 5 | Heart | Fibroblasts |
| ENSG00000167601 | ENSG00000167601.12 | AXL | AXL Receptor Tyrosine Kinase | heart | Fibroblasts |
| ENSG00000164530 | ENSG00000164530.15 | PI16 | Peptidase inhibitor 16 | heart | Fibroblasts |
| ENSG00000011028 | ENSG00000011028.14 | MRC2 | Mannose receptor 2 | Heart | Fibroblasts |
| ENSG00000123384 | ENSG00000123384.14 | LRP1 | Low density lipoprotein receptor-related protein 1 | Heart and Lung | Macrophages and fibroblasts |
| ENSG00000082781 | ENSG00000082781.12 | ITGB5 | Integrin beta 5 | Heart and Lung | Macrophages and fibroblasts |
| ENSG00000241399 | ENSG00000241399.7 | CD302 | CD302 | Lung | Macrophages and fibroblasts |
| ENSG00000174837 | ENSG00000174837.15 | ADGRE1 | Adhesion G protein-coupled receptor E1 | Heart and lung | Macrophages |
| ENSG00000177575 | ENSG00000177575.12 | CD163 | CD163 antigen | Heart and lung | Macrophages |
| ENSG00000168329 | ENSG00000168329.14 | CX3CR1 | C-X3-C motif chemokine receptor 1 | Heart and Lung | Macrophages |
| ENSG00000105383 | ENSG00000105383.15 | CD33 | CD33 antigen | Heart | macrophages |
| ENSG00000143119 | ENSG00000143119.14 | CD53 | CD53 antigen | Heart | macrophages |
| ENSG00000011600 | ENSG00000011600.12 | TYROBP | Transmembrane immune signaling adaptor TYROBP | Heart | Macrophages |
| ENSG00000121807 | ENSG00000121807.6 | CCR2 | C—C motif chemokine receptor 2 | Heart | Macrophages |
| ENSG00000169442 | ENSG00000169442.9 | CD52 | CD52 molecule | Heart | Macrophages |
| ENSG00000169896 | ENSG00000169896.18 | ITGAM | Integrin subunit alpha M | Heart | Macrophages |
| ENSG00000198223 | ENSG00000198223.17 | CSF2RA | Colony stimulating factor 2 receptor subunit alpha | Heart | Macrophages |
| ENSG00000131981 | ENSG00000131981.16 | LGALS3 | Galectin 3 | Heart | Macrophages |
| ENSG00000141655 | ENSG00000141655.17 | TNFRSF11A | TNF receptor superfamily member 11a | Heart | Macrophages |
| ENSG00000072135 | ENSG00000072135.13 | PTPN18 | Protein tyrosine phosphatase non-receptor Type 18 | Heart | Macrophages |
| ENSG00000117091 | ENSG00000117091.10 | CD48 | CD48 antigen | Heart | Macrophages |
| ENSG00000240505 | ENSG00000240505.9 | TNFRSF13B | TNF receptor superfamily member 13B | Heart | Macrophages |
| ENSG00000110876 | ENSG00000110876.10 | SELPLG | Selectin P ligand | Heart | Macrophages |
| ENSG00000169252 | ENSG00000169252.6 | ADRB2 | Adrenoceptor beta 2 | Heart | Macrophages |
| ENSG00000133800 | ENSG00000133800.9 | LYVE1 | Lymphatic vessel endothelial hyaluronan receptor 1 | Heart | Macrophages |
| ENSG00000140030 | ENSG00000140030.6 | GPR65 | G protein-coupled receptor 65 | Heart | Macrophages |
| ENSG00000169403 | ENSG00000169403.12 | PTAFR | Platelet activating factor receptor | Heart | Macrophages |
| ENSG00000171860 | ENSG00000171860.5 | C3AR1 | Complement component 3a receptor 1 | Heart | Macrophages |
| ENSG00000072694 | ENSG00000072694.21 | FCGR2B | Fc receptor | Heart | Macrophages |
| ENSG00000203747 | ENSG00000203747.11 | FCGR3A | Fc receptor | Heart | Macrophages |
| ENSG00000171631 | ENSG00000171631.14 | P2RY6 | Pyrimidinergic receptor P2Y. | Heart | Macrophages |
| ENSG00000150337 | ENSG00000150337.13 | FCGR1A | Fc receptor, IgG, high affinity I | Lung | Macrophages |
| ENSG00000162723 | ENSG00000162723.10 | SLAMF9 | SLAM family member 9 | Lung | Macrophages |
| ENSG00000106799 | ENSG00000106799.13 | TGFBR1 | Transforming growth factor, beta receptor I | Lung | Macrophages |
| ENSG00000196664 | ENSG00000196664.5 | TLR7 | Toll-like receptor 7 | Lung | Macrophages |
| ENSG00000101916 | ENSG00000101916.11 | TLR8 | Toll-like receptor 8 | Lung | Macrophages |
| ENSG00000095970 | ENSG00000095970.17 | TREM2 | Triggering receptor expressed on myeloid cells 2 | Lung | Macrophages |
| ENSG00000135077 | ENSG00000135077.9 | HAVCR2 | Hepatitis A virus cellular receptor 2 | Lung | Macrophages |
| ENSG00000147650 | ENSG00000147650.12 | LRP12 | Low density lipoprotein receptor-related protein 12 | Lung | Macrophages |
| ENSG00000163606 | ENSG00000163606.11 | CD200R1 | CD200 receptor 1 | Lung | Macrophages |
| ENSG00000167772 | ENSG00000167772.12 | ANGPTLA | Angiopoietin Like 4 | Lung | Macrophages |
| ENSG00000054219 | ENSG00000054219.11 | LY75 | Lymphocyte antigen 75 | Lung | Macrophages |
| ENSG00000181631 | ENSG00000181631.7 | P2RY13 | Purinergic receptor P2Y13 | Lung | Macrophages |
| ENSG00000109743 | ENSG00000109743.11 | BST1 | Bone marrow stromal cell antigen 1 | Lung | Macrophages |
| ENSG00000173391 | ENSG00000173391.9 | OLR1 | Oxidized low density lipoprotein receptor 1 | Lung | Macrophages |
| ENSG00000151490 | ENSG00000151490.15 | PTPRO | Protein tyrosine phosphatase receptor type O | Lung | Macrophages |

TABLE 3-continued

Exemplified receptors/markers for the targeting/delivery of the inhibitor of miR-21 to macrophages and/or fibroblasts in human lung and heart tissue as identified by RNA sequencing of purified primary cell fractions. Selection is based on abundance, cell type-specificity and receptor characteristics.

| Ensembl Gene ID | Ensembl Gene ID version | Gene name | Gene description | Cell type | Tissue |
|---|---|---|---|---|---|
| ENSG00000140564 | ENSG00000140564.13 | FURIN | Furin, paired basic amino acid cleaving enzyme | Lung | Macrophages |
| ENSG00000090659 | ENSG00000090659.18 | CD209 | CD209 molecule | Lung | Macrophages |
| ENSG00000171659 | ENSG00000171659.15 | GPR34 | G protein-coupled receptor 34 | Lung | Macrophages |
| ENSG00000069702 | ENSG00000069702.11 | TGFBR3 | Transforming growth factor | Heart | Fibroblasts |
| ENSG00000169439 | ENSG00000169439.12 | SDC2 | Syndecan 2 | Heart | Fibroblasts |
| ENSG00000159640 | ENSG00000159640.16 | ACE | Angiotensin I converting enzyme (peptidyl-dipeptidase A) 1 | Heart | Fibroblasts |
| ENSG00000169604 | ENSG00000169604.19 | ANTXR1 | Anthrax toxin receptor 1 | Heart | Fibroblasts |
| ENSG00000162733 | ENSG00000162733.19 | DDR2 | Discoidin domain receptor family | Heart | Fibroblasts |
| ENSG00000183098 | ENSG00000183098.11 | GPC6 | Glypican 6 | Heart | Fibroblasts |
| ENSG00000198121 | ENSG00000198121.13 | LPAR1 | Lysophosphatidic acid receptor 1 | Heart | Fibroblasts |
| ENSG00000179954 | ENSG00000179954.16 | SSC5D | Scavenger receptor cysteine rich family member with 5 domains | Heart | Fibroblasts |
| ENSG00000106538 | ENSG00000106538.10 | RARRES2 | Retinoic acid receptor responder 2 | Heart | Fibroblasts |
| ENSG00000100196 | ENSG00000100196.11 | KDELR3 | KDEL endoplasmic reticulum protein retention receptor 3 | Heart | Fibroblasts |
| ENSG00000182175 | ENSG00000182175.14 | RGMA | Repulsive guidance molecule BMP co-receptor A | Heart | Fibroblasts |
| ENSG00000129048 | ENSG00000129048.7 | ACKR4 | Atypical chemokine receptor 4 | Heart | Fibroblasts |
| ENSG00000160013 | ENSG00000160013.9 | PTGIR | Prostaglandin I2 receptor | Heart | Fibroblasts |
| ENSG00000144476 | ENSG00000144476.6 | ACKR3 | Atypical chemokine receptor 3 | Heart | Fibroblasts |
| ENSG00000104213 | ENSG00000104213.13 | PDGFRL | Platelet derived growth factor receptor like | Heart | Fibroblasts |
| ENSG00000128602 | ENSG00000128602.11 | SMO | Smoothened, frizzled class receptor | Heart | Fibroblasts |
| ENSG00000151892 | ENSG00000151892.15 | GFRA1 | GDNF family receptor alpha 1 | Heart | Fibroblasts |

The receptor(s) or cell surface molecule(s) indicated in table 3, above may be suitable for the binding of the moiety delivering the inhibitor of miR-21, or the targeting of the inhibitor of miR-21. Therefore, the moiety comprised in composition may bind to one or more of the receptor(s) or cell surface molecule(s) as indicated in table 3, above. The receptors or cell surface molecules indicated in table 3 were identified herein below to be comprised on macrophages and/or fibroblasts of human lung or heart tissue. Further, receptors or cell surface molecules may be identified by RNA sequencing of purified primary cell fractions. As illustrated in the appended examples, Mannose receptor C type 1 (Mrc1) is strongly expressed in macrophages. This renders MRC1 as a particularly desired and preferred target for a moiety "that delivers an inhibitor of miR-21 to a macrophage". A corresponding moiety is therefore a ligand binding to MRC1/a mannose receptor ligand. Such a ligand may comprise corresponding sugars like mannose. Other ligands for MRC1 are known in the art and comprise, but are not limited to, e.g. N-acetylgalactosamine (GalNAc). This is also illustrated in appended FIG. 22. Said figure documents that Mannose receptor C type 1 (MRC1) is expressed by macrophages in lung tissue. Appended FIG. 23 illustrates chemical structures of mannose receptor 1 ligands, whereby (A) shows a scheme of a non-limiting, yet, illustrative design of ligand conjugation and an inhibitor of miR-21, here "anti-miR-21" as defined herein.

Figure 23:
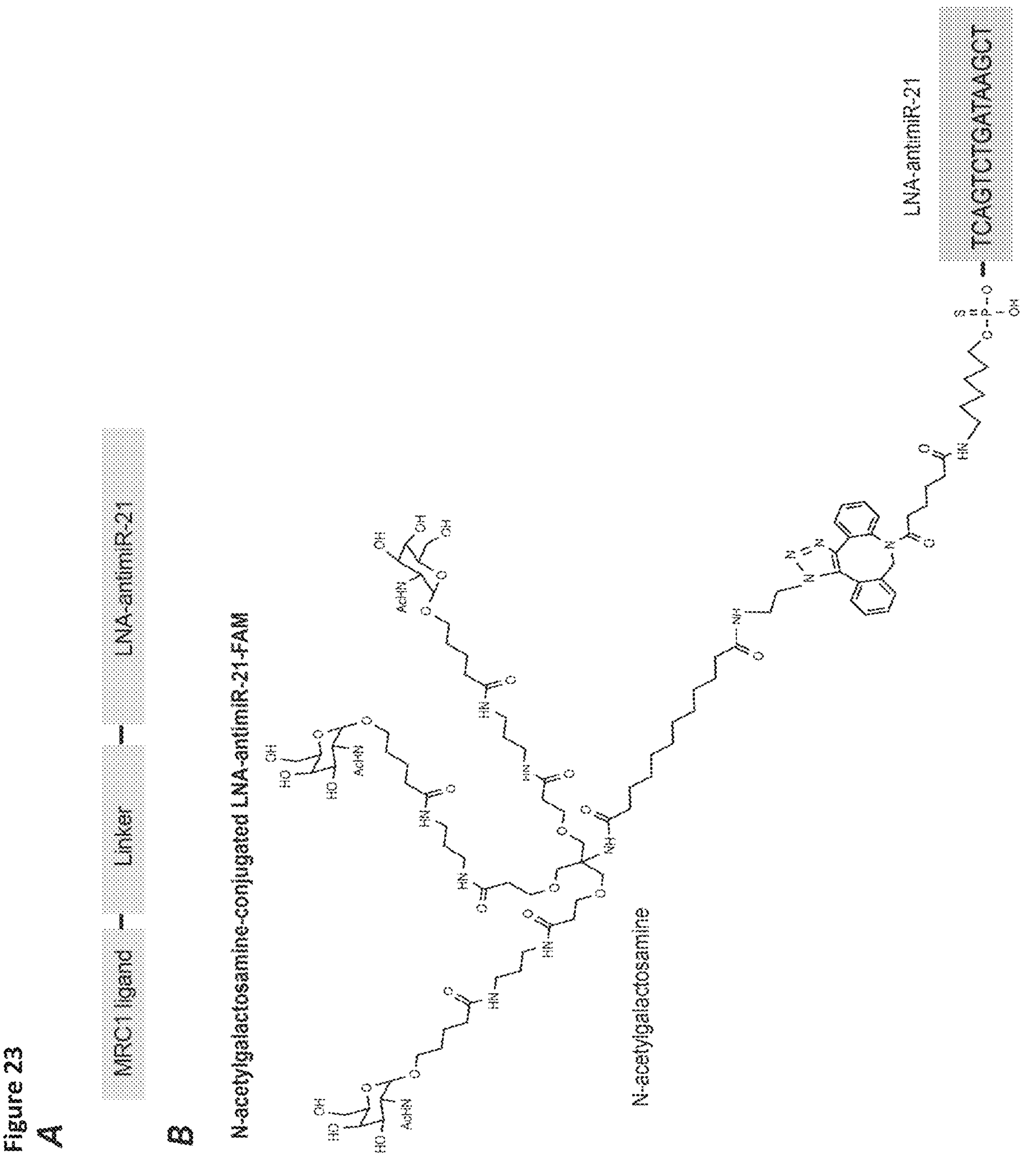
Figure 23:
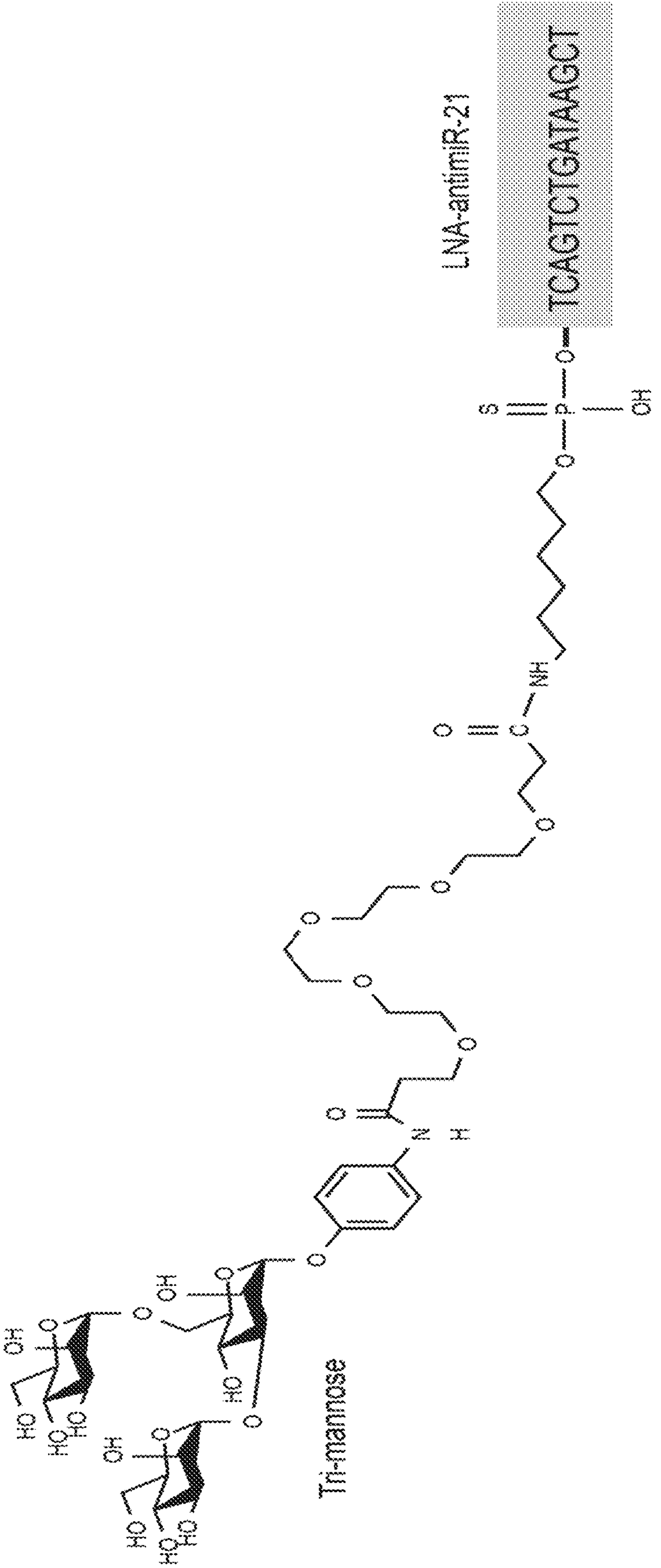

FIG. 23 (B) provides for exemplary and thereby non-limiting chemical structures of mannose-receptor ligand(s) conjugated to anti-miR-21 molecules. N-acetylgalactosamine (GalNAc) (Top) or mannose (here, tri-mannose, see Bottom of Figure) ligands were conjugated to 5'-end of (LNA-) anti-miR-21 (inhibitor of miR21). As known in the art, for example, Martinez-Pomares, L., (2012) have reported binding of mannose and N-acetylgalactosamine (GalNAc) ligands to MRC1. Further illustrative ligands for mannose receptor 1 (Mrc1) comprise but are not limited to specific antibodies directed to the extracellular part of MRC1.

Accordingly, and as illustrated in appended FIG. 23 (A), the general structure of a compound to be used in context of the present invention may have the format as follows:

inhibitor of miR-21-(linker)-binding/targeting/delivering moiety; or binding/targeting/delivering moiety-(linker)-inhibitor of miR-21

A non-limiting example of the later and comprising a binding/targeting/delivering moiety to macrophages is said construct shown in the scheme of FIG. 23 (A), Ligand to mannose receptor C type 1 (MRC1) as "binding moiety targeting/delivering to macrophages"; followed by (optional) linker/(linker); followed by LNA-anti-miR-21 as "inhibitor of miR-21"

Useful (biological) linker structures are very well known in the art and comprise, but are not limited to to click chemistry linkers (like, e.g. DBCO, tetrazine, TCO, BCN, carboxyl linkers (5'-COOH—C5, 3'-COOH—C6), aldehydes/hydrazides, monomethoxytrityl linkers, peptide linkers, ß-glucoronide linkers, spacer modifiers (like, e.g. Spacer C3, spacer C12), aromatic linkers, bifunctional linkers, etc. The person skilled in the art is aware that various "attachment/linker chemistry means and methods" are available to attach macrophage and/or fibroblast-specific ligands to the anti-miR-21 oligonucleotides via a in between linker moiety. Such "attachment/linker chemistry means and methods", comprise but are not limited to the addition of primary amino groups to the 5' position of the oligonucleotide. Examples for such means and methods include modifying 5'-aminohexyl linker and TFA-amino linker phosphoramidites which are used for the addition of a primary amine to the 5' position of an oligonucleotide. It is, e.g. also envisaged that "peptide linkers" are employed in context of this invention a discussed herein below, wherein peptides are also disclosed as "linker groups". Furthermore, it is also envisaged and within the knowledge of the skilled artisan that "cleavable linkers" may be employed. The person skilled in the art is readily in a position to also use such "cleavable-linker" in order to assemble the herein defined compounds of the invention comprising an inhibitor of miR-21 and a moiety that delivers said inhibitor of miR-21 to a macrophage. Such (a) "cleavable linker(s)" is/are, inter alia, described in Xue Y et al. Chem Soc Rev 2021 (DOI: 10.1039/d0cs01061h); Benizri (2019) Bioconjugate Chem. 2019, 30, 366-383 (in particular for oligonucleotides) or Jonathan (2019). Chem Soc Rev 48, 4361.

In the compounds of the present invention, one or more moieties that deliver said inhibitor of miR-21 to a macrophage, such as (for example) a (small molecule) ligand, like one or more sugar or modified sugar moieties as exemplified herein, or one or more (proteinaceous) ligands (or functional fragments thereof) or one or more antibodies (or functional fragments thereof), may linked to said inhibitor of miR-21, such as an anti-miR-21 oligonucleotide, preferably to a terminal phosphorothioate group of the oligonucleotide, either directly or via a linker group (hereinafter sometimes referred to merely as "linker"). Again, as pointed out herein, also further moieties that delivers said inhibitor of miR-21 can be employed that are bound to said inhibitor of miR-21 to a macrophage (and/or, optionally to a fibroblast) via "linker" structure.

As will be understood, the linker is not particularly limited and may be varied to a considerable degree while retaining the beneficial effects associated with the present invention.

For example, it is to be understood that the linker group may be linear or branched. In particular if the linker group is branched, more than one moiety that delivers said inhibitor of miR-21 to a macrophage (e.g. sugar or modified sugar moieties) may be attached to the linker group.

It is preferred, but nor limiting, that the linker group contains more than 20 and less than 100 non-hydrogen atoms (preferably less than 60 non-hydrogen atoms) in each linker chain between each sugar or modified sugar moiety and the terminal phosphorothioate group of the oligonucleotide. The number of non-hydrogen atoms in the linker group as a whole is preferably more than 20 and less than 200 atoms (preferably less than 150 atoms). The non-hydrogen atoms are preferably selected from carbon, nitrogen and oxygen. It is furthermore preferred that not more than 15 atom-% of the non-hydrogen atoms in the linker are part of aromatic groups.

More specifically, the linker may be a group L which is selected from $C_{10-40}$ alkylene, $C_{10-40}$ alkenylene, and $C_{10-40}$ alkynylene, wherein said alkylene, said alkenylene and said alkynylene are each optionally substituted with one or more groups independently selected from halogen, $C_{1-5}$ haloalkyl, —O($C_{1-5}$ haloalkyl), —CN, —$OR^{21}$, —$NR^{21}R^{21}$, —$NR^{21}OR^{21}$, —$COR^{21}$, —$COOR^{21}$, —$OCOR^{21}$, —$CONR^{21}R^{21}$, —$NR^{21}COR^{21}$, —$NR^{21}COOR^{21}$, —$OCONR^{21}R^{21}$, —$SR^{21}$, —$SOR^{21}$, —$SO_2R^{21}$, —$SO_2NR^{21}R^{21}$, —$NR^{21}SO_2R^{21}$, —$SO_3R^{21}$, and —$NO_2$, and further wherein one or more —$CH_2$— units comprised in said alkylene, said alkenylene or said alkynylene are each optionally replaced by a group independently selected from —O—, —$NR^{21}$—, —CO—, —S—, —SO—, and —$SO_2$—; in addition, it is envisaged that one or more —$CH_2$— units comprised in said alkylene, said alkenylene or said alkynylene are each optionally replaced by a group independently selected also from arylene, heteroarylene, cycloalkylene, and heterocycloalkylene, wherein said arylene, said heteroarylene; said cycloalkylene and said heterocycloalkylene are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl); among the arylene, heteroarylene, cycloalkylene, and heterocycloalkylene, arylene is preferred and phenylene is more preferred.

each $R^{21}$ is independently selected from hydrogen, $C_{1-5}$ alkyl, $C_{2-5}$ alkenyl, $C_{2-5}$ alkynyl, carbocyclyl, and heterocyclyl, wherein said alkyl, said alkenyl and said alkynyl are each optionally substituted with one or more groups $R^{Alk}$, and further wherein said carbocyclyl and said heterocyclyl are each optionally substituted with one or more groups $R^{Cyc}$;

any two $R^{21}$ are optionally linked to form a ring;

each $R^{Alk}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl);

each $R^{Cyc}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl).

In group L, the $C_{10-40}$ alkylene, $C_{10-40}$ alkenylene, and $C_{10-40}$ alkynylene are preferably $C_{20-35}$ alkylene, $C_{20-35}$ alkenylene, and $C_{20-35}$ alkynylene, respectively, wherein each of the alkylenes, alkenylenes and alkynylenes may be modified as set out above. It is further preferred that the linker is selected from $C_{10-40}$ alkylene and $C_{10-40}$ alkenylene, more preferably $C_{20-35}$ alkylene or $C_{20-35}$ alkenylene, even more preferably $C_{20-35}$ alkylene wherein each of the alkylenes and alkenylenes may be modified as set out above.

In the case of branched linkers, it is envisaged that each of the branches of the linker may be a group L as defined above and the main chain of the linker may consist of one or two group(s) L as defined above. If the main chain of the linker consists of two groups L, these are preferable sequentially linked -(group L)-(group L)- and may be chosen independently from each other.

As will be understood, the chain length of the $C_{10-40}$ alkylene, $C_{10-40}$ alkenylene, and $C_{10-40}$ alkynylene (including the optional substitution and the optional replacement(s) of —$CH_2$— units) in the branches of the linker may not necessarily be limited to $C_{10-40}$ but may also encompass $C_{4-9}$ alkylene, $C_{4-9}$ alkenylene, and $C_{4-9}$ alkynylene (including the optional substitution and the optional replacement(s) of —$CH_2$— units).

An example of a branched linker may thus have a structure as shown in the following:

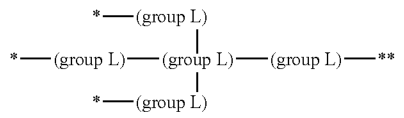

wherein * indicates attachment points for a moiety that delivers the inhibitor of miR-21 to a macrophage, and ** indicates an attachment point for an inhibitor of miR-21.

If the moiety that delivers the inhibitor of miR-21 to a macrophage may be a small molecule. Like, e.g. sugar or modified sugar moiety. In case the "delivery moiety" is a sugar or modified sugar moiety, it is preferred that the linker is attached to the sugar or modified sugar moiety via the anomeric oxygen of such a sugar.

If the "inhibitor of miR-2" is an oligonucleotide, it is preferred that the linker is attached to the oligonucleotide via a terminal phosphorothioate group of the oligonucleotide.

Two non-limiting examples of linkers are given in the following, one of which is branched, while the other is non-branched.

In a first example, the linker is branched, with three sugar or modified sugar moieties being attached (preferably via the anomeric oxygen) via first amide containing moieties to the hydroxy groups of a tris(hydroxymethyl)aminomethane, wherein the amino group of the tris(hydroxymethyl)aminomethane is linked via a second amide containing moiety to the oligonucleotide (or any other inhibitor of miR-21), preferably to a terminal phosphorothioate group of the oligonucleotide. The linker optionally contains a maker or label. Preferably, the first amide containing moieties are each aliphatic and each contain 10 to 15 atoms in the chain. More preferably, this branched linker group is as shown in the first structure of FIG. 23B, wherein it is to be understood that the N-acetylgalactosamine groups may independently be replaced by other sugar or modified sugar moieties (or other moieties that deliver said inhibitor of miR-21 to a macrophage) and the oligonucleotide may be varied (and stand as an example of the inhibitor of miR-21). In context of this invention, it is also understood that these sugar or modified sugar moieties are merely meant as an illustrative example of a (small molecule) ligand capable of interacting with a cell surface protein/receptor/marker on the surface of the "target cell" to which the "inhibitor of miR-21" is to be delivered (in the present example and in context of this invention to a macrophage and/or to a fibroblast and to a macrophage)

In a second example, the linker is not branched and contains 20 to 40 atoms selected from carbon, nitrogen and oxygen. Preferably, the linker contains or consists of a -phenylene-NHC(═O)$CH_2CH_2$—($OCH_2CH_2$)$_4$—$OCH_2CH_2$—C(═O)NH—($CH_2$)$_6$— group, wherein the phenylene groups is linked to the sugar or modified sugar moiety, preferably by a bond between the anomeric oxygen of a sugar and the phenylene group, and the ($CH_2$)$_6$— group is linked to the oligonucleotide, preferably via a terminal phosphorothioate group of the oligonucleotide. Preferably, this linker group is as shown in the second structure of FIG. 23B, wherein it is to be understood that the di(mannosyl) mannose group may be replaced by other sugar or modified sugar moieties (or other moieties that deliver said inhibitor of miR-21 to a macrophage and/or to a fibroblast and to a macrophage) and the oligonucleotide may be varied (and stand as an example of the inhibitor of miR-21).

The composition comprising an inhibitor of miR-21 and a moiety that delivers said inhibitor of miR-21 to a macrophage optionally furthermore contains a (e.g. fluorescence) maker or label. This marker may be in the inhibitor of miR-21, the moiety that delivers said inhibitor of miR-21 to a macrophage or in the linker. An example of such a marker or label in the linker is shown in the first formula of FIG. 23B.

As used herein above in the discussion of the "linker" structures, the term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl. As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene ($—CH_2—$), ethylene (e.g., $—CH_2—CH_2—$ or $—CH(—CH_3)—$), propylene (e.g., $—CH_2—CH_2—CH_2—$, $—CH(—CH_2—CH_3)—$, $—CH_2—CH(—CH_3)—$, or $—CH(—CH_3)—CH_2—$), or butylene (e.g., $—CH_2—CH_2—CH_2—CH_2—$). Unless defined otherwise, the term "alkylene" preferably refers to $C_{1-4}$ alkylene (including, in particular, linear $C_{1-4}$ alkylene), more preferably to methylene or ethylene, and even more preferably to methylene.

As used herein, the term "alkoxy" refers to an —O-alkyl group, wherein the alkyl moiety comprised in this group is as defined above.

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, "heterocyclyl" preferably refers to heteroaryl, heterocycloalkyl or heterocycloalkenyl.

As used herein, the term "cyclyl" refers to a carbocyclyl or a heterocyclyl, as defined herein above.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I). As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to $—CF_3$, $—CHF_2$, $—CH_2F$, $—CF_2—CH_3$, $—CH_2—CF_3$, $—CH_2—CHF_2$, $—CH_2—CF_2—CH_3$, $—CH_2—CF_2—CF_3$, or $—CH(CF_3)_2$. A particularly preferred "haloalkyl" group is $—CF_3$.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

The linker group may also contain or consist of a peptide. Such a peptide preferably comprises 1 to 100 amino acids, such as 1 to 25 amino acids, more preferably 12 to 20 amino acids, even more preferably 12 to 16 or 15 to 20 amino acids. The peptide linker may comprise one or more (G3S) and/or (G4S) motives, in particular 1, 2, 3, 4, 5 or 6 (G3S) and/or (G4S) motives, preferably 3 or 4 (G3S) and/or (G4S) motives, more preferably 3 or 4 (G4S) motives.

In other examples, the linker comprises 12 to 25 amino acids, preferably a sequence (G3S)3 or (G3S)4 or (G4S)3 or (G4S)4. Alternative peptide linkers may consist of or comprise the GEGTSTGSGGSGGSGGAD motive (see SEQ ID NO. 10). A peptide linker may be linked, either via its C-terminus or via its N-terminus, to the inhibitor of miR-21 by any means known to a skilled person. For example, the C-terminal acid may be reacted with an amino alcohol, such as an aminopropanol, to form an amide bond and the alcohol group of the aminopropanol may bind to the phosphor of a terminal phosphorothioate group of the inhibitor of miR-21. Alternatively, the N-terminus of the peptide linker may be reacted with an (optionally protected) hydroxy group containing acid (or anhydride, or lactone or acid chloride thereof), such as a hydroxypropanoic acid and (optionally after removing the protecting group from the hydroxy group) bind, via the hydroxy group of the hydroxy group containing carboxylic acid to the phosphor of a terminal phosphorothioate group of the inhibitor of miR-21.

Furthermore, the peptide linker may be linked, either via its C-terminus or via its N-terminus, to the moiety that delivers said inhibitor of miR-21 to a macrophage by any means known to a skilled person. For example the C-terminal acid may be reacted with an amino alcohol, such as an aminopropanol, to form an amide bond and the alcohol group of the aminopropanol may bind to an anomeric carbon of a sugar group of the moiety that delivers said inhibitor of miR-21 to a macrophage. Alternatively, the N-terminus of the peptide linker may be reacted with an (optionally protected) hydroxy group containing acid (or anhydride, or lactone or acid chloride thereof), such as a hydroxypropanoic acid and (optionally after removing the protecting group from the hydroxy group) bind, via the hydroxy group of the hydroxy group containing carboxylic acid to an anomeric carbon of a sugar group of the moiety that delivers said inhibitor of miR-21 to a macrophage.

A skilled person will understand that if the peptide linker is linked to the inhibitor of miR-21 via its C-terminus, it will be preferred that it is linked to the moiety that delivers said inhibitor of miR-21 to a macrophage via its N-terminus, and vice versa.

Suitably protected peptides can be prepared by any method known to the skilled person. These include, but are not limited to, solid-state peptide synthesis. Suitable protocols are known to the skilled person and e.g. mentioned in "Solid-phase peptide synthesis: from standard procedures to the synthesis of difficult sequences", Coin et al., Nature Protocols 2007, Vol. 2, pages 3247 to 3256. When using solid-state peptide synthesis, the peptides can be cleaved from the solid phase while leaving the protecting groups on the side chains of the peptides. In this state, the above discussed manipulations for attachment to the inhibitor of miR-21 and/or the moiety that delivers said inhibitor of miR-21 to a macrophage may most suitably be made.

As indicated above, the term "moiety" or "carrier" is interchangeable. In particular aspects, the moiety may be coupled to the inhibitor of miR-21, e.g. by a covalent bond. The carrier may comprise the inhibitor of miR-21 in particular aspects, e.g. the carrier may be selected from e.g., (targeting) liposomes, nano-particles, lipid nanoparticles (LNPs), mesoporous silica nanoparticles (MSNs), etc. comprising the inhibitor of miR-21. In certain context of the invention, the term "moiety may be used interchangeably with the term "part", of example in context of a compound of the invention wherein one "part" of said compound is able to inhibit miR-21 and another "part" is able to bind to, to target and/or to deliver said miR-21 inhibiting part to a target cell, preferably to a macrophages and/or to a fibroblast.

The binding/targeting/delivering moiety to macrophages and/or to fibroblast may also a specific protein ligand that interacts with a (specific) receptor macrophages and/or fibroblasts The binding/targeting/delivering moiety to macrophages and/or to fibroblasts may be an antibody or the functional binding fragment that specifically binds to at least one antigen that is found on: a macrophage; a fibroblast and a macrophage; a lung macrophage; or a lung fibroblast and a lung macrophage. In such particular aspects, the moiety may be an antibody or the functional binding fragment that specifically binds to at least one antigen that is exclusively found on: a macrophage; a fibroblast and a macrophage; a lung macrophage; or a lung fibroblast and a lung macrophage. As used herein, the functional binding fragment of the antibody may be an antigen binding fragment of the antibody.

The antibody or the functional binding fragment may (specifically bind) to at least one of antigens provided in the table above. Methods for identifying antibodies or antibody fragments thereof that are capable of (specifically) binding to at least one antigen are known to the skilled person. Moreover, antibodies and fragments thereof are known to the skilled person that bind to one of the antigens indicated in table 3, above. Therefore, the composition may comprise the inhibitor of miR-21 that is conjugated to an antibody or the binding fragment thereof, wherein the antibody or the binding fragment thereof delivers the inhibitor of mirR-21 to macrophage(s) and/or fibroblasts e.g. by binding to at least one of the antigens indicated in table 3, above. Antibodies or antibody fragments thereof binding to an antigen indicated above are known in the prior art. For example, the antibodies for the delivery of the inhibitor of miR-21 may be selected from the group consisting of antibodies directed against MRC1 (e.g. Abcam Cat. No. ab64693), against ADGRE1 (e.g. BioRAD Cat. No: MCA 2674), against CD14 (e.g. Abcam Cat. No. ab182032), against FCGR3A (e.g. Abcam Cat. No. ab89207), and against PDGFRA (e.g. Abcam Cat. No. ab96569).

As used herein, the term "antibody", in accordance with the present invention, comprises polyclonal and monoclonal antibodies as well as derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 (Harlow & Lane, 1988) and Harlow and Lane "Using Antibodies: A Laboratory Manual" Cold Spring Harbor Laboratory Press, 1999 (Harlow & Lane, 1999). The term "antibody" in accordance with the invention also includes embodiments such as chimeric, single chain and humanized antibodies, as well as antibody fragments, like, inter alia, Fab fragments, fusion proteins consisting of Eph receptors, ephrin or phosphatase extracellular domains and Fc. Antibody fragments or derivatives further comprise $F(ab')_2$, Fv fragments, scFvs, single domain $V_H$ or V-like domains, such as VhH or V-NAR-domains, as well as multimeric formats such as minibodies, diabodies, tribodies, tetrabodies or chemically conjugated Fab'-multimers; see, for example, Harlow and Lane (1988) and (1999)(Harlow & Lane, 1988, 1999), Altshuler (2010) Biochemistry (Moscow) 75, 1584-605 (Altshuler et al., 2010) or Holliger (2005) Nature Biotechnology 23, 1126-36 (Holliger & Hudson, 2005). Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody used herein is a monoclonal antibody. For the preparation of monoclonal antibodies, any technique, which provides antibodies produced by continuous cell line cultures, can be used. Examples for such techniques include the original hybridoma technique (Köhler & Milstein, 1975) as further developed by the art, the trioma technique, the human B-cell hybridoma technique (Kozbor & Roder, 1983) and the EBV-hybridoma technique to produce human monoclonal antibodies (Cole et al., 1985). The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: (Jones et al., 1986); (Riechmann et al., 1988) and (Presta, 1992). Various techniques have been developed for the production of antibody fragments. Traditionally, these fragments were derived via proteolytic digestion of intact antibodies (see (Morimoto et al., 1992); and (Brennan et al., 1985)). Antibody fragments can also be produced directly by recombinant host cells and the antibody phage libraries discussed above. Fab'-SH fragments can be directly recovered from *E. coli* and chemically coupled to form F(ab')2 fragments (Carter et al., 1992). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870. Such linear antibody fragments may be monospecific or bispecific. Bispecific antibodies with binding specificities for at least two different antigens or epitopes (Milstein & Cuello, 1983). For example, bispecific antibodies or fragments thereof can be used in the present invention, such that the bispecific antibody or the fragment thereof binds to macrophages and fibroblasts (e.g. one binding site of the antibody or the fragment thereof binds to macrophages and the other binding site of the antibody or the fragment thereof binds to fibroblasts). Techniques for generating bispecific antibodies from antibody fragments have also been described, such as using chemical linkage wherein intact antibodies are proteolytically cleaved to generate F(ab')2 fragments (Brennan et al., 1985). Fab'-SH fragments can be recovered from *E. coli* and chemically coupled to form bispecific antibodies (Shalaby et al., 1992). The "diabody" technology provides an alternative method for making bispecific antibody fragments (Holliger & Hudson, 2005). A "Fab fragment" generally is comprised of one light chain and the $C_H1$ and variable regions of one heavy chain. The heavy chain of a Fab molecule cannot form a disulfide bond with another heavy chain molecule. An "Fc" region generally contains two heavy chain fragments comprising the $C_H2$ and $C_H3$ domains of an antibody. The two heavy chain fragments are held together by two or more disulfide bonds and by hydrophobic interactions of the $C_H3$ domains. A "Fab' fragment" generally contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule. A "$F(ab')_2$ fragment" generally contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. The "Fv region" generally comprises the variable regions from both the heavy and light chains, but lacks the constant regions. Antibodies with more than two valencies are contemplated. Multivalent, "Octopus" antibodies with three or more antigen binding sites and two or more variable domains can be readily produced by recombinant expression of nucleic acid encoding the polypeptide chains of the antibody (US 2002/0004586; WO01/77342). For example, trispecific antibodies can be prepared (Tutt et al., 1991).

Figure 15:
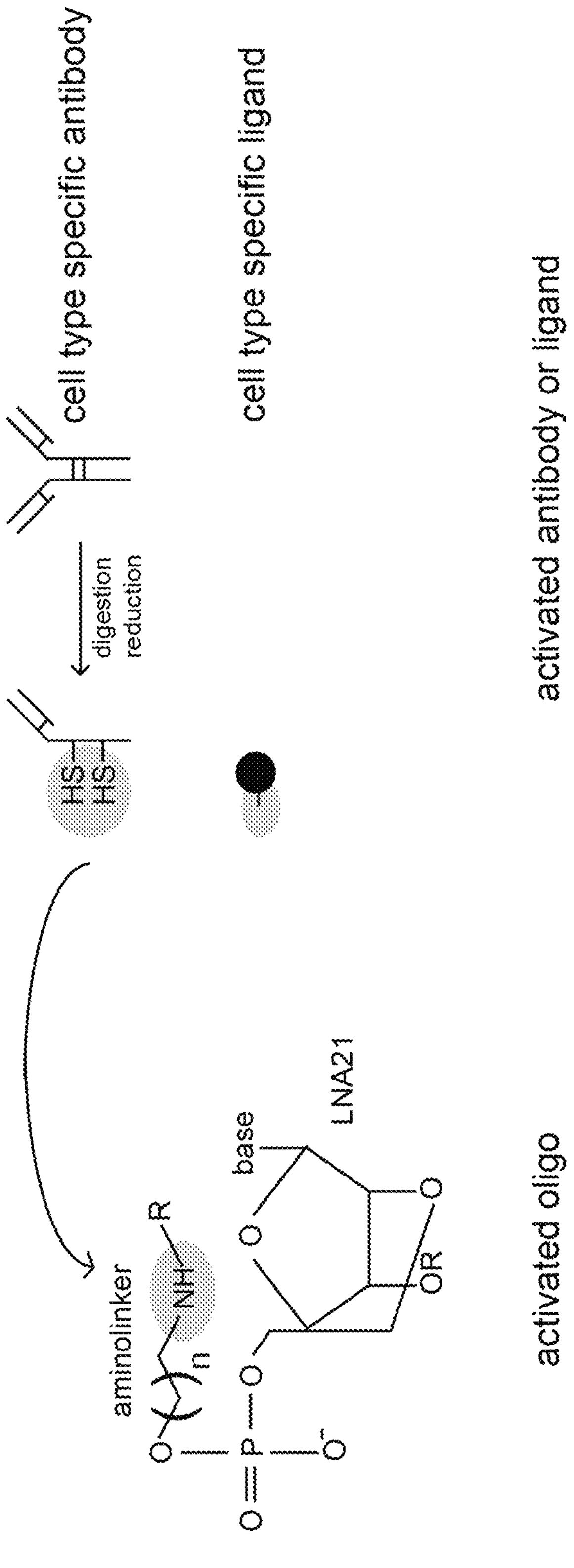

The inhibitor of miR-21 may be conjugated to the antibody or the functional fragment thereof (e.g. to the antibodies or the fragments thereof that are herein above exemplified). A conjugation to an antibody or a fragment thereof is illustrated in FIG. 15, below. In addition, the inhibitor of miR-21 may be conjugated to the cell type-specific targeting moiety As mentioned above, the inhibitor of miR-21 may also be comprised in "carriers", preferably in "carriers" that deliver to macrophages and/or fibroblasts. Such "carriers" may comprise liposomes, LNPs, nanoparticles and the like. Accordingly, in further aspects, the inhibitor of miR-21 may be, e.g. comprised in a nanoparticle. Such nanoparticle may be a lipid nanoparticle with or without PEGylation, a gold nanoparticle with oligonucleotide coat or a DNA nanostructure with oligonucleotide and targeting ligand incorporated. Further modalities represent the state-of-the-art and are listed in Juliano R L, Nucl Acids Res 2016 (see above).

The invention also relates to a method of producing the composition of claim. As indicated, the methods of production of the inhibitor of miR-21 and the inhibitor(s) of miR-21 per se are known to the skilled person. For example, antisense miR-21 can be provided by oligonucleotide synthesis. In further aspects, the method of producing the composition comprises conjugating the inhibitor of miR-21 to the moiety that delivers said inhibitor of miR-21 to a macrophage. An exemplary procedure is illustrated in FIG. 15, below. For example, the inhibitor of miR-21 may be conjugated to a small molecule, or antibody or functional fragment thereof. For instance, the antisense miR-21 or the inhibitor of miR-21 may be coupled to a linker (e.g. an amino acid linker) that couples to the moiety that delivers the inhibitor to the target cell. Alternatively, the antisense miR-21 or the inhibitor of miR-21 may be coupled to the moiety that delivers the inhibitor to the target cell. Click chemistry can be used for such a method. However, further methods for coupling the moiety to the inhibitor of miR-21 are known, e.g. by covalently coupling. In particular aspects, the method comprises conjugating the antisense miRNA-21 with the moiety. Further, the method of producing the composition may comprise introducing the inhibitor of miR-21 into a moiety that delivers said inhibitor of miR-21 to a macrophage.

As used herein, the inhibitor of miR21 may be any molecule so long it derepresses or overexpresses the targets of miR-21. Methods to determine the derepression or overexpression are known to the skilled person as also indicated above. In preferred aspects, the inhibitor of miR-21 comprises or is an antisense miRNA-21 (examples comprise, but are not limited to SEQ ID NOs 1 to 3 and 7 to 9). Antisense miRNA-21 molecules are known to the skilled person; see e.g. Khvorova & Watts Nature Biotechnology 2017 (Khvorova & Watts, 2017); and Rupaimoole &Slack MicroRNA therapeutics: towards a new era for the management of cancer and other diseases (Rupaimoole & Slack, 2017). Nature Reviews in Drug discovery 2017, which are herein incorporated by reference. Further, antisense miRNA-21 is also disclosed in WO 2009/106367 A1, or EP 2260 101 B1, which are herein incorporated by reference. For example, an antisense oligonucleotide is to be understood as a oligonucleotide which has a certain sequence complementary to another sequence, in particular a sequence complementary to miR-21. A target of miRm21 may also be understood to encompass a downstream target of miR-21. It is important to note that an inhibition of miR-21, e.g. via an oligonucleotide with a sequence at least complementary to miR-21 will lead to a derepression or even an overexpression of targets of miR-21, like the "target" Sprouty (a developmental protein involved in cell signaling) and the like. Herein below in the appended examples, exemplary antisense miRNA-21 are provided. In general, the antisense miRNA to be employed in context of this invention may be an oligonucleotide that comprises a sequence complementary to miR-21. In one particular embodiment of the invention, the antisense miRNA-21 may be a locked nucleic acid, or preferably is a phosphorothioated LNA/DNA mixmer. For example, the inhibitor of miR-21 may be an antisense-miR-21 that may be 3'-tCgAaTaGtCtGaCT-5' (SEQ ID NO:1), and/or 3'-TCgAaTagTCtgAcT-5' (SEQ ID NO: 2). Further useful antisense-miR-21 molecules are provided in SEQ ID NO:3 (a LNA construct comprising the same nucleotide sequence as SEQ ID Nos: 1 and 2, but with all nucleotides locked, 5'-Methyl-Cytosine modifications and a phosphorothioate backbone), SEQ ID NO: 7 (a LNA construct comprising the same nucleotide sequence as SEQ ID Nos: 1 and 2, but with all nucleotides locked, with 5'-Methyl-Cytosine modifications, but without a phosphorothioate backbone), SEQ ID NO:8 (a LNA construct comprising the same nucleotide sequence as SEQ ID Nos: 1 and 2, but with all nucleotides locked, with a phosphorothioate backbone, but without 5'-Methyl-Cytosine modifications) and SEQ ID NO: 9 (a LNA construct comprising the same nucleotide sequence as SEQ ID Nos: 1 and 2, but with all nucleotides locked and without any 5'-Methyl-Cytosine modifications and without a phosphorothioate backbone). In the sequences provided herein, capital letters refer to LNA, lower case letters refer to DNA bases. Every capital C denotes 5-Methyl-Cytosine. The antisense miRs against miR-21 may have a fully PS (Phosphorothioate) backbone; see also, e.g. SEQ ID NO. 1. Particularly useful antisense-miR-21 molecules are provided in SEQ ID NO: 1 and 2, most preferred and as illustrated in the appended examples is the "anti-miR-21" as follows: 3'-tCgAaTaGtCtGaCT-5' (SEQ ID NO:1)

As discussed herein, the present invention provides for compositions that comprise an inhibitor of miR-21 and that comprise a moiety that delivers said inhibitor of miR-21 to a macrophage, like a lung macrophage. As discussed herein above, said composition may also comprise a single molecule that has said at least two functional moieties/parts, namely a functional moiety/part that is an inhibitor of miR-21 and a functional moiety/part that delivers said inhibitor of miR-21 to said macrophage. Yet, as discussed herein above, said "compound" as well as the herein described composition, may also comprise further functional moieties or parts, like, e.g. a moiety or part that targets and/or delivers said inhibitor of miR-21 to other target cells", like, e.g. fibroblasts. Accordingly and as discussed and illustrated herein, in context of this invention compounds/compositions are provided that have at least said to functional features, namely feature (a) relating to the inhibition of miR-21 and feature (b) relating to the delivery of said inhibiting moiety/part ("inhibitor of miR-21") to the desired target cell (this delivery may also be a "carrier" as defined herein, like, e.g. a targeting liposome, nano-particles, a targeting lipid nanoparticle (LNP), a targeting mesoporous silica nanoparticle (MSN), etc). Said target cell(s) is/are (a) macrophage(s) and/or (a) fibroblast(s), preferably the target cell(s) is/are (a) macrophage(s). In preferred aspects, the macrophage(s) and/or fibroblast(s) is/are lung macrophages(s) and/or lung fibroblast(s). In more preferred aspects, the macrophage(s) and/or fibroblast(s) is/are alveolar macrophage(s) and/or alveolar fibroblast(s); and/or interstitial macrophage(s) and/or interstitial fibroblast(s). Accordingly, the present invention provides for compositions/compounds for (medical and/or pharmaceutical) uses as described herein as well as for, for the inventive compositions/compounds per se, for methods of producing said inventive compositions/compounds as well as for the methods of treatment as disclosed herein, wherein said compositions/compounds comprises an inhibitor of miR-21 and a moiety that delivers said inhibitor of miR-21 to a macrophage. In one embodiment of the invention, and as explained above, the inventive composition may be a single molecule, i.e. a compound that comprises the inhibitor of miR-21 and the moiety/part that is able to deliver said inhibitor of miR-21 to a macrophage/that is able to target said inhibitor of miR-21 to a macrophage. Said inhibitor of miR-21 and said delivering/targeting moiety/part may be linked via a "linker" (structure). Accordingly, the present invention also provides for compositions comprising an inhibitor of miR-21 and comprising at least one moiety that delivers said inhibitor of miR-21 to a macrophage, wherein said inhibitor of miR-21 and said moiety that delivers said inhibitor of miR-21 to a macrophage are linked via a linker, wherein the linker contains, or consists of, a group L which is selected from $C_{10-40}$ alkylene, $C_{10-40}$ alkenylene, and $C_{10-40}$ alkynylene, wherein said alkylene, said alkenylene and said alkynylene are each optionally substituted with one or more groups independently selected from halogen, $C_{1-5}$ haloalkyl, —O($C_{1-5}$ haloalkyl), —CN, —$OR^{21}$, —$NR^{21}R^{21}$, —$NR^{21}OR^{21}$, —$COR^{21}$, —$COOR^{21}$, —$OCOR^{21}$, —$CONR^{21}R^{21}$, —$NR^{21}COR^{21}$, —$NR^{21}C_{00}R^{21}$, —$OCONR^{21}R^{21}$, —$SR^{21}$, —$SOR^{21}$, —$SO_2R^{21}$, —$SO_2NR^{21}R^{21}$, —$NR^{21}SO_2R^{21}$, —$SO_3R^{21}$, and —$NO_2$, and further wherein one or more —$CH_2$— units comprised in said alkylene, said alkenylene or said alkynylene are each optionally replaced by a group independently selected from —O—, —$NR^{21}$, —CO—, —S—, —SO—, —$SO_2$—, arylene, heteroarylene, cycloalkylene, and heterocycloalkylene, wherein said arylene, said heteroarylene, said cycloalkylene and said heterocycloalkylene are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl);

each $R^{21}$ is independently selected from hydrogen, $C_{1-5}$ alkyl, $C_{2-5}$ alkenyl, $C_{2-5}$ alkynyl, carbocyclyl, and heterocyclyl, wherein said alkyl, said alkenyl and said alkynyl are each optionally substituted with one or more groups $R^A$k, and further wherein said carbocyclyl and said heterocyclyl are each optionally substituted with one or more groups $R^{Cyc}$;

any two $R^2$ are optionally linked to form a ring;

each $R^{Alk}$ is independently selected from —OH, —O($C_{1-5}$ alkyl), —O($C_{1-5}$ alkylene)-OH, —O($C_{1-5}$ alkylene)-O ($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO ($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH ($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl);

each $R^{Cyc}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O($C_{1-5}$ haloalkyl), —CN, —$NO_2$, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N ($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH ($C_{1-5}$ alkyl), and —N($C_{1-5}$ alkyl)($C_{1-5}$ alkyl).

In one embodiment of the inventive composition/compound, said composition/compound may comprise more than one moiety said inhibitor of miR-21 to a macrophage. Accordingly, also compositions are provided, wherein said composition (also compound) comprises two or moieties/parts that deliver said inhibitor of miR-21 to a macrophage. Accordingly, said inhibitor of miR-21 and said two or more moieties/parts that deliver said inhibitor of miR-21 to a macrophage may be linked via a branched linker, wherein each of the branches of the linker are a group L as defined in the preceding claim and the main chain of the linker comprises, or consists of, one or two group(s) L as defined in the preceding claim, wherein preferably the main chain is attached to the inhibitor of miR-21 and the branches are attached to the moieties that deliver said inhibitor of miR-21 to a macrophage.

Each group L may be selected from $C_{10-40}$ alkylene, wherein said alkylene is optionally substituted with one or more groups independently selected from halogen, $C_{1-5}$ haloalkyl, —O($C_{1-5}$ haloalkyl), —CN, —$OR^{21}$, —$NR^{21}R^{21}$, —$NR^{21}OR^{21}$, —$COR^{21}$, —$COOR^{21}$, —$OCOR^{21}$, —$CONR^{21}R^{21}$, —$NR^{21}COR^{21}$, —$NR^{21}COOR^{21}$, —$OCONR^{21}R^{21}$, —$SR^{21}$, —$SOR^{21}$, —$SO_2R^{21}$, —$SO_2NR^{21}R^{21}$, —$NR^{21}SO_2R^{21}$, —$SO_3R^{21}$, and —$NO_2$, and further wherein one or more —$CH_2$— units comprised in said alkylene are, each independently, replaced by a group selected from —O—, —$NR^{21}$—, —CO—, —S—, —SO—, —$SO_2$—, arylene, heteroarylene, cycloalkylene, and heterocycloalkylene, wherein said arylene, said heteroarylene, said cycloalkylene and said heterocycloalkylene are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

In one embodiment of the inventive composition/compound said linker may be represented by

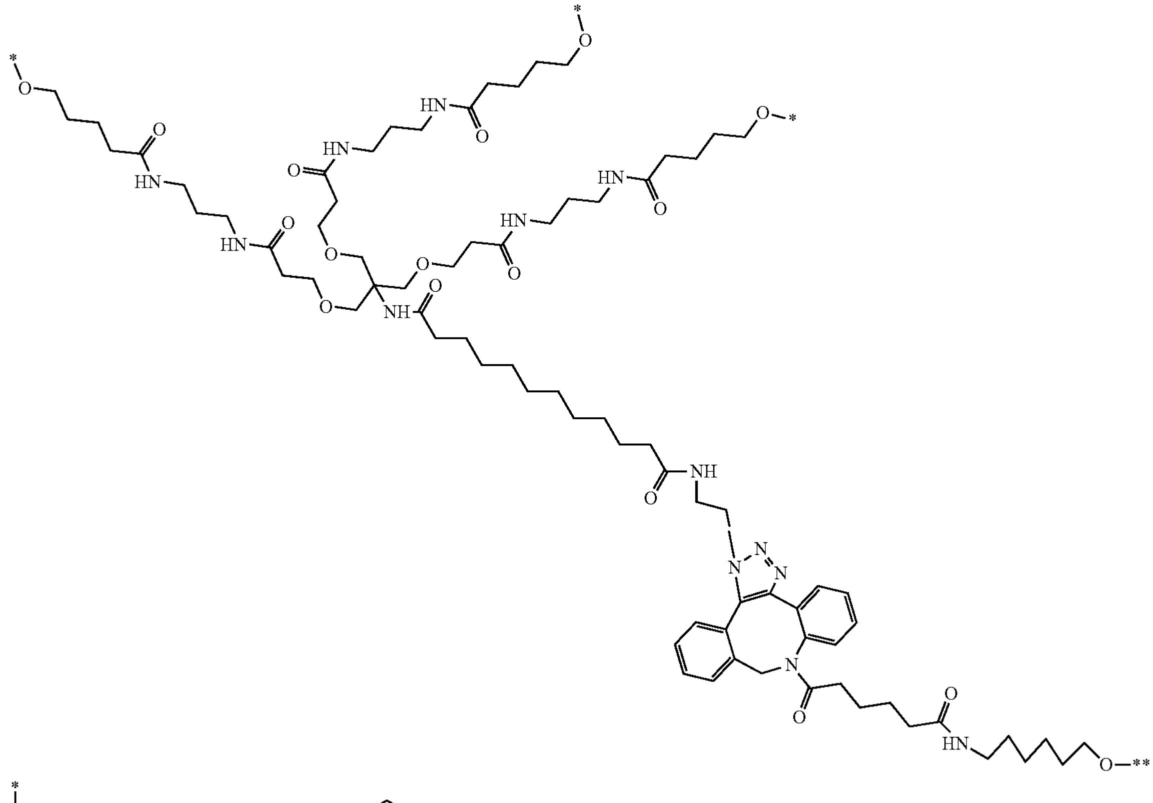

or

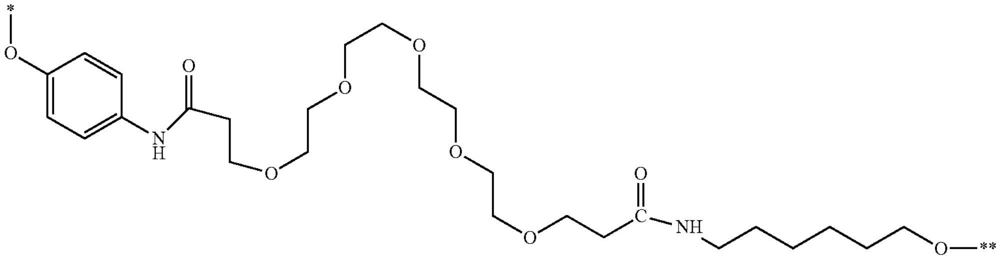

wherein * represents a bond to a moiety that delivers said inhibitor of miR-21 to a macrophage and ** represents a bond to an inhibitor of miR-21.

In the inventive composition/compounds said inhibitor of miR-21 may preferably be bound to the linker via the phosphor atom of a terminal phosphorothioate group.

The one or more moieties/parts in the inventive compounds/compositions that deliver said inhibitor of miR-21 to a macrophage may comprise a sugar, may preferably comprise or consist of one or more selected from mannose and N-acetylgalactosamine, more preferably consist of mannose, dimannosylmannose and N-acetylgalactosamine. As exemplified in the appended, non-limiting examples, also trimannose was used to target the inhibitor of miR-21 to macrophages (via the interaction with mannose receptor C type 1)

The one or more moieties that deliver said inhibitor of miR-21 to a macrophage may be selected from the following:

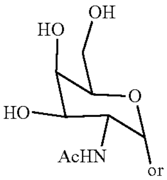

or

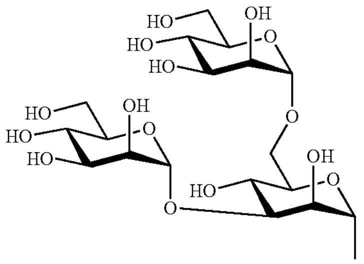

wherein the linker is attached at the anomeric carbon at the lower right hand part of each structure.

Figure 23C:
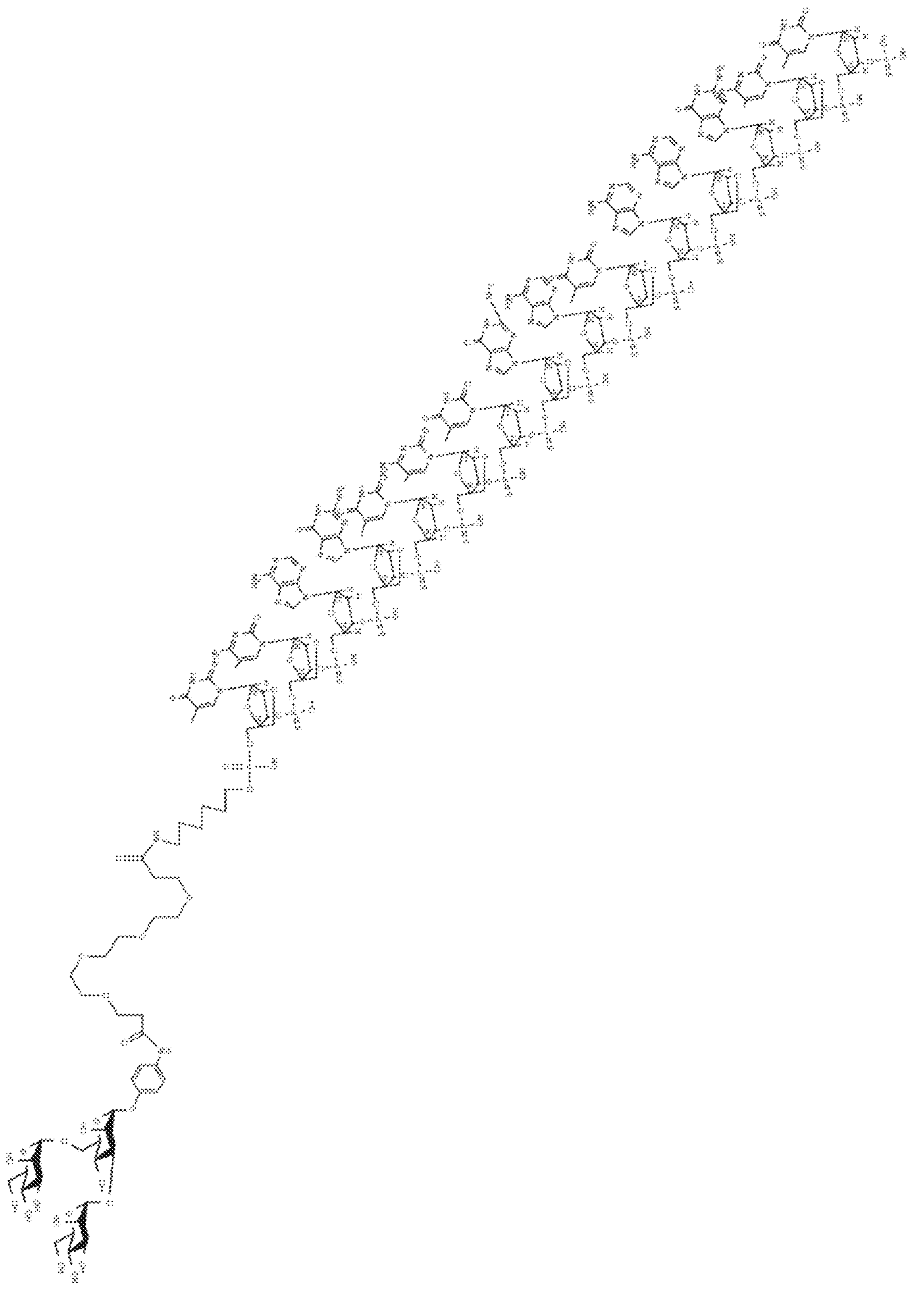
Figure 23D:
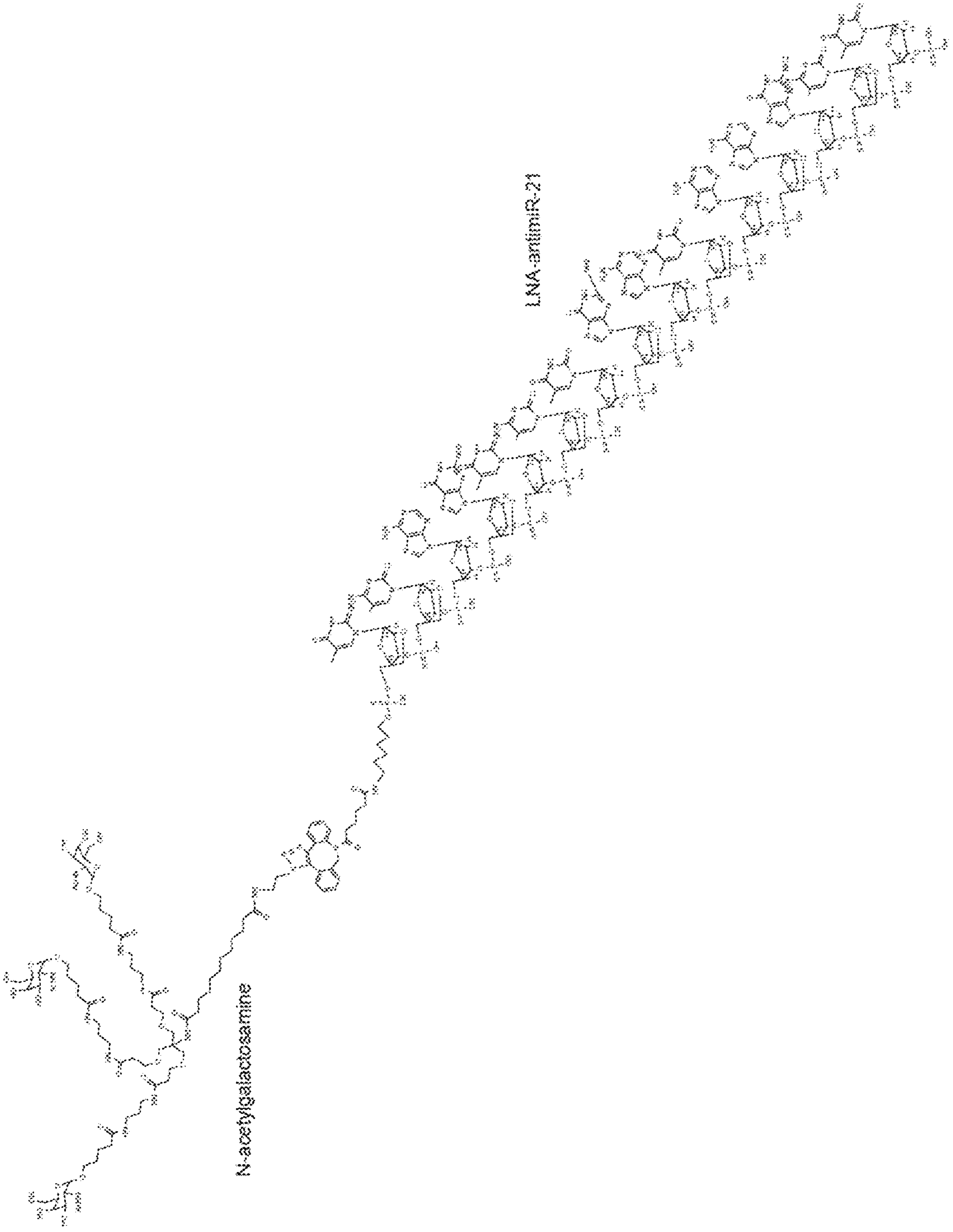

The inventive composition may contain or comprise one or both of the compounds as defined in FIG. 23B and/or one or both of the compounds in FIGS. 23C and 23D.

As indicated herein, the composition/compounds of the present invention comprising an inhibitor of miR-21 and comprising a moiety that delivers said inhibitor of miR-21 to a macrophage, preferably to a lung macrophage, are particularly useful in medical setting and in particular in the prevention and/or treatment of pulmonary fibrosis. The definitions and explanation for the compositions/compounds of the invention as provided herein above and below apply to these compositions/compounds to be used as pharmaceuticals and/or in the herein provide methods of treatment of fibrotic disorders, in particular in the treatment of pulmonary fibrosis. In particular aspects, the corresponding pharmaceutical composition comprising the compounds/compositions of the present invention are in aerosol form. The pharmaceutical composition may be beneficially used in medicine and/or for the use of a medicament. Without being limiting, but in a preferred embodiment, it is envisaged that in the treatment of pulmonary fibrosis the compositions/compounds of the invention are to be inhaled by the patient in need of medical intervention.

The term "treatment" as used herein or grammatical variants thereof covers any treatment of a disease/medical condition/disorder in a subject and includes: (a) preventing and/or ameliorating the disease/medical condition/disorder in a subject which may be predisposed to the disease/medical condition/disorder; (b) inhibiting the disease/medical condition/disorder, i.e. arresting its development; or (c) relieving the disease/medical condition/disorder, i.e. causing regression of the disease/medical condition/disorder. For example, the herein provided composition can be used in the prevention of the pulmonary fibrosis.

The composition provided herein may also be referred to as a pharmaceutical composition. Said pharmaceutical composition comprises an inhibitor of miR-21 and a moiety that delivers said inhibitor of miR-21 to a macrophage. Said inhibitor of miR-21 and said moiety that delivers said inhibitor of miR-21 to a macrophage may be linked/conjugated etc. as also illustrated and explained herein. The pharmaceutical composition may be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations. Embodiments described herein in particular for the medical and/or pharmaceutical uses apply, *mutatis mutantis*, for the here described pharmaceutical compositions.

The composition provided herein may be combined with further drugs/medicaments. For example, the composition provided herein will be administered in the treatment in combination with a pharmaceutical composition for the treatment of viral and/or bacterial infection(s) and anti-inflammatory treatments. Such treatments may include but are not limited to antiviral agents (for example: Remdesivir), beta-adrenergic receptor agonists (for example Salbutamol) and glucocorticoids (for example Dexamethason).

Pharmaceutical compositions or composition may comprise a pharmaceutically acceptable carrier. By "pharmaceutically acceptable carrier" is liquid filler, diluent, encapsulating material or formulation auxiliary of any type.

The invention relates to the use of the composition(s)/compound(s) as provided herein and comprising in particular an inhibitor of miR-21 as well as a moiety that delivers said inhibitor of miR-21 to a macrophage in the treatment of a pulmonary fibrosis. The invention further relates to the use of the composition for the manufacture of a medicament for the treatment of pulmonary fibrosis, wherein the composition comprises said inhibitor of miR-21 and said moiety that delivers said inhibitor of miR-21 to a macrophage. The invention also relates to a method of treatment for pulmonary fibrosis comprising administering to a subject in need of such treatment a composition/compound comprising said inhibitor of miR-21 and said moiety that delivers said inhibitor of miR-21 to a macrophage. In context of this invention also a method of treatment for od of pulmonary fibrosis is provided. Said method of treatment comprising administering to a subject in need of such treatment, in particular a human patient suffering from pulmonary fibrosis or prone to suffer from pulmonary fibrosis, a composition/compound described herein and comprising an inhibitor of miR-21 and a moiety that delivers said inhibitor of miR-21 to a macrophage, preferably to a lung macrophage. The embodiments described herein for the medical and/or pharmaceutical uses apply to this inventive method of treatment *mutatis mutantis*. It is of note that also the herein desired method of treatment of pulmonary fibrosis may comprise also the (co-)administration of further drugs aimed at the amelioration and/or even prevention of a fibrotic conditions. Such drugs may comprise, but are not limited to, glucocorticoids such as dexamethasone, tyrosine kinase inhibitors such as Nintedanib, a receptor blocker for multiple tyrosine kinases or Pirfenidone, an antifibrotic agent that inhibits transforming growth factor beta (TGF-b)-stimulated collagen synthesis.

Again, embodiments described herein in particular for the medical and/or pharmaceutical uses apply, *mutatis mutantis*, for the here described methods of treatment of pulmonary fibrosis and/or pulmonary fibrosis associated or causing fibrosis. A particular method of treatment of the present invention is the treatment of a patient in need of such treatment wherein said patient suffers from pulmonary fibrosis is caused or associated by pulmonary support or mechanical ventilation, in particular following Adult Respiratory Distress Syndrome (ARDS). Such a patient may also comprise a COVD-19 patient.

As used herein, the terms “comprising” and “including” or grammatical variants thereof are to be taken as specifying the stated features, integers, steps or components but do not preclude the addition of one or more additional features, integers, steps, components or groups thereof. This term encompasses the terms “consisting of” and “consisting essentially of.” Thus, the terms “comprising”/“including”/“having” mean that any further component (or likewise features, integers, steps and the like) can/may be present.

The term “consisting of” means that no further component (or likewise features, integers, steps and the like) is present.

The term “about” preferably refers to ±10% of the indicated numerical value, more preferably to ±5% of the indicated numerical value, and in particular to the exact numerical value indicated.

As used herein, the term “about” refers to ±10% of the indicated numerical value, and in particular to ±5% of the indicated numerical value. Whenever the term “about” is used, a specific reference to the exact numerical value indicated is also included. If the term “about” is used in connection with a parameter that is quantified in integers, such as the number of nucleotides in a given nucleic acid, the numbers corresponding to ±10% or ±5% of the indicated numerical value are to be rounded to the nearest integer.

The present invention is further described by reference to the following non-limiting figures and examples. Unless otherwise indicated, established methods of recombinant gene technology were used as described, for example, in Sambrook, Russell “Molecular Cloning, A Laboratory Manual”, Cold Spring Harbor Laboratory, N.Y. (2001) (Sambrook & Russell, 2001)) which is incorporated herein by reference in its entirety.

The present invention is further described by reference to the following non-limiting figures and examples. The Figures show:

FIG. 1. Efficiency of miR-21 inhibition using locked nucleic acid-modified antisense miR-21. (A) Expression of miR-21 in postischemic myocardium. SHAM n=3; I/R injury n=3-6. (B) Experimental strategy. Pigs underwent catheterization with balloon occlusion of the left anterior descending (LAD) coronary artery for 60 minutes, followed by reperfusion for 33 days. The miR inhibitor, locked nucleic acid-modified antisense miR-21 (LNA-antimiR-21) was applied regionally with a catheter at day 5 and day 19 during reperfusion injury. 10 mg LNA-antimiR-21 was infused into the left anterior descending artery (LAD) and the left circumflex artery (LCx) in the ratio 3:2. Upper panel: sequences of miR-21 (SEQ ID NO: 4), LNA-antimiR-21 (SEQ ID NO: 1) and LNA-antimiR-Control (SEQ ID NO: 5). Grey region indicates the seed sequence and bases complementary to miR-21 are shown in red. (C) Quantitative analysis of miR-21 expression after regional application of LNA-antimiR-21 or LNA-antimiR-Control. HF Control n=4; HF LNA-antimiR-Control n=3; HF LNA-antimiR-21 n=5. Data denote mean and individual values and were analysed using one-way ANOVA (B) or two-way ANOVA (C) with Sidak’s post-test. **P<0.01.

Figure 2:
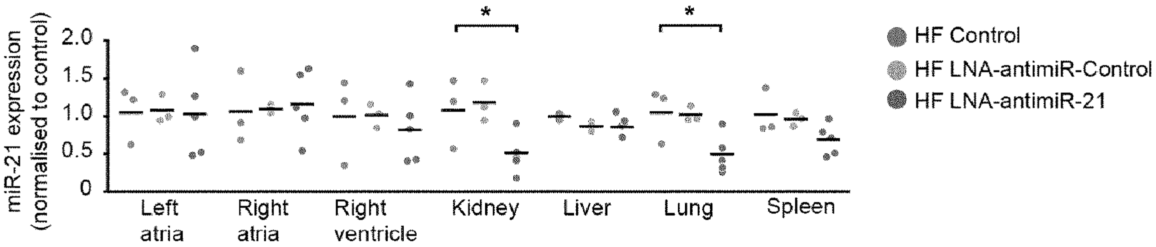

FIG. 2. Quantification of miR-21 expression in right ventricle, left atria, right atria, liver, lung, kidney and spleen after inhibition of miR-21 using LNA-antimiR-21. LNA-antimiR-21 was applied regionally with a catheter at day 5 and day 19 during reperfusion injury. Expression of miR-21 in other regions of the heart (left atrium, right atrium and right ventricle) and in other organs (kidney, liver, lung and spleen). HF Control n=3; HF LNA-antimiR Control n=3; HF LNA-antimiR-21 n=5. Data denote mean and individual values and were analyzed using one-way ANOVA with Sidak’s post-test. *P<0.05.

FIG. 3. Inhibition of miR-21 protects pig hearts from I/R-induced cardiac hypertrophy and myocardial fibrosis. (A) Ratio of heart weight to body weight (HW/BW). (B) Top, wheat germ agglutinin staining in representative myocardial sections in the border zone of hearts. Bottom, quantification of data. (C) Top, representative stainings of myocardial samples by Sirius red/Fast green. Bottom, quantification of data. (D) Quantitative analysis of vimentin staining (fibroblast marker) for the border zone of hearts. (E) Quantitative analysis of CD68 staining (macrophage marker) for the border zone of hearts. (F) Capillary density was determined by staining myocardial sections with an antibody against CD31 in the border region. Representative images and quantification. (G) Quantitative assessment of mRNA levels of collagen genes (Col1a1, Col1a2 and Col3a1), smooth muscle actin (Acta2) and myocyte hypertrophy-associated genes (Nppa, Nppb and Myh7). Scale bars: 50 μm (B), 500 μm (C) and (D). n>300 cells with central nuclei per heart (B). n>10000 cells per heart (D, E and F). Sham Control n=3; HF Control n=4; HF LNA-antimiR Control n=3; HF LNA-antimiR-21 n=5. Data denote mean and individual values and were analysed using one-way ANOVA with Sidak’s post-test. *P<0.05, P<0.01, *P<0.001 and ****P<0.0001.

FIG. 4. Catheter-based local application of LNA-antimiR-21 improves global and regional myocardial function. Pigs underwent percutaneous ischemia/reperfusion (60 min/33 days) injury and LNA-antimiR-21 or LNA-antimiR-Control was applied regionally with a catheter at day 5 and day 19 during reperfusion injury. (A) Representative pressure-volume loop tracings obtained at d33 after I/R. (B-E) Indices of global myocardial function as measured by PV-analysis; (B) left ventricular end-diastolic pressure, (C) stroke volume, (D) Contraction velocity, (E) relaxation velocity of the left ventricle. (F) Subendocardial segment shortening as determined by sonomicrometry as a measure of regional myocardial function. Analysis was performed 33 days after ischemia/reperfusion injury under rest or after pacing with 120 bpm and 140 bpm. (G) Ejection fraction as determined by fluoroscopy before I/R injury and at day 33 after reperfusion. HF Control n=4; HF LNA-antimiR Control n=3; HF LNA-antimiR-21 n=5. Data denote mean and individual values and were analysed using-two-way ANOVA with Sidak’s post-test. *P<0.05, P<0.01 and *P<0.001.

Figure 5:
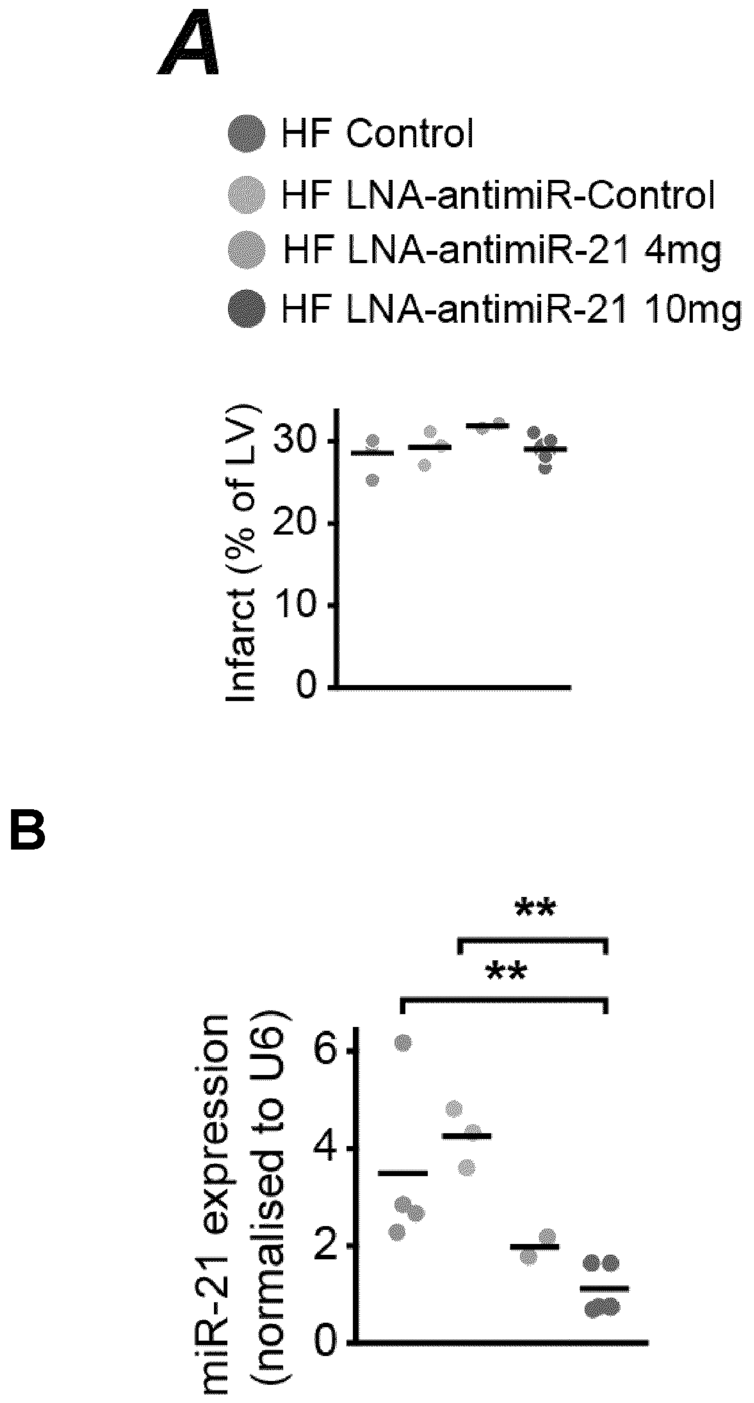
Figure 5:
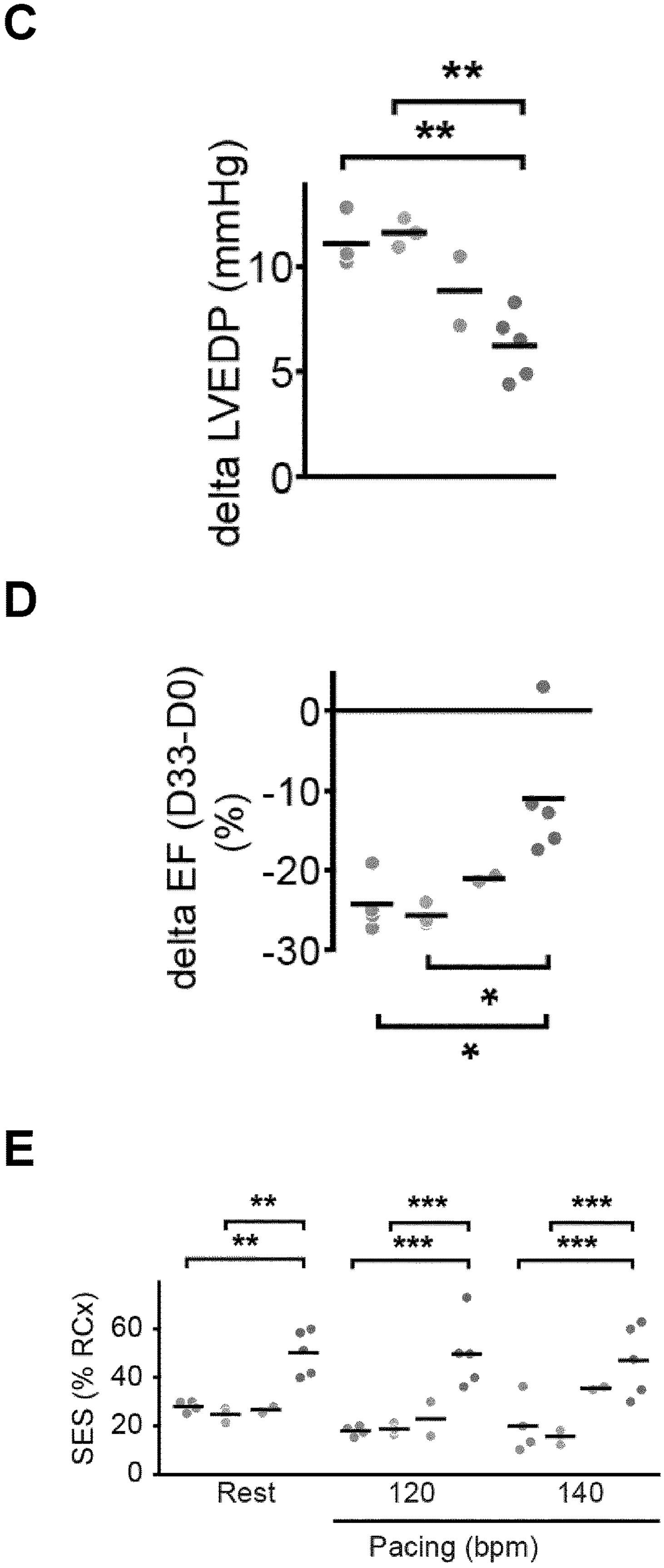

FIG. 5. Inhibition of miR-21 prevented I/R-induced loss of cardiac function in a dose-dependent manner. Pigs underwent ischemia/reperfusion injury and received either 4 mg or, 10 mg of LNA-antimiR-21 at day 5 and day 19 after surgery. This figure also refers to data presented in FIG. 1C, 4 to directly compare 4 mg LNA-antimiR-21 dosage to that of 10 mg. (A) Quantification of infarct sizes. (B) Quantitative analysis of miR-21 expression. (C) Analysis of left ventricular end-diastolic pressure. (D) Quantification of ejection fraction. (E) Analysis of regional myocardial function using sonomicrometry. HF Control n=4; HF LNA-antimiR-Control n=3; HF LNA-antimiR-21 (4 mg) n=2; HF LNA-antimiR-21 (10 mg) n=5. Data denote mean and individual values and were analysed using unpaired one-way ANOVA. P<0.01 and *P<0.001.

FIG. 6. Differential expression analysis reveals de-repression of miR-21 targets after LNA-antimiR-21 application. (A) Scheme for RNA sequencing. RNA sequencing libraries were generated from 4 μg total RNA samples isolated from myocardial ischemic tissue using TruSeq Stranded mRNA sample preparation kit. Sequencing was carried out on a HiSeq4000 (Illumina) and the analysis was carried out using an in-house Galaxy platform. n=3 per group. (B) Principal component analysis. Principal Component 1 (PC1, x-axis) represents 59.5% and PC2 (y-axis) represents 40.5% of total variation in the data (TPM>=3; n=8432). (C) Cumulative distribution and median fold change plots of differential expression for all genes and broadly conserved miR-21 targets containing 8-mer, 7-mer-m8 or 7-mer-A1 binding sites as predicted by TargetScan Human (version 7). Bar graphs show median mRNA fold change with interquartile range. Data was analyzed using Kolmogorov-Smirnov test. ***P<0.001. (D) Gene ontology enrichment of biological processes for highly deregulated genes (log fold change greater than 2 or less than −2, adjusted p-value<0.05) between HF LNA-antimiR-Control and Sham (left), and HF LNA-antimiR-21 and HF LNA-antimiR-Control (right). Grey dotted line indicates P<0.05 for the GO terms. (E) Chord diagram showing the deregulated genes and their associated gene ontology terms. (F) Immunoblot directed against phosphorylated (p-ERK) and unphosphorylated ERK (t-ERK) performed on myocardial tissue lysates. GAPDH was used as loading control. (G) Percentage of phospho-ERK positive cardiac fibroblasts in the pig myocardial tissue. Immunofluorescent staining was performed on myocardial sections against phospho-ERK, Vimentin (VIM; mesenchymal cell marker) and CD31 (endothelial cell marker). Nuclei was stained with DAPI. Cells that were positive for VIM and negative for CD31 were considered as cardiac fibroblasts. Scale bar: 50 μm. Sham Control n=3; HF Control n=4; HF LNA-antimiR-Control n=3; HF LNA-antimiR-21 n=5. Data denote mean and individual values and were analysed using one-way ANOVA. *P<0.05.

Figure 7:
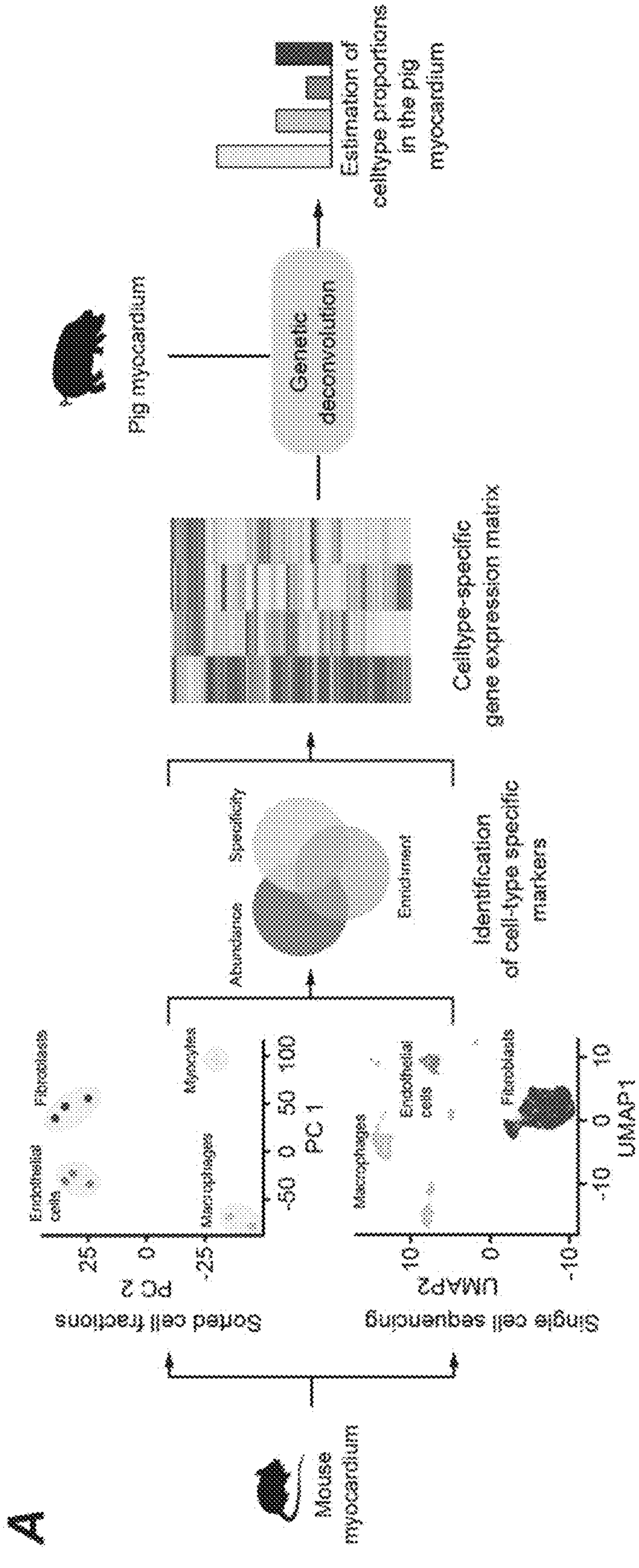
Figure 7:
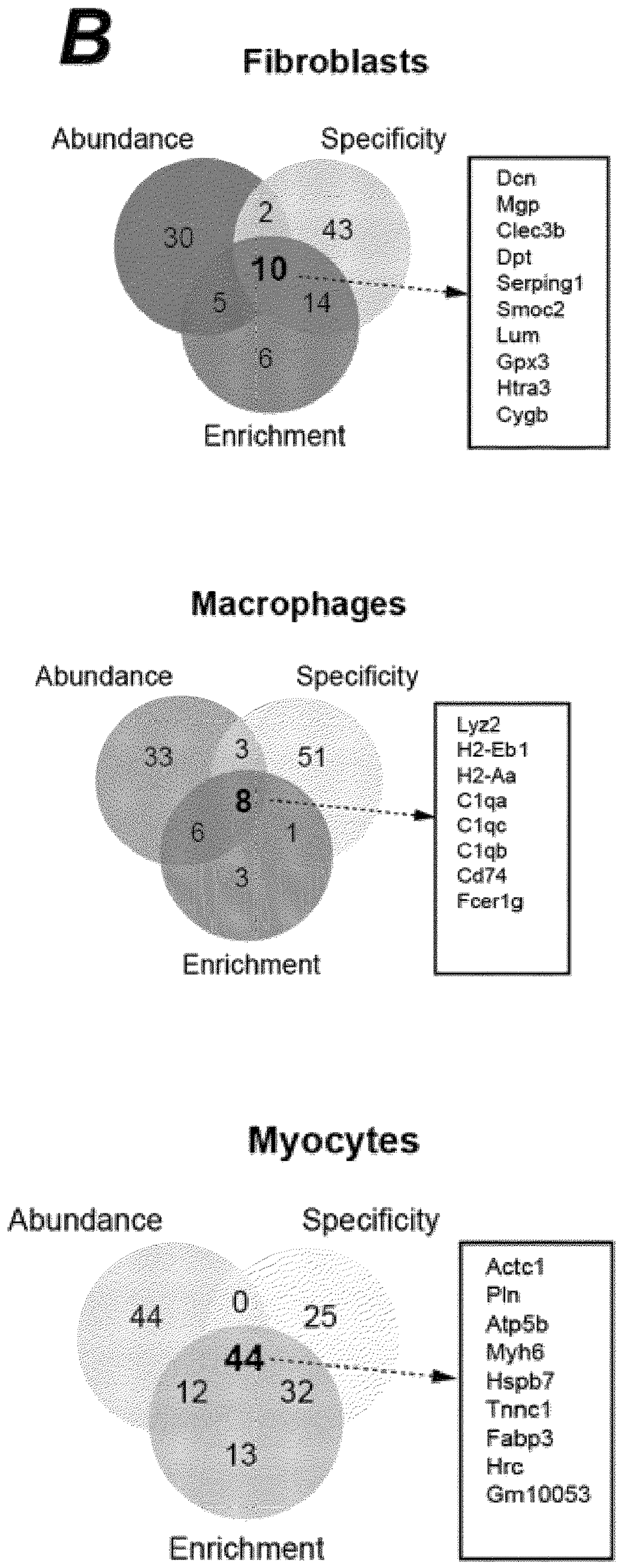
Figure 7:
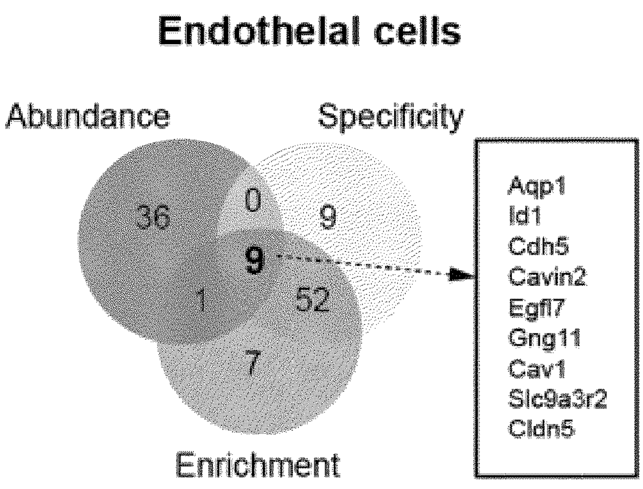
Figure 7:
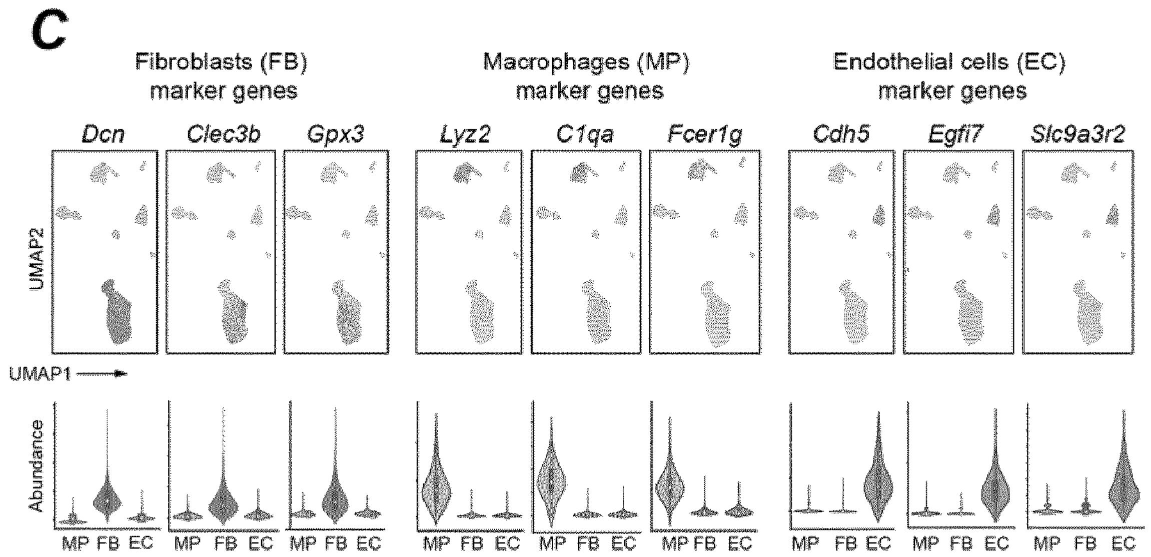
Figure 7:
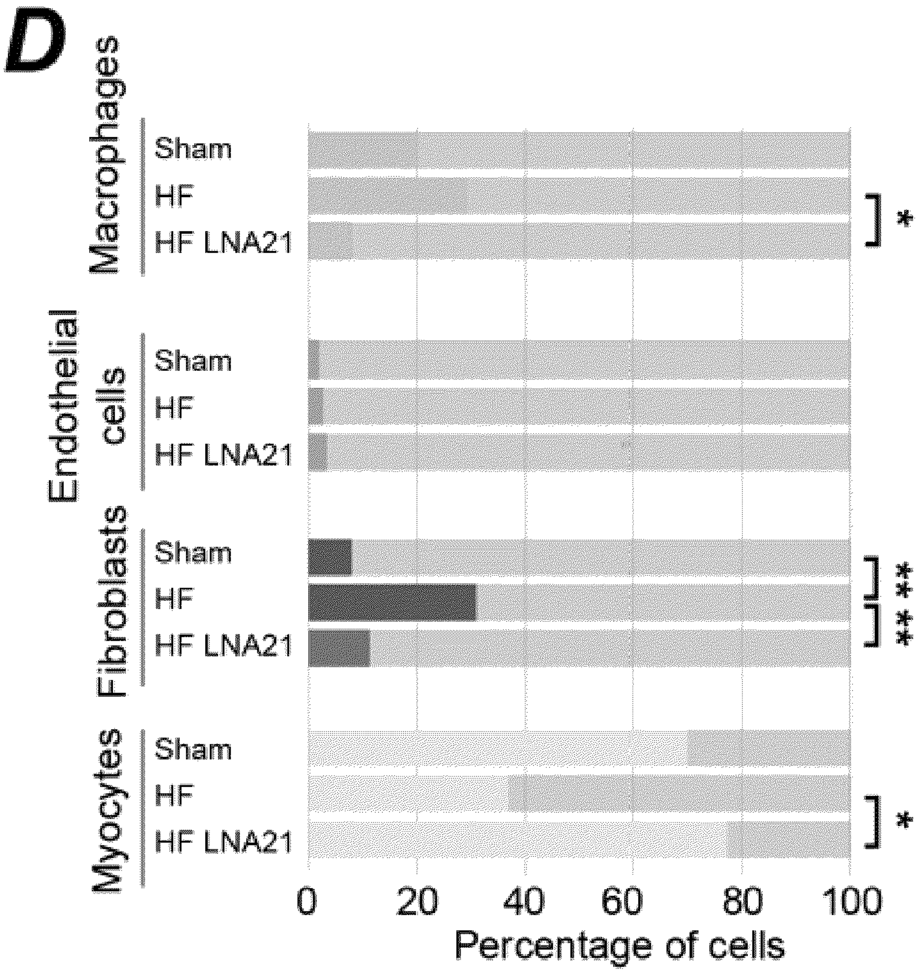

FIG. 7. Next generation RNA sequencing coupled with genetic deconvolution reveals a critical role of macrophages and fibroblasts in antimiR-21-treated pig myocardium. (A) Overview of genetic deconvolution. (B) Intersections among genes for consensus rankings based on abundance, specificity and enrichment for the gene across cell types. (C) UMAP feature and violin plots of the top three enriched genes in the signature matrix for macrophages, endothelial cells and fibroblasts. (D) Relative cell type proportion estimates for pig myocardium from bulk and single cell RNA expression for myocytes, endothelial cells, fibroblasts and macrophages. Sham Control n=3; HF Control n=3; HF LNA-antimiR-21 n=5. Data denote mean and individual values and were analyzed using one-way ANOVA with Sidak's post-test. *P<0.05 and **P<0.01.

FIG. 8. miR-21 is the most abundant and enriched microRNA in cardiac macrophages. (A) Scheme for cell isolation. (B) MiRNA expression profiles in different myocardial celltypes. Pie graph representation of miRNAs in cardiac macrophages and other myocardial cell types (myocytes, fibroblasts and endothelial cells) isolated from hearts of wildtype mice. (C) Expression of miR-21a-5p in different myocardial cell types. (D) Wild type mice were either subjected to transverse aortic constriction (TAC) or received sham surgery as a negative control. Pie graph representation of miRNAs in cardiac macrophages isolated from hearts of wildtype mice 6 days after pressure overload. 6 days after TAC n=5. (E) Relative expression of miR-21-5p as determined by SYBR-green based quantitative real time PCR in cardiac macrophages isolated from hearts 6 or 21 days after pressure overload. Sham n=6; 6 days after TAC n=5, 21 days after TAC n=3. (F) Measured copies of miRNA (bars) and corresponding 3'-UTR target pools (black line) in total reads per million (TPM) for the top expressed miRNAs in cardiac macrophages isolated from WT mice after sham or TAC surgery. miR-21 is denoted in red colour. Y-axis is log scale. n=3 per group. (G) Macrophage-specific miR-21-deficient (miR-21 cKO) mice was generated by crossing miR-21-floxed mice with a mouse line expressing Cre recombinase driven by Cx3cr1 promotor that is specifically active in resident macrophages. Expression of miR-21 in cardiac macrophages. Data denote mean and individual values and were analyzed using one-way analysis of variance (ANOVA). WT n=3; miR-21 cKO n=5. Data denote mean and individual values and were analyzed using either Students' t-test. *P<0.05, P<0.01 and P<0.001.

FIG. 9. Macrophage-specific deletion of miR-21 prevents pressure overload-induced myocardial remodeling in mice. Eight-weeks old wildtype and miR-21 cKO mice were subjected to either TAC or Sham surgery and harvested the hearts four weeks later. Cardiac function was monitored by echocardiography carried out before surgery, 2-weeks after surgery and at the end of the experiment (4-weeks after surgery). (A) Experimental strategy. (B) Sirius red/fast green staining of representative myocardial sections and quantification of extracellular matrix. (C) Representative myocardial sections stained with wheat germ agglutinin (WGA) and quantification of cardiomyocyte area. (D) Quantitative PCR assessment of mRNA levels of Collagen genes (Col1a1, Col1a2), Acta2, Myh7 and Nppa. (E) Assessment of cardiac function as measured by left ventricular ejection fraction. (F) Representative speckle tracings of cardiac strain measured using Vevostrain software at systole and diastole. (G) Quantification of peak radial strain (%), peak longitudinal strain (%) and peak circumferential strain (%). Scalebar represents 2 mm (B) and 100 mm (C). WT Sham n=6; miR-21 cKO Sham n=7; WT TAC n=10; miR-21cKO TAC n=7. Data denote mean and individual values and were analyzed using either Students' t-test (A) or two-way analysis of variance (ANOVA) with Sidaks' post test (B-G). *P<0.05, P<0.01 and *P<0.001.

FIG. 10. Single cell sequencing reveals accumulation of resident-like macrophages in the heart after specific deletion of miR-21 in cardiac macrophages. (A) Experimental workflow of single cell sequencing of non-cardiac myocyte cells isolated from wildtype and miR-21 cKO mice hearts 6 days after TAC surgery. Barcoded cDNA libraries were generated using 10× Chromium Single Cell 3'-Library kit reagents, sequencing was carried out using HiSeq4000 and analysed using cell ranger and Seurat packages. (B) UMAP-distributed plots showing dimensional reduction of the distribution of wildtype and miR-21 cKO single cell transcriptomes, and the grouping of cells based on their gene expression. (C) Violin plots showing expression of marker genes for macrophages, resident-like and inflammatory macrophages. (D) Pie graph representing different macrophage clusters. (E) Gene ontology (GO) enrichment analysis on Biological processes of top 200 deregulated genes in resident-like macrophages in WT TAC vs WT Sham and miR-21 cKO TAC vs WT TAC. Chord diagram showing associations of genes related to top over-represented gene ontology terms.

(F) RNA velocity indicates a faster shift to M2-like macrophages from M1-like macrophages in miR-21 cKO mice compared to WT controls. (G) Expression of pro-inflammatory genes (Tnf, Il6, Nos2) in LNA-antimiR-21 or LNA-antimiR control treated bone marrow-derived macrophages with and without stimulation with 5 ng/mL of lipopolysaccharide (LPS). n=6. Data denote mean and individual values and were analyzed using two-way analysis of variance (ANOVA) with Sidaks' post test. P<0.01, *P<0.001 and ****P<0.0001.

FIG. 11. Analysis of ligand receptor pairing in single cell transcriptomics data sets identifies the cardiac macrophage as primary paracrine inducer of fibroblast activation. (A) Chord diagram summarizing significantly upregulated paracrine and autocrine interactions among different cardiac cell fractions in WT and miR-21 cKO mice. The line color indicates ligands broadcast by the cell population of the same color. The line thickness is proportional to the number of ligands where cognate receptors are present in the recipient cell population and numbers indicate the quantity of ligand-receptor pairs for each inter-population link. Ligand or receptor is considered to be expressed when it is detected in at least 20 percent of a cell population. Largest number of interactions occurred from M1-like macrophages towards activated fibroblasts (Postn+) in wildtype that was repressed in miR-21 cKO mice. (B) Detailed view of Paracrine interactions from M1-like macrophages towards activated fibroblast (Postn+) cells. (C) RNA velocity indicates a repression of differentiation of activated fibroblasts to myofibroblasts in miR-21 cKO mice compared to WT controls. (D) Pie graph representing different macrophage clusters. (E) Experimental strategy for co-culture of adult mouse cardiac fibroblasts (AMCF) and bone marrow-derived macrophages (BMDM). Macrophages were differentiated form bone marrow progenitor cells and then transfected with either 100 nM LNA-antimiR-21 or LNA-antimiR-Control and stimulated with LPS. Freshly isolated AMCFs were co-cultured with LNA-antimiR-21-treated BMDMs (after washing with PBS) for 48 hours. Monocultures of AMCF served as negative control. Immunofluorescent staining was carried out against Vimentin (VIM; marker for fibroblasts) and c-smooth muscle actin (ACTA2; marker for myofibroblasts). Nuclei were stained with DAPI. Fibroblast activation was measured by ACTA2 expression. (F) Percentage of ACTA2 positive cardiac fibroblasts. N=4-6 independent experiments carried out in triplicates. Data are mean and individual values and were analysed using two-way ANOVA with Sidak's post-test. ***P<0.001.

FIG. 12. MiR-21 is the most abundant and enriched microRNA in lung macrophages. (A) Flow cytometry strategy for the isolation of alveolar and interstitial macrophages. (B) MicroRNA expression profiles determined by small RNA sequencing of total lung cells and macrophage populations. Pie graph representation of miRNAs in total lung cells, alveolar and interstitial macrophages isolated from lungs of wildtype mice. n=3 mice per group. (C) Expression of miR-21 by quantitative real time PCR in different pulmonary cell types showed an enrichment of miR-21 in macrophage populations. n=3. Data are mean±s.e.m.

FIG. 13. MiR-21 is upregulated in mice and humans after lung injury. (A) MiR-21 is elevated in mice after lung injury. Expression of miR-21 in lung tissues harvested from mice 14 days after administration with either PBS or bleomycin. PBS n=8; Bleomycin n=9. (B) MiR-21 is increased in lung tissue from idiopathic pulmonary fibrosis (IPF) patients. (C-D) Inhibition of miR-21 protects pig hearts from I/R-induced lung fibrosis. (C) LNA-antimiR-21 was applied regionally with a catheter at day 5 and day 19 during ischemia reperfusion injury in pigs (see also FIG. 1). Quantitative analysis of miR-21 expression in lung tissue after regional application of LNA-antimiR-21 or LNA-antimiR Control in pig hearts. HF LNA-antimiR Control n=3; HF LNA-antimiR-21 n=5. (D) Quantification of I/R-induced lung fibrosis. Data are mean±s.e.m. and were analysed using Student's t-test. *P<0.05 and **P<0.01.

FIG. 14. Myofibroblast-specific deletion of miR-21 prevents pressure myocardial infarction-induced myocardial remodeling in mice. Myofibroblast-specific miR-21-deficient (Postn miR-21 cKO) mice was generated by crossing miR-21-floxed mice with a mouse line expressing inducible mer-cre-mer recombinase (MCM) driven by periostin (Postn) promotor that is specifically active in myofibroblasts. Eight-weeks old wildtype and miR-21 cKO mice were subjected to either myocardial infarction (MI) or Sham surgery. Echocardiography was carried out in mice 1 week after surgery to assess cardiac dysfunction and tamoxifen (40 mg/kg/d) was administered intraperitoneally into the mice for 5 days to achieve deletion of miR-21 specifically in myofibroblasts. Hearts were harvested four weeks later. (A) Experimental strategy. (B) Expression of miR-21 in cardiac fibroblasts in mice two days after the last tamoxifen injection. (C) Ratio of heart weight to tibia length (HW/TL). (D) Ratio of lung weight to tibia length (LW/TL). (E) Assessment of cardiac function as measured by left ventricular ejection fraction at day 28 after MI surgery. (F) Quantification of end diastolic volume and end systolic volume at day 28 after MI. (G) Quantification of peak radial strain (%). WT Sham n=4; Postn miR-21cKO Sham n=5; WT MI n=7; Postn miR-21cKO MI n=8. Data denote mean and individual values and were analyzed using two-way analysis of variance (ANOVA) with Sidaks' post test. *P<0.05, P<0.01 and *P<0.001.

FIG. 15. Antibody-conjugated oligonucleotides. An exemplary method to conjugate a 5'-amine-modified oligonucleotides to ligands or antibody (or antibody fragments thereof) to receptors that are specifically enriched in the target cell type. Antibodies can be digested with pepsin to obtain smaller antibody fragments.

FIG. 16. Table1. Serological analysis of selected biochemical parameters of liver and kidney function.

FIG. 17. Table2. Cardiovascular events.

Figure 18:
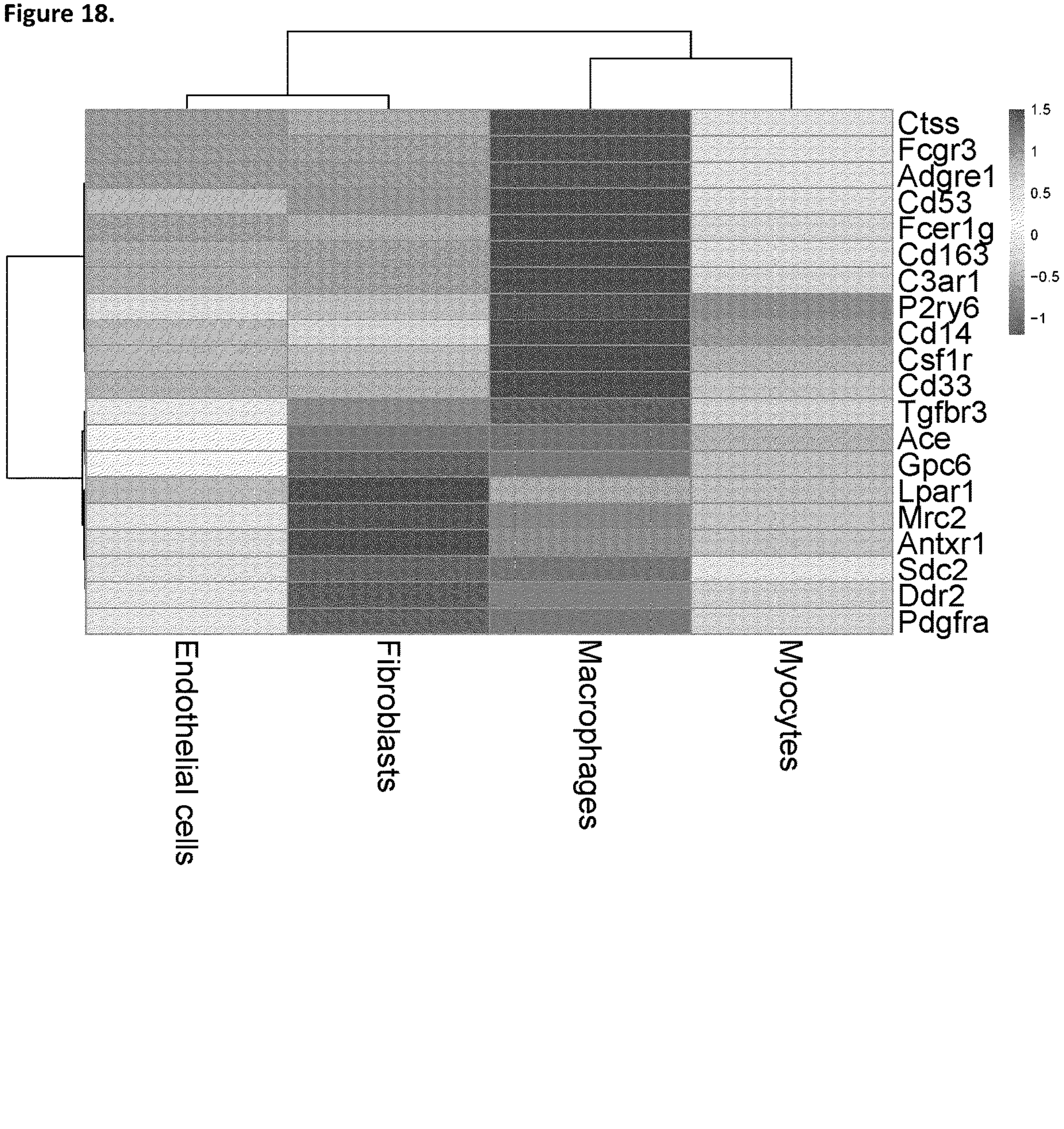

FIG. 18. Heat map depicting candidate receptors for the targeting of anti-miR-21 to macrophages and/or fibroblasts in human lung and heart tissue as identified by RNA sequencing of purified primary cell fractions. Data are from deep RNA sequencing of whole transcriptomes, filtered for cell type-specificity and then clustered. Red depicts relative enrichment, blue relative depletion compared to the other cell types depicted. The lower left corner lists top candidate surface receptors that represent candidate targets for macrophage targeting.

The present invention is additionally described by way of the following illustrative non-limiting examples that provide a better understanding of the present invention and of its many advantages.

Figure 19:
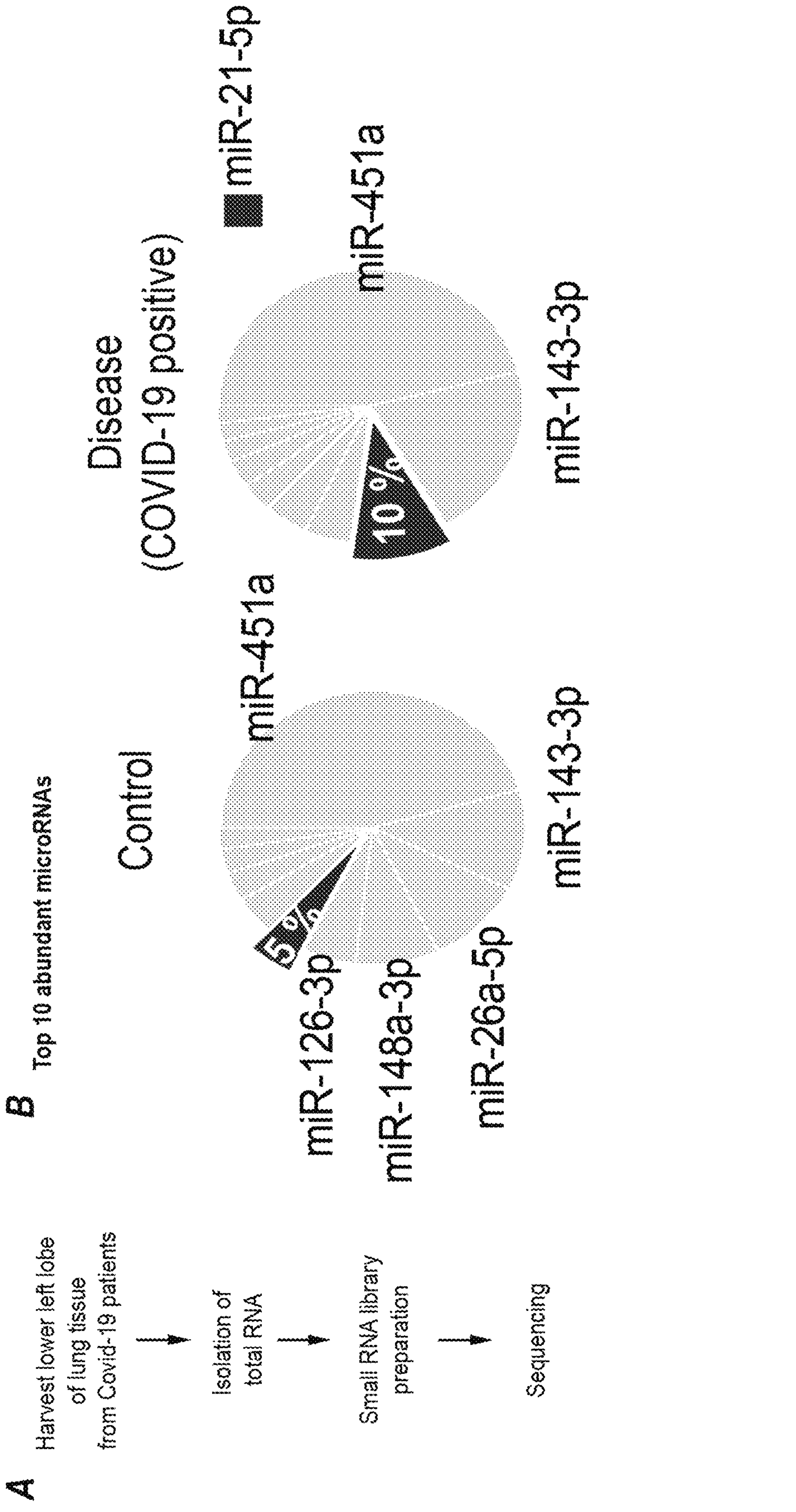

FIG. 19. MiRNA-21 is upregulated in lung tissue harvested from Covid-19 patients. (A) Scheme. Human lung tissues were harvested and similar regions of the lower left lobes from Covid-19 patients and control subjects were used for RNA extraction. Small RNA library was generated using the NEB Next Small RNA library kit and the samples were sequenced using MiSeq. (B) MiRNA expression profile in the lung tissue. Pie graph representation of the top 10 abundant miRNAs in the lung tissue in Covid-19 patients and control subjects. Control subjects n=3; Covid-19 patients n=3.

Figure 20:
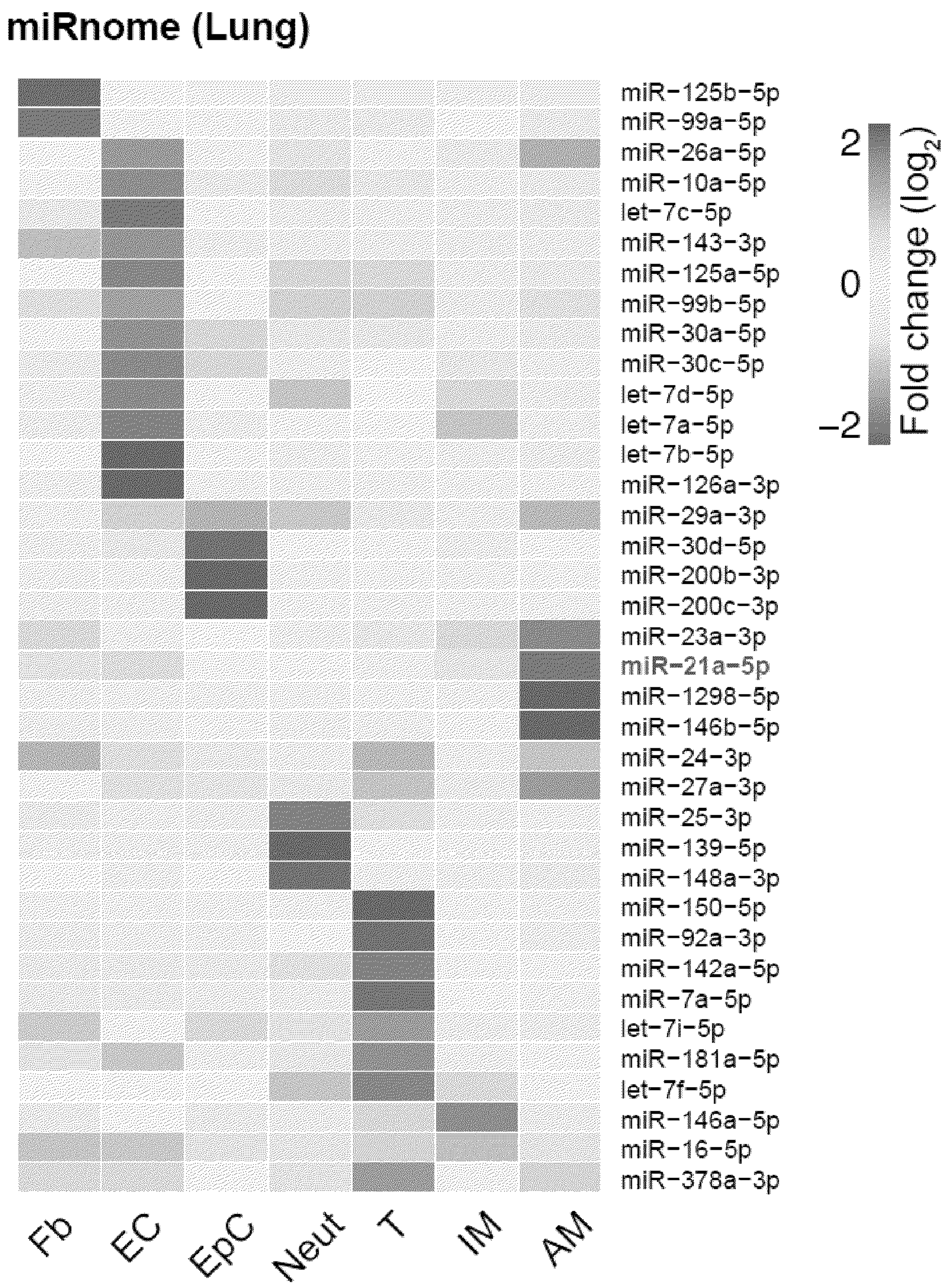

FIG. 20. MiR-21 is enriched in macrophages in murine lung. MiR-21 is enriched in alveolar macrophages (AM) in the mouse lung. Heatmap representation of differentially expressed miRNAs (log 2 foldchange >=1 or log 2 foldchange <=−1 and p-adjusted value <=0.05) across pulmonary cell types (n=1-3 for each cell type) in different cell types: Fibroblasts (Fb), endothelial cells (EC), epithelial cells (EpC), neutrophils (NeuT), T-cells (T) and interstitial macrophages (IM).

Figure 21:
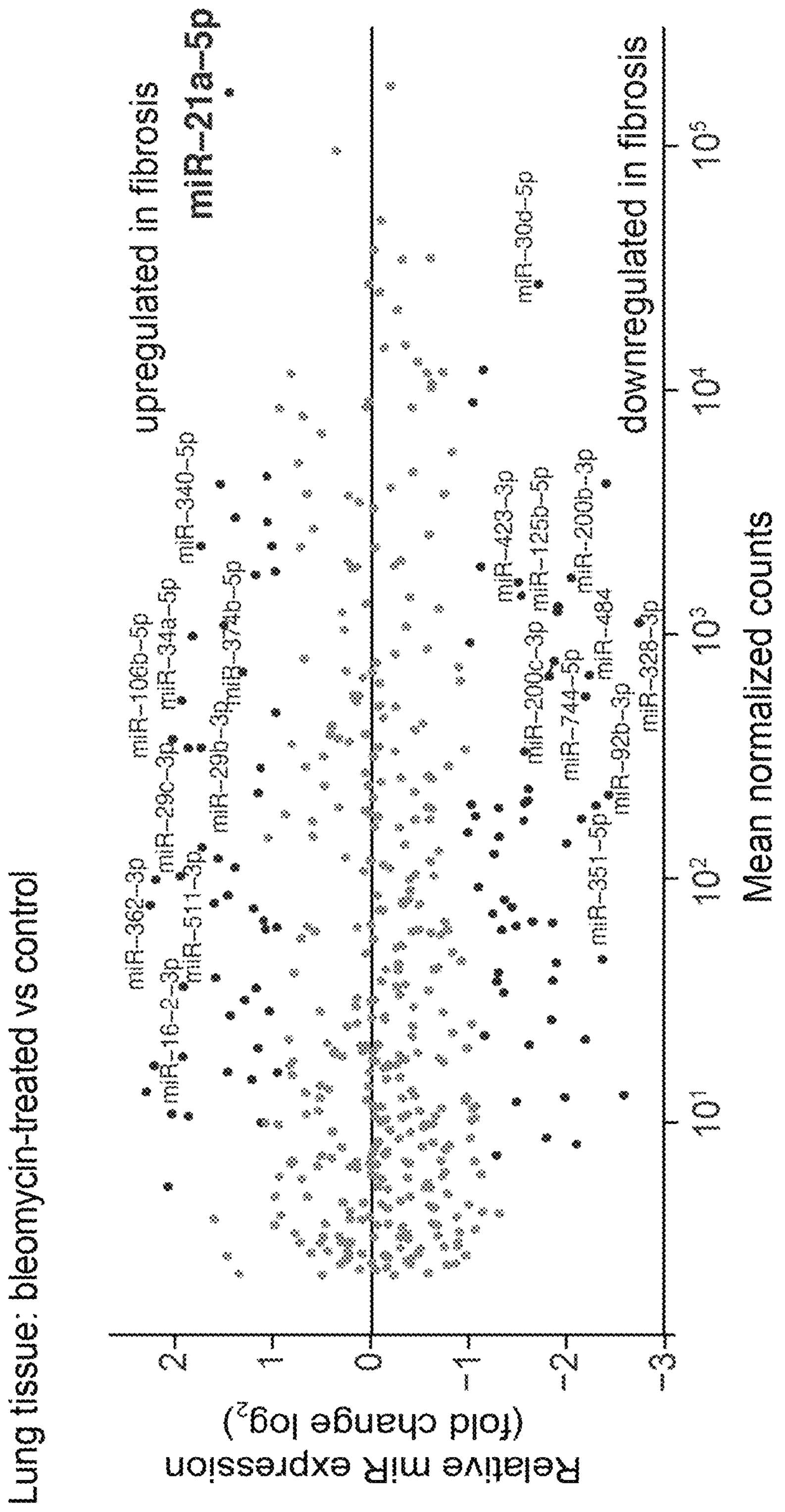

FIG. 21. MiR-21 is upregulated in lung tissue from a mouse model of pulmonary fibrosis. Bleomycin was administered into the mouse lungs using a microsprayer and 7 days later the lung tissue was harvested. Total RNA was extracted, and the miRNA libraries were prepared using NEBNext Small RNA library preparation kit and sequenced in MiSeq sequencer. Sequencing reads were analysed using miRDeep2 and the differentially expressed miRNAs were identified by DESeq. Significantly de-regulated microRNAs (FDR<0.05) are indicated in red colour.

FIG. 22. Mannose receptor C type 1 (MRC1) is expressed by macrophages in lung tissue. (A) Strategy to identify candidate surface receptors that are enriched in lung macrophages. (B) Relative abundance of Mrc1 in alveolar and interstitial macrophages. (C) Expression of Mrc1 in different pulmonary cell types. (D) Feature plot showing expression of Mrc1 in single cell transcriptomes generated from mouse lungs 14 days after bleomycin (GSE141259; PBS n=7; bleomycin n=4). (E) Representative immunofluorescence staining of 5 m mouse bleomycin-treated lung sections using an antibody against MRC1. Nuclei were stained with Sytox green. Scalebar represents 200 μm. (F) Feature plot showing expression of Mrc1 in single cell transcriptomes generated from control and IPF (idiopathic pulmonary fibrosis) human lungs (GSE135893; Control n=10; IPF n=12).

FIG. 23. Exemplary chemical structures of mannose receptor C type 1 ligands. (A) Scheme showing design of ligand conjugation and antimiR-21. (B) Exemplary chemical structures of mannose-receptor ligand conjugated antimiR-21 molecules. N-acetylgalactosamine (GalNAc) (Top) or mannose (Bottom) ligands were conjugated to 5'-end of LNA-antimiR-21 (SEQ ID NO: 1). (C & D) Exemplary chemical structures of mannose-receptor ligand conjugated antimiR-21 molecules. N-acetylgalactosamine (GalNAc) (D) or mannose (C) ligands were conjugated to 5'-end of LNA-antimiR-21.

FIG. 24. Ligand-conjugated anti-miR-21 for targeted delivery to macrophages. (A) Experimental strategy. Wild type mice were administered with 1.25 mg/kg of either mannose, -GalNAc- or unconjugated LNA-antimiR-21-FAM by inhalation using Flexivent nebulization unit. Mice that received PBS served as negative control. Two hours later, mice were sacrificed and bronchoalveolar lavage fluid (BALF) was collected by sequential instillation and aspiration of ice-cold PBS containing 2 mM EDTA. Lungs were then harvested, subjected to enzymatic digestion and enriched for immune cells by magnetic microbeads-conjugated anti-CD45 antibody. Immune cell enriched fractions were either stained with antibodies against CD45, F4/80 and MRC1 for macrophages (MP), or with antibodies against CD45, CD3 and Ly6G for T cells and neutrophils (N). The flow through cell suspension enriched for non-immune cell fractions were stained with antibodies against CD45, EPCAM, CD105 and CD140a to analyse epithelial cells (Ep), endothelial cells (EC) and fibroblasts (FB) respectively. Anti-CD45 antibody was used in the non-immune cell fractions to exclude leukocytes. The cells were then assessed for FAM signal intensity using flow cytometry. (B) Percentage of FAM-positive macrophages isolated from BALF. (C) Percentage of FAM-positive cells in different cell types of the lung. Unconjugated: PBS n=3, 0.625 mg/kg n=3, 1.25 mg/kg n=3, 2.5 mg/kg n=3. Mannose-conjugated: PBS n=3, 1.25 mg/kg n=3. GalNAc-conjugated: PBS n=2, 0.625 mg/kg n=2, 1.25 mg/kg n=2, 2.5 mg/kg n=2. Data are mean and individual values and were analysed using two-way ANOVA with Tukey's post-test. Comparison was only carried out between unconjugated- and mannose-conjugated LNA-antimiR-21-FAM groups. *P<0.05. GalNAc: N-acetylgalactosamine. FAM: fluorescein amidites.

FIG. 25. Assessment of mannose-conjugated LNA-antimiR-21-FAM uptake by macrophages from BALF and lung tissue using flow cytometry. (A) Median fluorescence intensity of FAM signal in macrophages from BALF and lung tissue. (B) Representative histogram of macrophage subsets. Unconjugated: PBS n=3, 1.25 mg/kg n=3. Mannose-conjugated: PBS n=3, 1.25 mg/kg n=3. Data are mean and individual values and were analysed using Students' t-test. *P<0.05. FAM: fluorescein amidites.

FIG. 26. Inhibition of miR-21 reduced bleomycin-induced pulmonary remodeling and lung dysfunction. (A) Experimental strategy. Mice were administered with PBS or bleomycin (2 U/kg) into the mouse lungs using a microsprayer. The mannose-conjugated micro-ribonucleic acid (miR) inhibitor locked nucleic acid (LNA)-modified antisense miR-21 (2.5 mg/kg) was applied by inhalation using a Flexivent nebulizer at day 4 after bleomycin-induced lung injury. 10 days after antimiR application, lung function was assessed using Flexivent and lungs were harvested for morphometric analysis. (Bottom) Sequences of miR-21 (SEQ ID NO: 4), LNA-antimiR-21 (SEQ ID NO: 1) and LNA-antimiR-mismatch-21 (control) (SEQ ID NO: 5). (B) Representative staining of lung tissues using Sirius red/Fast green and quantification of the same. Scale bar represents 100 μm. (C) Mean tracings of pressure-volume loop curves. Gray shaded area behind the curves indicates standard error mean. (D-F) Lung function as indicated by quasi-static elastance (D), quasi-static compliance (E) and inspiration capacity (F). Mannose-conjugated LNA-antimiR-mismatch-21: PBS n=3, bleomycin n=7. Mannose-conjugated LNA-antimiR-21: PBS n=3, bleomycin n=6. Data are mean and individual values and were analyzed using 2-way ANOVA with Tukey's post test. *P<0.05, P<0.01 and *P<0.001.

FIG. 27. Mannose receptor C type 1 (MRC1) is expressed by macrophages in mouse hearts. (A) Strategy to identify candidate surface receptors that are enriched in heart. (B) Relative enrichment and abundance of surface receptors in macrophages compared to other myocardial cell types. (C) Expression of Mrc1 in different myocardial cell types. (D) Feature plot showing expression of Mrc1 in single cell transcriptomes generated from mouse hearts 6 days after pressure overload. (E) Relative enrichment and abundance of surface receptors in fibroblasts compared to other myocardial cell types.

EXAMPLE 1

Inhibition of miR-21 by Local Delivery of LNA-antimiR-21

The expression of miR-21 in left ventricular (LV) myocardium of a large animal model of heart failure was determined, namely in pigs subjected to transient occlusion (60 min) of the left anterior descending artery (LAD). In a pilot experiment, animals were followed for 1, 7 or 28 days before euthanasia and removal of the hearts for further analysis (FIG. 1A). The expression of miR-21 was progressively upregulated in both remote and border zone regions of LV myocardium (FIG. 1A). Because of this expression kinetics and a reported anti-apoptotic role for miR-21 in cardiac myocytes in acute ischemia (Sayed et al., 2010), the following experimental design was employed: pigs were subjected to I/R, left untreated for 5 days to allow for scar formation and were then given two times (days 5 and 19 after I/R) locked nucleic acid (LNA)-modified antimiR-21 (LNA-antimiR-21) locally into the coronaries (FIG. 1B). We chose a phosphorothioate-modified, 15 nucleotide, LNA/DNA mixmer design to inhibit miR-21 with high specificity and efficacy. 10 mg of LNA-antimiR-21 (a phosphorothioate-modified, 15 nucleotide, LNA/DNA mixmer) or control was infused into the left anterior descending artery (LAD) and the left circumflex artery (LCx) in a ratio of 3:2 and over a time period of 3 minutes per vessel with concomitant occlusion of the vessel by an angioplasty balloon (FIG. 1B). At 33 days after I/R injury, intracoronary delivery of LNA-antimiR-21 led to a significant reduction of miR-21 (−66%) as detected by quantitative RT-PCR on RNA prepared from LV ischemic myocardium (FIG. 1C). Interestingly, the repression of miR-21 appeared to preferentially occur in the border zone vs. remote region of the myocardium, suggesting preferential uptake in ischemic tissue. Regional application of LNA-antimiR-21 likewise did not alter miR-21 levels in other regions of the heart, right ventricle, left atria and right atria (FIG. 2). Consistent with previous results of local antimiR application in pigs (Hinkel et al., 2013), we observed a modest, but significant reduction of miR-21 in the kidney and in the lung (FIG. 2), organs known for very high uptake of systemic oligonucleotide therapeutics (Stenvang et al., 2012). Serum concentrations of routine clinical chemistry parameters for kidney and liver function were in the normal range, indicating intact kidney and liver function. (Table 1). Also, upon application of LNA-antimiR-21, we did not observe episodes of arrhythmia or deaths, which occurred only prior to the application of the antimiR (Table 2). Taken together, catheter-based, local delivery of LNA-antimiR-21 was effective in long-term suppression of miR-21 in LV myocardium of a large animal model of heart failure.

TABLE 1

Serological analysis of selected biochemical parameters of liver and kidney function

| n | HF Control 3 | HF LNA-antimiR-Control 3 | HF LNA-antimiR-21 5 | p-value |
|---|---|---|---|---|
| | | Day 0 | | |
| AST (GOT) (U/l) | 32 ± 3.8 | 23 ± 3.1 | 29 ± 3.8 | n.s. |
| ALT (GPT) (U/l) | 42 ± 5.0 | 36 ± 3.7 | 46 ± 8.8 | n.s. |
| γ-GT (U/l) | 33 ± 10.7 | 28 ± 8.4 | 30 ± 7.5 | n.s. |
| Creatinine (μmol/l) | 87 ± 5.9 | 72 ± 5.4 | 88 ± 2.4 | n.s. |
| Urea (mmol/μl) | 2.5 ± 0.6 | 3.6 ± 0.7 | 3.1 ± 0.9 | n.s. |
| | | Day 5 | | |
| AST (GOT) (U/l) | 33 ± 7.1 | 32 ± 7.3 | 30 ± 1.3 | n.s. |
| ALT (GPT) (U/l) | 47 ± 7.4 | 55 ± 1.2 | 63 ± 10.6 | n.s. |
| γ-GT (U/l) | 48 ± 22.8 | 23 ± 3.5 | 32 ± 7 | n.s. |
| Creatinine (μmol/l) | 93 ± 10.5 | 58 ± 5.2 | 99 ± 5.4 | n.s. |
| Urea (mmol/μl) | 2.7 ± 0.6 | 3.9 ± 0.3 | 3.2 ± 0.6 | n.s. |
| | | Day 33 | | |
| AST (GOT) (U/l) | 31 ± 3.3 | 22 ± 7.3 | 27 ± 4.9 | n.s. |
| ALT (GPT) (U/l) | 44 ± 12.6 | 22 ± 3.7 | 53 ± 9.5 | n.s. |
| γ-GT (U/l) | 49 ± 11.7 | 25 ± 4.7 | 33 ± 4.8 | n.s. |

TABLE 1-continued

Serological analysis of selected biochemical parameters of liver and kidney function

| n | HF Control 3 | HF LNA-antimiR-Control 3 | HF LNA-antimiR-21 5 | p-value |
|---|---|---|---|---|
| Creatinine (μmol/l) | 120 ± 20.7 | 97 ± 0.8 | 111 ± 2.3 | n.s. |
| Urea (mmol/μl) | 3.3 ± 0.8 | 3.4 ± 0.2 | 4.3 ± 0.7 | n.s. |

(MEAN ± SEM, p-value HF Control vs. HF LNA-antimiR-21)
Reference values:
AST (GOT) (<59 U/l);
ALT (GPT) (<68 U/l);
γ-GT (<54 U/l);
Creatinine (<160 μmol/l);
Urea (2.5-6.7 mmol/μl).

TABLE 2

Cardiovascular events

| | Sham | HF Control | HF LNA-antimiR-21 |
|---|---|---|---|
| | | Day0 | |
| Ventricular extrasystoly | 0% | 67% | 85% |
| Reanimation (Defibrillation) | 0% | 33% | 14% |
| Cardiac death | 0% | 16% | 14% |
| | | Day 5 | |
| Ventricular extrasystoly | | 20% | 16% |
| Reanimation (Defibrillation) | | 20% | 16% |
| Cardiac death | | 20% | 16% |
| | | Day 19 | |
| Ventricular extrasystoly | | 0% | 0% |
| Reanimation (Defibrillation)n | | 0% | 0% |
| Cardiac death | | 0% | 0% |
| | | Day 33 | |
| Ventricular extrasystoly | 0% | 0% | 0% |
| Reanimation (Defibrillation) | 0% | 0% | 0% |
| Cardiac death | 0% | 0% | 0% |

(MEAN ± SEM, p-value HF Control vs. HF LNA-antimiR-21)

Inhibition of miR-21 Decreases/R-Induced Adverse Myocardial Remodeling

Moreover effect of LNA-antimiR-21 on myocardial remodeling was determined (FIG. 3). At 33 days after I/R, the two different treatment groups exhibited similar infarct. Prominent adverse cardiac remodeling was observed at this time point, evident as a significant increase in heart weight to body weight, cardiac myocyte hypertrophy and cardiac fibrosis, all of which were significantly reduced in the LNA-antimiR-21-treated pigs (FIGS. 3A-C). We then assessed key pathological processes that have been associated with myocardial remodeling, namely fibroblast proliferation, inflammation and angiogenesis (FIG. 3D-F). Immunofluorescent staining of LV myocardium indicated fibroblast proliferation and macrophage infiltration, both of which were significantly repressed by LNA-antimiR-21 compared to control-treated animals. In contrast, we found no evidence for alterations in capillary density in this model, nor was this affected by antimiR-21 (FIG. 3F). Analysis of myocardial total RNA by QRT-PCR yielded a gene expression signature indicative of myocardial remodeling in other species including humans and that was likewise significantly reversed in the LNA-antimiR-21 group (FIG. 3G). Comparative analyses of remote LV myocardium indicated only minimal changes of the parameters characterizing myocardial remodeling.

Catheter-Based Local Delivery of LNA-antimiR-21 Improves Global and Regional Myocardial Function To evaluate the impact of miR-21 inhibition on cardiac function, invasive hemodynamic measurements (pressure-volume analysis, PV analysis) were carried out before ischemia (d0), and at day (d) 5 (before LNA-antimiR-21 administration) and 33 post ischemia (d33 also with cardiac pacing to obtain rate-contraction relationships). This was complemented with contrast agent fluoroscopy before (d0) and after (d33) ischemia to determine ejection fraction (EF) and myocardial perfusion under resting conditions. Before sacrifice and tissue harvesting on d33, sonomicrometry with cardiac pacing was performed upon implantation of ultrasonic crystals into the border zone (10 mm distal of the occlusion site) and remote myocardium (see scheme in FIG. 1B for an overview as to the experimental strategy).

The control-treated animals displayed a marked decline in global myocardial function with increased LVEDP, decreased LV stroke volume and a negative rate-contraction-relationship indicative of overt heart failure (FIG. 4A-E). In contrast, treatment with LNA-antimiR-21 significantly prevented a decline in cardiac function (FIGS. 4A-E). Consistently, LNA-antimiR-21 application led to a significant gain of functional reserve of the left ventricle as evidenced by a positive rate-contraction-relationship (FIGS. 4D and E). Analysis of LV volumes likewise indicated a significant reduction of LV end-systolic volume (HF 58.5-3.4, HF LNA-antimiR-Control 58-0.4, HF LNA-antimiR-21 40.2±5.3), while the modest reduction in LV end diastolic volume observed with LNA-antimiR-21 did not reach statistical significance (HF 112.7±3.5, HF LNA-antimiR-Control 107.6±3, HF LNA-antimiR-21 103±2.7). As an independent measure for LV function, we employed sonomicrometry to determine subendocardial segment shortening (FIG. 4F). In line with the hemodynamic analyses, LNA-antimiR-21 improved regional contractility compared to LNA-antimiR-control-treated animals both under resting and at pacing (140 bpm) conditions (FIG. 4F). Fluoroscopy upon injection of a contrast agent likewise indicated a marked decline in EF at day33, which was prevented in the LNA-antimiR-21 group (FIG. 4G). While our study design did not aim for a quantitative determination of tissue perfusion such as MRI or PET, we not observe any difference between the groups with regard to coronary flow (by contrast agent injection) with a TIMI value of 3 indicating normal perfusion of the LAD including its microcirculation. Finally, the effect of LNA-antimiR-21 appeared to be dose-dependent, as the present data obtained from treatment with 4 mg instead of 10 mg of oligonucleotide suggest (FIG. 5). In summary, these findings demonstrate that local application of a miR-21 inhibitor significantly improved cardiac function in this model of post-ischemic heart failure.

AntimiR-21 Normalizes Transcriptomic Signatures of Failing Pig Myocardium

Further the consequences were determined that interfering with miR-21 has on the disease-associated gene expression signature in this large animal model. Using TruSeq Illumina sequencing of polyA-enriched RNA isolated from left ventricular ischemic myocardium (border zone) treated with LNA-antimiR-21 or control as well as from Sham-treated animals (n=3 from each group) yielded approximately 126.6 million reads per sample after removing the adaptors and filtering (>99.9% of reads qualified). Mapping the reads to the pig genome (*Sus scrofa* v11.1), we were able to successfully align 112 million reads (FIG. 6A). This corresponds to 95±0.4% of all reads aligned with high confidence, illustrating the high data quality of data set, which to our knowledge is the first extensive deep sequencing data set of myocardial disease in the adult pig.

A principal component analysis revealed clear separation between and high homogeneity within the three different experimental groups studied, underlining the validity of this data set for subsequent analyses (FIG. 6B). Ischemia lead to a pronounced deregulation of the pig cardiac transcriptome, which was partially reverted by antimiR-21 treatment.

To assess, whether these transcriptome changes indeed related to the modulation of miR-21 activity in the myocardium, we determined the distributions of mRNA-fold changes for all genes and compared them to those of conserved miR-21 targets, predicted by TargetScan Human 7 (FIG. 6C). Inhibition of miR-21 resulted in significant derepression of miR-21 targets compared to mRNAs containing no sites for miR-21 (FIG. 6C).

AntimiR-21 Inhibits Pro-Fibrotic and Inflammatory Transcriptional Signatures in Failing Myocardium We then sought to identify the biological processes primarily activated during HF and modulated by interfering with miR-21. Gene ontology (GO) enrichment analysis of all mRNAs deregulated in HF (log fold change >2 or log fold change <−2 and q-value <0.05) showed an enrichment for processes related to tissue remodeling including extracellular matrix organization, cell adhesion, osteoblast differentiation and inflammatory response (left panels in FIGS. 6D and E). Interfering with miR-21 had the strongest effect on the inflammatory and immune response, followed by repression of ERK-MAP-kinase (right panels in FIGS. 6D and E). To further validate the latter and to determine, whether this transcriptional signature resulted in altered protein activity of ERK-MAPkinase, we performed Western blotting and immunofluorescence stainings for activated MAPK3 (pERK) on cardiac tissue (FIGS. 6F and G). AntimiR-21 resulted in a significant inhibition of HF-induced ERK-MAPkinase activity (FIG. 6F). Remodeling-associated ERK activation and its repression by antimiR-21 was found to primarily occur in cardiac fibroblasts (FIG. 6G).

a Genetic Deconvolution Approach for the Pig Identifies the Cardiac Macrophage and Fibroblast as the Key Cell Types Affected by antimiR-21 Treatment.

The transcriptional changes observed in the myocardium putatively originates from changes in cell states but may also result from variations in cell type proportions. To analyze the latter, a genetic deconvolution approach for the pig was developed. Deep transcriptome data derived from the four principal myocardial cell types (myocytes, fibroblasts, macrophages and endothelial cells) sorted from mouse heart was included and was employed in addition to a mouse scRNA-Seq data set (re-processed data reported by Skelly et al (Skelly et al., 2018)) (FIG. 7A). We then identified the top enriched, highly specific and most abundant genes in each cell type of interest and combined these for the scRNA-Seq and deep RNA-Seq data sets (FIGS. 7A and B). Finally, we computed the overlap regarding the top abundant, specific and enriched mRNAs for all four cell types (FIG. 7B) and these markers were then used to build the signature matrix for deconvolution (FIG. 7C). We then applied this novel genetic deconvolution approach to determine the relative cell type proportions under Sham conditions, upon cardiac remodeling during heart failure and the effect of antimiR-21 (FIG. 7D). Failing myocardium was characterized by a prominent increase in macrophage and fibroblast numbers. Treatment with anti-miR-21 reversed the increase of macrophage and fibroblast numbers. This unbiased approach to analyze RNA-Seq data from cardiac tissue is able to determine cell fractions in a quantitative manner. It indicates that treatment with antimiR-21 led to normalization of the increased cell numbers of macrophages and also fibroblasts (FIG. 7D).

An alternative approach to target a specific organ is to localize the application of antimiR-21. Cardiac catheterization has become a routine procedure in clinical cardiology with the vast majority of all patients presenting with an acute coronary syndrome receiving this intervention (Bashore et al., 2012). Complications of cardiac catheterization have become a very rare event, allowing for a low threshold towards its application. Here, we applied antimiR-21 through the related coronary arteries, which offers the advantage of preferential exposure of the injured tissue to high concentrations of the antimiR. Interestingly, our data indicate that after ischemia, uptake of antimiR-21 in the myocardium appears facilitated, potentially due to leakiness of endothelia and dissolution of the extracellular matrix (FIGS. 1C and 2), supporting the idea of further concentrating antimiR-21 at the site of injury.

Administration of the inhibitor of miR-21 at least 5 days after ischemia, in particular myocardial infarction, unexpectedly provided an increased uptake and therapeutic efficacy in postischemic myocardium:

The finding of the increased uptake of the inhibitor of miR-21 was unexpected at 5 days after ischemia since we expected the increased uptake of the inhibitor of miR-21 only directly after ischemia or myocardial infarction. Thus, it is surprisingly documented herein that the administration of the antimiR-21 5 days after ischemia results in an increased uptake of therapeutic antimiR 5 days after ischemia. Therefore, the administration of the inhibitor of miR-21 5 days after ischemia is safe for the delivery of antimiRs since it avoids the detrimental effects in the acute setting.

In the years following its original description, upregulation of miR-21 has been reported as a hallmark of myocardial remodeling originating from causes such diverse as pressure overload, myocardial infarction and atrial fibrillation. Subsequently, multiple studies have demonstrated the therapeutic efficacy of inhibiting miR-21 in the respective disease models (Adam et al., 2012; Cardin et al., 2012; Thum et al., 2008). Yet, overexpression of miR-21 in myocytes protected myocytes from apoptosis during acute ischemia (Sayed et al., 2010). In line with such a suspected beneficial role of miR-21 in cardiac myocytes, modest or neutral effects for global, genetic deletion of miR-21 was observed (Patrick et al., 2010; Ramanujam et al., 2016) (Patrick et al., 2010; Ramanujam et al., 2016)(Patrick et al., 2010; Ramanujam et al., 2016)(Patrick et al., 2010; Ramanujam et al., 2016). However, a deletion of miR-21 in myocytes was detrimental, but the deletion of miR21 in non-myocytes provided cardioprotection (Ramanujam et al., 2016). It was the ingenious idea of the inventors to avoid potential detrimental consequences of promoting the death of cardiac macrophages by antimiR-21 in the acute ischemic setting. Thus, the inventors administered the miR-21 inhibitor at day 5. As demonstrated herein below, the administration of the inhibitor of miR-21 at day 5 after the ischemia does not promote the loss of myocytes. This strategy of delayed application post myocardial infarction avoids acute detrimental effects and fully exploits the beneficial effects of upregulated miR-21 in later disease states.

In this model, inhibition of miR-21 lead to sustained reshaping of the myocardial transcriptome 4 weeks after initiation of the treatment, suggesting a remarkably long-lasting suppression of miR-21 activity. Unbiased gene ontology analysis identified inflammation-related and MAP kinase signaling to be most significantly affected by manipulation of miR-21. This analysis indicated that antimiR-21 led to reduction in macrophage infiltration as well as fibroblast proliferation. These data suggest that anti-miR-21 can exert its anti-fibrotic activity not only through its effect in fibroblasts, but also through its action in macrophages. Therefore, the therapeutic efficacy may be further increased by applying anti-miR-21 molecules targeted to macrophages and/or fibroblasts.

Accordingly, the experimental data herein provided demonstrate that the local delivery delayed until day 5 after ischemia yielded unexpectedly increased uptake and therapeutic efficacy in postischemic myocardium. Furthermore, the herein provided RNA sequencing analyses showed that this unexpectedly interferes with macrophages accumulation, pointing towards the cardiac macrophage as a primary target of anti-miR-21.

EXAMPLE 2

MiR-21 as a Therapeutic Target in Macrophages miR-21 is Highly Expressed in Cardiac Macrophages and Increases in Heart Failure In order to obtain an inventory of the entire small RNA transcriptomes of the major cell fractions of the mouse heart (FIG. 8), a cell isolation strategy starting with retrograde perfusion of the isolated heart (Langendorff preparation), followed by fractionation into myocytes, endothelial cells, fibroblasts and macrophages using magnetic and fluorescence activated cell sorting (MACS and FACS) was used (see FIG. 8 and scheme in FIG. 8A). Sequencing of small RNAs of different myocardial cell fractions (n=3 from each group) yielded approximately 1 million reads per sample (approximately 85% valid reads) after removing the adaptor sequences, and filtering low quality (Phred Q<30) and small (less than 12 nucleotides) reads. High quality reads mapped to small RNA reference library (miRNA hairpins from miRBase 21) were then filtered for miRNAs that had non-zero values in replicates of at least one cell type and that the average counts per million across all samples was greater than 3. Using these criteria we detected 307 unique individual transcripts that were confidently annotated as microRNA (FIG. 8B). In agreement with small RNA transcriptomes obtained in different cell types and tissues (Sood et al., 2006; Wessels et al., 2019), we likewise observed a unilateral distribution of the absolute abundance of the individual miRNA molecules, with very few miRNAs constituting for half of the entire miRnome (FIG. 8B). Interestingly, several of those miRNAs at the upper end of the expression spectrum also exhibited very pronounced cell type specificity when compared to the other myocardial cell types (FIG. 1C). We found miR-21 to be the highest expressed miR in cardiac macrophages c(MPs), constituting about one quarter of all microRNA molecules in this cell type (FIG. 8B). This is far higher than in other cardiac cell fractions including fibroblasts (FIGS. 8B, C). To investigate whether this molecule also played a role in the development of cardiac disease, we tested it in a disease model for left ventricular pressure overload induced by transverse aortic constriction (TAC). Interestingly, expression of miR-21 in cMPs further increased in a progressive manner 6 and 21 days after the initiation of pressure overload (FIGS. 8D,E). Effective target mRNA regulation through a microRNA requires that its concentration in a given cell type matches that of its target sites (i.e. the entire targetome in a cell) (Bosson et al., 2016; Brown et al., 2007). We therefore determined the absolute abundance of all mRNAs that contain canonical target site for the top 40 expressed miRNAs and set it in relation to the absolute copy numbers of the respective miRNA (FIG. 8F). While only few miRNAs match their targetome in cMPs, miR-21 also exerted the highest miRNA:target ratio among all macrophage miRNAs both under Sham and disease conditions, suggestive of a strong regulatory effect of this miR-21 in cMPs (FIG. 8E). To further examine the role of miR-21 in cMPs in vivo, macrophage (MP)-specific miR-21-deficient mice (miR-21 cKO) were generated by crossing miR-21-floxed-mice with a mouse line expressing Cre-recombinase driven by the Cx3cr1-promotor which is specifically active in macrophages (Yona et al., 2013). Cx3cr1-Cretg/0; miR-21flox/flox mice (miR-21 cKO) exhibited greatly decreased levels of miR-21 in cMPs, with preserved miR-21 levels in other cardiac cell types, myeloid and lymphoid cells (FIG. 8G). We found miR-21-cKO to develop normally and they exhibited normal cardiac function as determined by echocardiography compared to WT littermate controls. Thus, miR-21-cKO mice are a well-suited model to study the function of miR-21 in macrophages, and in particular in cardiac macrophages.

Genetic Deletion of miR-21 Specifically in MPs Improves Heart Function after Pressure Overload of the Left Ventricle (by Transverse Aortic Constriction, TAC)

In order to investigate the contribution of macrophage miR-21 to pathological cardiac remodeling and dysfunction, WT and miR-21 cKO mice were subjected to TAC and determined the extent of fibrosis and cardiac hypertrophy (FIG. 9A). Staining extracellular matrix proteins in myocardial cross-sections indicated that fibrosis in the miR-21 cKO group had been significantly prevented compared with TAC-treated WT mice (FIG. 9B). MiR-21 cKO mice were also protected from TAC-induced cardiac hypertrophy at the morphologic and cellular level (FIG. 9C). Consistent with these findings, the expression of hypertrophy-related genes (Acta1, Myh7, Nppa) and fibrosis-related genes (Col1a1, Col1a2), were significantly reduced in TAC-treated miR-21 cKO mice compared to WT littermates (FIG. 9D).

Echocardiography carried out before surgery and at days 14 and 28 after sham or TAC surgery was used to assess cardiac function. Both WT and miR-21 cKO mice in the sham groups were healthy and normal, in contrast to the typical impairment of cardiac function that was evident in TAC-treated WT (FIGS. 9E and F). Interestingly, TAC-treated miR-21 cKO mice displayed significantly better left ventricular ejection fraction (LVEF) compared to WT mice (FIG. 9E). This was also reflected by other echocardiography parameters such as left ventricular anterior wall thickness in TAC-treated miR-21 cKO mice compared to WT littermates. In addition, we applied a very sensitive and accurate measurement of left ventricular (LV) function by assessing LV strain using speckle-tracking analysis of 2-dimensional echocardiography (FIG. 9F). Also, this analysis indicated significantly better LV function with higher levels of radial strain in miR-21 cKO mice, almost reaching levels typically observed in the sham-treated mice (FIG. 9G).

Together, these findings suggest a crucial role for macrophage miR-21 in cardiac remodeling and dysfunction.

Single Cell Sequencing Analysis Revealed that miR-21 Depletion in Macrophages Favors M2 Polarization.

In order to better understand the mechanism through which miR-21 exerts its function in cardiac macrophages and how this then determines responses in other myocardial cell fractions, we carried out single cell sequencing using the non-myocyte cell population isolated from either wildtype or miR-21 cKO mice 6 days after pressure overload (FIG. 10A). The transcriptional profiles of single cells were obtained using the 10× Chromium platform and analysed 8,343 wildtype and 6,421 knockout cells that passed quality control for which an average of ~2000 median genes per cell were detected (in total 21,436 genes were detected across cell types) (FIG. 10B).

Figure 10E:
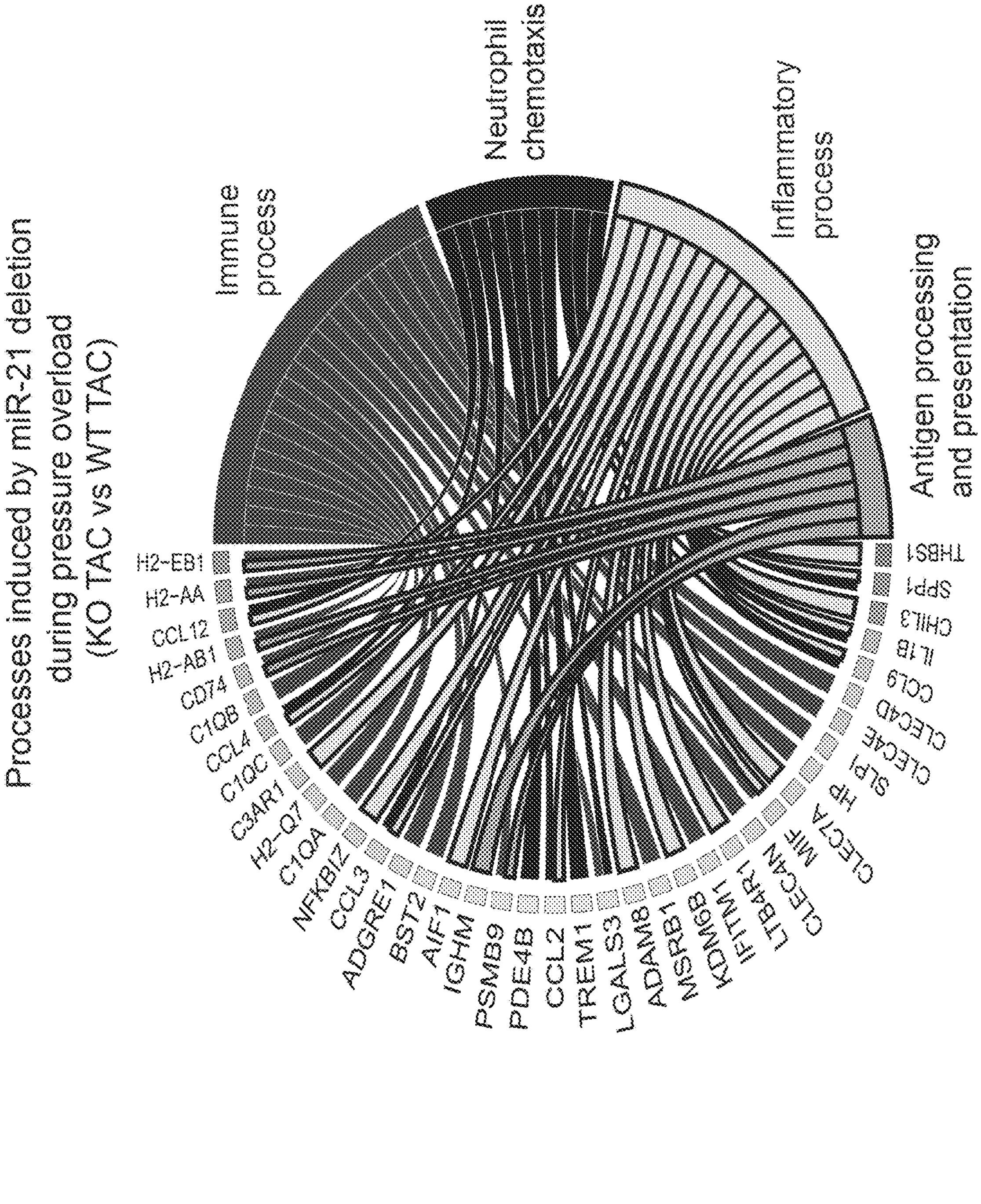
Figure 10:
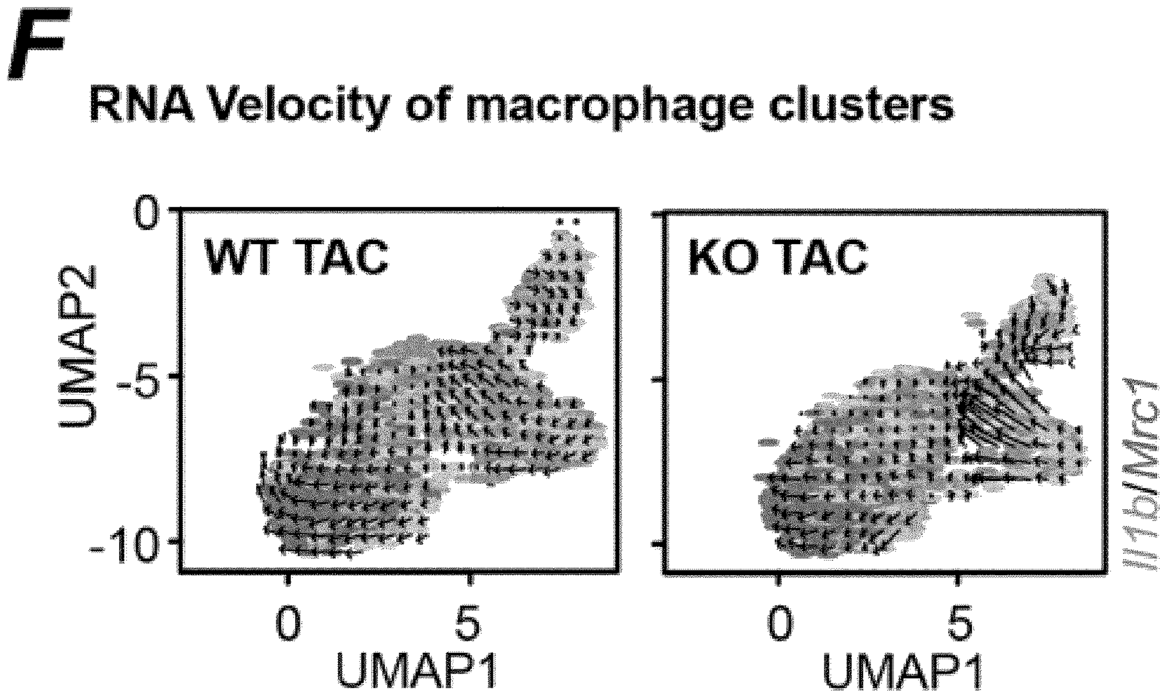
Figure 10:
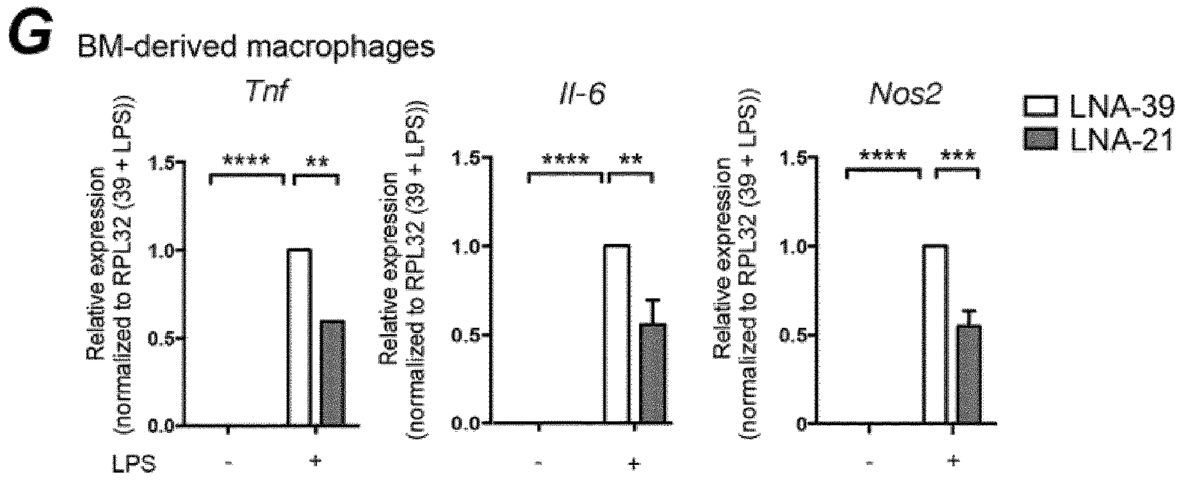

Analysis of the scRNA-seq data set including cells from both wildtype and miR-21 cKO mice pooled together and analysed by the Seurat package showed two clusters of macrophages (2 and 4), three clusters of fibroblasts (1, 3 and 6), three clusters of endothelial cells (0, 5 and 12) and including other myocardial cells. Using known genetic markers, subset analysis of macrophages further classified this cell type into two different cell populations—M2-like macrophages and M1-like pro-inflammatory macrophages (FIG. 10C). Comparative sequencing analysis revealed a reduction in the number of M1-like macrophages upon deletion of miR-21 in macrophages compared to those isolated from a WT background (FIG. 10D). Gene ontology analysis of the macrophage clusters revealed that genes associated to pro-inflammatory signaling and upregulated after pressure overload were largely repressed upon deletion of miR-21 (FIG. 10E). These findings were corroborated with corresponding analysis carried out separately on individual macrophage subclusters and that largely confirmed a repression of disease-associated pro-inflammatory pathways in M1-like macrophages upon deletion of miR-21. Likewise, M2-like macrophages (cluster 2) showed a pronounced reversal of the pressure overload-associated changes upon deletion of miR-21.

RNA velocity analysis of spliced vs. unspliced reads confirmed that miR-21 deficiency in cMPs resulted in a polarization of cells from a pro-inflammatory Il1b-expressing (M1-like) towards an M2-like state as denoted by Mrc1 expression concomitant with very low levels of Il1b (FIG. 10F). In order to corroborate these findings in a more defined setting in vitro, we assessed the extent of pro-inflammatory signaling in cultured bone marrow-derived macrophages (BMDM) that were either treated with LNA-antimiR-control or LNA-antimiR-21 and after stimulation with lipopolysaccharide (LPS), a potent pro-inflammatory stimulus. Consistent with the single cell data obtained from miR-21 cKO mice, the expression of pro-inflammatory-related genes (Tnf, 116, Nos2) were significantly reduced in LNA-antimiR-21-treated compared to LNA-antimiR-control-treated BMDMs (FIG. 10G).

Altogether, our data suggest that miR-21 is a key molecule necessary for the pro-inflammatory activation of macrophages in the mammalian heart.

Analysis of Ligand Receptor Pairing in Single Cell Transcriptomics Data Sets Identifies the Cardiac Macrophage as Primary Paracrine Inducer of Fibroblast Activation.

Our phenotypic characterization of miR-21 cKO mice (FIG. 9) had revealed a prominent effect of macrophage miR-21 on myocardial remodeling during pressure overload, including a significant prevention of myocardial fibrosis (FIG. 9B). We therefore asked, whether the cardiac macrophage, upon disease induction, would directly signal to cardiac fibroblasts. Recent advances in bioinformatic analysis of single cell transcriptomic data sets from complex multicellular tissues allow to systematically map paracrine intercellular communication based on ligand-receptor pairing (Ramilowski et al., 2015).

We thereby analysed about 2500 validated ligand-receptor interaction pairs within and between cell types and created a cellular interaction map first for homeostatic conditions. Next we sought to identify changes of cellular interaction that occur as a response to pressure overload of the heart, again in an unbiased way, incorporating all potential ligand-receptor interaction pairs (FIG. 11A). Interestingly, upon induction of pressure-overload, the most changes in interaction were observed between M1-like macrophages and activated fibroblasts of the Postn+ subtype (FIG. 11A). Intriguingly, we found paracrine interactions from M1-like MP to Postn+ fibroblast to be the most significantly repressed of all intercellular interactions originating from M1-like MPs, when we compared miR-21-deficient mice subjected to TAC to WT mice (right panel in FIG. 11A). The remarkable extent of these changes made us hypothesize, that the activated MP may indeed mediate the pro-fibrotic activation of the cardiac fibroblast. We then examined in more detail these ligand-receptor pairs as candidate signaling mechanisms underlying the fibrotic response in this model and its inhibition by deletion of miR-21 (FIG. 11B). Intriguingly, we found the top upregulated candidate ligands with predicted receptor signaling to activated fibroblasts to all exhibit documented pro-fibrotic activity. All of these fibroblast-activating signaling pathways were found down-regulated when we analyzed signaling emanating from miR-21-deficient macrophages under pressure overload (4 out of 8 passed the threshold of regulation applied in FIG. 11B). In addition, we found a single signaling pathway to be activated in pressure-overloaded miR-21 cKO mice, namely Lrp1-dependent signaling (FIG. 11B). Lrp1, a member of the low-density lipoprotein receptor family of proteins, has been reported as a potent integrator of diverse anti-fibrotic signals such as ApoE, and C1qb (Potere et al., 2019). Together, these data suggest the cardiac macrophage to send a powerful array of pro-fibrotic mediators to the cardiac fibroblast upon pressure overload of the heart. The induction of the underlying M1-like and secretory phenotype of the cardiac macrophage depends on the function of miR-21.

We next sought to study the effect of these signals on the cardiac fibroblast. To this end, we assessed the dynamic transcriptional response of the cardiac fibroblast population upon pressure overload and the relevance of miR-21 therein. RNA velocity analysis of the single cell sequencing data showed that the fraction of activated fibroblasts (denoted by Postn) were pushed towards myofibroblasts (denoted by Acta2 and Postn abundance) upon pressure overload (FIG. 11C). This transcriptional response towards a future myofibroblast phenotype was largely abolished in miR-21 cKO mice (FIG. 11C). In good agreement with these dynamic changes, we also found cell numbers for myofibroblasts to be increased upon pressure overload. Again, deletion of miR-2 in macrophages reversed these effects (FIG. 11D). Finally, we thought to obtain proof that indeed the macrophage secretome was sufficient to provide for myofibroblast differentiation in general and its dependence on miR-21. To do so, we devised a defined co-culture setting of activated macrophages and cardiac fibroblasts (FIG. 11E). BMDM progenitor cells were differentiated to mature macrophages, transfected with either LNA-antimiR-21 or LNA-antimiR-Control for 24 hours and stimulated with LPS. These* macrophages were then added to the surrounding 8 wells of 9-well coculture slides such that a ratio of fibroblast: macrophages of 3:1 was achieved, closely mimicking cell ratios in myocardium in vivo. Automated, high-content image analysis of immunostaining for Acta2 (Metamorph) was then employed as a parameter for myofibroblast formation (FIG. 11F). Unstimulated, quiescent macrophages did not induce myofibroblast transformation in this assay and inhibition of miR-21 had no detectable effect under these conditions (FIG. 11F). Pro-inflammatory polarization of cultured macrophages with LPS conditioned their secretome to promote strong myofibroblast transformation. Consistent with the data obtained from the miR-21 cKO mice, macrophage-dependent myofibroblast transformation was significantly reduced upon pretreatment of the macrophages with LNA-antimiR-21 (FIG. 11F).

The regulatory role of miR-21 in fibroblasts has been regarded as the primary mechanism underlying the pathological role of miR-21 in tissue fibrosis and disease and hence the therapeutic effects of anti-miR-21 (resp. RG-012). The experimental results provided herein of quantitative small RNA sequencing of purified myocardial cell fractions revealed an enormous concentration of miR-21 in the cardiac macrophage, where miR-21 has its highest expression of all myocardial cell types and where it ranks #1 among all microRNAs. This key finding was the starting point of the present study and prompted us to delineate the contribution of cMP miR-21 as to tissue fibrosis and cardiac function. The effects we report to be mediated by macrophage miR-21 are profound and go far beyond primary immune functions.

Accordingly, the experimental data demonstrate that, firstly, miR-21 has extremely high concentrations in macrophages and is further upregulated in cardiac macrophages (MPs) in a disease or disorder. This suggests that it is important in this cell type. The extremely high numbers of miR-21 molecules per cell in diseased myocardium also might be one reason why conventional methods using systemic administration to suppress endogenous miR-21 might be ineffective.

Secondly, the experimental data shows that miR-21 is a key regulator of pro-inflammatory (M1-like) macrophage polarization.

Thirdly, the experimental data provided herein demonstrate that miR-21 in cardiac macrophages controls paracrine, pro-fibrotic signaling towards fibroblasts. This macrophage-derived, pro-fibrotic secretory signal is strong enough to control pathological tissue fibrosis. Accordingly, the targeting of macrophages provides an improved and new concept of the treatment of fibrosis.

EXAMPLE 3

To determine the expression of small RNAs and in particular microRNAs, we devised a flow cytometry-based strategy to purify primary cell fractions from intact mouse lungs. After cell sorting using the well-established cell surface markers depicted in FIG. 12, RNA was prepared according to standard procedures and small RNA sequencing carried out using the Illumina platform. Methodological details are as follows:

Flow cytometry/cell sorting for lung tissues: Primary cells were isolated from lungs extracted from wild type C57BL/6N mice. A 20G cannula was inserted into the trachea and was ligated using a nylon thread. Lungs were then instilled with 1 mL of ice cold 2 mM EDTA/PBS solution, incubated for 5 seconds with constant pressing of the lungs and the broncho alveolar fluid (BALF) was collected in a 15 mL falcon tube. This process was repeated 5 times. After the collection of BALF cells, blood was cleared from the body by perfusing 5 mL of ice-cold 2 mM EDTA/PBS solution into the left ventricle until the lung is completely white. The lungs were then extracted from the mice and was cut into very small pieces using a scissor in 3 mL of DMEM-based digestion buffer containing collagenase type II (1 mg/mL), DNaseI (0.3 mg/mL), dispase (50 U/mL) and $CaCl_2$ (0.03% v/v). Lungs were digested in a 37° C. shaker for 25 min, following which the cells were centrifuged at 400 g for 7 min. The cells were then treated with 1 mL of erythrocyte lysis buffer (nine parts of 155 mM $NH_4Cl$ and one part of 0.1 mM Tris HCL pH 7.65) for 5 min at room temperature before neutralizing with 2 mL PBS. Cells were then washed with FACS buffer (2 mM EDTA, 0.5% BSA in PBS). Primary cells were then treated with rat anti-mouse CD16/CD32 (clone 2.4G2) at 4° C. for 10 minutes before being incubated with fluorescent-conjugated antibodies at 4° C. for 60 minutes. The leukocyte fraction was then separated from other cell fractions using MACS columns. Cells were first incubated with biotin-conjugated CD45 antibody at 4° C. for 30 min followed by incubated with Streptavidin microbeads at 4° C. for 15 min. Both flow-through and leukocytes-enriched cells were then stained with primary fluorescent antibodies for flow cytometry based cell sorting. The following antibodies were used. Leukocyte-enriched fraction: anti-CD45-FITC, anti-CD11b-PE, anti-CD24-PE/Dazzle594, anti-CD11c-PECy5, Ly6G-PerCP/Cy5.5 and F4/80-PECy7. Flow-through: anti-CD45-FITC, anti-CD105-PE, anti-Epcam-PE/Dazzle594 and anti-PDGFRA-PECy7. Both cell suspensions were triturated through a 40 μm Nylon cell strainer (Falcon) and then subjected to FACS analysis using a Sony SH800S cell sorter.

Flow cytometry/cell sorting for heart tissues: Primary cells were isolated as described previously (Ramanujam et al., 2016). For FACS sorting, the cardiac cell suspension was separated into cardiomyocytes-(pellet) and non-myocytes-enriched fractions (supernatant) by centrifugation (900×g for 1 minute). While cardiac myocytes were sorted based on morphology, non-myocyte fractions were further subjected to antibody-based flow cytometry procedures. Non-myocyte-enriched supernatant was centrifuged at 400×g for 5 minutes and washed with FACS buffer (2 mM EDTA, 0.5% BSA in PBS). Primary cells were then treated with rat anti-mouse CD16/CD32 (clone 2.4G2) at 4° C. for 10 minutes before being incubated with fluorescent-conjugated antibodies at 4° C. for 60 minutes. The following antibodies were used: anti-PDGFRα-PECy7 (clone APA5), anti-CD105-PE (clone MJ7/18) and anti-CD45-FITC (clone 30-F11). The dye DRAQ7 was used to control for viability. Cell suspensions were triturated through a 40 μm Nylon cell strainer (Falcon, Tewksbury, USA) and then subjected to FACS analysis using a Biorad S3 cell sorter.

RNA sequencing: Total RNA was extracted from tissue using peqGOLD RNA pure (Peqlab). Libraries were constructed in a strand-specific manner from 4 μg of DNase-treated RNA using TruSeq Stranded mRNA sample preparation kit (Illumina, San Diego, California). This kit includes a poly-adenylation selection to enrich mRNA. RNA was then fragmented, subjected to two rounds of cDNA synthesis and adapters were then ligated to ds cDNA. All libraries were sequenced on Illumina HiSeq 2000 generating 100 bp paired-end reads. High quality reads were obtained by trimming adapter sequences, invalid and low quality reads from the raw reads. The clean reads were then mapped to *Sus scrofa* 11.1 reference genome by HISAT2 software (v 2.1.0) using default parameters. Then, transcript assemblies were constructed using StringTie software (v 1.3.6). StringTie merge software (v 1.3.6) was used to merge transcripts and DESeq2 software (v 2.11.40.2) was used to compute differential expression. The genes were then selected based on abundance, cell type-specificity and receptor characteristics using ADAPTS R package.

As found surprisingly herein, miR-21 is the most abundant and enriched microRNA in lung macrophages. Our data reveal that microRNA-21 represents approx. 20% of all microRNA molecules expressed in lung alveolar macrophages and thereby is the top 1 expressed microRNA species in this cell type. Similar high expression levels were found in the lung interstitial macrophage cell population, where 12% of all miRNA reads could be attributed to miR-21. Relative expression of miR-21 was further validated by quantitative real time PCR in different pulmonary cell types and again showed a relative enrichment of miR-21 in macrophage populations (FIG. 12). Given the very high abundance of macrophages in the mammalian lung, these data suggest that the vast majority of miR-21 of the lung derives from the lung macrophage.

We then asked, whether miR-21 is upregulated in mice and humans after lung injury. Thus, we tested, whether the expression of miR-21 was altered in pulmonary disease and employed a well-established model of pulmonary fibrosis, namely pulmonary fibrosis induced by application of the chemotherapeutic agent bleomycin. Expression of miR-21 was determined in lung tissues harvested from mice 14 days after administration with either control solution (PBS) or bleomycin. We found expression of miR-21 to be strongly increased in diseased lungs (FIG. 13 A).

We then studied the expression of miR-21 in biopsies from patients with idiopathic pulmonary fibrosis. Again, we found a significant increase in miR-21 in lung tissue (FIG. 13 B).

Finally, we tested, whether inhibition of miR-21 with a synthetic oligonucleotide inhibitor against miR-21 (LNA-anti-miR-21) would suffice to repress miR-21 in the lung and whether this would interfere with pulmonary fibrosis. Here, we studied pigs, who had received intracoronary LNA-anti-miR-21 (see FIG. 1 from the present application) and that develop a moderate degree of pulmonary consolidation and fibrosis. The pulmonary disease is a well-known consequence of pulmonary congestion, which results from cardiac dysfunction post myocardial infarction. Intracoronary application of LNA-anti-miR-21 effectively suppressed miR-21 in the congested lungs (FIG. 13 C). Importantly, LNA-anti-miR-21 significantly prevented pulmonary fibrosis in this model of heart failure-related pulmonary congestion and fibrosis.

Collectively, these data suggest that inhibition of miR-21, presumably through affecting miR-21 in macrophages including cardiac macrophages has a strong anti-fibrotic effect in the lung. As documented below, inhibition of miR-21 specifically in lung macrophages has indeed a similarly strong anti-fibrotic effect.

EXAMPLE 4

Genetic deletion of miR-21 in activated cardiac fibroblasts prevents cardiac remodeling and dysfunction.

While miR-21 has been shown to promote fibroblast proliferation, survival and myofibroblast transformation, it has not been demonstrated to date, that the activity of miR-21 in cardiac fibroblasts is indeed a determinant of tissue remodeling and dysfunction such as observed in cardiac failure. We employed the well-established Postn- MCM transgenic mouse line, that allows for the specific expression of Cre recombinase in activated fibroblasts and thereby recombination of loxP site-flanked genetic loci. Of note, the transgenic Postn-MCM line is an inducible transgenic line, i.e. Cre recombinase is expressed in response to the application of tamoxifen. We then crossed this mouse line to mice with a floxed miR-21 locus, thereby aiming for a loss of miR-21 in activated cardiac fibroblasts. These mice were subjected to myocardial infarction (MI), which induces progressive cardiac remodeling and dysfunction (FIG. 14A). Four weeks after MI, the mice were subjected to an analysis of cardiac dimensions and function by echocardiography and the hearts and lungs were harvested for further analysis. Genetic deletion of miR-21 in the activated fibroblast population lead to a significant reduction of miR-21 in the failing myocardium (FIG. 14B), suggesting a marked contribution of the fibroblast miR-21 to the overall miR-21 content in the failing heart. Fibroblast deletion of miR-21 significantly prevented heart failure-associated increase in myocardial mass (termed hypertrophy (FIG. 14C) and likewise prevented the increase in lung weight-to-body weight (FIG. 14D). These beneficial effects of deleting miR-21 in the activated cardiac fibroblast population likewise reflected in a significant improvement of cardiac function, as determined by the left ventricular ejection fraction (FIG. 14E). Furthermore, echocardiography indicated favorable effects on cardiac structural remodeling, namely a reduction of the heart failure-associated increase in enddiastolic and endsystolic volumes (FIG. 14 F). The improvement in cardiac function was further confirmed by a significant increase of radial strain peak compared to the wild type group (FIG. 14G).

Collectively, these data suggest, that also fibroblast-specific inhibition of miR-21 is a valid therapeutic strategy to target tissue fibrosis.

EXAMPLE 5

MiR-21 is Upregulated in Lung Tissue Harvested from COVID-19 Patients and in an Animal Model of Pulmonary Fibrosis We initially sought to obtain the small RNA transcriptome profiles of the lungs harvested from COVID-19 patients and non-fibrotic control subjects (FIG. 19A). Post-mortem lung tissues were harvested from regions in the left lower lobe a predilection site for COVID-19-induced remodeling in human lung. We found miR-21 to be a highly expressed microRNA in lungs from control subjects, constituting about 5% of all microRNA molecules in human lung (FIG. 19B). Interestingly, expression of miR-21 further increased in the lungs of COVID-19 patients and was also found to be the single most upregulated miRNA (fold change of about 2) among the top 10 expressed miRNAs (FIG. 19B).

We next obtained small RNA expression profiles for different pulmonary cell types to assess miR-21 expression across cell types. As a source of freshly isolated cells, we used lungs from mice at 10 weeks of age and examined miR-21 expression in different pulmonary cell types of murine lung using a strategy involving magnetic-activated (MACS) and fluorescence-activated cell sorting (FACS). Interestingly, miR-21 was the single highest expressed microRNA in alveolar macrophages, which was also highly enriched in this cell type compared to other cell types (FIG. 20). Together, this unique expression pattern suggests a strong regulatory role for miR-21 in pulmonary macrophages.

To investigate the contribution of miR-21 to the development of pulmonary fibrosis and dysfunction, we subjected wild type mice to lung injury by single dose intratracheal application of bleomycin using a microsprayer. Lung dysfunction was confirmed 7 days after bleomycin application using Flexivent instrument (data not shown). MicroRNA expression profiles obtained from saline- or bleomycin-treated lungs showed miR-21 to be significantly upregulated 7 days after bleomycin administration (FIG. 21). Among the top expressed miRNAs, miR-21 was the one with the strongest degree of upregulation.

Ligand-Conjugated antimiR-21 for Targeted Delivery to Macrophages

We had employed a screening strategy that identified mannose receptor C type 1 (Mrc1) as strongly expressed in macrophages, where it was also enriched compared to other cell types. (see Table 3 herein above).

In an attempt to identify cell-surface receptors on lung and cardiac macrophages and or fibroblasts, respectively, we performed unbiased transcriptome sequencing of pulmonary and cardiac cell types from the mouse and then extended these analyses to human transcriptomic data (FIG. 22). RNA sequencing of pulmonary subtypes identified more than 18,000 genes across all cell types. Among those we detected more than 1000 surface receptors out of which 106 there are enriched in macrophages. Among the latter, we found 13 to be highly abundant and specific for macrophages. These macrophage-specific candidate surface receptors for anti-miR-21/inhibitor of miR-21 delivery include, in particular:

| | | |
|---|---|---|
| Mannose receptor C type 1 | Heart and Lung | macrophages |
| Folate receptor beta | Heart and Lung | Macrophages |
| Leukocyte immunoglobulin like receptor A5 | Heart and Lung | Macrophages |
| C-Type lectin domain containing 10A | Heart and Lung | Macrophages |
| Macrophage receptor with collagenous structure | Lung | Macrophages |
| Formyl peptide receptor 2 | Lung | Macrophages |
| Integrin subunit alpha X | Lung | Macrophages |
| Peroxisome proliferator activated receptor gamma | Lung | Macrophages |
| CD74 antigen | Heart | Macrophages |
| Colony stimulating factor 1 receptor | Heart | Macrophages |
| Fc receptor | Heart | Macrophages |
| CD14 antigen | Heart | Macrophages |
| CD68 antigen | Heart | Macrophages |

We next compared the relative abundance of our top ranked candidate surface receptor MRC1 in alveolar and interstitial macrophages and in leucocytes, epithelial, and endothelial cells, showing a much stronger expression of MRC1 in macrophages. Corresponding data were obtained for cardiac cell types including macrophages. Corresponding data were also obtained for fibroblasts from lung and heart.

The expression of MRC on lung macrophages was then corroborated by its detection on the protein level by immunofluorescence using an antibody directed against MRC1. Here, MRC1 was clearly detected in cells, that morphologically resemble pulmonary macrophages. In lung tissue, derived from mice treated with bleomycin, there was a strong increase of MRC1 positive cells, identified as macrophages.

We next sought to validate these data by the bioinformatic analysis of publicly available human single cell data sets derived from lung tissue of patients treated with bleomycin or suffering from idiopathic pulmonary fibrosis and the respective controls. When we plotted the expression of human MRC1 in these datasets, we found strong and almost exclusive expression of MRC1 in human pulmonary macrophages. The number of MRC1 positive cells increased in lungs from humans treated with bleomycin as well as in tissue derived from patients suffering from IPF.

To identify candidates surface receptors for cardiac macrophages and fibroblasts, we pursued an approach similar as to the one described above for the lung. We performed sequencing of the major cardiac cell types and identified more than 14,000 genes across all cell types (Total reads per million >1). Among those we identified more than 800 surface receptors, with 89 surface receptors enriched in macrophages and 86 surface receptors expressed and enriched in fibroblasts, respectively. We further stratified 16 surface receptors that were abundant and specifically expressed only in macrophages and 10 surface receptors which were abundant and specifically expressed only in fibroblasts. Among those 16 selected surface receptors for cardiac macrophages, again Mrc1 stood out as the single candidate surface receptor with the highest abundance. Single cell sequencing of primary cells isolated from the hearts of mice that had been subjected to pressure overload of the left ventricle or control/sham mice corrobated highly specific expression of MRC1 in cardiac macrophages.

A similar corresponding analysis of fibroblast surface receptors yielded Scara5 as the top candidate molecule.

Further candidate surface receptor molecules for the cardiac macrophage include

| | | |
|---|---|---|
| CD33 antigen | Heart | macrophages |
| CD53 antigen | Heart | macrophages |
| Transmembrane immune signaling adaptor TYROBP | Heart | Macrophages |
| C—C motif chemokine receptor 2 | Heart | Macrophages |
| CD52 molecule | Heart | Macrophages |
| Integrin subunit alpha M | Heart | Macrophages |
| Colony stimulating factor 2 receptor subunit alpha | Heart | Macrophages |
| Galectin 3 | Heart | Macrophages |
| TNF receptor superfamily member 11a | Heart | Macrophages |
| Protein tyrosine phosphatase non-receptor Type 18 | Heart | Macrophages |
| CD48 antigen | Heart | Macrophages |
| TNF receptor superfamily member 13B | Heart | Macrophages |
| Selectin P ligand | Heart | Macrophages |
| Adrenoceptor beta 2 | Heart | Macrophages |
| Lymphatic vessel endothelial hyaluronan receptor 1 | Heart | Macrophages |
| G protein-coupled receptor 65 | Heart | Macrophages |
| Platelet activating factor receptor | Heart | Macrophages |
| Complement component 3a receptor 1 | Heart | Macrophages |
| Fc receptor | Heart | Macrophages |
| Fc receptor | Heart | Macrophages |
| Pyrimidinergic receptor P2Y | Heart | Macrophages |

Further candidate surface receptor molecules for the cardiac fibroblast include

| | | |
|---|---|---|
| Transforming growth factor | Heart | Fibroblasts |
| Syndecan 2 | Heart | Fibroblasts |
| Angiotensin I converting enzyme (peptidyl-dipeptidase A) 1 | Heart | Fibroblasts |

-continued

| | | |
|---|---|---|
| Anthrax toxin receptor 1 | Heart | Fibroblasts |
| Discoidin domain receptor family | Heart | Fibroblasts |
| Glypican 6 | Heart | Fibroblasts |
| Lysophosphatidic acid receptor 1 | Heart | Fibroblasts |
| Scavenger receptor cysteine rich family member with 5 domains | Heart | Fibroblasts |
| Retinoic acid receptor responder 2 | Heart | Fibroblasts |
| KDEL endoplasmic reticulum protein retention receptor 3 | Heart | Fibroblasts |
| Repulsive guidance molecule BMP co-receptor A | Heart | Fibroblasts |
| Atypical chemokine receptor 4 | Heart | Fibroblasts |
| Prostaglandin I2 receptor | Heart | Fibroblasts |
| Atypical chemokine receptor 3 | Heart | Fibroblasts |
| Platelet derived growth factor receptor like | Heart | Fibroblasts |
| Smoothened, frizzled class receptor | Heart | Fibroblasts |
| GDNF family receptor alpha 1 | Heart | Fibroblasts |

Using immunofluorescent staining of lung tissue using an antibody directed against mannose receptor C type 1 (MRC1) indicated both strong and selective expression of mannose receptor C type 1 (MRC1) in cells that display the morphological characteristics of macrophages (FIG. 22).

Several studies (for example, Martinez-Pomares, L., 2012) have reported binding of Mannose and N-acetylgalactosamine (GalNAc) ligands to mannose receptor C type 1 (MRC1). We next conjugated an oligonucleotide directed against miR-21 (LNA-antimiR-21) with a moiety consisting of these ligands and a synthetic linker molecule (FIG. 23).

In particular, the preparation of carbohydrate ligand conjugated LNA oligonucleotide was carried out as follows:

Commercially available carbohydrate 4-aminophenyl 3,6-di-O-(α-D-mannopyranosyl)-α-D-mannopyranoside (Synthose, Toronto, Canada, #AM853, 24.8 mg) was reacted with 18.1 mg Acid-PEG5-NHS ester (Broadpharm, San Diego, California, #BP-22220) in 248 μL DMF containing 4.4 μL Diisopropylethylamine (DIPEA). Once TLC showed consumption of the starting carbohydrate the product formed was precipitated by addition of ether. Solids were collected by filtration and re-dissolved in pyridine (500 μL). Acetic anhydride (500 μL) was added to block all free hydroxyl groups on the tri-saccharide. The solution was evaporated to dryness and purified by Sephadex LH20 column chromatography using a 1:1 mixture of methanol and dichloromethan.

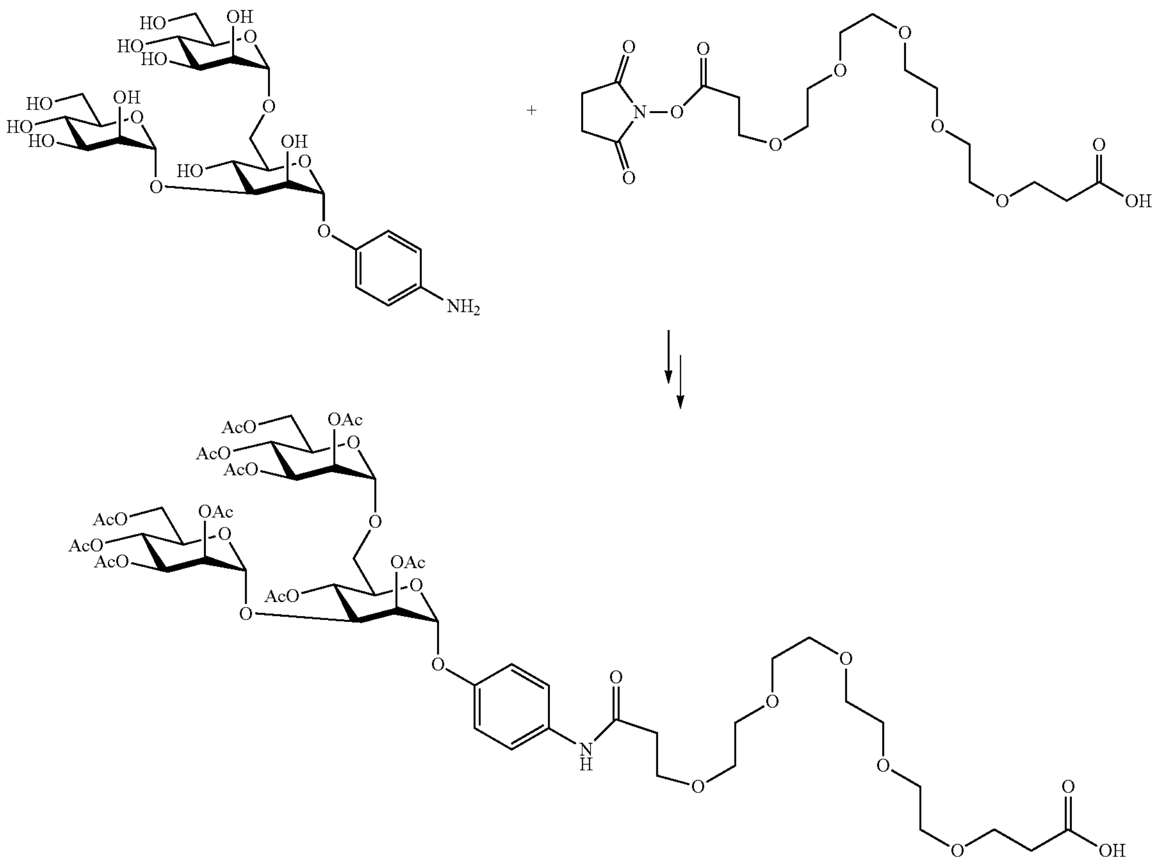

The 30 mg of obtained carbohydrate carboxylic acid was activated by 2.9 mg N-hydroxy-succinimide (NHS) in the presence of 3.7 μL diisopropylcarbodiimide and 303 μL DMF. The solution was stirred overnight at ambient temperature and was used without further purification for the conjugation reaction with the oligonucleotide.

Fully phosphorothioated LNA oligonucleotides were synthesized employing the conventional phosphoramidite oligomerization chemistry on solid phase. The oligonucleotides were equipped with an aminohexyl linker at the 5'-end which served as the reactive handle for ligand conjugation. Oligonucleotides were prepared as follows:

Oligonucleotides were assembled on a Mermade 12 synthesizer (LGC Biosearch, Alexandria, MN, USA). Syntheses were performed on a solid support made of controlled pore glass (CPG, 600 Å) derivatized with 2'-deoxy-thymidine with a loading of 87 μmol/g (obtained from LGC Biosearch). To assemble the required sequences phosphoramidites as well as ancillary reagents were purchased from SAFC (Hamburg, Germany). Specifically, the following locked nuclei acid (LNA) and DNA phosphoramidites were used:

(5'-O-dimethoxytrityl-$N^6$-(benzoyl)-(2'-O, 4'-C methylene)-adenosine-3'-O-(2-cyanoethyl-N,N-diisopropylamino) phosphoramidite, 5'-O-dimethoxytrityl-$N^4$-(benzoyl)-(2'-O, 4'-C methylene)-5-methylcytidine-3'-O-(2-cyanoethyl-N,N-diisopropylamino) phosphoramidite, (5'-O-dimethoxytrityl-$N^2$-(dimethylformamidine)-(2'-O, 4'-C methylene)-guanosine-3'-O-(2-cyanoethyl-N,N-diisopropylamino) phosphoramidite, and 5'-O-dimethoxytrityl-(2'-O, 4'-C methylene)-5-methyluridine-3'-O-(2-cyanoethyl-N,N-diisopropylamino) phosphoramidite. DNA phosphoramidites, including 5-methylcytidine, carried the same protecting groups as the LNA phosphoramidites. All amidites were dissolved in anhydrous acetonitrile (100 mM) and molecular sieves (3 Å) were added. In order to introduce the $C_6$-amino linkers at the 5'-end of the oligomers the corresponding aminohexyl N-(trifluoroacetylamido)-phosphoramidites available from Chemgenes (Wilmington, MA, USA) were used. The TFA protected aminolinker was introduced without any modification of the synthesis cycle except for the capping step which was omitted. 5-Ethyl thiotetrazole (ETT, 500 mM in acetonitrile) was used as activator solution. Coupling times for DNA amidites was 4 minutes other amidites were coupled for 6-8 minutes. Phosphorothioate linkages were generated using a 50 mM solution of 3-((dimethylamino-methylidene)amino)-3H-1,2,4-dithiazole-3-thione (DDTT, obtained from AM Chemicals, Oceanside, CA, USA) in anhydrous acetonitrile/pyridine (1:1 v/v).

After finalization of the solid phase synthesis, cyanoethyl protecting groups were removed by a 30 minute treatment with 20% diethyl amine in acetonitrile without cleaving the oligonucleotides from the support. Subsequently, the dried solid support was transferred to a polypropylene tube and treated with concentrated aqueous ammonia (Aldrich) for at least 18 hours at 55° C. After centrifugation the supernatant was transferred to a new tube and the CPG was washed with aqueous ammonia. The combined solutions were evaporated and the residue was reconstituted in buffer A (see below).

Crude oligonucleotides were purified by reversed phase (RP) HPLC using a C18 XBridge Prep column (5 μm, 19×50 mm) from Waters (Eschborn, Germany) and an AKTA Pure HPLC system (GE Helthcare) equipped with a fraction collector and a sample pump. Buffer A was 100 mM triethylammonium acetate (TEAAc, pH 7 from Biosolve, Valkenswaard, the Netherlands) and buffer B contained 95% acetonitrile in buffer A. A flow rate of 15 mL/min was used and gradient of 0-100% B within 120 column volumes was employed. Buffers were heated to 60° C. and the column was maintained in a column oven at the same temperature. Product elution was monitored at 280 nm and 2 mL fractions were collected.

Product containing fractions were pooled and desalted using size exclusion using a column packed with Sephadex G25 (GE Healthcare).

| ID | Sequence 5'-3' | Mol weight calc | Mol weight found |
|---|---|---|---|
| X89911 | (NH2C6)sTbsCbsdAsGbsdTsCbsd TsGbsdAsTbsdAsAbsdGsCbsdT | 5253.3 | 5252.7 |

-continued

| ID | Sequence 5'-3' | Mol weight calc | Mol weight found |
|---|---|---|---|
| X89913 | (NH2C6)sTbsCbsdAsGbsdTsdAsd TsTbsdAsGbsCbsAbsdGsCbsdT | 5253.3 | 5252.7 |

Key: dA, dC, dG, dT: DNA nucleotides
Ab, Cb, Gb, Tb: LNA nucleotides
s: phosphorothioate linkage
(NH2C6): aminohexyl linker Purified oligonucleotides were dissolved in 50 mM sodium carbonate buffer (pH 9.5) and DMSO in a ratio of 1:1.5 at a oligonucleotide concentration of 700 OD/mL. The NHS activated carbohydrate ligand was added in two portions separated by 90 min.

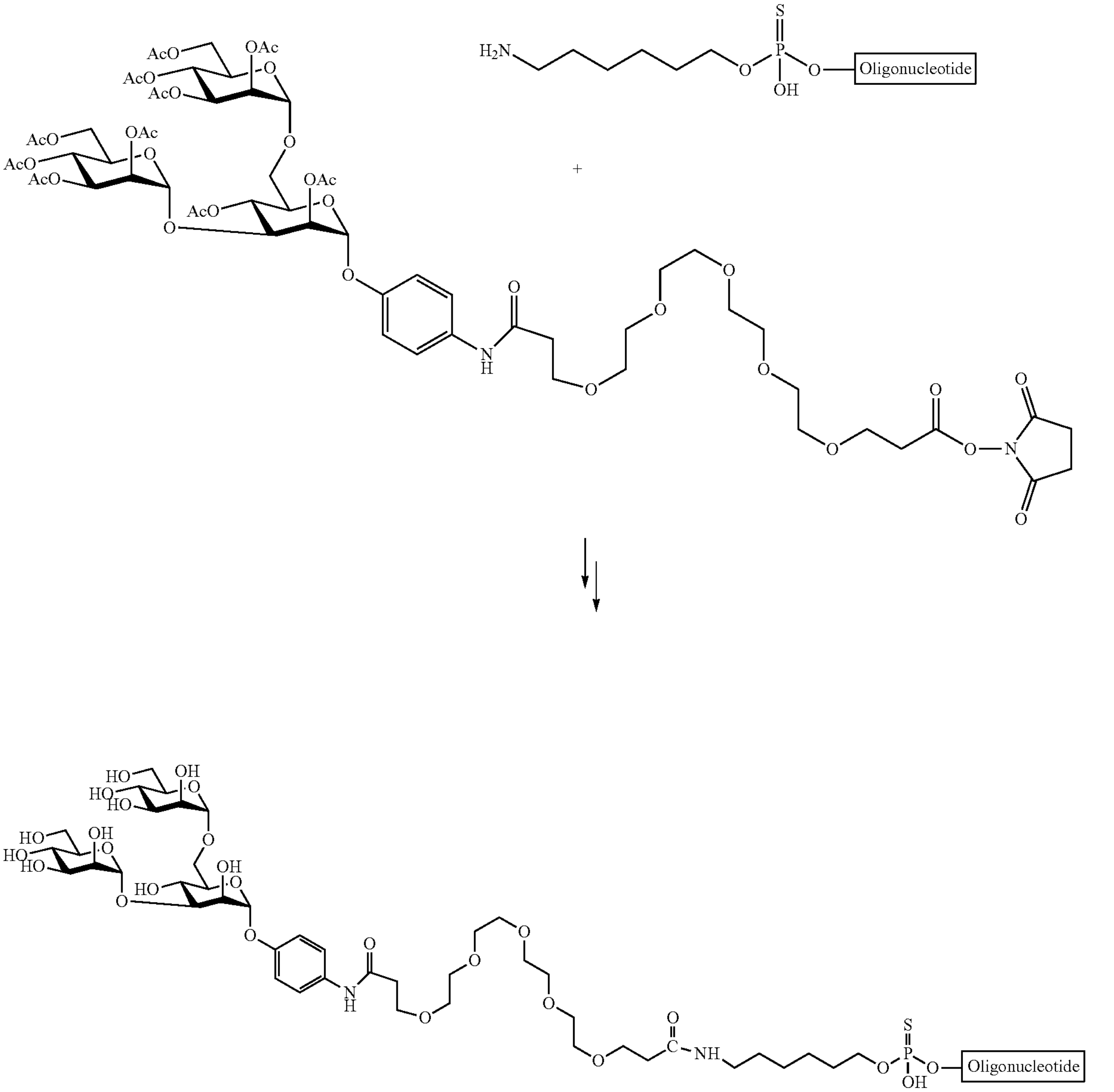

The reaction mixture was purified by RP HPLC employing the same method as described for the purification of the oligonucleotide. Product containing fractions were pooled together and precipitated by addition of ethanol. The pellet was collected by centrifugation. The supernatant was discarded and the pellet reconstituted in 500 mM NaCl. This solution was desalted using size exclusion chromatography with Sephadex G25 as stationary phase and water as eluent. The product containing aqueous solution was quantified by measuring the absorption at 260 nm. Finally, the solution was freeze dried.

| ID | Sequence (5'-3') |
|---|---|
| X89912 | (Tri-Man-PEG5)(NHC6)sTbsCbsdAsGbsdTsCbsd TsGbsdAsTbsdAsAbsdGsCbsdT |
| X89914 | (Tri-Man-PEG5)(NHC6)sTbsCbsdAsGbsdTsdAsd TsTbsdAsGbsCbsAbsdGsCbsdT |

| ID | Mol weight calculated | Mol weight found | Purity (%, RP HPLC) |
|---|---|---|---|
| X89912 | 6151.2 | 6150.0 | 91.3 |
| X89914 | 6151.2 | 6150.0 | 86.7 |

We next aimed to test for the delivery of the composition comprising these ligand-coupled oligonucleotides to the cells of the murine lung upon their inhalation in an aerosolized form. To this end, locked nucleic acid (LNA)/deoxyribonucleic acid mixmer of antimiR-21 (LNA-antimiR-21) was linked to fluorescein amidite derivative (FAM) at its 3'-end and ligand conjugated to its 5'-end. An exemplary structure of the mannose ligand-conjugated oligonucleotide used in this study is shown in FIG. 23.

We then administered the indicated doses of mannose- or GalNAc-conjugated LNA-antimiR-21-FAM into wild type mouse lungs by inhalation of the aerosolized composition using a dedicated mouse inhalation device (flexiVent system, SCIREQ, Canada; Yang et al., 2019) (FIG. 24A). Unconjugated LNA-antimiR-21 served as control while PBS-treated mouse lungs served as negative controls. Two hours after the application of the composition comprising the miR-21 inhibitor, bronchoalveolar lavage (BAL) fluid and lung tissue were collected from each animal as described in the methods section. Uptake of LNA-antimiR-21 in pulmonary cell types was assessed by determination of FAM signal intensity using flow cytometry (FIG. 24A). FAM signals were detected in cells isolated from both BALF and lung tissue and increased with increasing concentration of LNA-antimiR-21 (all groups described in FIGS. 24B and C).

Next, we determined the percentage of positive cells in both leukocyte and non-leukocyte fractions isolated from lung tissue. Flow cytometry analysis indicated that the relative fraction of FAM positive macrophages was increased when the composition comprising the mannose-conjugated LNA-antimiR-21 was administered compared to unconjugated LNA-antimiR-21 (FIG. 24C). We then estimated the relative amount of LNA-antimiR-21 molecules delivered to this cell type by determining the median fluorescence intensity of macrophage populations and normalized this to data from cells isolated from PBS-administered lungs. Compared to controls (unconjugated oligo-treated group), we observed a significantly higher median FAM fluorescence intensity in macrophages isolated from mannose-coupled LNA-antimiR-21-treated BALF or lungs (FIGS. 25A and B).

In summary, aerosolized inhalation of composition comprising the mannose-conjugated LNA-antimiR-21 resulted in higher delivery to pulmonary macrophages.

EXAMPLE 6

Inhibition of miR-21 Reduced Bleomycin-Induced Pulmonary Remodelling and Dysfunction To determine the effect of the inhaled mannose-conjugated LNA-antimiR-21 composition on pulmonary remodelling, we subjected wild type mice to bleomycin-induced lung injury and then administered the mannose-conjugated LNA-antimiR-21 composition locally into the lungs by inhalation on day 4 after lung injury (FIG. 26A). Staining extracellular matrix proteins in lung sections indicated that fibrosis is increased in mice administered with bleomycin. However, inhalation of the mannose-conjugated LNA-antimiR-21 composition led to a significant reduction of pulmonary fibrosis (FIG. 26B).

We then evaluated the impact of miR-21 inhibition on lung function by subjecting the mouse lungs to different breathing perturbations using the flexiVent ventilator. In order to determine the intrinsic elastic properties (or quasi-static mechanical properties) of the respiratory system, pressure-volume (PV) loops were obtained from PBS- and bleomycin-treated mice on day 14 after lung injury. Data from the PV loops from bleomycin-exposed mice with pulmonary fibrosis showed a downwards shift (see gray and black curves in FIG. 26C) indicating a reduction in lung capacity and compliance. Measurements revealed that quasi-static elastance, quasi-static compliance and inspiratory capacity parameters derived from the PV loops were significantly reduced in bleomycin-exposed mannose-conjugated LNA-antimiR-mismatch-21 mice (FIG. 26D-F). Aerosolized inhalation of mannose-conjugated LNA-antimiR-mismatch-21-treated mice prevented this decline in pulmonary function (see red curve in FIG. 26C).

Taken together, these data demonstrate the therapeutic efficacy of local delivery of macrophage-targeted, mannose-conjugated antimiR-21 composition by inhalation in a murine model of pulmonary fibrosis.

Methodological details in particular for Example 5 and Example 6 herein above are as follows:

Experimental animals and study design: All animal studies were performed in accordance with relevant guidelines and regulations of the responsible authorities and approval was obtained from the IRB at the Regierung von Oberbayern (ROB-55.2-2532.Vet_02-19-82).

Intratracheal administration of bleomycin: 10-weeks old C57BL/6N wild type mice were administered with bleomycin hydrochloride (Sigma Aldrich Taufkirchen, Germany) diluted in 50 µl sterile PBS at 2 U/kg body weight of mice using a microsprayer (Penn Century device distributed by BioJane Limited, China).

Aerosolized application of oligonucleotide inhibitors: AntimiRs were synthesized as fully phosphorothioated locked nucleic acid (LNA)/deoxyribonucleic acid mixmers (FAM-labeled antimiRs: BaseClick, Munich, Germany; Axolabs GmbH, Kulmbach, Germany). AntimiRs were applied using a flexiVent rodent ventilator FX2 (SciReq Inc., Canada) attached to a nebulizer unit (Aeroneb Lab—small droplet diameter 2.5-4 µm, Ireland) as described previously 2. For each mouse, the nebulizer was filled with 20 µl of 2.5, 5 or 10 mg/mL antimiR and the nebulizer was active for 40 ms per breath (at duty cycle of 25%) during ventilation of the mouse with 150 breaths per minute, 15 mL/Kg bodyweight tidal volume and an inhalation-exhalation time ratio of 2:1.

Lung function analysis: Lung function was assessed using a flexiVent rodent ventilator FX2 for mice. Mice were tracheotomized under deep anaesthesia, and a 20 G tracheal cannula inserted into the trachea was fixed tightly using a 4-0 silk suture to ensure no leaks and reliable measurements. The cannula was then connected to the flexiVent unit for mechanical ventilation (150 breaths per minute, 15 mL/Kg bodyweight tidal volume and an inhalation-exhalation time ratio of 0.67:1) and the lung function was assessed with different breathing manoeuvres—deep inflation, Prime-8 and pressure-driven ramp-style pressure-volume perturbation. Inspiration capacity, quasi-static compliance and quasi-static elastance parameters were derived from the PV loops.

Isolation of primary cells from adult mouse lung: Prior to harvesting the lungs, bronchoalveolar lavage fluid was collected by sequential (about 5 times) instillation and aspiration of PBS containing 2 mM EDTA through insertion of cannula in the trachea. Lungs were harvested and washed in ice-cold PBS containing 2 mM EDTA. The right lobes of the lung were cut into very small pieces in 3 ml enzyme digestion solution containing Collagenase II (Worthington, Lakewood, NJ), dispase I (Gibco) and DNaseI (Corning, Bedford, USA) followed by incubation at 37° C. for 25 minutes. Enzymatic digestion of the lungs was stopped by addition of 500 μl of foetal calf serum and the cell suspension was then mixed by pipetting up and down using a 1 mL syringe. Cells were then filtered through a 100 μm cell strainer and centrifuged at 400 g at 4° C. for 7 minutes. The cells were then treated with 1 mL of erythrocyte lysis buffer (nine parts of 155 mmol/1 $NH_4Cl$ and one part of 0.1 mol/l Tris-HCl pH 7.65) for about 5 minutes at room temperature before neutralizing with 4 mL of PBS. Cells were then washed in FACS buffer (PBS containing 2 mM EDTA and 0.5% biotin-free bovine serum albumin) and filtered through a 70 μm cell strainer.

Flow cytometry/cell sorting: Cell pellets were then treated with anti-mouse CD16/CD32 at 4° C. for 15 min before being incubated with magnetic microbeads-conjugated anti-CD45 primary antibody at 4° C. for 20 min in a shaker. Leukocyte fraction was separated from other cell fractions using AutoMACS (Miltenyi Biotec, Bergish Gladbach, Germany).

Immune cell enriched fractions from the lung were either stained with antibodies against CD45, F4/80, SIGLECF and MRC1 to isolate macrophages, or with antibodies against CD45, Ly6G and CD3 to isolate neutrophils and T cells. The flow through lung cell suspension enriched for non-immune cell fractions were stained with antibodies against CD45, CD140a, CD105 and EPCAM to analyse fibroblast, endothelial and epithelial cells, respectively. Anti-CD45 antibody was used in the non-immune cell fractions to exclude leukocytes. Cells were analysed using Sony SH800 sorter.

Mouse treated with PBS was included on each experiment day to normalize the background fluorescence and to facilitate comparison across replicate and treatment groups performed on different days. We then analyzed the data using FlowJo software (v 10.7.1) to calculate the number of FAM-positive cells and median fluorescence intensity.

MicroRNA library preparation: Total RNA was then extracted using Trizol reagent and small RNA libraries were prepared using NEBNext small RNA library prep set for Illumina (NEB) following manufacturer's protocol. The amplified PCR products were purified using a Monarch kit and were run on 6% urea-PAGE for selection based on amplification length. The bands corresponding to miRNAs (approximately 150 bp) were cut out and eluted overnight using the lexogen Gel extraction module kit. Libraries were multiplexed, pooled and the deep sequencing run was performed on a MiSeq sequencer (50 cycles single run) using a paired read chip at 75 bp read length.

Bioinformatics: Then, FASTQ files were generated from raw BCL output from the sequencer. Sequencing of small RNAs yielded approximately 1.5 million reads per sample (approximately % valid reads) after removing the adaptor sequences, and filtering low quality (Phred Q<20) and small (less than 12 nucleotides) reads. The remaining high-quality reads were further filtered for unique sequences, counted for each sample, aligned to small RNA reference library (miRNA hairpins from miRBase v22) and read abundances normalized to counts per million using miRDeep2 tool. We then then filtered for microRNAs that showed average detection range across all samples of >5 counts per million. DESeq2 was used to test for differential expression of small RNAs between the samples and an "ashr" adaptive shrinkage estimator (Stephens (2017); Biostatistics 18(2): 275-294) was used for the log fold changes. R package tool pHeatmap was used to test for differential expression of small RNAs between the samples. Image in FIG. 6A was generated using BioRender online tool and the chemical structures were generated using ChemDraw (v20.0).

Histology: The left lung lobe still connected to the trachea and cannula was perfused with PBS and 4% paraformaldehyde (PFA) prior to storing the tissues in 4% PFA for 24 hours for paraffin embedding. For the analysis of collagen deposition, paraffin sections (8 μm) of left ventricular myocardium were stained with Sirius red and Fast green. Whole heart images were taken with a 10× objective using a AxioObserver.Z1 (Zeiss, Jena, Germany) motorized scanning-stage microscopy (130×85; Marzhauser, Wetzlar, Germany) and analysed using Metamorph software (Molecular Devices). Fibrosis was quantified as the ratio of signals from Sirius red to Fast green in each section.

For Kryoblocks, a piece of the lung tissue (left lobe) was kept in 30% sucrose/PBS solution at 4° C. overnight 2 hours after incubation in 4% PFA. Lung kryosections (5 μm) were fixed with methanol (at −20° C. for 10 min), washed thoroughly with tap water and treated with acetone (at −20° C. for 1 min). The sections were then blocked with 5% goat serum diluted in PBS and stained with primary antibodies against MRC1 (#AB64693, RRID: AB_1523910, Abcam) at 4° C. overnight. The sections were then stained with the respective secondary antibodies. Nuclei were stained with Sytox green (Life Technologies). Images were acquired by confocal microscopy using 63× glycerol objective (Leica SP5).

Statistical analysis: Data denote mean and individual values. Statistical analysis was performed using Graphpad Prism software package (version 8). Data distribution was assessed by Shapiro-Wilk test for normality. Bartlett's test was performed to test homogeneity of variance, and Spearman's rank correlation test was performed to test heteroscedasticity. Differences among two means were assessed by Students' t-test. Differences among multiple means were assessed by two-way analysis of variance (ANOVA) followed by Tukey's post test. A P-value of less than 0.05 was considered significant.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

REFERENCES

Adam (2012); Basic Research in Cardiology 107(5): 278
Altshuler (2010); Biochemistry (Moscow) 75(13): 1584-1605
Bahit (2018); JACC: Heart Failure 6(3): 179-186
Bartel (2018); Cell 173(1): 20-51
Bashore (2012); Journal of the American College of Cardiology 59(24): 2221-2305.
Bosson (2016); Mol Cell 56(3): 347-359
Brennan (1985); Science 229(4708): 81-83
Brown (2007); Nature Biotechnology 25(12): 1457-1467
Cardin (2012); Circulation: Arrhythmia and Electrophysiology 5(5): 1027-1035
Carter (1992); Bio/Technology 10(2): 163-167
Cole (1985); Journal of Immunological Methods 78(2): 271-278
Harlow (1988); Antibodies: a laboratory manual. Cold Spring Harbor Laboratory
Harlow (1999); Using antibodies: a laboratory manual. Cold Spring Harbor Laboratory Press
Hinkel (2012); Circulation 128(10): 1066-1075
Hollinger (2005); Nature Biotechnology 23: 1126-1136
Jones (1986); Nature 321(6069): 522-525
Juliano (2016); Nucleic Acids Research, 44(14)
Khvorova (2017); Nature Biotechnology 35: 238-248
Köhler (1975); Nature, 256(5517), 495-497
Kozbor (1983); Immunol Today 4(3): 72-79
Li (2014); Nature Reviews Drug Discovery, 13(8), 622-638
Lu (2019); Nature Reviews Cardiology 16: 661-674
Martinez-Pomares (2012); J. Leukoc. Biol. 92: 1177-1186
Mendell (2012); Cell 148(6): 1172-1187
Milstein 1983); Nature, 305(5934), 537-540
Morimoto (1992); J Biol Chem 267(31): 21987-21990
Patrick (2010); Journal of Clinical Investigation, 120(11), 3912-3916
Pellicori (2019); Heart Failure Review 25: 147-159
Potere (2019); Front Cardiovasc Med 2019 Apr. 26; 6:51
Presta (1992); Current Opinion in Biotechnology 3(4): 394-398
Ramanujam (2016); Molecular Therapy 24(11): 1939-1948
Ramilowski (2015); Nat. Commun. 6(1): 7866
Riechmann (1988); Nature, 332(6162), 323-327
Rupaimoole (2017); Nature Reviews Drug Discovery 16: 203-222
Sambrook (2001); Molecular Cloning: A Laboratory Manual (Fourth Edition). Cold Spring
Harbor Laboratory Press.
Sayed (2010); Journal of Biological Chemistry, 285(26), 20281-20290
Sgalla (2018); Respiratory Research, 19(1), 1-18
Shalaby (1992); The Journal of Experimental Medicine, 175(1), 217-225
Skelly (2018); Cell Reports, 22(3), 600-610
Sood (2006); Proceedings of the National Academy of Sciences of the United States of
America, 103(8), 2746-2751
Stenvang (2012); Silence 3(1): 1
Stephens (2017); Biostatistics 18, 275-294
Thum (2008); Nature 456: 980-984
Tutt (1991); Journal of Immunology 147(1): 60-69
Wessels (2019); Nature Communications 10(1): 1626
Xu (2020); Journal of Infection 80: 394-400
Yang (2019); ACS Nano 13: 1029-1041
Yona (2013); Immunity 38(1): 79-91

The invention claimed is:

1. A method of treating pulmonary fibrosis associated with and/or caused by a viral infection, the method comprising administering to a subject in need thereof a composition comprising an inhibitor of miR-21 and a moiety that delivers said inhibitor of miR-21 selectively to a lung macrophage, wherein said moiety comprises mannose, wherein the inhibitor of miR-21 is conjugated to said moiety via a linker, and wherein:

(i) the linker is:

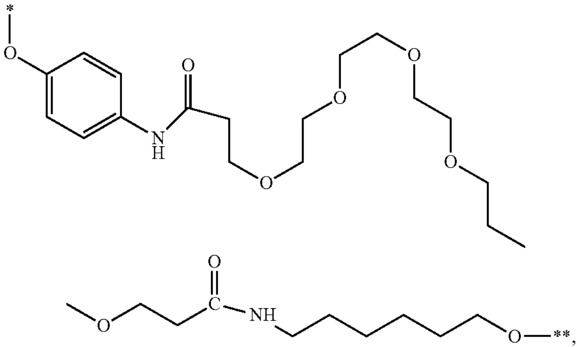, wherein * represents a bond to the moiety that delivers said inhibitor of miR-21 selectively to a lung macrophage and ** represents a bond to the inhibitor of miR-21; and/or (ii) the moiety that delivers said inhibitor of miR-21 to a macrophage is:

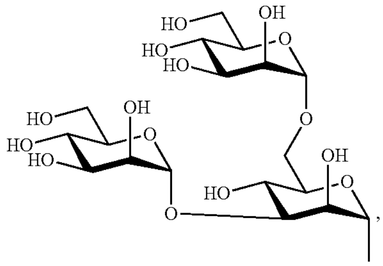, wherein the linker is attached at the anomeric carbon at the lower right hand part of the structure.

2. The method of claim 1, wherein the selectively delivery means a selective and preferential binding to said macrophage over non-target cells.

3. The method of claim 1, wherein the composition is administered by a pulmonary administration.

4. The method of claim 3, wherein the composition is administered by an aerosolized composition to the lung of the subject by inhalation or by other means of local administration to the lung, bronchi and/or airways.

5. The method of claim 1, wherein the viral infection is a corona virus infection.

6. The method of claim 1, wherein the pulmonary fibrosis is associated with and/or caused by pulmonary support or mechanical ventilation, optionally following Adult/Acute Respiratory Distress Syndrome (ARDS).

7. The method of claim 1, wherein the composition is administered to the subject at least about 5 days after Adult/Acute Respiratory Distress Syndrome (ARDS).

8. The method of claim 1, wherein the composition is administered by intraarterial administration.

9. The method of claim 1, wherein the inhibitor of miR-21 comprises or is an antisense miRNA-21.

10. The method of claim 9, wherein the antisense miRNA-21 is an oligonucleotide that comprises a sequence complementary to miR-21.

11. The method of claim 9, wherein the antisense miRNA-21 is a locked nucleic acid (LNA) or a phosphorothioated LNA/DNA mixmer.

12. The method of claim 1, wherein the inhibitor of miR-21 is selected from SEQ ID NO:1, SEQ ID NO:2, SEQ ID NO:3, SEQ ID NO: 7, SEQ ID NO:8 and SEQ ID NO: 9.

13. The method of claim 1, wherein the composition contains the following compound, wherein the LNA-anti-miR-21 is SEQ ID NO:1:

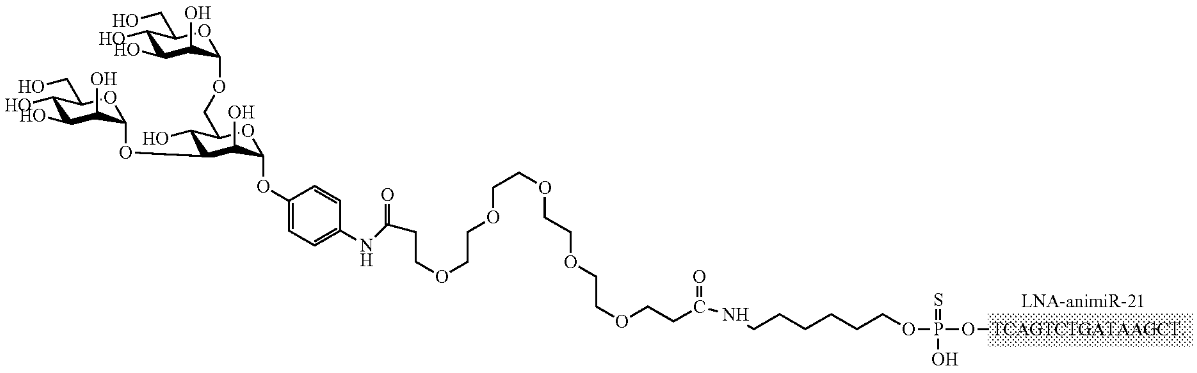

14. The method of claim 7, wherein the composition is further to be administered to the subject at least about 19 days after Adult/Acute Respiratory Distress Syndrome (ARDS).

15. The method of claim 8, wherein the composition is administered by intracardial administration, intracoronary administration, and/or by administration via inhalation.

16. The method of claim 12, wherein the inhibitor of miR-21 is bound to the linker via the phosphor atom of a terminal phosphorothioate group.

17. The method of claim 1, wherein the linker is:

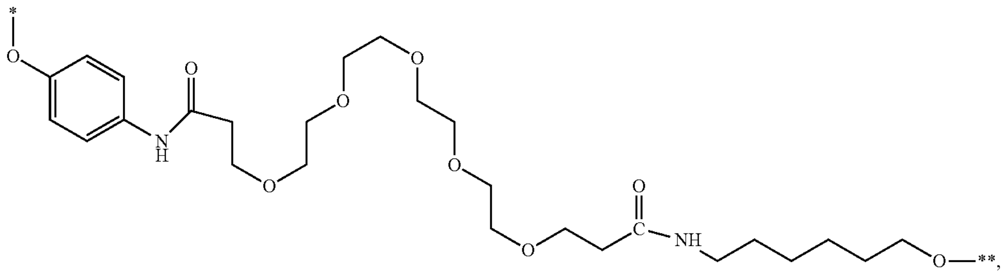

wherein * represents a bond to the moiety that delivers said inhibitor of miR-21 selectively to a lung macrophage and ** represents a bond to the inhibitor of miR-21; and the moiety that delivers said inhibitor of miR-21 to a macrophage is:

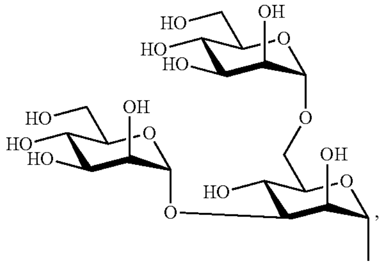

wherein the linker is attached at the anomeric carbon at the lower right hand part of the structure.

* * * * *

SEQUENCE LISTING

<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: 1
<223> OTHER INFORMATION: /note="Is a locked nucleotide"
<220> FEATURE:
<221> NAME/KEY: misc_feature
<222> LOCATION: 1..15
<223> OTHER INFORMATION: /note="Phosphorothioate backbone"
<220> FEATURE:
<221> NAME/KEY: misc_feature
<222> LOCATION: 2
<223> OTHER INFORMATION: /note="Is a locked nucleotide"
/note="Is a 5-methyl-cytosine"
<220> FEATURE:
<221> NAME/KEY: misc_feature
<222> LOCATION: 4
<223> OTHER INFORMATION: /note="Is a locked nucleotide"
<220> FEATURE:
<221> NAME/KEY: misc_feature
<222> LOCATION: 6
<223> OTHER INFORMATION: /note="Is a locked nucleotide"
/note="Is a 5-methyl-cytosine"
<220> FEATURE:
<221> NAME/KEY: misc_feature

```
<222> LOCATION: 8
<223> OTHER INFORMATION: /note="Is a locked nucleotide"
<220> FEATURE:
<221> NAME/KEY: misc_feature
<222> LOCATION: 10
<223> OTHER INFORMATION: /note="Is a locked nucleotide"
<220> FEATURE:
<221> NAME/KEY: misc_feature
<222> LOCATION: 12
<223> OTHER INFORMATION: /note="Is a locked nucleotide"
<220> FEATURE:
<221> NAME/KEY: misc_feature
<222> LOCATION: 14
<223> OTHER INFORMATION: /note="Is a locked nucleotide"
      /note="Is a 5-methyl-cytosine"

<400> SEQUENCE: 1

tcagtctgat aagct                                                  15


<210> SEQ ID NO 2
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: 1
<223> OTHER INFORMATION: /note="Is a locked nucleotide"
<220> FEATURE:
<221> NAME/KEY: misc_feature
<222> LOCATION: 1..15
<223> OTHER INFORMATION: /note="Phosphorothioate backbone"
<220> FEATURE:
<221> NAME/KEY: misc_feature
<222> LOCATION: 3
<223> OTHER INFORMATION: /note="Is a locked nucleotide"
<220> FEATURE:
<221> NAME/KEY: misc_feature
<222> LOCATION: 6
<223> OTHER INFORMATION: /note="Is a locked nucleotide"
      /note="Is a 5-methyl-cytosine"
<220> FEATURE:
<221> NAME/KEY: misc_feature
<222> LOCATION: 7
<223> OTHER INFORMATION: /note="Is a locked nucleotide"
<220> FEATURE:
<221> NAME/KEY: misc_feature
<222> LOCATION: 10
<223> OTHER INFORMATION: /note="Is a locked nucleotide"
<220> FEATURE:
<221> NAME/KEY: misc_feature
<222> LOCATION: 12
<223> OTHER INFORMATION: /note="Is a locked nucleotide"
<220> FEATURE:
<221> NAME/KEY: misc_feature
<222> LOCATION: 14
<223> OTHER INFORMATION: /note="Is a locked nucleotide"
      /note="Is a 5-methyl-cytosine"
<220> FEATURE:
<221> NAME/KEY: misc_feature
<222> LOCATION: 15
<223> OTHER INFORMATION: /note="Is a locked nucleotide"

<400> SEQUENCE: 2

tcagtctgat aagct                                                  15


<210> SEQ ID NO 3
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
```

<222> LOCATION: 1..15
<223> OTHER INFORMATION: /note="Is a locked nucleotide"
/note="Phosphorothioate backbone"
<220> FEATURE:
<221> NAME/KEY: misc_feature
<222> LOCATION: 2
<223> OTHER INFORMATION: /note="Is a 5-methyl-cytosine"
<220> FEATURE:
<221> NAME/KEY: misc_feature
<222> LOCATION: 6
<223> OTHER INFORMATION: /note="Is a 5-methyl-cytosine"
<220> FEATURE:
<221> NAME/KEY: misc_feature
<222> LOCATION: 14
<223> OTHER INFORMATION: /note="Is a 5-methyl-cytosine"

<400> SEQUENCE: 3
tcagtctgat aagct 15

<210> SEQ ID NO 4
<211> LENGTH: 22
<212> TYPE: RNA
<213> ORGANISM: Homo sapiens

<400> SEQUENCE: 4
uagcuuauca gacugauguu ga 22

<210> SEQ ID NO 5
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: 1..15
<223> OTHER INFORMATION: /note="Is a locked nucleotide"
/note="Phosphorothioate backbone"
<220> FEATURE:
<221> NAME/KEY: misc_feature
<222> LOCATION: 2
<223> OTHER INFORMATION: /note="Is a 5-methyl-cytosine"
<220> FEATURE:
<221> NAME/KEY: misc_feature
<222> LOCATION: 11
<223> OTHER INFORMATION: /note="Is a 5-methyl-cytosine"
<220> FEATURE:
<221> NAME/KEY: misc_feature
<222> LOCATION: 14
<223> OTHER INFORMATION: /note="Is a 5-methyl-cytosine"

<400> SEQUENCE: 5
tcagtattag cagct 15

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 6

Cys Ser Pro Gly Ala Lys Val Arg Cys
1 5

<210> SEQ ID NO 7
<211> LENGTH: 15
<212> TYPE: DNA
<213> ORGANISM: Artificial Sequence
<220> FEATURE:
<223> OTHER INFORMATION: An artificially synthesized sequence -continued

```
<220> FEATURE:
<221> NAME/KEY: misc_feature
<222> LOCATION: 1..15
<223> OTHER INFORMATION: /note="Is a locked nucleotide"
<220> FEATURE:
<221> NAME/KEY: misc_feature
<222> LOCATION: 2
<223> OTHER INFORMATION: /note="Is a 5-methyl-cytosine"
<220> FEATURE:
<221> NAME/KEY: misc_feature
<222> LOCATION: 6
<223> OTHER INFORMATION: /note="Is a 5-methyl-cytosine"
<220> FEATURE:
<221> NAME/KEY: misc_feature
<222> LOCATION: 14
<223> OTHER INFORMATION: /note="Is a 5-methyl-cytosine"

<400> SEQUENCE: 7

tcagtctgat aagct                                                     15


<210> SEQ ID NO 8
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: 1..15
<223> OTHER INFORMATION: /note="Is a locked nucleotide"
      /note="Phosphorothioate backbone"

<400> SEQUENCE: 8

tcagtctgat aagct                                                     15


<210> SEQ ID NO 9
<211> LENGTH: 15
<212> TYPE: DNA
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: 1..15
<223> OTHER INFORMATION: /note="Is a locked nucleotide"

<400> SEQUENCE: 9

tcagtctgat aagct                                                     15


<210> SEQ ID NO 10
<211> LENGTH: 18
<212> TYPE: PRT
<213> ORGANISM: Artificial Sequence
<220> FEATURE:
<223> OTHER INFORMATION: An artificially synthesized sequence

<400> SEQUENCE: 10

Gly Glu Gly Thr Ser Thr Gly Ser Gly Gly Ser Gly Gly Ser Gly Gly
1               5                   10                  15

Ala Asp
```